(12) United States Patent
Kasturirangan et al.

(10) Patent No.: US 10,457,732 B2
(45) Date of Patent: Oct. 29, 2019

(54) BISPECIFIC BINDING PROTEINS AND USES THEREOF

(71) Applicant: MEDIMMUNE, LLC, Gaithersburg, MD (US)

(72) Inventors: Srinath Kasturirangan, Gaithersburg, MD (US); Changshou Gao, Gaithersburg, MD (US); Godfrey Rainey, Gaithersburg, MD (US); Michelle Morrow, Cambridge (GB); Claire Louise Dobson, Cambridge (GB); Stacey Drabic, Gaithersburg, MD (US); Darren Schofield, Cambridge (GB); Gianluca Carlesso, Gaithersburg, MD (US); Kristen Pollizzi, Gaithersburg, MD (US); Yariv Mazor, Gaithersburg, MD (US); Michael Oberst, Gaithersburg, MD (US); Scott A. Hammond, Gaithersburg, MD (US); Brian Lobo, Gaithersburg, MD (US); Prakash Manikwar, Gaithersburg, MD (US); Jonathan Seaman, Cambridge (GB); Simon Dovedi, Cambridge (GB); Ronald Herbst, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 26 days.

(21) Appl. No.: 15/588,271

(22) Filed: May 5, 2017

(65) Prior Publication Data

US 2018/0022807 A1 Jan. 25, 2018

Related U.S. Application Data

(60) Provisional application No. 62/332,788, filed on May 6, 2016.

(51) Int. Cl.
*C07K 16/28* (2006.01)

(52) U.S. Cl.
CPC ...... *C07K 16/2818* (2013.01); *C07K 16/2803* (2013.01); *C07K 16/2827* (2013.01); *C07K 16/2878* (2013.01); *C07K 2317/31* (2013.01); *C07K 2317/35* (2013.01); *C07K 2317/41* (2013.01); *C07K 2317/51* (2013.01); *C07K 2317/515* (2013.01); *C07K 2317/52* (2013.01); *C07K 2317/524* (2013.01); *C07K 2317/526* (2013.01); *C07K 2317/53* (2013.01); *C07K 2317/55* (2013.01); *C07K 2317/622* (2013.01); *C07K 2317/73* (2013.01); *C07K 2317/732* (2013.01); *C07K 2317/76* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 2015/0274844 A1 | 10/2015 | Blankenship et al. | |
| 2015/0352225 A1 | 12/2015 | Rabuka et al. | |
| 2016/0145355 A1* | 5/2016 | Saha | C07K 16/3038 424/136.1 |

FOREIGN PATENT DOCUMENTS

WO  WO 2013/070565 A1  5/2013

* cited by examiner

*Primary Examiner* — Peter J Reddig

(57) ABSTRACT

The disclosure generally provides proteins that bind two epitopes (e.g., a first and a second epitope) and that are bivalent for binding to each of the first and second epitopes. The disclosure also provides for specific binding proteins, including antibodies, which bind to a target protein. The disclosure also provides compositions comprising such proteins, nucleic acid molecules encoding such proteins and methods of making such proteins. The disclosure provides methods of inducing an immune response in a subject as well as methods for treating or preventing cancer in a subject by administering the proteins, nucleic acid molecules and/or compositions to the subject.

12 Claims, 115 Drawing Sheets

Specification includes a Sequence Listing.

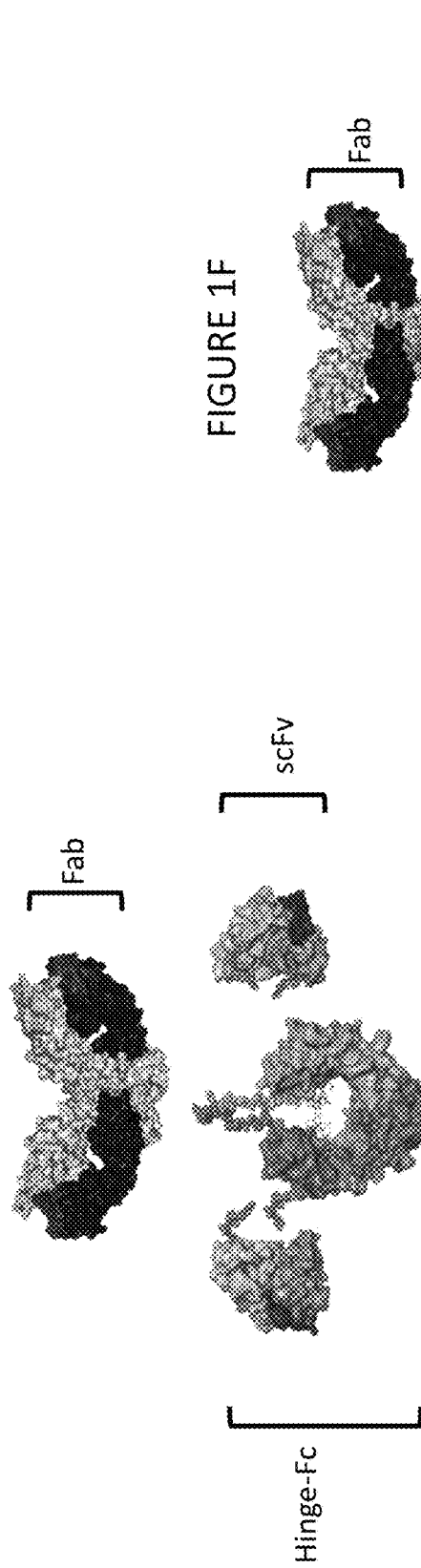
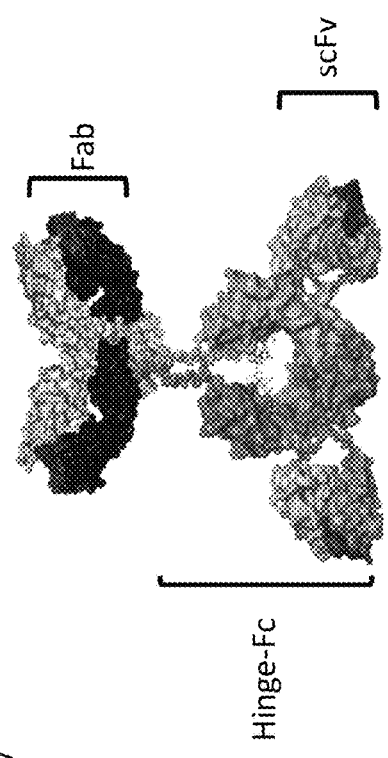
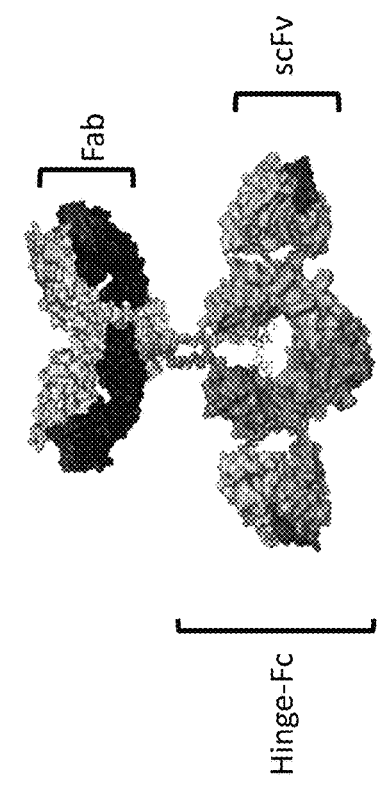

AK—scfv—GQP B

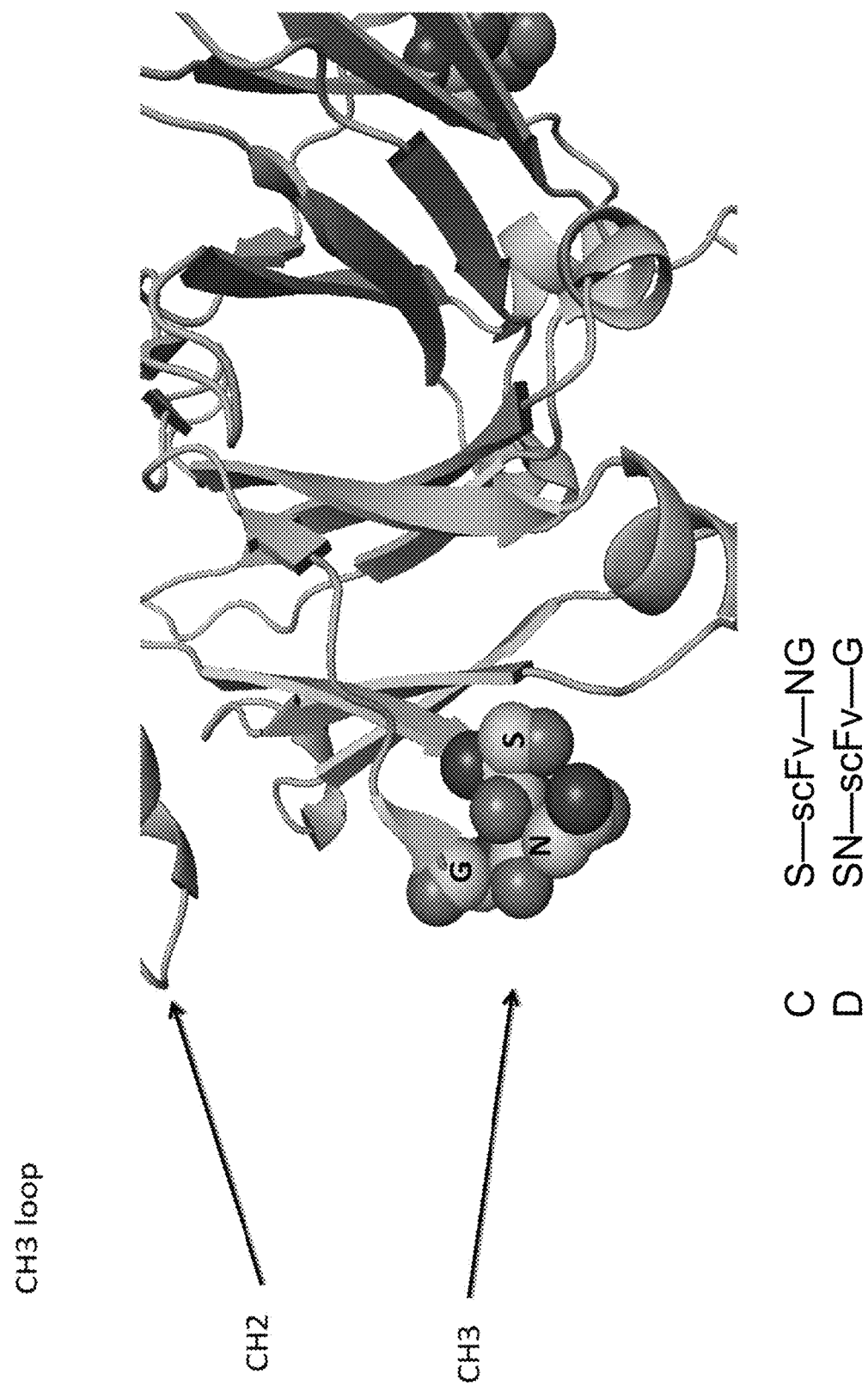

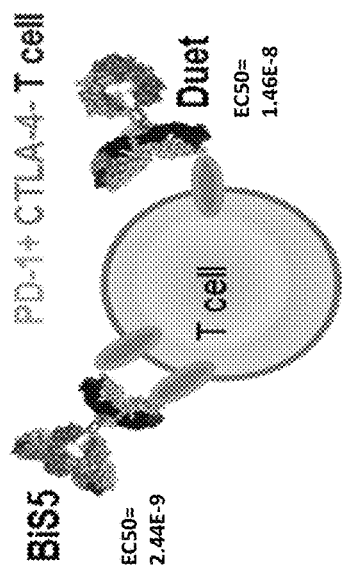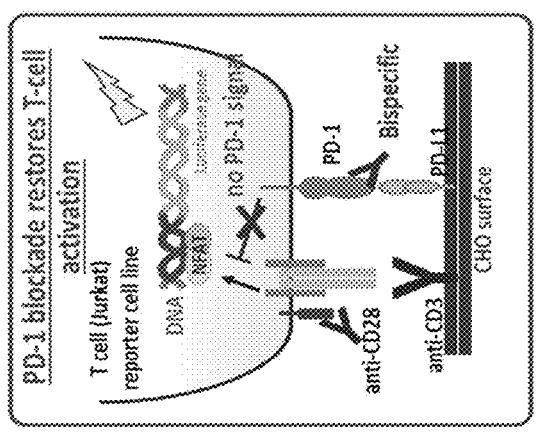
FIGURE 6A
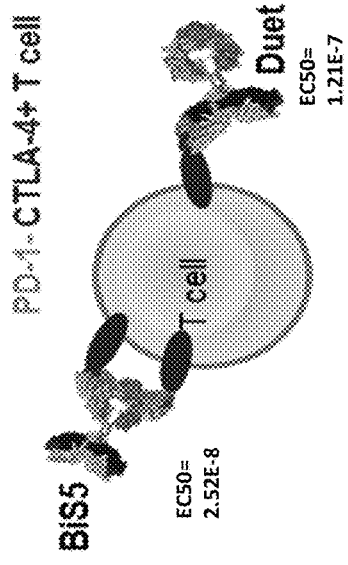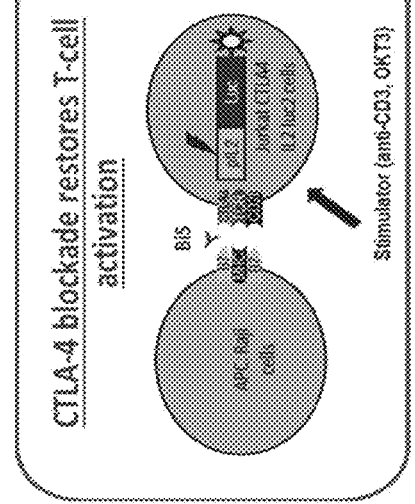
FIGURE 6B

FIGURE 16
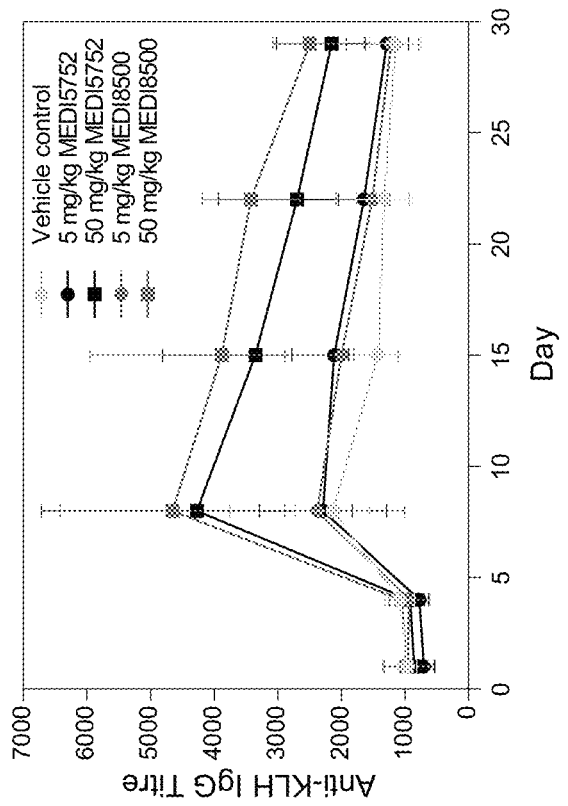
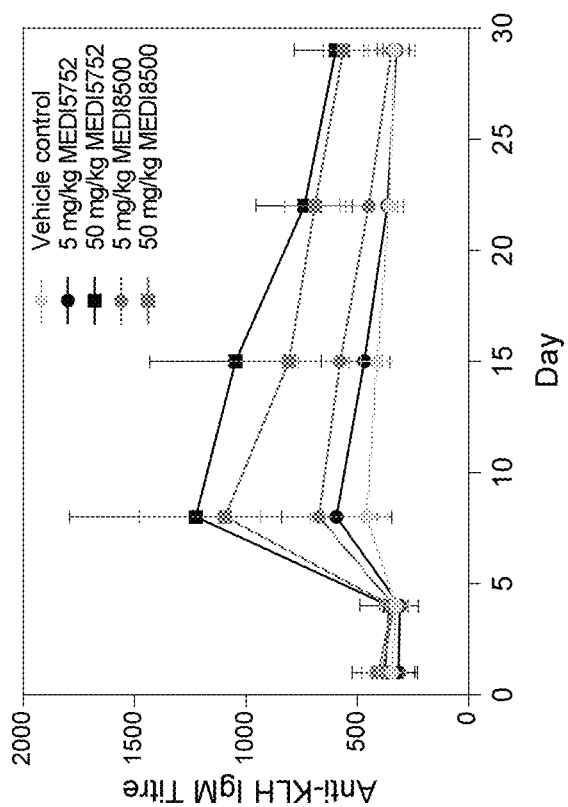

FIGURE 17

| CHO cell | PD-1 receptor density | CTLA-4 receptor density | PD-1/CTLA-4 ratio |
|---|---|---|---|
| | $2.4 \times 10^6$ | - | - |
| | - | $7.3 \times 10^4$ | - |
| | $7.3 \times 10^5$ | $5.5 \times 10^4$ | ~10:1 |
| | $1.4 \times 10^6$ | $3.9 \times 10^4$ | ~40:1 |

CHO cells expressing
PD-1:CTLA-4 (10:1)

CHO cells expressing
PD-1:CTLA-4 (40:1)

CHO cells expressing
PD-1:CTLA-4 (10:1)

CHO cells expressing
PD-1:CTLA-4 (40:1)

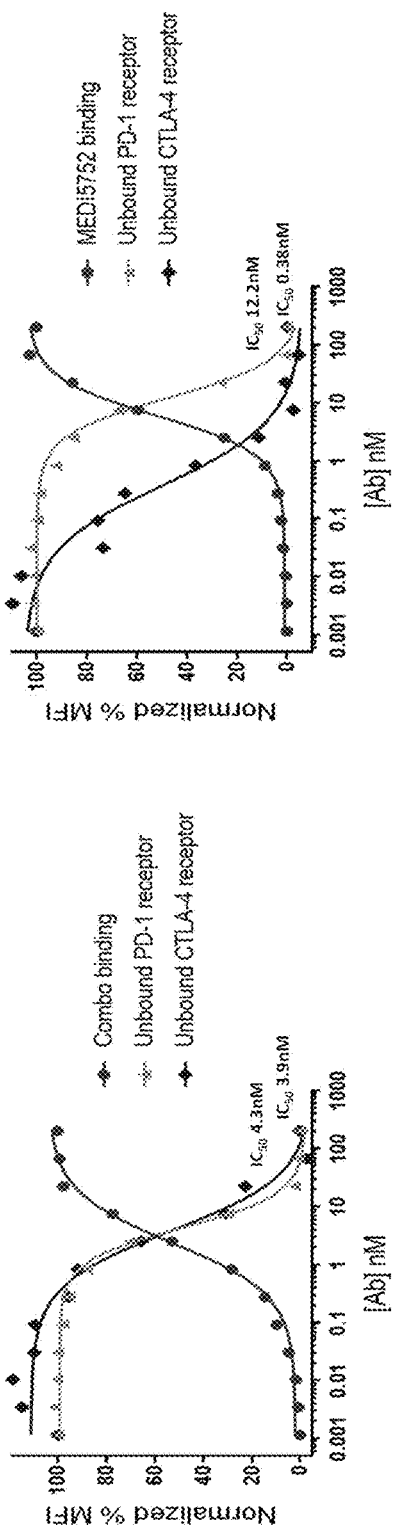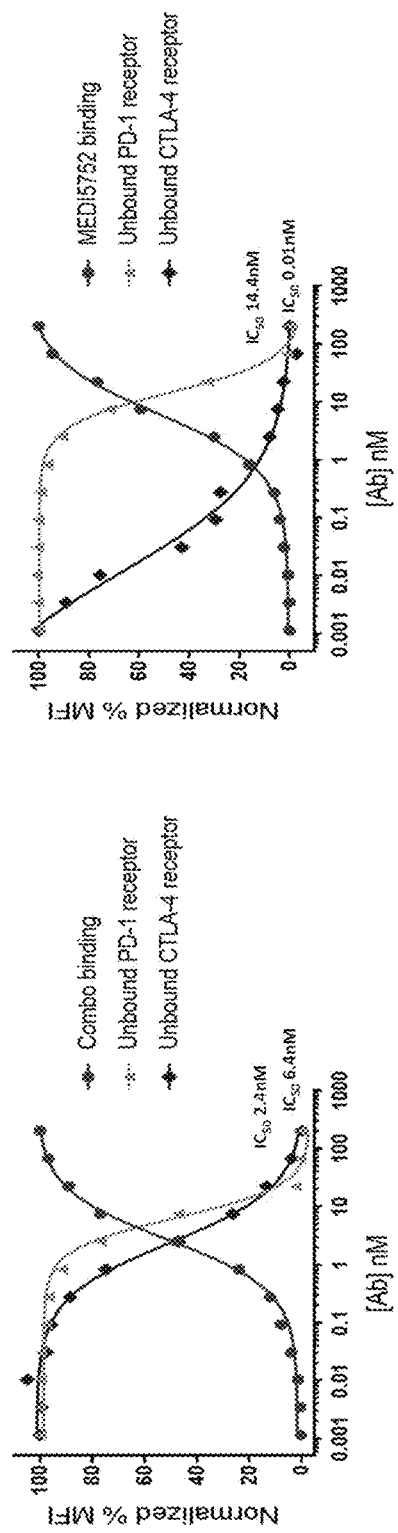

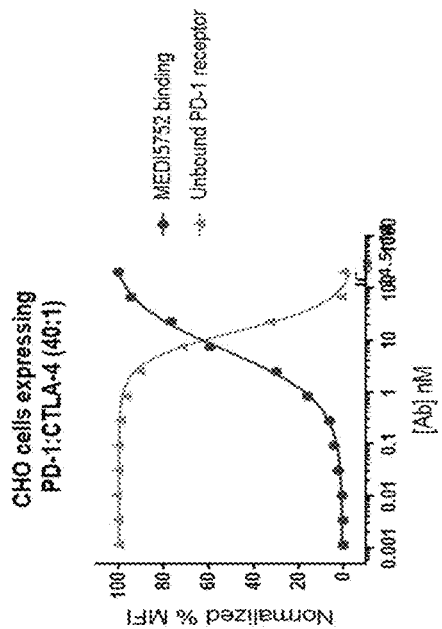
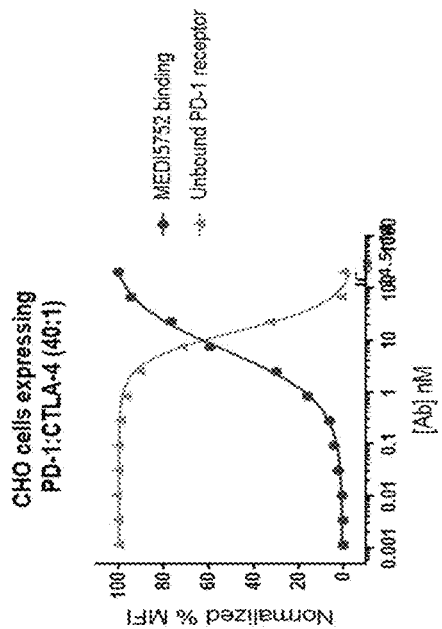
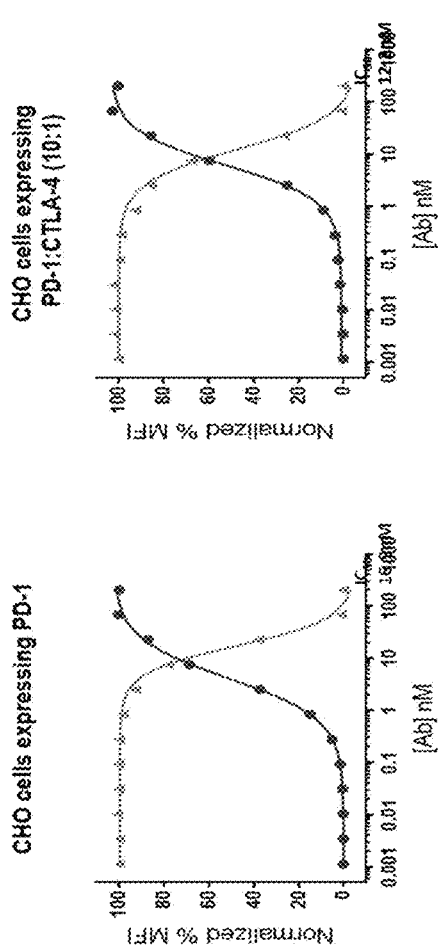
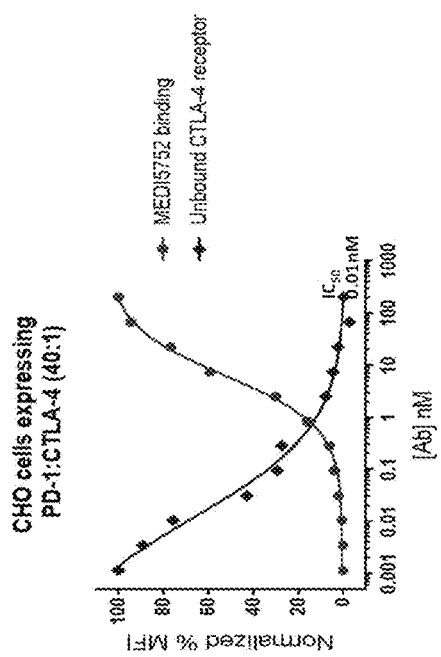
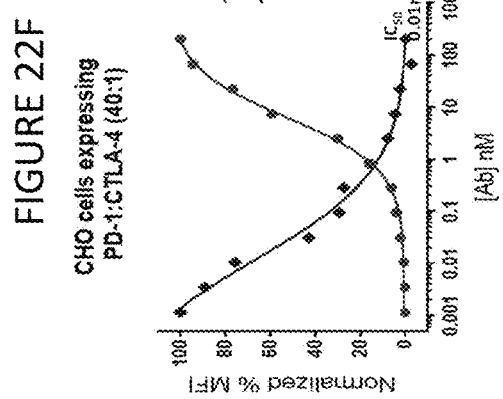
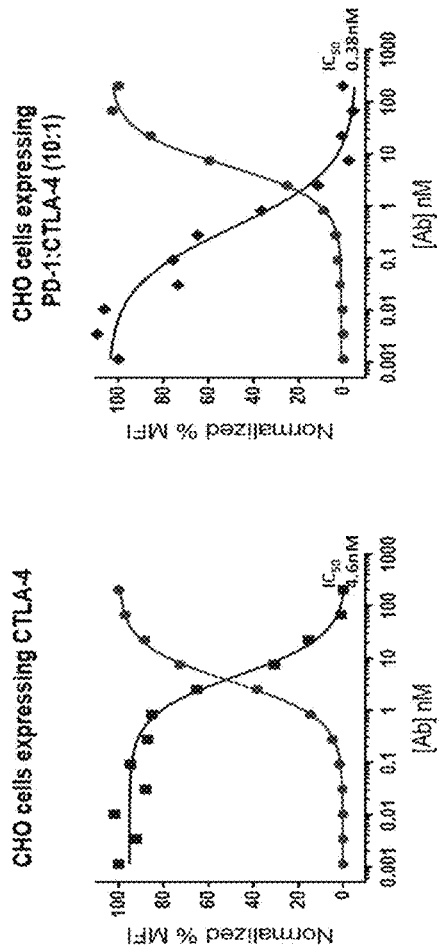

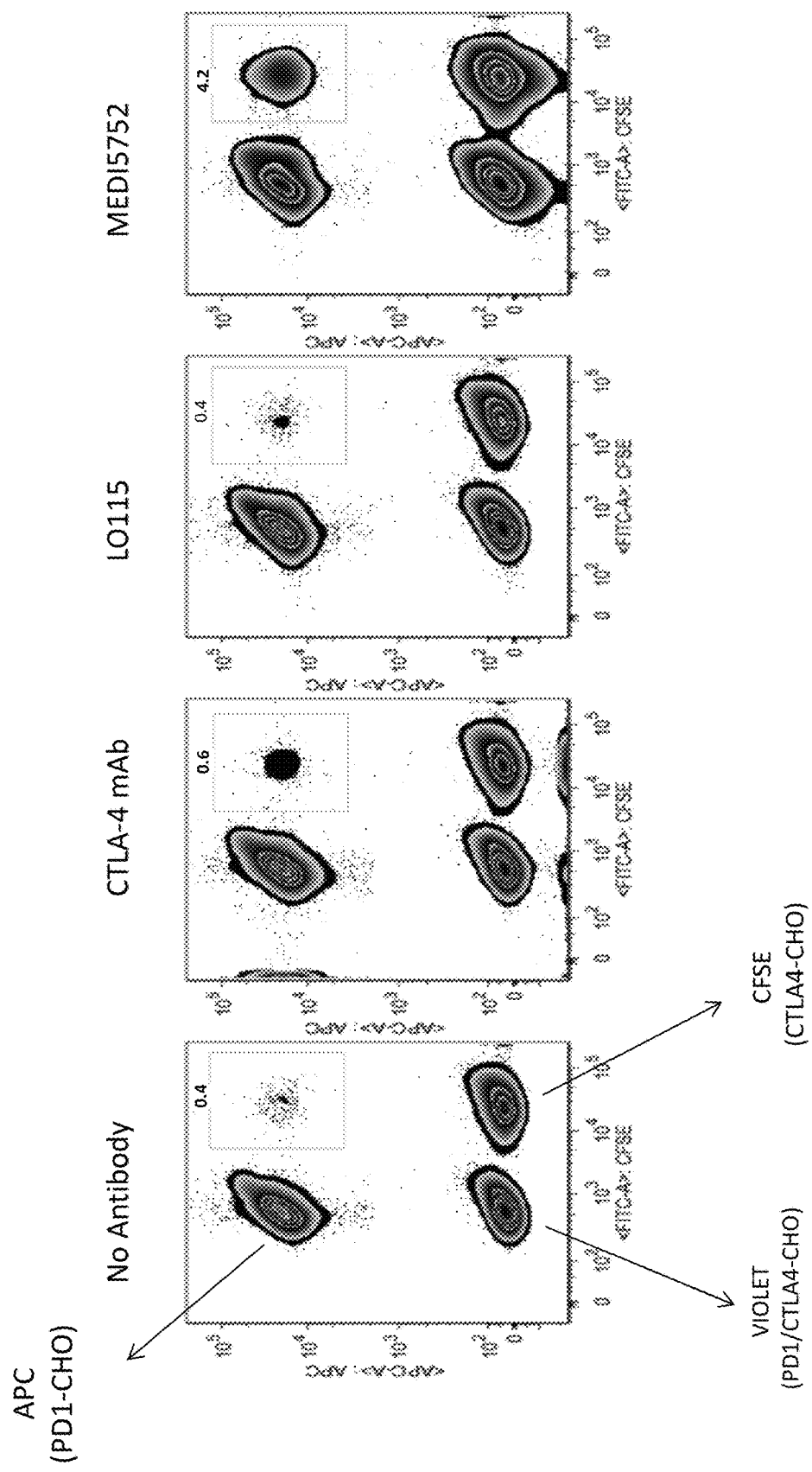

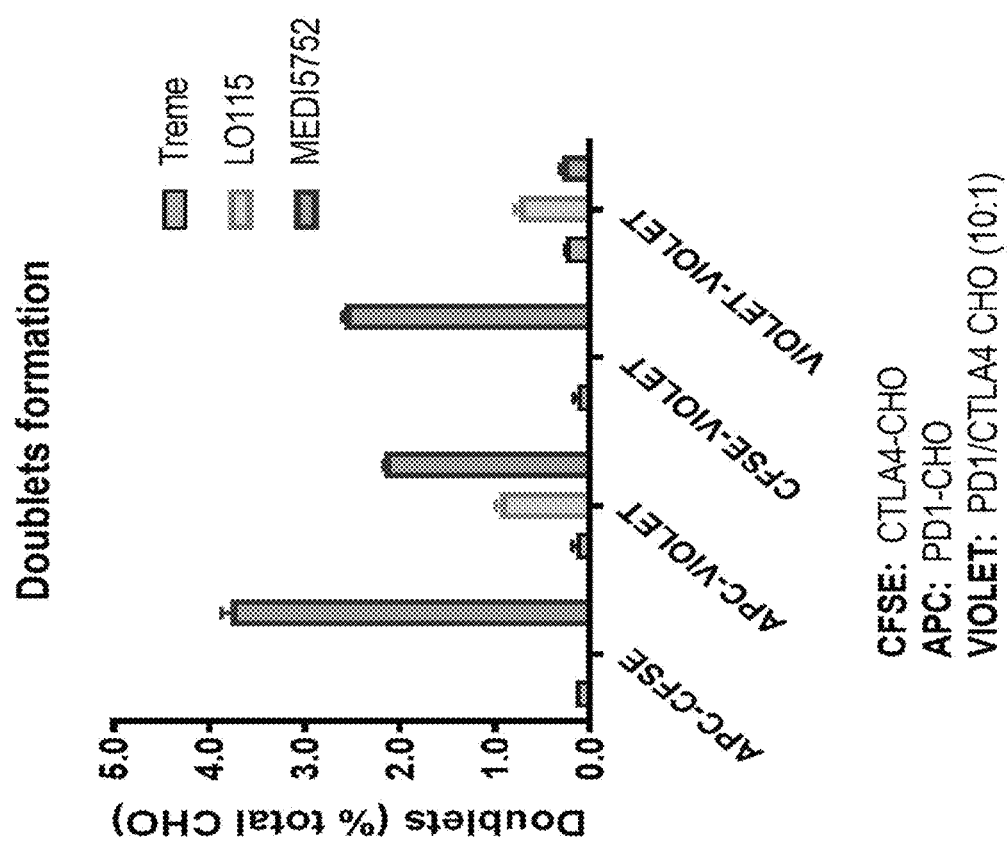

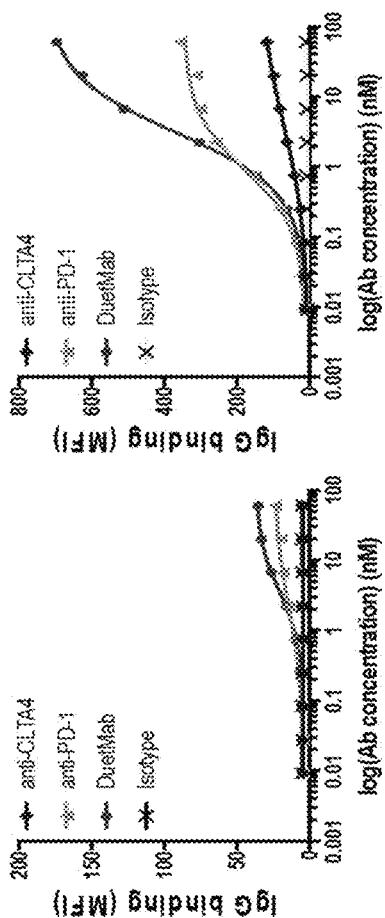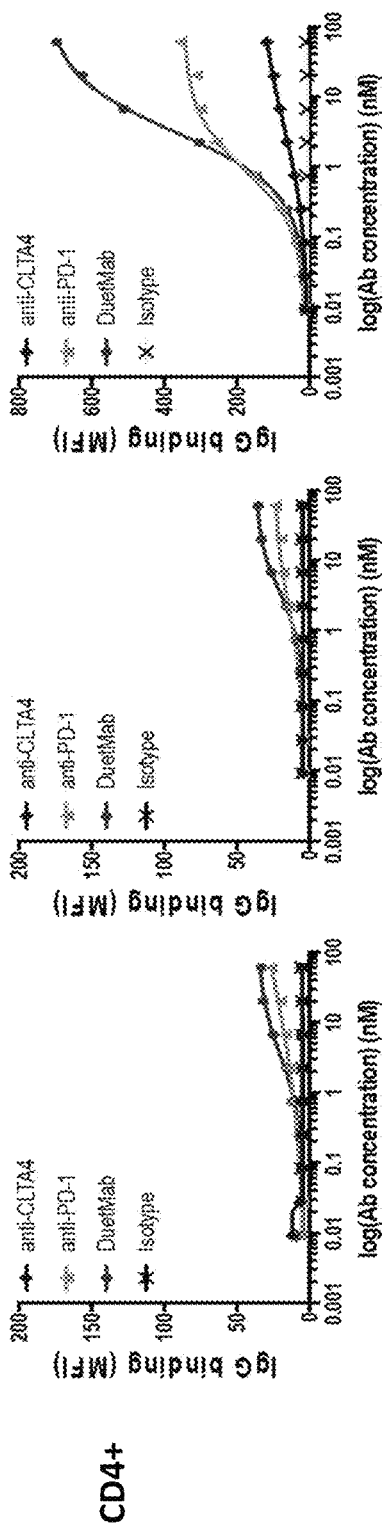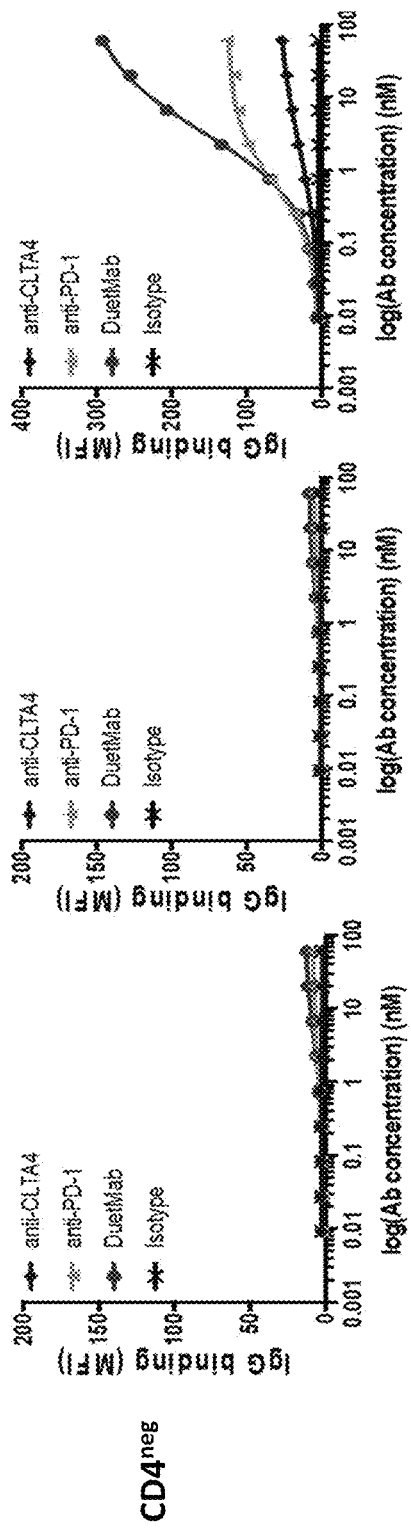
FIGURE 24A Unstim
FIGURE 24B anti-CD3
FIGURE 24C anti-CD3+anti-CD28

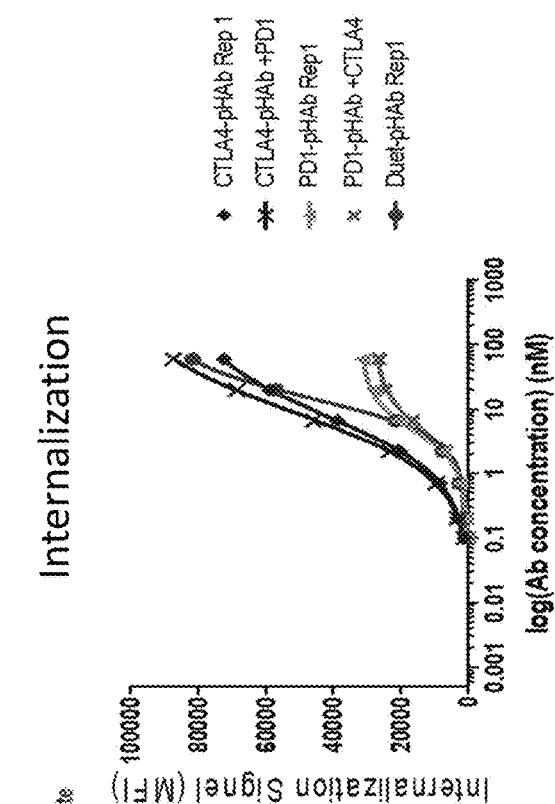
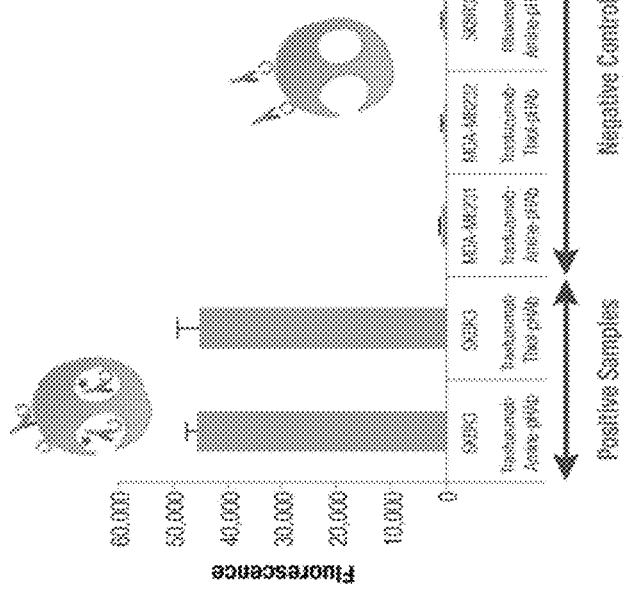
FIGURE 25A
FIGURE 25B
Internalization

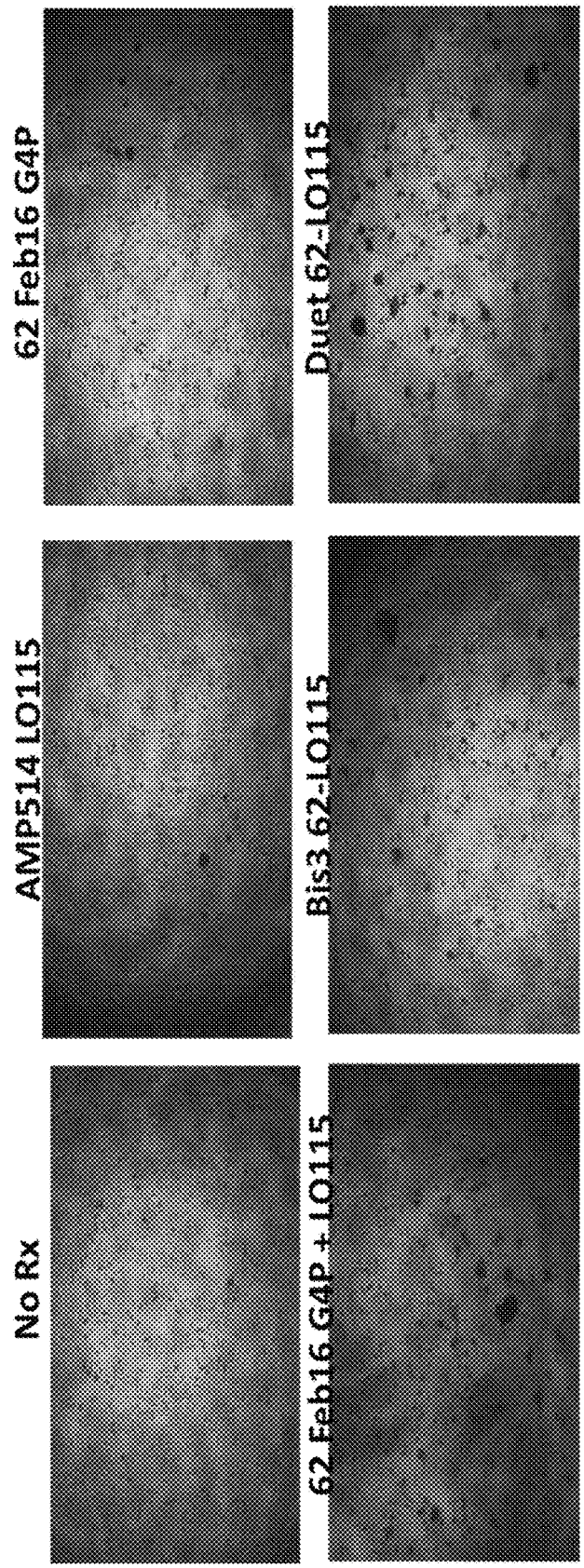

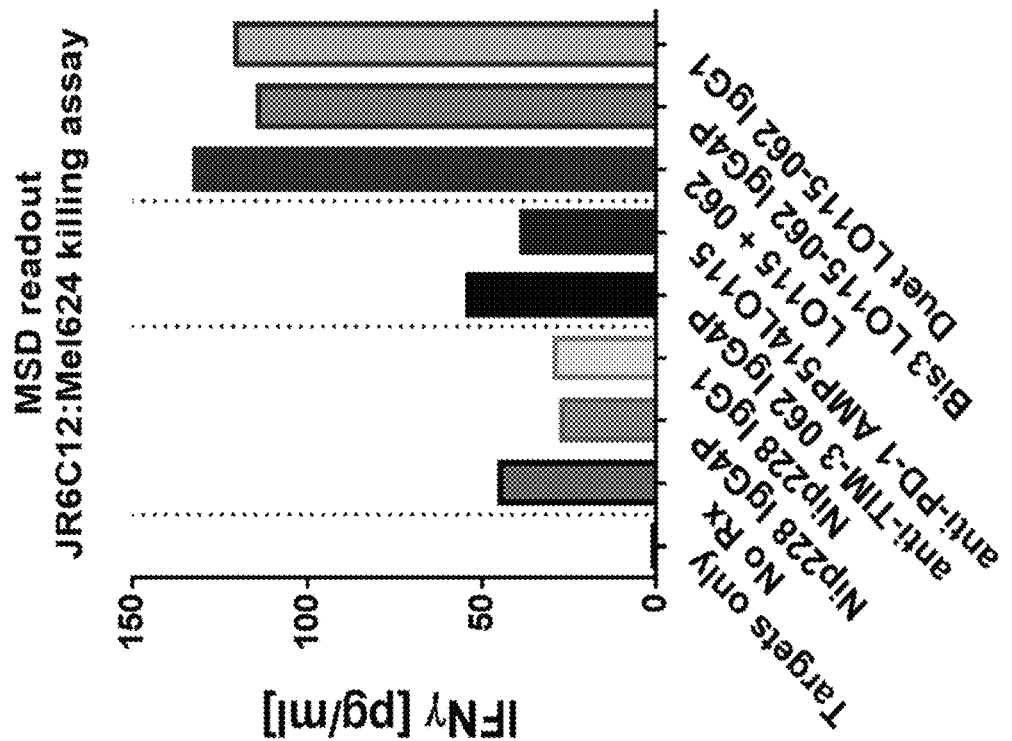
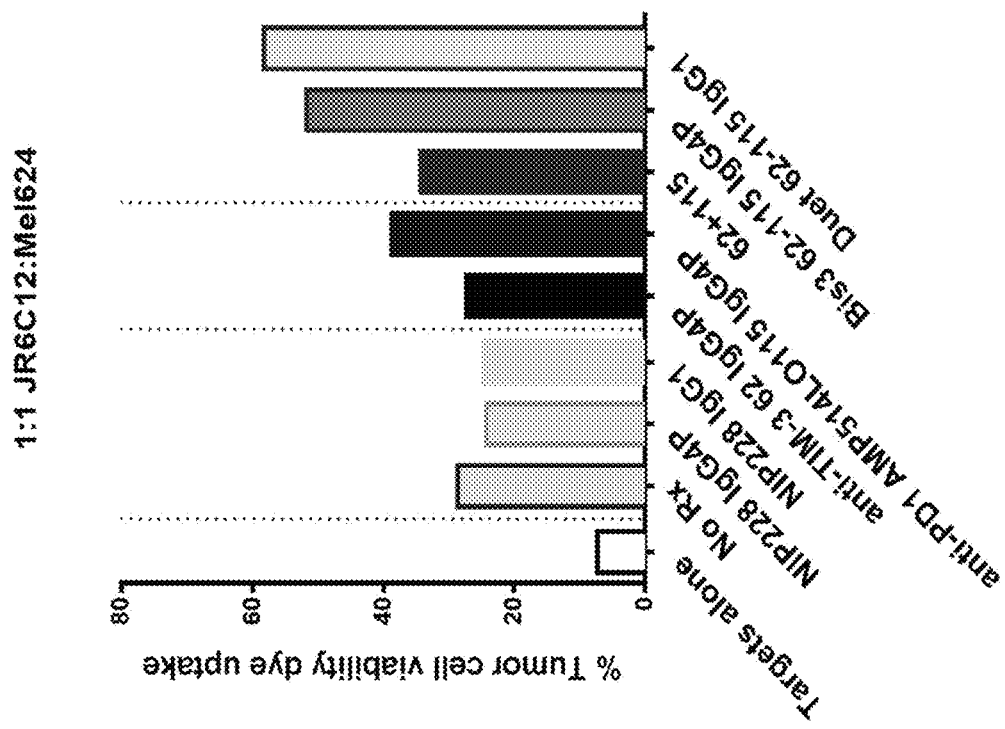

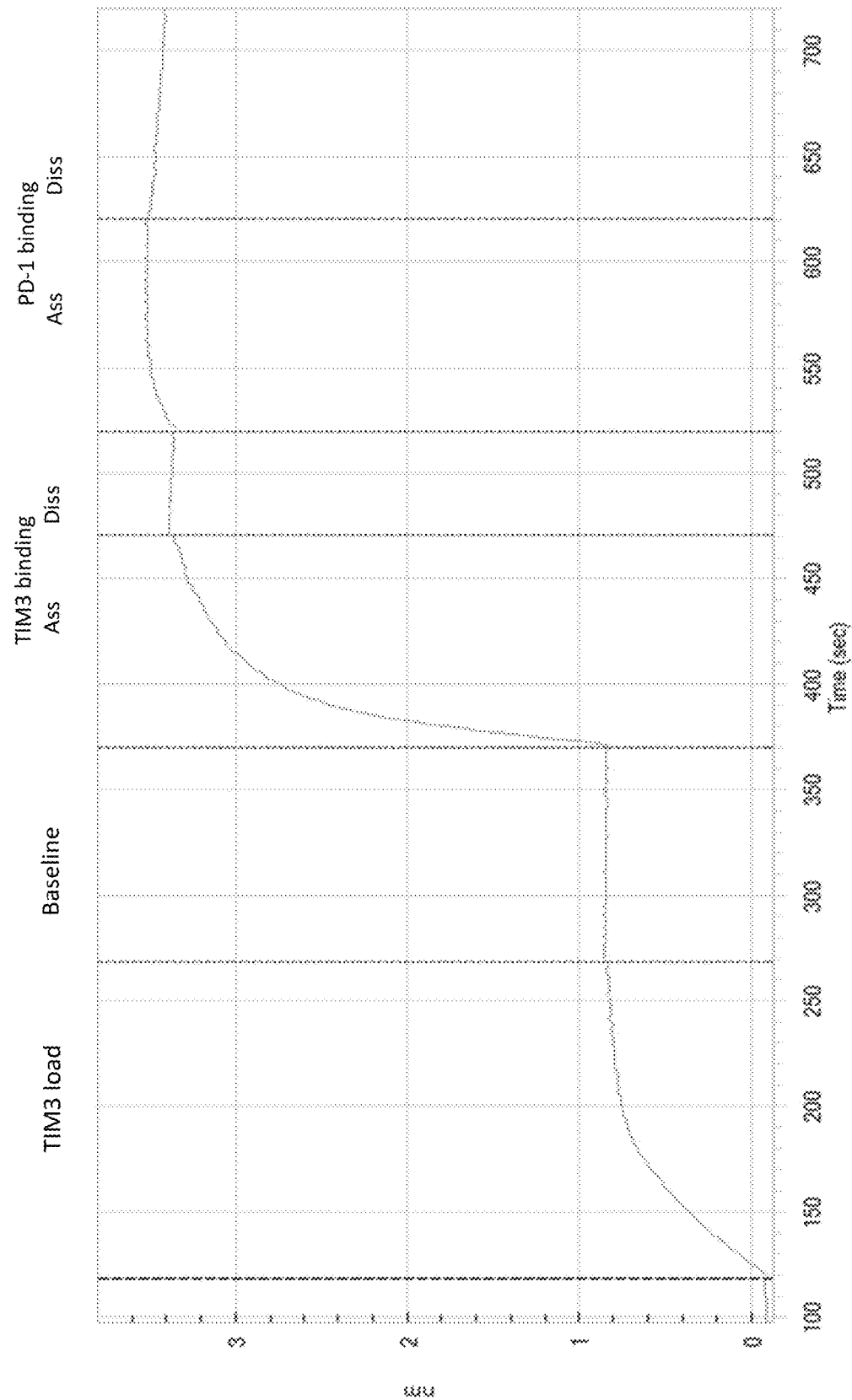

FIGURE 30
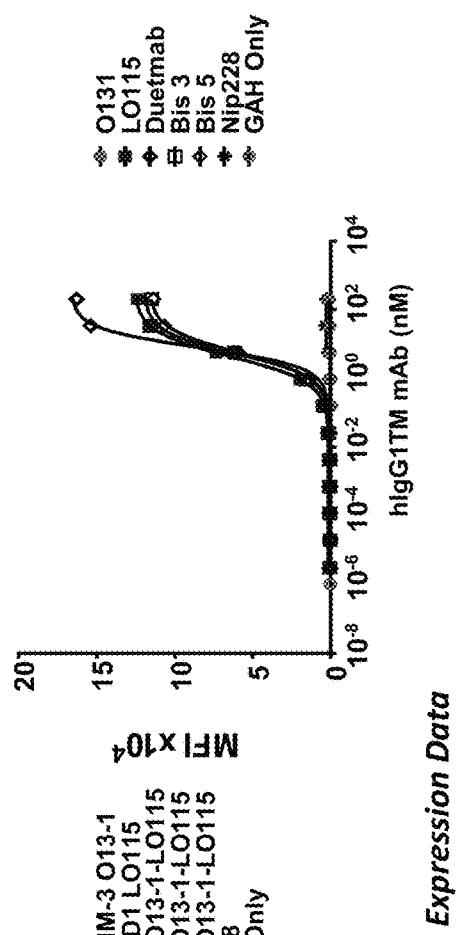
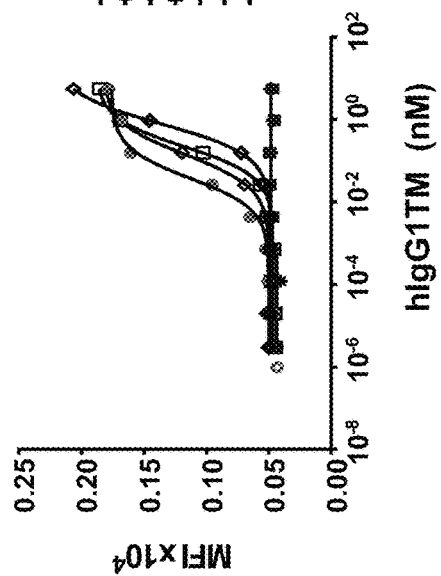
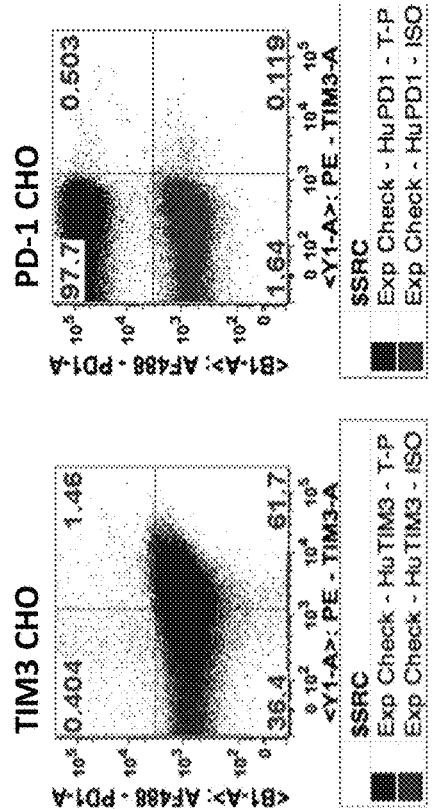

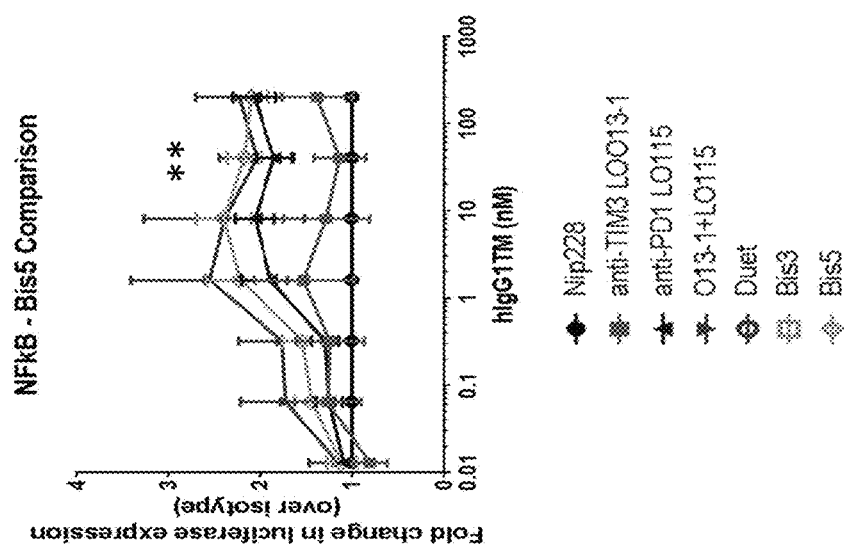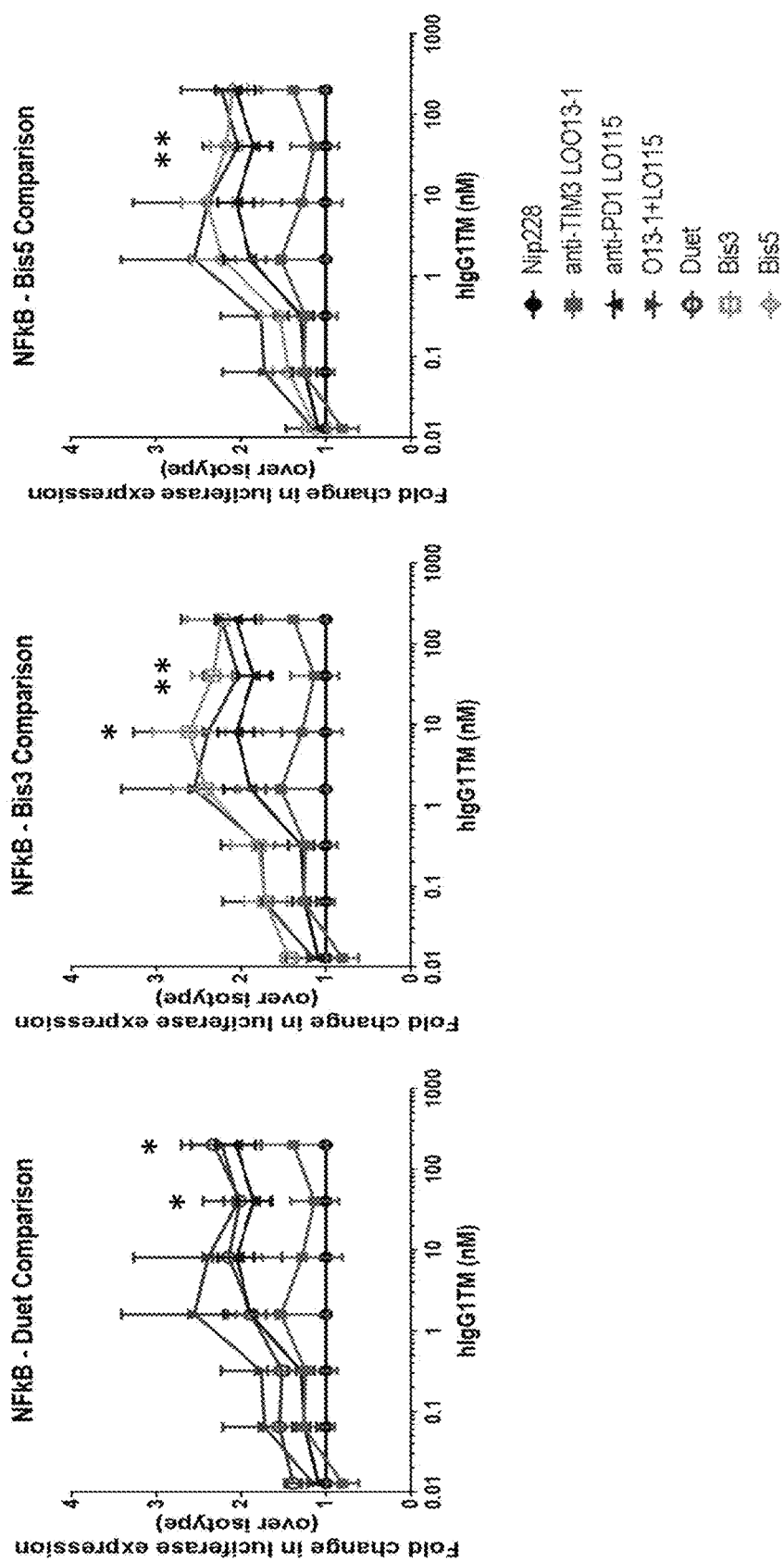

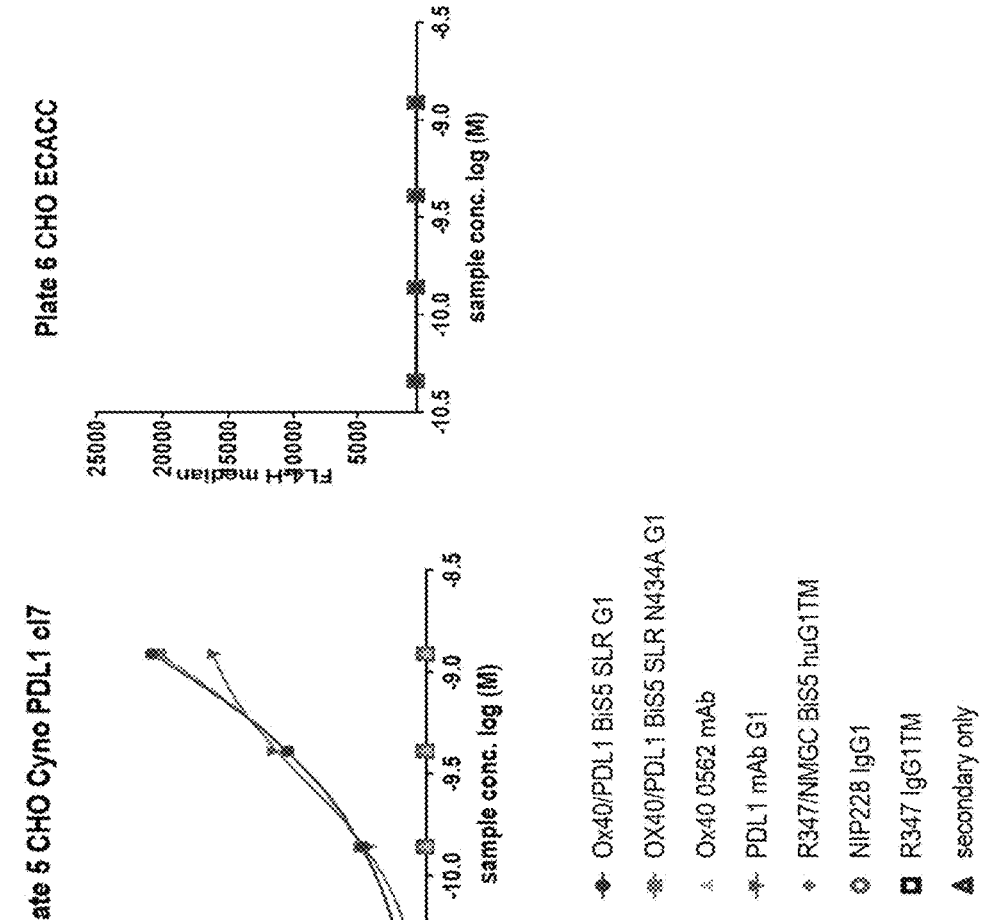
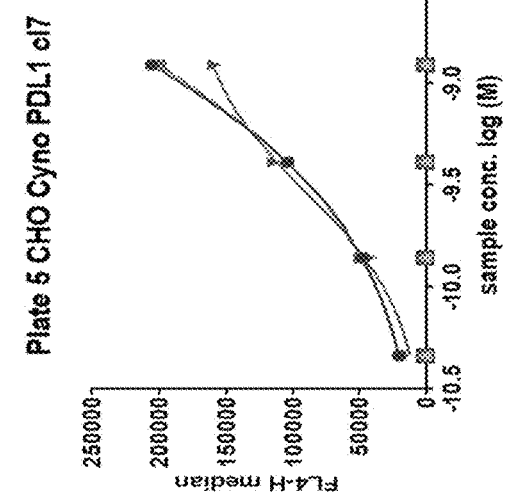
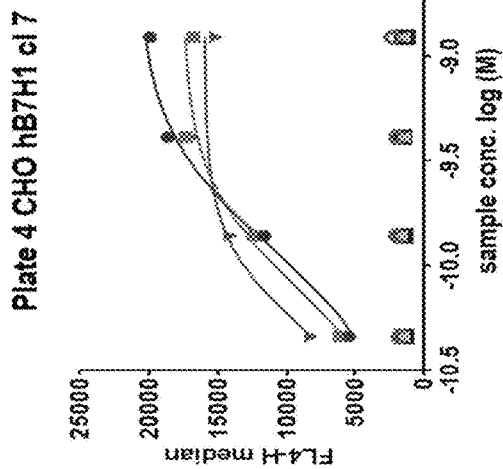
FIGURE 40D
FIGURE 40E
FIGURE 40F

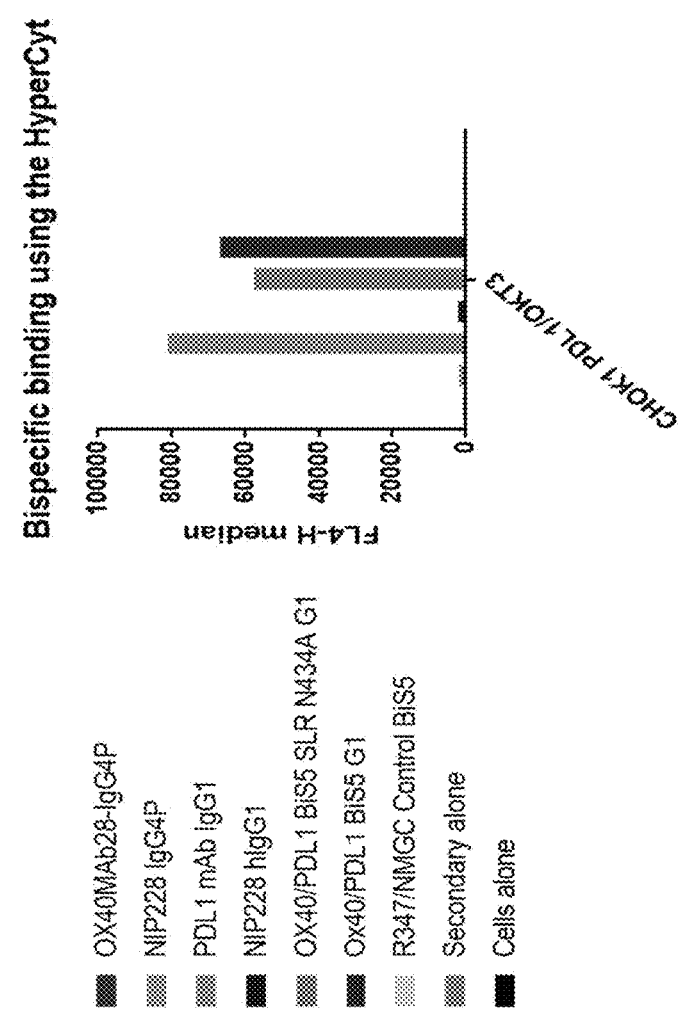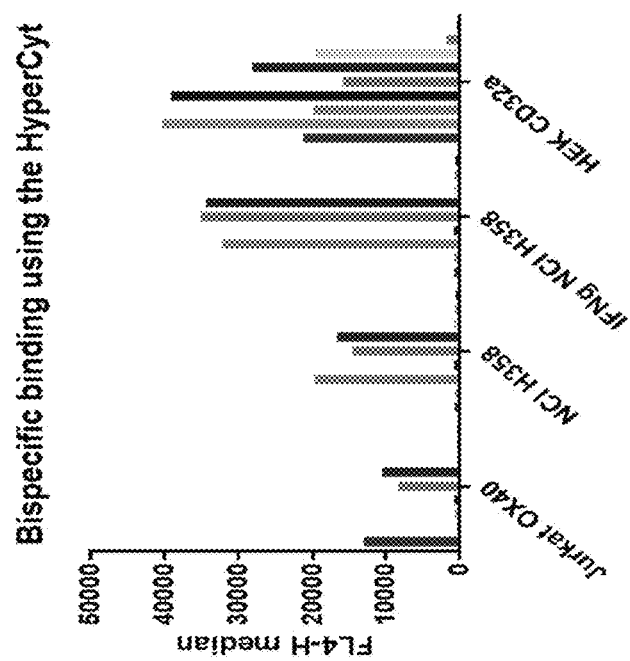
FIGURE 41A
FIGURE 41B

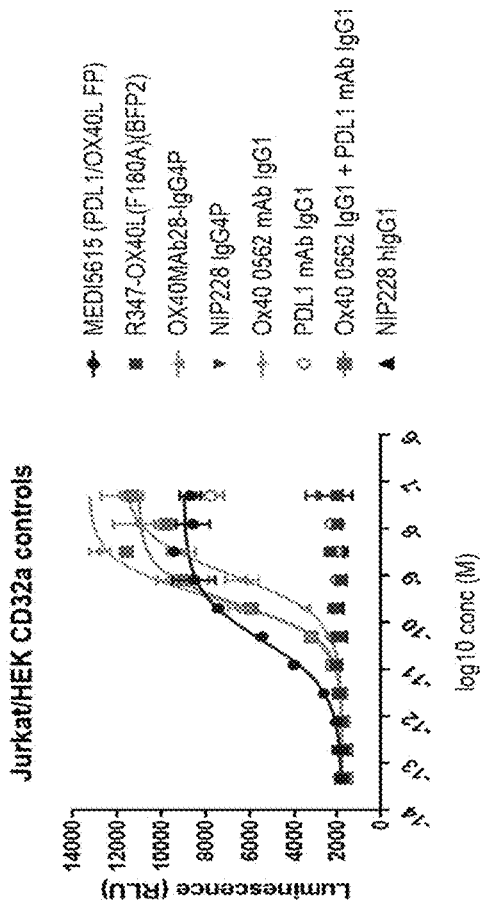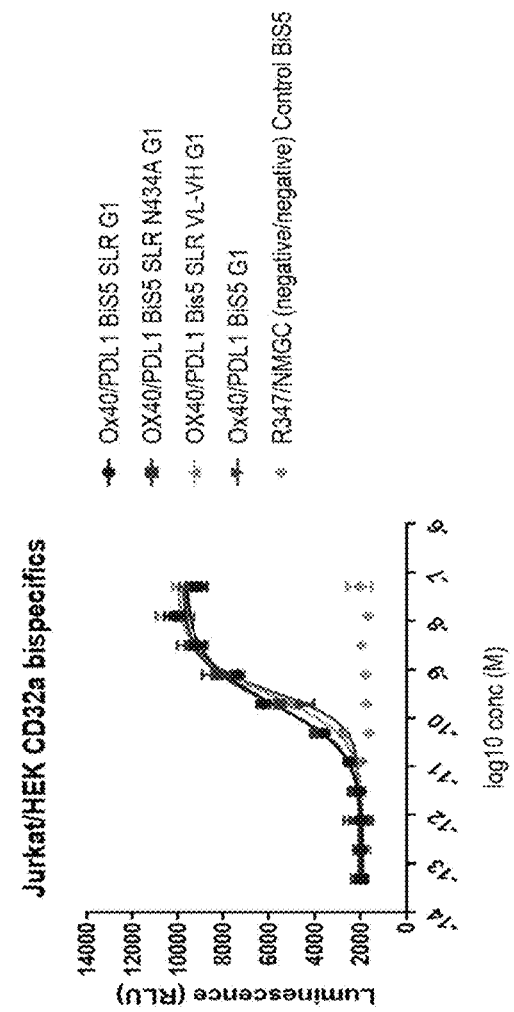

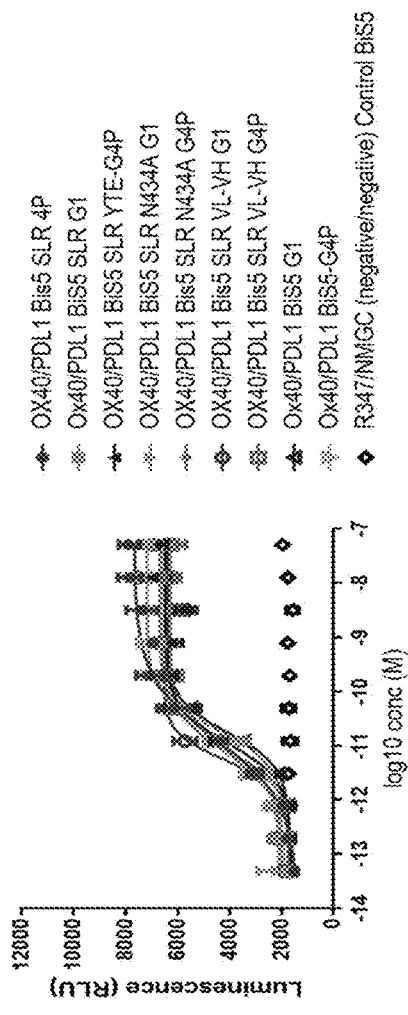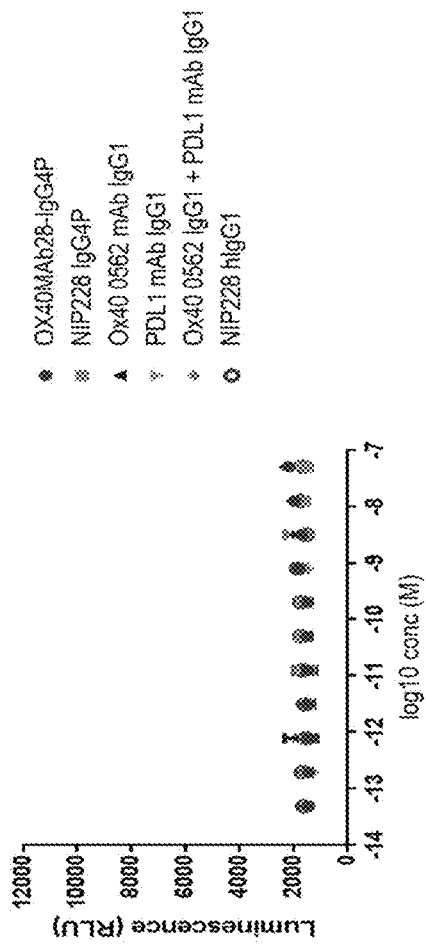

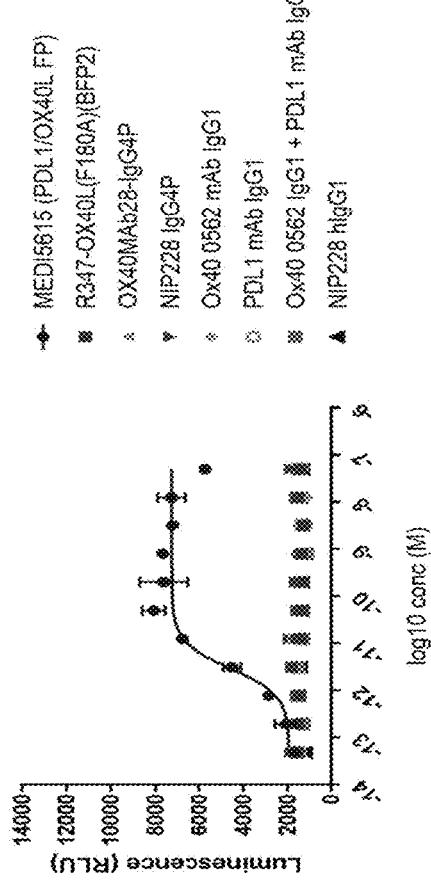
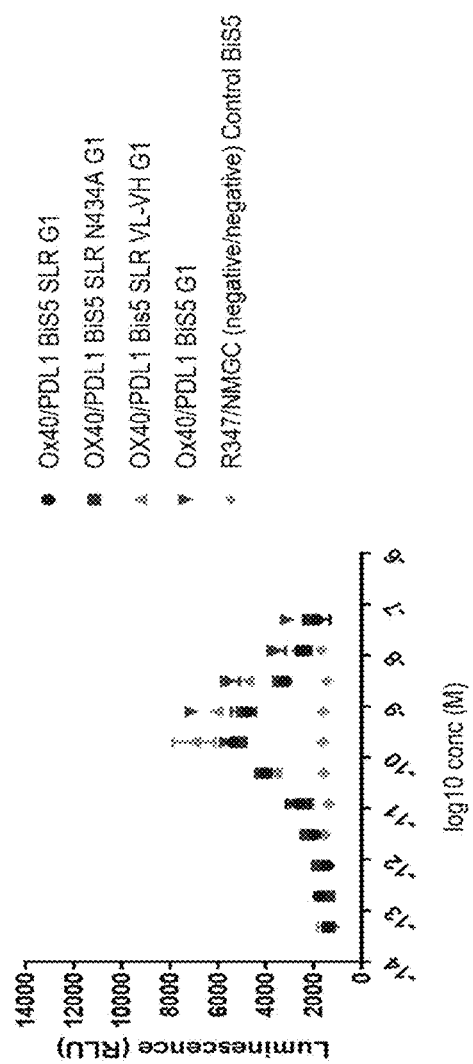
FIGURE 45A
FIGURE 45B

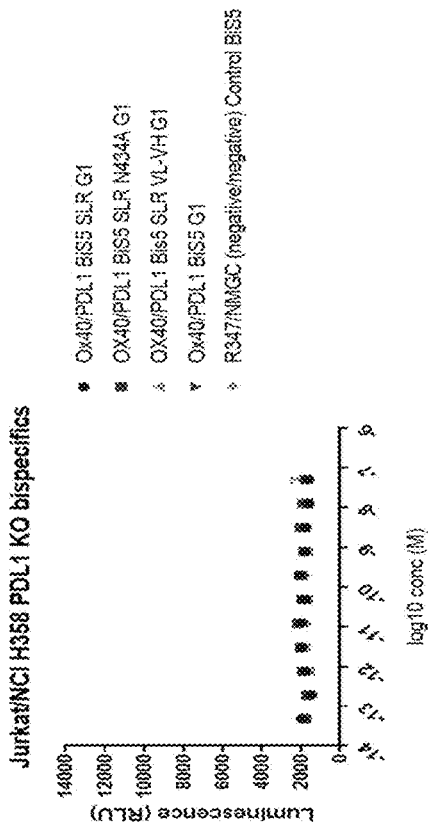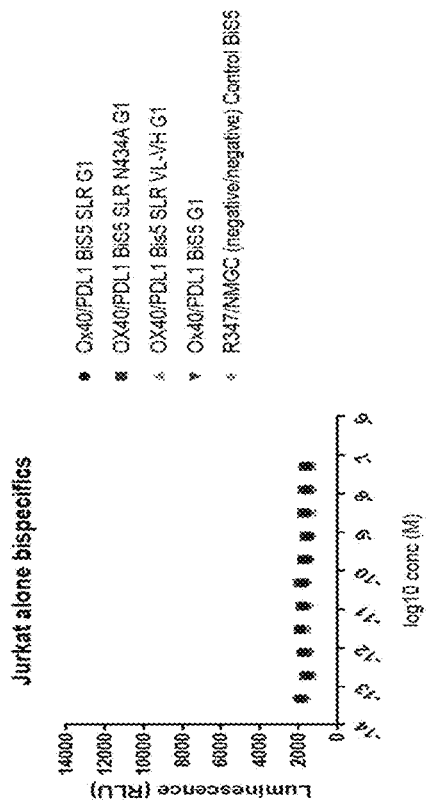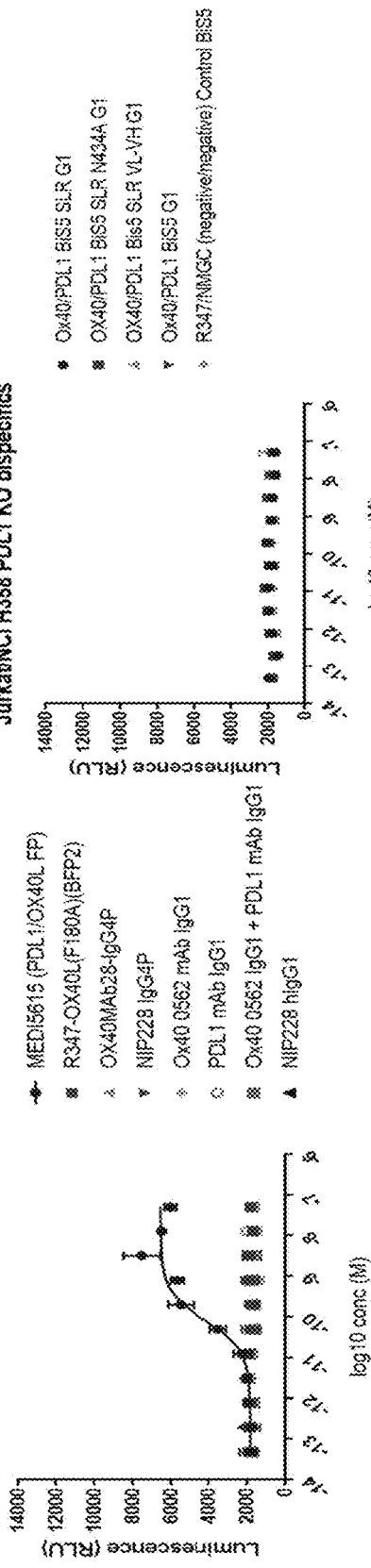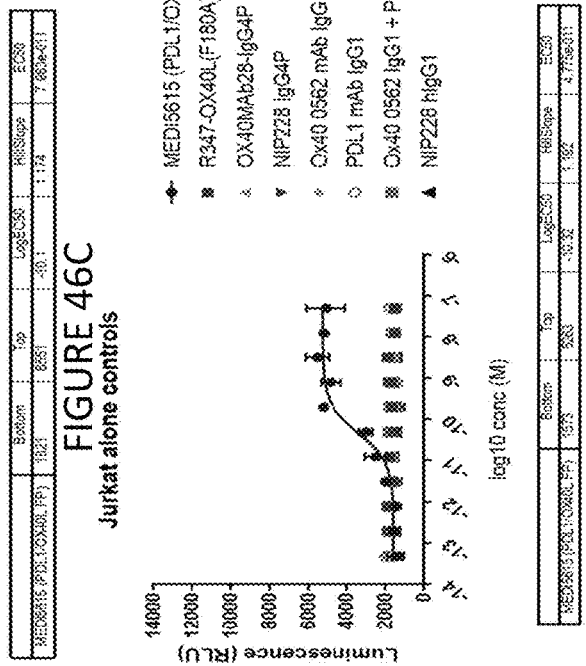

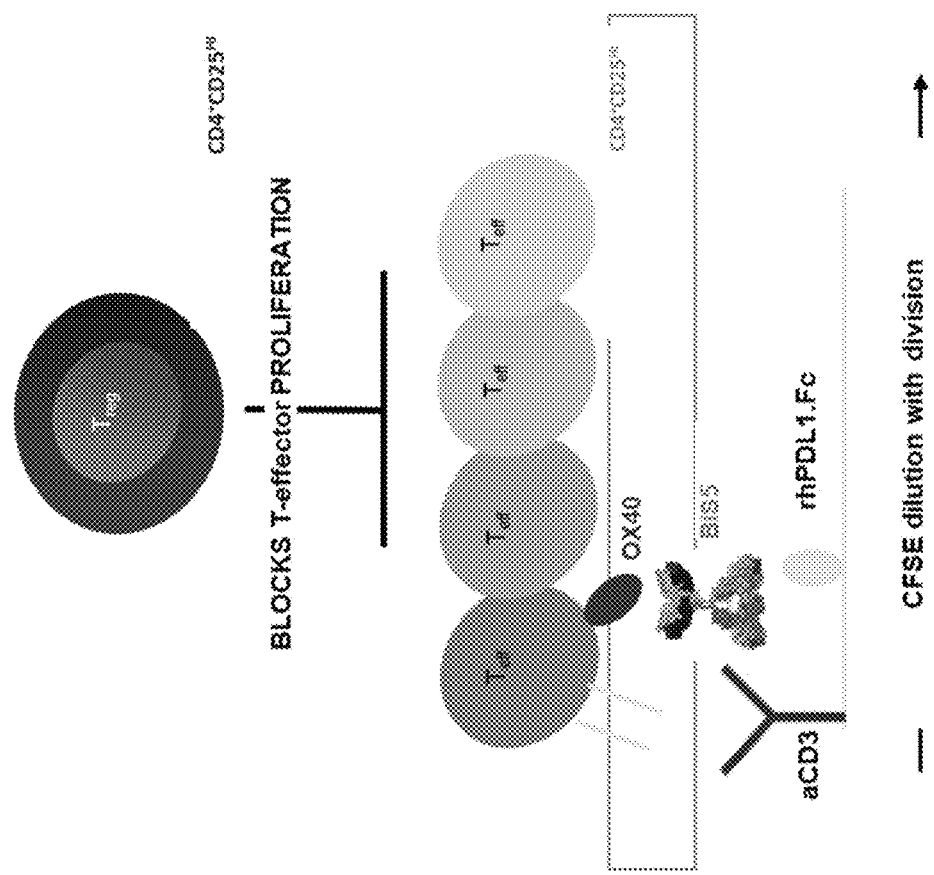

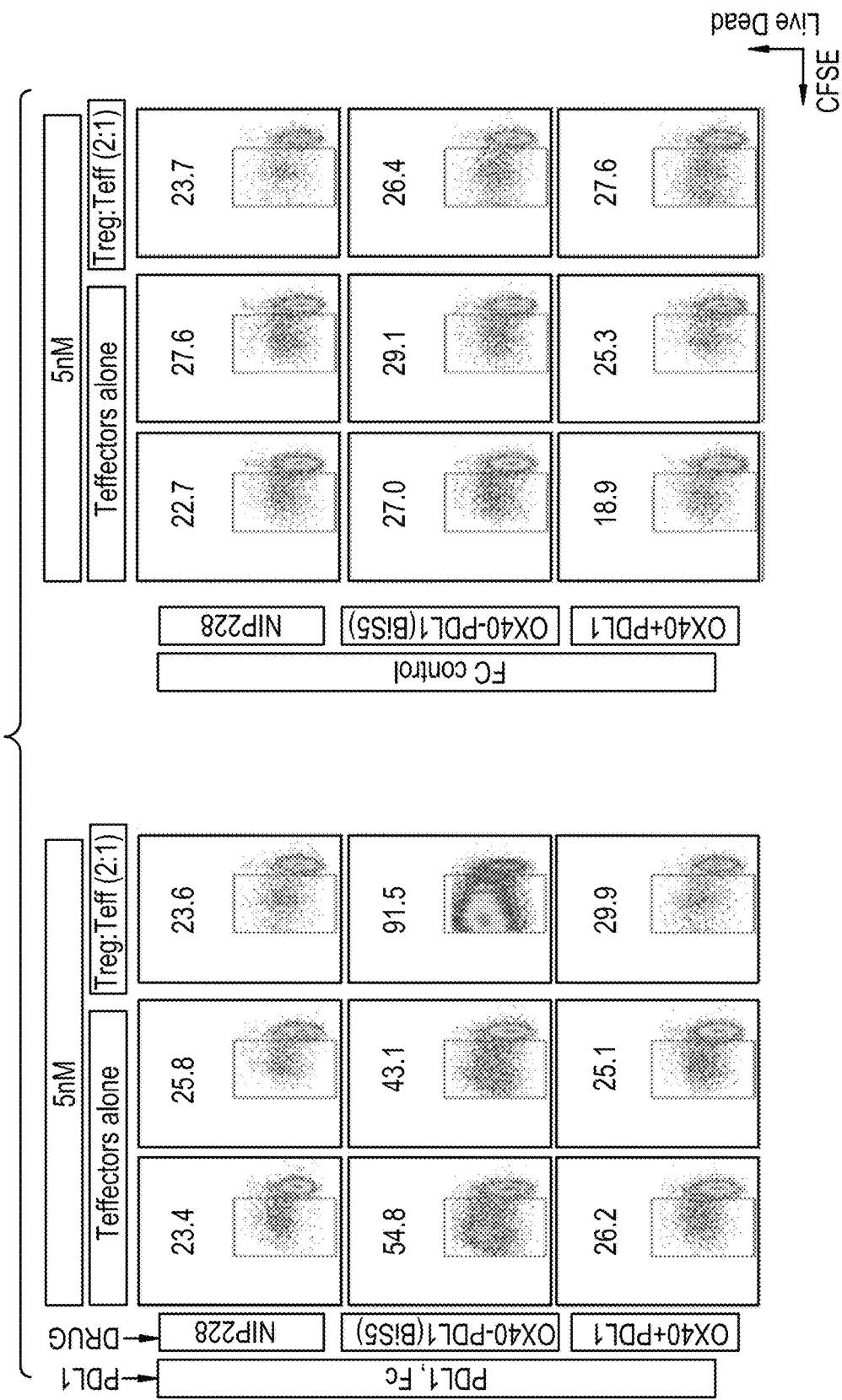

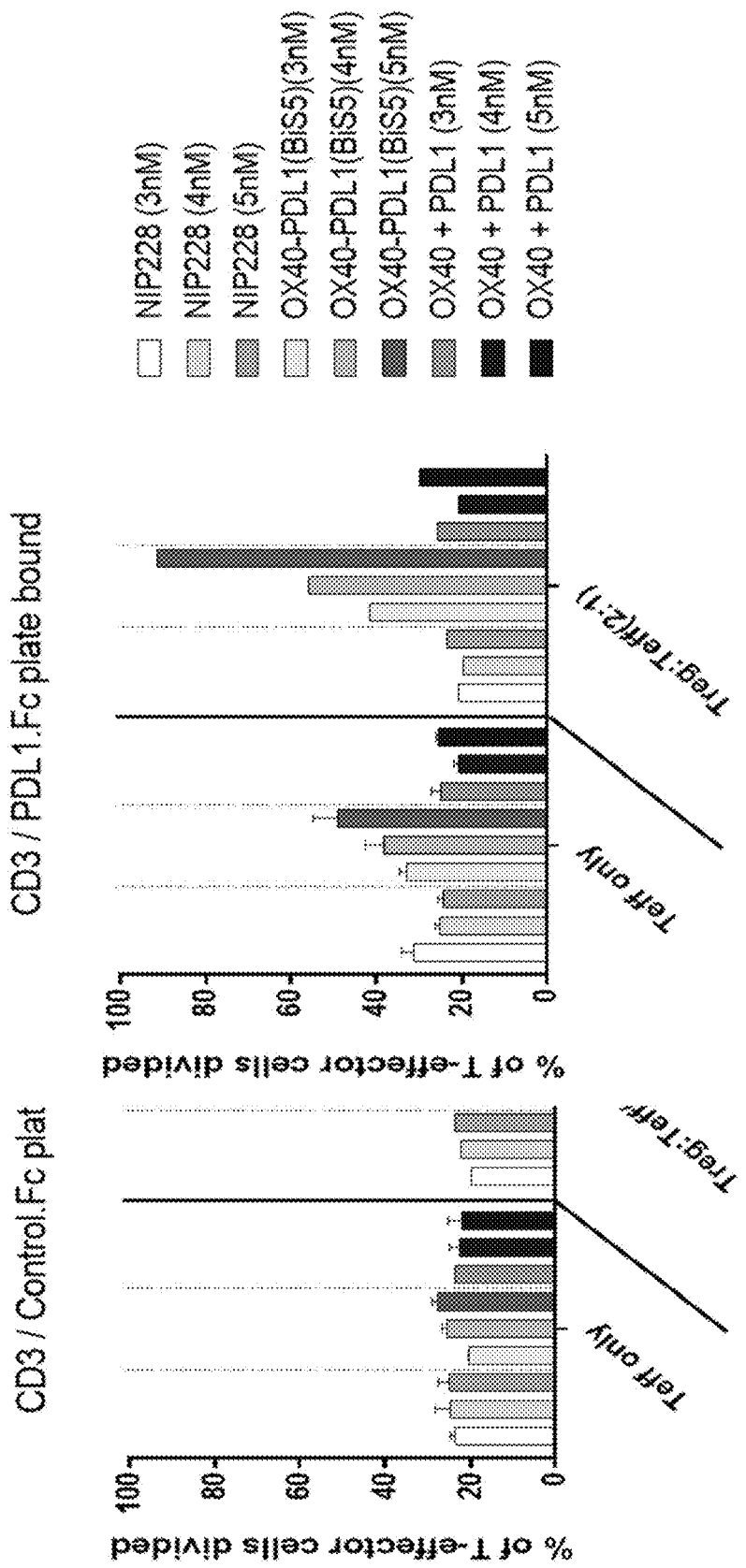

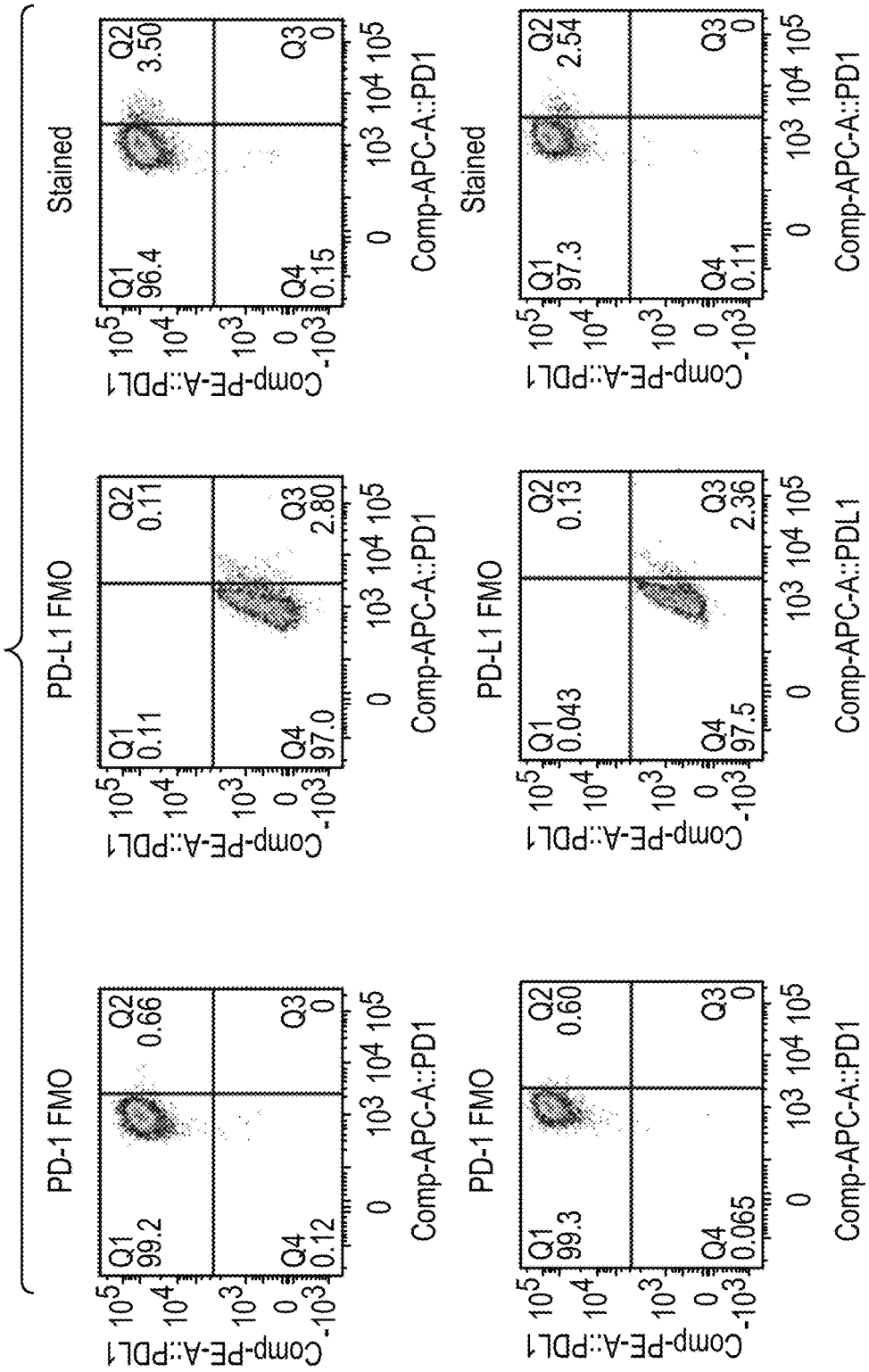

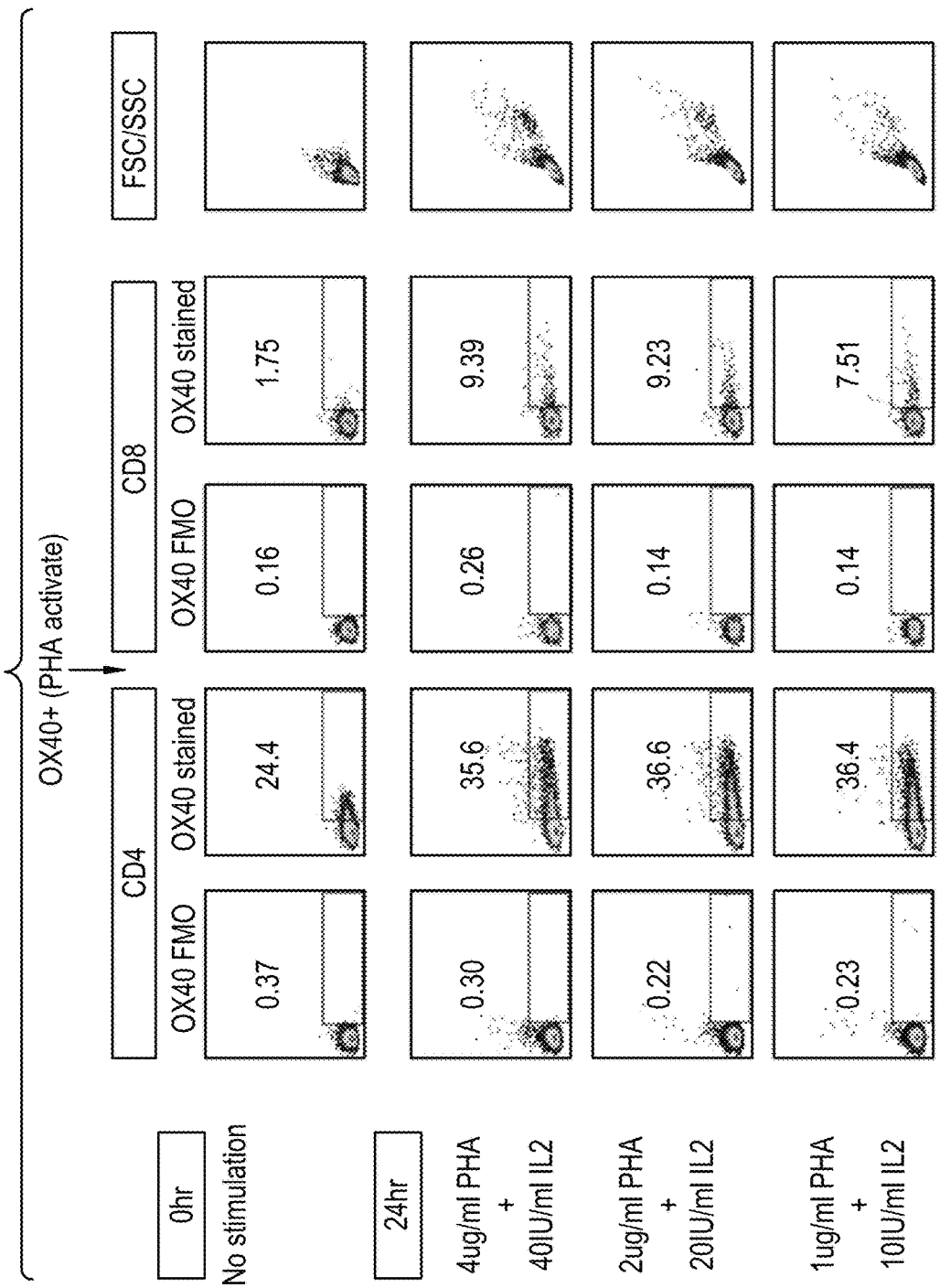

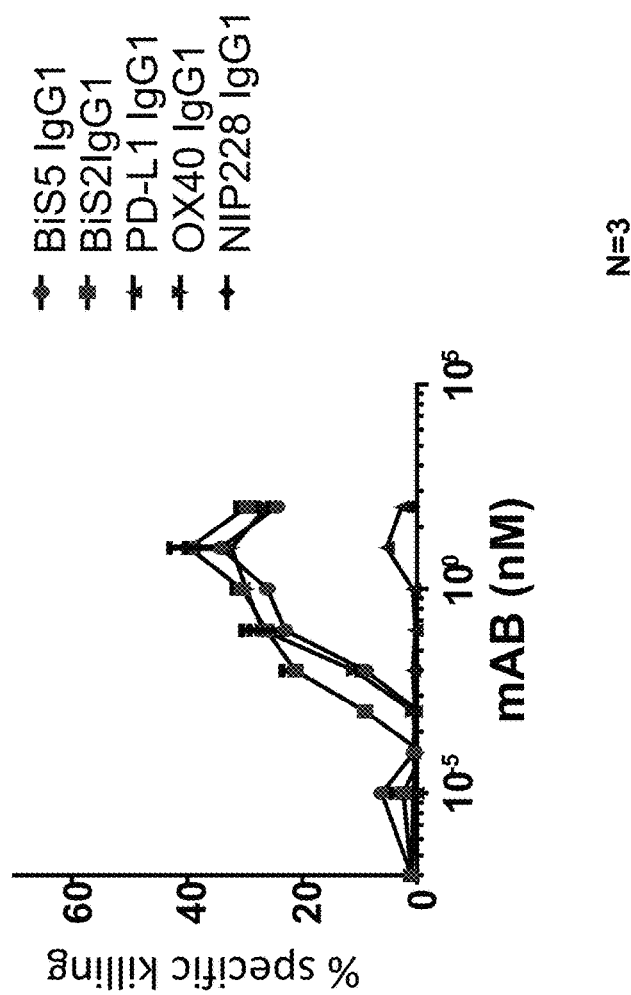
FIGURE 53A CHO-K1 B7H1
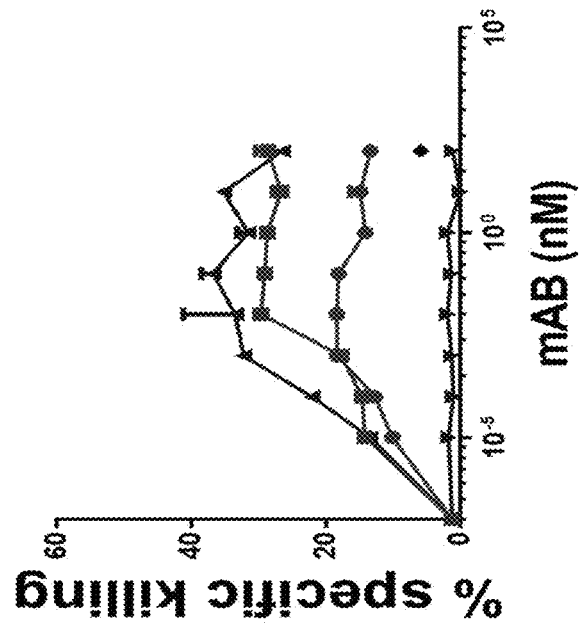
FIGURE 53B CHO-K1 OX40

NB: baseline defined as mean of Day -5 and Day 0 pre-dose

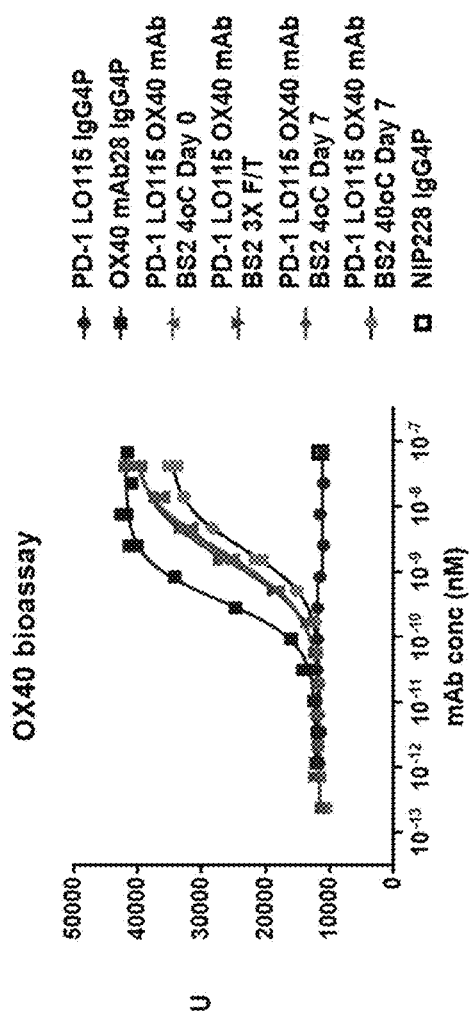
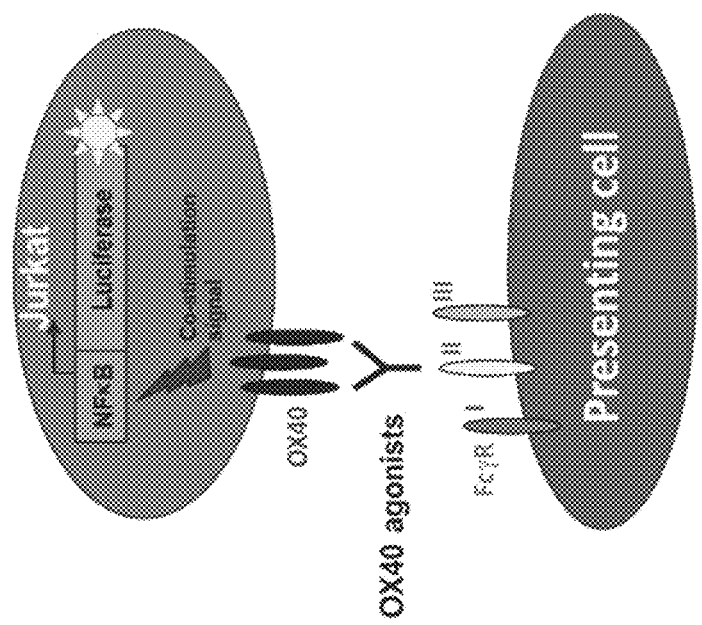
FIGURE 65A
FIGURE 65B

Monomer Loss Rate vs pH at 40C

Fragmentation Rate vs pH at 40C

Aggregation Rate vs pH at 40C

SEB Assay Format

SEQUENCE LISTING

```
<160> NUMBER OF SEQ ID NOS: 97

<210> SEQ ID NO 1
<211> LENGTH: 711
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Val Glu Ser Gly Gly Val Val Gln Pro Gly Arg Ser
    130                 135                 140

Leu Arg Leu Ser Cys Ala Ala Ser Gly Phe Thr Phe Ser Ser Tyr Gly
145                 150                 155                 160

Met His Trp Val Arg Gln Ala Pro Gly Lys Cys Leu Glu Trp Val Ala
                165                 170                 175

Val Ile Trp Tyr Asp Gly Ser Asn Lys Tyr Tyr Ala Asp Ser Val Lys
            180                 185                 190
```

```
Gly Arg Phe Thr Ile Ser Arg Asp Asn Ser Lys Asn Thr Leu Tyr Leu
            195                 200                 205

Gln Met Asn Ser Leu Arg Ala Glu Asp Thr Ala Val Tyr Tyr Cys Ala
    210                 215                 220

Arg Asp Pro Arg Gly Ala Thr Leu Tyr Tyr Tyr Tyr Gly Met Asp
225                 230                 235                 240

Val Trp Gly Gln Gly Thr Thr Val Thr Val Ser Ser Gly Gly Gly
                245                 250                 255

Ser Gly Gly Gly Gly Ser Glu Val Gln Leu Val Glu Ser Gly Gly
            260                 265                 270

Leu Val Gln Pro Gly Gly Ser Leu Arg Leu Ser Cys Ala Ala Ser Gly
            275                 280                 285

Phe Thr Phe Ser Asp Tyr Gly Met His Trp Val Arg Gln Ala Pro Gly
        290                 295                 300

Lys Gly Leu Glu Trp Val Ala Tyr Ile Ser Ser Gly Ser Tyr Thr Ile
305                 310                 315                 320

Tyr Ser Ala Asp Ser Val Lys Gly Arg Phe Thr Ile Ser Arg Asp Asn
                325                 330                 335

Ala Lys Asn Ser Leu Tyr Leu Gln Met Asn Ser Leu Arg Ala Glu Asp
            340                 345                 350

Thr Ala Val Tyr Tyr Cys Ala Arg Arg Ala Pro Asn Ser Phe Tyr Glu
            355                 360                 365

Tyr Tyr Phe Asp Tyr Trp Gly Gln Gly Thr Thr Val Thr Val Ser Ser
        370                 375                 380

Ala Ser Thr Lys Gly Pro Ser Val Phe Pro Leu Ala Pro Cys Ser Arg
385                 390                 395                 400

Ser Thr Ser Glu Ser Thr Ala Ala Leu Gly Cys Leu Val Lys Asp Tyr
                405                 410                 415

Phe Pro Glu Pro Val Thr Val Ser Trp Asn Ser Gly Ala Leu Thr Ser
            420                 425                 430

Gly Val His Thr Phe Pro Ala Val Leu Gln Ser Ser Gly Leu Tyr Ser
            435                 440                 445

Leu Ser Ser Val Val Thr Val Pro Ser Ser Ser Leu Gly Thr Lys Thr
    450                 455                 460

Tyr Thr Cys Asn Val Asp His Lys Pro Ser Asn Thr Lys Val Asp Lys
465                 470                 475                 480

Arg Val Glu Ser Lys Tyr Gly Pro Pro Cys Pro Pro Cys Pro Ala Pro
                485                 490                 495

Glu Phe Leu Gly Gly Pro Ser Val Phe Leu Phe Pro Pro Lys Pro Lys
            500                 505                 510

Asp Thr Leu Met Ile Ser Arg Thr Pro Glu Val Thr Cys Val Val Val
            515                 520                 525

Asp Val Ser Gln Glu Asp Pro Glu Val Gln Phe Asn Trp Tyr Val Asp
    530                 535                 540

Gly Val Glu Val His Asn Ala Lys Thr Lys Pro Arg Glu Glu Gln Phe
545                 550                 555                 560

Asn Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Gly Leu
            580                 585                 590

Pro Ser Ser Ile Glu Lys Thr Ile Ser Lys Ala Lys Gly Gln Pro Arg
            595                 600                 605
```

Glu Pro Gln Val Tyr Thr Leu Pro Pro Ser Gln Glu Met Thr Lys
610             615                 620

Asn Gln Val Ser Leu Thr Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Tyr Ser
                660                 665                 670

Arg Leu Thr Val Asp Lys Ser Arg Trp Gln Gly Asn Val Phe Ser
                675                 680                 685

Cys Ser Val Met His Glu Ala Leu His Asn His Tyr Thr Gln Lys Ser
690                 695                 700

Leu Ser Leu Ser Leu Gly Lys
705                 710

<210> SEQ ID NO 2
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Lys His Thr Asn Leu
                20                  25                  30

Tyr Trp Ser Arg His Met Tyr Trp Tyr Gln Gln Lys Pro Gly Gln Ala
            35                  40                  45

Pro Arg Leu Leu Ile Tyr Leu Thr Ser Asn Arg Ala Thr Gly Ile Pro
50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Gln Gln Trp
                85                  90                  95

Ser Ser Asn Pro Phe Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 3
<211> LENGTH: 711
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Tyr Thr Ile Tyr Ser Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Pro Asn Ser Phe Tyr Glu Tyr Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

385             390             395             400
Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys Gly Gly Gly Ser Gly Gly Gly Ser Asp Ile Gln Met Thr
    450                 455                 460

Gln Ser Pro Ser Ser Leu Ser Ala Ser Val Gly Asp Arg Val Thr Ile
465                 470                 475                 480

Thr Cys Arg Ala Ser Gln Ser Ile Asn Ser Tyr Leu Asp Trp Tyr Gln
                485                 490                 495

Gln Lys Pro Gly Lys Ala Pro Lys Leu Leu Ile Tyr Ala Ala Ser Ser
            500                 505                 510

Leu Gln Ser Gly Val Pro Ser Arg Phe Ser Gly Ser Gly Ser Gly Thr
        515                 520                 525

Asp Phe Thr Leu Thr Ile Ser Ser Leu Gln Pro Glu Asp Phe Ala Thr
    530                 535                 540

Tyr Tyr Cys Gln Gln Tyr Tyr Ser Thr Pro Phe Thr Phe Gly Cys Gly
545                 550                 555                 560

Thr Lys Val Glu Ile Lys Gly Gly Gly Ser Gly Gly Gly Gly Ser
                565                 570                 575

Gly Gly Gly Gly Ser Gly Gly Gly Ser Gln Val Gln Leu Val Glu
        580                 585                 590

Ser Gly Gly Gly Val Val Gln Pro Gly Arg Ser Leu Arg Leu Ser Cys
    595                 600                 605

Ala Ala Ser Gly Phe Thr Phe Ser Ser Tyr Gly Met His Trp Val Arg
        610                 615                 620

Gln Ala Pro Gly Lys Cys Leu Glu Trp Val Ala Val Ile Trp Tyr Asp
625                 630                 635                 640

Gly Ser Asn Lys Tyr Tyr Ala Asp Ser Val Lys Gly Arg Phe Thr Ile
                645                 650                 655

Ser Arg Asp Asn Ser Lys Asn Thr Leu Tyr Leu Gln Met Asn Ser Leu
            660                 665                 670

Arg Ala Glu Asp Thr Ala Val Tyr Tyr Cys Ala Arg Asp Pro Arg Gly
        675                 680                 685

Ala Thr Leu Tyr Tyr Tyr Tyr Gly Met Asp Val Trp Gly Gln Gly
    690                 695                 700

Thr Thr Val Thr Val Ser Ser
705                 710

<210> SEQ ID NO 4
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Lys His Thr Asn Leu
            20                  25                  30

```
Tyr Trp Ser Arg His Met Tyr Trp Tyr Gln Gln Lys Pro Gly Gln Ala
             35                  40                  45

Pro Arg Leu Leu Ile Tyr Leu Thr Ser Asn Arg Ala Thr Gly Ile Pro
 50                  55                  60

Ala Arg Phe Ser Gly Ser Gly Ser Gly Thr Asp Phe Thr Leu Thr Ile
 65                  70                  75                  80

Ser Ser Leu Glu Pro Glu Asp Phe Ala Val Tyr Tyr Cys Gln Gln Trp
                 85                  90                  95

Ser Ser Asn Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 5
<211> LENGTH: 721
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
             20                  25                  30

Gly Met His Trp Val Arg Gln Ala Pro Gly Lys Gly Leu Glu Trp Val
             35                  40                  45

Ala Tyr Ile Ser Ser Gly Ser Tyr Thr Ile Tyr Ser Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Ala Pro Asn Ser Phe Tyr Glu Tyr Tyr Phe Asp Tyr Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

```
Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gly Gly Gly Ser Gly Gly Gly Gly Ser Asp Ile Gln Met
385                 390                 395                 400

Thr Gln Ser Pro Ser Ser Leu Ser Ala Ser Val Gly Asp Arg Val Thr
                405                 410                 415

Ile Thr Cys Arg Ala Ser Gln Ser Ile Asn Ser Tyr Leu Asp Trp Tyr
            420                 425                 430

Gln Gln Lys Pro Gly Lys Ala Pro Lys Leu Leu Ile Tyr Ala Ala Ser
            435                 440                 445

Ser Leu Gln Ser Gly Val Pro Ser Arg Phe Ser Gly Ser Gly Ser Gly
    450                 455                 460

Thr Asp Phe Thr Leu Thr Ile Ser Ser Leu Gln Pro Glu Asp Phe Ala
465                 470                 475                 480

Thr Tyr Tyr Cys Gln Gln Tyr Tyr Ser Thr Pro Phe Thr Phe Gly Cys
                485                 490                 495

Gly Thr Lys Val Glu Ile Lys Gly Gly Gly Gly Ser Gly Gly Gly Gly
            500                 505                 510

Ser Gly Gly Gly Gly Ser Gly Gly Gly Gly Ser Gln Val Gln Leu Val
            515                 520                 525

Glu Ser Gly Gly Gly Val Val Gln Pro Gly Arg Ser Leu Arg Leu Ser
    530                 535                 540

Cys Ala Ala Ser Gly Phe Thr Phe Ser Ser Tyr Gly Met His Trp Val
545                 550                 555                 560

Arg Gln Ala Pro Gly Lys Cys Leu Glu Trp Val Ala Val Ile Trp Tyr
                565                 570                 575

Asp Gly Ser Asn Lys Tyr Tyr Ala Asp Ser Val Lys Gly Arg Phe Thr
            580                 585                 590
```

```
Ile Ser Arg Asp Asn Ser Lys Asn Thr Leu Tyr Leu Gln Met Asn Ser
            595                 600                 605

Leu Arg Ala Glu Asp Thr Ala Val Tyr Tyr Cys Ala Arg Asp Pro Arg
610                 615                 620

Gly Ala Thr Leu Tyr Tyr Tyr Tyr Gly Met Asp Val Trp Gly Gln
625                 630                 635                 640

Gly Thr Thr Val Thr Val Ser Ser Gly Gly Gly Ser Gly Gly Gly
                645                 650                 655

Gly Ser Gly Gln Pro Glu Asn Asn Tyr Lys Thr Thr Pro Val Leu
            660                 665                 670

Asp Ser Asp Gly Ser Phe Phe Leu Tyr Ser Arg Leu Thr Val Asp Lys
            675                 680                 685

Ser Arg Trp Gln Glu Gly Asn Val Phe Ser Cys Ser Val Met His Glu
690                 695                 700

Ala Leu His Asn His Tyr Thr Gln Lys Ser Leu Ser Leu Ser Leu Gly
705                 710                 715                 720

Lys

<210> SEQ ID NO 6
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Lys His Thr Asn Leu
            20                  25                  30

Tyr Trp Ser Arg His Met Tyr Trp Tyr Gln Gln Lys Pro Gly Gln Ala
        35                  40                  45

Pro Arg Leu Leu Ile Tyr Leu Thr Ser Asn Arg Ala Thr Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Gln Gln Trp
                85                  90                  95

Ser Ser Asn Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 7
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Lys His Thr Asn Leu
            20                  25                  30

Tyr Trp Ser Arg His Met Tyr Trp Tyr Gln Gln Lys Pro Gly Gln Ala
        35                  40                  45

Pro Arg Leu Leu Ile Tyr Leu Thr Ser Asn Arg Ala Thr Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Gln Gln Trp
                85                  90                  95

Ser Ser Asn Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 8
<211> LENGTH: 610
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
cgagagagcc accctgagct gctccgcctc ctccaagcac accaacctgt actggtcccg      60
gcacatgtac tggtatcagc agaagcccgg ccaggcccct cggctgctga tctacctgac     120
ctctaaccgg gccaccggca tccctgccag attctccggc tctggctccg gcaccgactt     180
caccctgacc atctccagcc tggaacccga ggacttcgcc gtgtactact gccagcagtg     240
gtcctccaac cccttcacct cggccaggg caccaagctg gaaatcaagc gtacggtggc     300
tgcaccatct gtcttcatct tcccgccatc tgatgagcag ttgaaatctg gaactgcctc     360
tgttgtgtgc ctgctgaata acttctatcc cagagaggcc aaagtacagt ggaaggtgga     420
taacgccctc caatcgggta actcccagga gagtgtcaca gagcaggaca gcaaggacag     480

-continued

```
cacctacagc ctcagcagca ccctgacgct gagcaaagca gactacgaga aacacaaagt    540
ctacgcctgc gaagtcaccc atcagggcct gagctcgccc gtcacaaaga gcttcaacag    600
gggagagtgt                                                          610
```

<210> SEQ ID NO 9
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Tyr Thr Ile Tyr Ser Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Pro Asn Ser Phe Tyr Glu Tyr Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
```

```
                    325                 330                 335
Ile Glu Lys Thr Ile Ser Lys Ala Lys Gly Gln Pro Arg Glu Pro Gln
                340                 345                 350

Val Cys Thr Leu Pro Pro Ser Arg Glu Glu Met Thr Lys Asn Gln Val
            355                 360                 365

Ser Leu Ser Cys Ala Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
        450

<210> SEQ ID NO 10
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gaggtgcagc tggtggaatc cggcggagga ctggtgcagc tggcggctc cctgagactg      60 tcttgcgccg cctccggctt cacattctcc gactacggca tgcactgggt ccgacaggcc    120
cctggaaagg gcctggaatg ggtggcctac atctcctccg ctcctacac catctactcc     180 gccgactccg tgaagggccg gttcaccatc tcccgggaca cgccaagaa ctccctgtac     240 ctgcagatga actccctgcg ggccgaggac acagccgtgt actactgtgc cagacgggcc    300
cctaactcct tctacgagta ctacttcgac tactggggcc agggcaccac cgtgaccgtg    360
tcctctgcta gcaccaaagg tccgagcgtt tttccgctgg caccgagcag caaaagcacc    420
tctggtggca ccgcagcact gggttgtctg gtgaaagatt attttccgga accggttacc    480
gtttcttgga tagcggtgc actgaccagc ggtgttcata cctttccggc agttctgcag    540
agcagcggtc tgtatagcct gtctagcgtt gttaccgttc cgagcagcag cctgggcacc    600
cagacctata tttgcaatgt gaatcataaa ccgagcaata aaagtgtga taacgcgtt     660 gaaccgaaaa gctgtgacaa aactcacacg tgcccaccgt gcccagcacc tgagttcgag    720
gggggaccgt cagtcttcct cttccccccca aaacccaagg acaccctcat gatctcccgg    780
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagccagcat cgagaaaacc   1020
atctccaaag ccaaagggca gccccgagaa ccacaggtct gcaccctgcc cccatcccgg   1080
gaggagatga ccaagaacca ggtcagcctg agctgcgcgg tcaaaggctt ctatcccagc   1140
gacatcgccg tggagtggga gagcaatggg cagccggaga caactacaa gaccacgcct   1200 cccgtgctgg actccgacgg ctccttcttc ctcgttagca agctcaccgt ggacaagagc   1260
```

```
aggtggcagc agggggaacgt cttctcatgc tccgtgatgc atgaggctct gcacaaccac      1320
tacacgcaga agagcctctc cctgtctccg ggtaaa                                 1356
```

<210> SEQ ID NO 11
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gacatccaga tgacccagtc tccatcctcc ctgtctgcat ctgtaggaga cagagtcacc       60
atcacttgcc gggcaagtca gagcattaac agctatttag attggtatca gcagaaacca      120
gggaaagccc ctaaactcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag tattacagta ctccattcac tttcggccct      300
gggaccaaag tggaaatcaa aggtcagccc aaggcggccc cctcggtcac tctgttcccg      360
ccctgctctg aggagcttca agccaacaag gccacactgg tgtgtctcat aagtgacttc      420
tacccgggag ccgtgacagt ggcctggaag gcagatagca gccccgtcaa ggcgggagtg      480
gagaccacca cacctccaa acaaagcaac aacaagtacg cggccagcag ctacctgagc       540
ctgacgcctg agcagtggaa gtcccacaga agctacagct gccaggtcac gcatgaaggg      600
agcaccgtgg agaagacagt ggcccctaca gaagtgtca                             639
```

<210> SEQ ID NO 12
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Cys Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
```

```
            165                 170                 175
Thr Phe Pro Ala Val Leu Gln Ser Ser Gly Leu Tyr Ser Leu Ser Ser
        180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
        210                 215                 220

Pro Lys Ser Val Asp Lys Thr His Thr Cys Pro Pro Cys Pro Ala Pro
225                 230                 235                 240

Glu Phe Glu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Ser Ile Glu Lys Thr Ile Ser Lys Ala Lys Gly Gln Pro Arg
            340                 345                 350

Glu Pro Gln Val Tyr Thr Leu Pro Pro Cys Arg Glu Glu Met Thr Lys
        355                 360                 365

Asn Gln Val Ser Leu Trp Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
450                 455

<210> SEQ ID NO 13
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
caggtgcagc tggtggagtc tgggggaggc gtggtccagc ctggggaggtc cctgagactc      60 tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagatccg     300 agggagcta cccttttacta ctactactac ggtatggacg tctggggcca agggaccacg     360
```

```
gtcaccgtct cctcagcgtc gaccaaaggt ccgagcgtgt gcccgctggc accgagcagc    420
aaaagcacct ctggtggcac cgcagcactg ggttgtctgg tgaaagatta ttttccggaa    480
ccggttaccg tttcttggaa tagcggtgca ctgaccagcg tgttcatac ctttccggca     540 gtcctgcaga gcagcggtct gtatagcctg tctagcgttg ttaccgttcc gagcagcagc    600
ctgggcaccc agacctatat ttgcaatgtg aatcataaac cgagcaatac caaagttgat    660
aaacgcgttg aaccgaaaag cgtggacaaa actcacacgt gcccaccgtg cccagcacct    720
gagttcgagg ggggaccgtc agtcttcctc ttccccccaa acccaagga caccctcatg     780 atctcccgga cccctgaggt cacatgcgtg gtggtggacg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca aagccctccc agccagcatc   1020
gagaaaacca tctccaaagc caaagggcag ccccgagaac cacaggtcta caccctgccc   1080
ccatgccggg aggagatgac caagaaccag gtcagcctgt ggtgcctggt caaaggcttc   1140
tatcccagcg acatcgccgt ggagtgggag agcaatgggc agccggagaa caactacaag   1200
accacgcctc ccgtgctgga ctccgacggc tccttcttcc tctatagcaa gctcaccgtg   1260
gacaagagca ggtggcagca ggggaacgtc ttctcatgct ccgtgatgca tgaggctctg   1320
cacaaccact acacgcagaa gagcttaagc ctgtctccgg gtaaa                    1365
```

<210> SEQ ID NO 14
<211> LENGTH: 710
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Val Glu Ser Gly Gly Val Val Gln Pro Gly Arg Ser
    130                 135                 140

Leu Arg Leu Ser Cys Ala Ala Ser Gly Phe Thr Phe Ser Ser Tyr Gly
145                 150                 155                 160

Met His Trp Val Arg Gln Ala Pro Gly Lys Cys Leu Glu Trp Val Ala
                165                 170                 175

Val Ile Trp Tyr Asp Gly Ser Asn Lys Tyr Tyr Ala Asp Ser Val Lys
```

-continued

```
              180                 185                 190
Gly Arg Phe Thr Ile Ser Arg Asp Asn Ser Lys Asn Thr Leu Tyr Leu
            195                 200                 205
Gln Met Asn Ser Leu Arg Ala Glu Asp Thr Ala Val Tyr Tyr Cys Ala
            210                 215                 220
Arg Asp Pro Arg Gly Ala Thr Leu Tyr Tyr Tyr Tyr Gly Met Asp
225                 230                 235                 240
Val Trp Gly Gln Gly Thr Thr Val Thr Val Ser Ser Gly Gly Gly
            245                 250                 255
Ser Gly Gly Gly Ser Glu Val Gln Leu Val Glu Ser Gly Gly Gly
            260                 265                 270
Leu Val Gln Pro Gly Gly Ser Leu Arg Leu Ser Cys Ala Ala Ser Gly
            275                 280                 285
Phe Thr Phe Ser Arg Tyr Trp Met Ser Trp Val Arg Gln Ala Pro Gly
            290                 295                 300
Lys Gly Leu Glu Trp Val Ala Asn Ile Lys Gln Asp Gly Ser Glu Lys
305                 310                 315                 320
Tyr Tyr Val Asp Ser Val Lys Gly Arg Phe Thr Ile Ser Arg Asp Asn
                325                 330                 335
Ala Lys Asn Ser Leu Tyr Leu Gln Met Asn Ser Leu Arg Ala Glu Asp
                340                 345                 350
Thr Ala Val Tyr Tyr Cys Ala Arg Glu Gly Gly Trp Phe Gly Glu Leu
                355                 360                 365
Ala Phe Asp Tyr Trp Gly Gln Gly Thr Leu Val Thr Val Ser Ser Ala
                370                 375                 380
Ser Thr Lys Gly Pro Ser Val Phe Pro Leu Ala Pro Cys Ser Arg Ser
385                 390                 395                 400
Thr Ser Glu Ser Thr Ala Ala Leu Gly Cys Leu Val Lys Asp Tyr Phe
                405                 410                 415
Pro Glu Pro Val Thr Val Ser Trp Asn Ser Gly Ala Leu Thr Ser Gly
                420                 425                 430
Val His Thr Phe Pro Ala Val Leu Gln Ser Ser Gly Leu Tyr Ser Leu
                435                 440                 445
Ser Ser Val Val Thr Val Pro Ser Ser Ser Leu Gly Thr Lys Thr Tyr
450                 455                 460
Thr Cys Asn Val Asp His Lys Pro Ser Asn Thr Lys Val Asp Lys Arg
465                 470                 475                 480
Val Glu Ser Lys Tyr Gly Pro Pro Cys Pro Pro Cys Pro Ala Pro Glu
                485                 490                 495
Phe Leu Gly Gly Pro Ser Val Phe Leu Phe Pro Pro Lys Pro Lys Asp
                500                 505                 510
Thr Leu Met Ile Ser Arg Thr Pro Glu Val Thr Cys Val Val Val Asp
                515                 520                 525
Val Ser Gln Glu Asp Pro Glu Val Gln Phe Asn Trp Tyr Val Asp Gly
                530                 535                 540
Val Glu Val His Asn Ala Lys Thr Lys Pro Arg Glu Glu Gln Phe Asn
545                 550                 555                 560
Ser Thr Tyr Arg Val Val Ser Val Leu Thr Val Leu His Gln Asp Trp
                565                 570                 575
Leu Asn Gly Lys Glu Tyr Lys Cys Lys Val Ser Asn Lys Gly Leu Pro
                580                 585                 590
Ser Ser Ile Glu Lys Thr Ile Ser Lys Ala Lys Gly Gln Pro Arg Glu
                595                 600                 605
```

Pro Gln Val Tyr Thr Leu Pro Pro Ser Gln Glu Met Thr Lys Asn
            610                 615                 620

Gln Val Ser Leu Thr Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                    645                 650                 655

Thr Pro Pro Val Leu Asp Ser Asp Gly Ser Phe Phe Leu Tyr Ser Arg
                660                 665                 670

Leu Thr Val Asp Lys Ser Arg Trp Gln Glu Gly Asn Val Phe Ser Cys
            675                 680                 685

Ser Val Met His Glu Ala Leu His Asn His Tyr Thr Gln Lys Ser Leu
            690                 695                 700

Ser Leu Ser Leu Gly Lys
705                 710

<210> SEQ ID NO 15
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 16
<211> LENGTH: 710
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380
```

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
    435                 440                 445

Gly Gly Gly Gly Ser Gly Gly Gly Ser Asp Ile Gln Met Thr Gln
450                 455                 460

Ser Pro Ser Ser Leu Ser Ala Ser Val Gly Asp Arg Val Thr Ile Thr
465                 470                 475                 480

Cys Arg Ala Ser Gln Ser Ile Asn Ser Tyr Leu Asp Trp Tyr Gln Gln
            485                 490                 495

Lys Pro Gly Lys Ala Pro Lys Leu Leu Ile Tyr Ala Ala Ser Ser Leu
        500                 505                 510

Gln Ser Gly Val Pro Ser Arg Phe Ser Gly Ser Gly Ser Gly Thr Asp
    515                 520                 525

Phe Thr Leu Thr Ile Ser Ser Leu Gln Pro Glu Asp Phe Ala Thr Tyr
530                 535                 540

Tyr Cys Gln Gln Tyr Tyr Ser Thr Pro Phe Thr Phe Gly Cys Gly Thr
545                 550                 555                 560

Lys Val Glu Ile Lys Gly Gly Gly Gly Ser Gly Gly Gly Gly Ser Gly
            565                 570                 575

Gly Gly Ser Gly Gly Gly Gly Ser Gln Val Gln Leu Val Glu Ser
    580                 585                 590

Gly Gly Gly Val Val Gln Pro Gly Arg Ser Leu Arg Leu Ser Cys Ala
        595                 600                 605

Ala Ser Gly Phe Thr Phe Ser Ser Tyr Gly Met His Trp Val Arg Gln
610                 615                 620

Ala Pro Gly Lys Cys Leu Glu Trp Val Ala Val Ile Trp Tyr Asp Gly
625                 630                 635                 640

Ser Asn Lys Tyr Tyr Ala Asp Ser Val Lys Gly Arg Phe Thr Ile Ser
            645                 650                 655

Arg Asp Asn Ser Lys Asn Thr Leu Tyr Leu Gln Met Asn Ser Leu Arg
        660                 665                 670

Ala Glu Asp Thr Ala Val Tyr Tyr Cys Ala Arg Asp Pro Arg Gly Ala
    675                 680                 685

Thr Leu Tyr Tyr Tyr Tyr Tyr Gly Met Asp Val Trp Gly Gln Gly Thr
690                 695                 700

Thr Val Thr Val Ser Ser
705             710
```

<210> SEQ ID NO 17
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30
```

```
Tyr Leu Ala Trp Tyr Gln Gln Lys Pro Gly Gln Ala Pro Arg Leu Leu
            35                  40                  45

Ile Tyr Asp Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Leu Pro
                 85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210             215

<210> SEQ ID NO 18
<211> LENGTH: 720
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Gly Trp Phe Gly Glu Leu Ala Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

```
            165                 170                 175
Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gly Gly Ser Gly Gly Gly Ser Asp Ile Gln Met Thr
385                 390                 395                 400

Gln Ser Pro Ser Ser Leu Ser Ala Ser Val Gly Asp Arg Val Thr Ile
                405                 410                 415

Thr Cys Arg Ala Ser Gln Ser Ile Asn Ser Tyr Leu Asp Trp Tyr Gln
            420                 425                 430

Gln Lys Pro Gly Lys Ala Pro Lys Leu Leu Ile Tyr Ala Ala Ser Ser
        435                 440                 445

Leu Gln Ser Gly Val Pro Ser Arg Phe Ser Gly Ser Gly Ser Gly Thr
    450                 455                 460

Asp Phe Thr Leu Thr Ile Ser Ser Leu Gln Pro Glu Asp Phe Ala Thr
465                 470                 475                 480

Tyr Tyr Cys Gln Gln Tyr Tyr Ser Thr Pro Phe Thr Phe Gly Cys Gly
                485                 490                 495

Thr Lys Val Glu Ile Lys Gly Gly Gly Ser Gly Gly Gly Gly Ser
            500                 505                 510

Gly Gly Gly Gly Ser Gly Gly Gly Ser Gln Val Gln Leu Val Glu
        515                 520                 525

Ser Gly Gly Gly Val Val Gln Pro Gly Arg Ser Leu Arg Leu Ser Cys
    530                 535                 540

Ala Ala Ser Gly Phe Thr Phe Ser Ser Tyr Gly Met His Trp Val Arg
545                 550                 555                 560

Gln Ala Pro Gly Lys Cys Leu Glu Trp Val Ala Val Ile Trp Tyr Asp
                565                 570                 575

Gly Ser Asn Lys Tyr Tyr Ala Asp Ser Val Lys Gly Arg Phe Thr Ile
            580                 585                 590
```

```
Ser Arg Asp Asn Ser Lys Asn Thr Leu Tyr Leu Gln Met Asn Ser Leu
            595                 600                 605

Arg Ala Glu Asp Thr Ala Val Tyr Tyr Cys Ala Arg Asp Pro Arg Gly
610                 615                 620

Ala Thr Leu Tyr Tyr Tyr Tyr Gly Met Asp Val Trp Gly Gln Gly
625                 630                 635                 640

Thr Thr Val Thr Val Ser Ser Gly Gly Gly Ser Gly Gly Gly Gly
                645                 650                 655

Ser Gly Gln Pro Glu Asn Asn Tyr Lys Thr Thr Pro Pro Val Leu Asp
            660                 665                 670

Ser Asp Gly Ser Phe Phe Leu Tyr Ser Arg Leu Thr Val Asp Lys Ser
            675                 680                 685

Arg Trp Gln Glu Gly Asn Val Phe Ser Cys Ser Val Met His Glu Ala
690                 695                 700

Leu His Asn His Tyr Thr Gln Lys Ser Leu Ser Leu Ser Leu Gly Lys
705                 710                 715                 720

<210> SEQ ID NO 19
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

```
<210> SEQ ID NO 20
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Cys Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Gly Thr Tyr Tyr Gly Asn Tyr Phe Glu Tyr Trp
            100                 105                 110

Gly Arg Gly Thr Leu Val Thr Val Ser Ser Gly Gly Gly Gly Ser Gly
        115                 120                 125

Gly Gly Gly Ser Gly Gly Gly Ser Gly Gly Gly Ser Gln Thr
    130                 135                 140

Val Leu Thr Gln Pro Pro Ser Val Ser Val Ala Pro Gly Lys Thr Ala
145                 150                 155                 160

Ser Ile Ser Cys Gly Gly Asp Asn Ile Gly Gly Lys Ser Val His Trp
                165                 170                 175

Tyr Gln Gln Lys Pro Gly Gln Ala Pro Val Leu Val Ile Tyr Tyr Asp
            180                 185                 190

Ser Asp Arg Pro Ser Gly Ile Pro Gln Arg Phe Ser Gly Ser Asn Ser
        195                 200                 205

Gly Asn Thr Ala Thr Leu Thr Ile His Arg Val Glu Ala Gly Asp Glu
    210                 215                 220

Ala Asp Tyr Tyr Cys Gln Val Leu Asp Arg Arg Ser Asp His Trp Leu
225                 230                 235                 240

Phe Gly Cys Gly Thr Lys Leu Thr Val Leu
                245                 250

<210> SEQ ID NO 21
<211> LENGTH: 709
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Tyr Thr Ile Tyr Ser Ala Asp Ser Val
```

```
            50                  55                  60
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Pro Asn Ser Phe Tyr Glu Tyr Tyr Phe Asp Tyr Trp
                    100                 105                 110

Gly Gln Gly Thr Thr Val Thr Val Ser Ser Ala Ser Thr Lys Gly Pro
                115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Lys Gly Gly Gly Gly Ser Gly Gly Gly Gly Ser Glu Val Gln Leu Leu
                450                 455                 460

Glu Ser Gly Gly Gly Leu Val Gln Pro Gly Gly Ser Leu Arg Leu Ser
465                 470                 475                 480
```

```
Cys Ala Ala Ser Gly Phe Thr Phe Ser Ser Tyr Ala Met Ser Trp Val
                485                 490                 495

Arg Gln Ala Pro Gly Lys Cys Leu Glu Trp Val Ser Ala Ile Ser Gly
            500                 505                 510

Ser Gly Gly Ser Thr Tyr Tyr Ala Asp Ser Val Lys Gly Arg Phe Thr
        515                 520                 525

Ile Ser Arg Asp Asn Ser Lys Asn Thr Leu Tyr Leu Gln Met Asn Ser
    530                 535                 540

Leu Arg Ala Glu Asp Thr Ala Val Tyr Tyr Cys Ala Arg Gly Ser Tyr
545                 550                 555                 560

Gly Thr Tyr Tyr Gly Asn Tyr Phe Glu Tyr Trp Gly Arg Gly Thr Leu
                565                 570                 575

Val Thr Val Ser Ser Gly Gly Gly Ser Gly Gly Gly Ser Gly
            580                 585                 590

Gly Gly Gly Ser Gly Gly Gly Ser Gln Thr Val Leu Thr Gln Pro
        595                 600                 605

Pro Ser Val Ser Val Ala Pro Gly Lys Thr Ala Ser Ile Ser Cys Gly
    610                 615                 620

Gly Asp Asn Ile Gly Gly Lys Ser Val His Trp Tyr Gln Gln Lys Pro
625                 630                 635                 640

Gly Gln Ala Pro Val Leu Val Ile Tyr Tyr Asp Ser Asp Arg Pro Ser
                645                 650                 655

Gly Ile Pro Gln Arg Phe Ser Gly Ser Asn Ser Gly Asn Thr Ala Thr
                660                 665                 670

Leu Thr Ile His Arg Val Glu Ala Gly Asp Glu Ala Asp Tyr Tyr Cys
            675                 680                 685

Gln Val Leu Asp Arg Arg Ser Asp His Trp Leu Phe Gly Cys Gly Thr
            690                 695                 700

Lys Leu Thr Val Leu
705

<210> SEQ ID NO 22
<211> LENGTH: 719
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Tyr Thr Ile Tyr Ser Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Pro Asn Ser Phe Tyr Glu Tyr Tyr Phe Asp Tyr Trp
            100                 105                 110

Gly Gln Gly Thr Thr Val Thr Val Ser Ser Ala Ser Thr Lys Gly Pro
```

-continued

```
                115                 120                 125
Ser Val Phe Pro Leu Ala Pro Cys Ser Arg Ser Thr Ser Glu Ser Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Lys Thr Tyr Thr Cys Asn Val Asp
                195                 200                 205
His Lys Pro Ser Asn Thr Lys Val Asp Lys Arg Val Glu Ser Lys Tyr
        210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
                260                 265                 270
Pro Glu Val Gln Phe Asn Trp Tyr Val Asp Gly Val Glu Val His Asn
                275                 280                 285
Ala Lys Thr Lys Pro Arg Glu Glu Gln Phe Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Gln Glu Glu Met Thr Lys Asn Gln Val Ser Leu Thr
                355                 360                 365
Cys Leu Val Lys Gly Phe Tyr Pro Ser Asp Ile Ala Val Glu Trp Glu
        370                 375                 380
Ser Asn Gly Gly Gly Gly Ser Gly Gly Gly Gly Ser Glu Val Gln Leu
385                 390                 395                 400
Leu Glu Ser Gly Gly Gly Leu Val Gln Pro Gly Gly Ser Leu Arg Leu
                405                 410                 415
Ser Cys Ala Ala Ser Gly Phe Thr Phe Ser Ser Tyr Ala Met Ser Trp
                420                 425                 430
Val Arg Gln Ala Pro Gly Lys Cys Leu Glu Trp Val Ser Ala Ile Ser
        435                 440                 445
Gly Ser Gly Gly Ser Thr Tyr Tyr Ala Asp Ser Val Lys Gly Arg Phe
        450                 455                 460
Thr Ile Ser Arg Asp Asn Ser Lys Asn Thr Leu Tyr Leu Gln Met Asn
465                 470                 475                 480
Ser Leu Arg Ala Glu Asp Thr Ala Val Tyr Tyr Cys Ala Arg Gly Ser
                485                 490                 495
Tyr Gly Thr Tyr Tyr Gly Asn Tyr Phe Glu Tyr Trp Gly Arg Gly Thr
                500                 505                 510
Leu Val Thr Val Ser Ser Gly Gly Gly Gly Ser Gly Gly Gly Gly Ser
                515                 520                 525
Gly Gly Gly Gly Ser Gly Gly Gly Gly Ser Gln Thr Val Leu Thr Gln
        530                 535                 540
```

```
Pro Pro Ser Val Ser Val Ala Pro Gly Lys Thr Ala Ser Ile Ser Cys
545                 550                 555                 560

Gly Gly Asp Asn Ile Gly Gly Lys Ser Val His Trp Tyr Gln Gln Lys
            565                 570                 575

Pro Gly Gln Ala Pro Val Leu Val Ile Tyr Tyr Asp Ser Asp Arg Pro
            580                 585                 590

Ser Gly Ile Pro Gln Arg Phe Ser Gly Ser Asn Ser Gly Asn Thr Ala
            595                 600                 605

Thr Leu Thr Ile His Arg Val Glu Ala Gly Asp Glu Ala Asp Tyr Tyr
            610                 615                 620

Cys Gln Val Leu Asp Arg Arg Ser Asp His Trp Leu Phe Gly Cys Gly
625                 630                 635                 640

Thr Lys Leu Thr Val Leu Gly Gly Gly Ser Gly Gly Gly Gly Ser
                645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Arg Leu Thr Val Asp Lys Ser Arg
            675                 680                 685

Trp Gln Glu Gly Asn Val Phe Ser Cys Ser Val Met His Glu Ala Leu
            690                 695                 700

His Asn His Tyr Thr Gln Lys Ser Leu Ser Leu Ser Leu Gly Lys
705                 710                 715

<210> SEQ ID NO 23
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Lys His Thr Asn Leu
            20                  25                  30

Tyr Trp Ser Arg His Met Tyr Trp Tyr Gln Gln Lys Pro Gly Gln Ala
        35                  40                  45

Pro Arg Leu Leu Ile Tyr Leu Thr Ser Asn Arg Ala Thr Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Gln Gln Trp
                85                  90                  95

Ser Ser Asn Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
```

```
                    180                 185                 190
Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 24
<211> LENGTH: 709
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Tyr Thr Ile Tyr Ser Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Pro Asn Ser Phe Tyr Glu Tyr Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys Gly Gly Gly Gly Ser Gly Gly Gly Gly Ser Glu Val Gln Leu Leu
450                 455                 460

Glu Ser Gly Gly Gly Leu Val Gln Pro Gly Gly Ser Leu Arg Leu Ser
465                 470                 475                 480

Cys Ala Ala Ser Gly Phe Thr Phe Ser Ser Tyr Ala Met Ser Trp Val
                485                 490                 495

Arg Gln Ala Pro Gly Lys Cys Leu Glu Trp Val Ser Ala Ile Ser Gly
            500                 505                 510

Ser Gly Gly Ser Thr Tyr Tyr Ala Asp Ser Val Lys Gly Arg Phe Thr
        515                 520                 525

Ile Ser Arg Asp Asn Ser Lys Asn Thr Leu Tyr Leu Gln Met Asn Ser
530                 535                 540

Leu Arg Ala Glu Asp Thr Ala Val Tyr Tyr Cys Ala Arg Gly Ser Tyr
545                 550                 555                 560

Gly Thr Tyr Tyr Gly Asn Tyr Phe Glu Tyr Trp Gly Arg Gly Thr Leu
                565                 570                 575

Val Thr Val Ser Ser Gly Gly Gly Gly Ser Gly Gly Gly Gly Ser Gly
            580                 585                 590

Gly Gly Gly Ser Gly Gly Gly Gly Ser Gln Thr Val Leu Thr Gln Pro
        595                 600                 605

Pro Ser Val Ser Val Ala Pro Gly Lys Thr Ala Ser Ile Ser Cys Gly
610                 615                 620

Gly Asp Asn Ile Gly Gly Lys Ser Val His Trp Tyr Gln Gln Lys Pro
625                 630                 635                 640

Gly Gln Ala Pro Val Leu Val Ile Tyr Tyr Asp Ser Asp Arg Pro Ser
                645                 650                 655

Gly Ile Pro Gln Arg Phe Ser Gly Ser Asn Ser Gly Asn Thr Ala Thr
            660                 665                 670

Leu Thr Ile His Arg Val Glu Ala Gly Asp Glu Ala Asp Tyr Tyr Cys
        675                 680                 685

Gln Val Leu Asp Arg Arg Ser Asp His Trp Leu Phe Gly Cys Gly Thr
690                 695                 700

Lys Leu Thr Val Leu
705

<210> SEQ ID NO 25
<211> LENGTH: 452
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 25

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asp | Tyr |
| | | | 20 | | | | | 25 | | | | | 30 | | |
| Gly | Met | His | Trp | Val | Arg | Gln | Ala | Pro | Gly | Lys | Gly | Leu | Glu | Trp | Val |
| | | 35 | | | | | 40 | | | | | 45 | | | |
| Ala | Tyr | Ile | Ser | Ser | Gly | Ser | Tyr | Thr | Ile | Tyr | Ser | Ala | Asp | Ser | Val |
| 50 | | | | | 55 | | | | | 60 | | | | | |
| Lys | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Arg | Ala | Pro | Asn | Ser | Phe | Tyr | Glu | Tyr | Tyr | Phe | Asp | Tyr | Trp |
| | | | 100 | | | | | 105 | | | | | 110 | | |
| Gly | Gln | Gly | Thr | Thr | Val | Thr | Val | Ser | Ser | Ala | Ser | Thr | Lys | Gly | Pro |
| | | 115 | | | | | 120 | | | | | 125 | | | |
| Ser | Val | Phe | Pro | Leu | Ala | Pro | Ser | Ser | Lys | Ser | Thr | Ser | Gly | Gly | Thr |
| 130 | | | | | 135 | | | | | 140 | | | | | |
| Ala | Ala | Leu | Gly | Cys | Leu | Val | Lys | Asp | Tyr | Phe | Pro | Glu | Pro | Val | Thr |
| 145 | | | | | 150 | | | | | 155 | | | | | 160 |
| Val | Ser | Trp | Asn | Ser | Gly | Ala | Leu | Thr | Ser | Gly | Val | His | Thr | Phe | Pro |
| | | | | 165 | | | | | 170 | | | | | 175 | |
| Ala | Val | Leu | Gln | Ser | Ser | Gly | Leu | Tyr | Ser | Leu | Ser | Ser | Val | Val | Thr |
| | | | 180 | | | | | 185 | | | | | 190 | | |
| Val | Pro | Ser | Ser | Ser | Leu | Gly | Thr | Gln | Thr | Tyr | Ile | Cys | Asn | Val | Asn |
| | | 195 | | | | | 200 | | | | | 205 | | | |
| His | Lys | Pro | Ser | Asn | Thr | Lys | Val | Asp | Lys | Arg | Val | Glu | Pro | Lys | Ser |
| 210 | | | | | 215 | | | | | 220 | | | | | |
| Cys | Asp | Lys | Thr | His | Thr | Cys | Pro | Pro | Cys | Pro | Ala | Pro | Glu | Leu | Leu |
| 225 | | | | | 230 | | | | | 235 | | | | | 240 |
| Gly | Gly | Pro | Ser | Val | Phe | Leu | Phe | Pro | Pro | Lys | Pro | Lys | Asp | Thr | Leu |
| | | | | 245 | | | | | 250 | | | | | 255 | |
| Met | Ile | Ser | Arg | Thr | Pro | Glu | Val | Thr | Cys | Val | Val | Val | Asp | Val | Ser |
| | | | 260 | | | | | 265 | | | | | 270 | | |
| His | Glu | Asp | Pro | Glu | Val | Lys | Phe | Asn | Trp | Tyr | Val | Asp | Gly | Val | Glu |
| | | 275 | | | | | 280 | | | | | 285 | | | |
| Val | His | Asn | Ala | Lys | Thr | Lys | Pro | Arg | Glu | Glu | Gln | Tyr | Asn | Ser | Thr |
| 290 | | | | | 295 | | | | | 300 | | | | | |
| Tyr | Arg | Val | Val | Ser | Val | Leu | Thr | Val | Leu | His | Gln | Asp | Trp | Leu | Asn |
| 305 | | | | | 310 | | | | | 315 | | | | | 320 |
| Gly | Lys | Glu | Tyr | Lys | Cys | Lys | Val | Ser | Asn | Lys | Ala | Leu | Pro | Ala | Pro |
| | | | | 325 | | | | | 330 | | | | | 335 | |
| Ile | Glu | Lys | Thr | Ile | Ser | Lys | Ala | Lys | Gly | Gln | Pro | Arg | Glu | Pro | Gln |
| | | | 340 | | | | | 345 | | | | | 350 | | |
| Val | Cys | Thr | Leu | Pro | Pro | Ser | Arg | Glu | Glu | Met | Thr | Lys | Asn | Gln | Val |
| | | 355 | | | | | 360 | | | | | 365 | | | |
| Ser | Leu | Ser | Cys | Ala | Val | Lys | Gly | Phe | Tyr | Pro | Ser | Asp | Ile | Ala | Val |
| 370 | | | | | 375 | | | | | 380 | | | | | |

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 26
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Thr Val Leu Thr Gln Pro Pro Ser Val Ser Val Ala Pro Gly Lys
1               5                   10                  15

Thr Ala Ser Ile Ser Cys Gly Gly Asp Asn Ile Gly Lys Ser Val
            20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Gln Arg Phe Ser Gly Ser
        50                  55                  60

Asn Ser Gly Asn Thr Ala Thr Leu Thr Ile His Arg Val Glu Ala Gly
65                  70                  75                  80

Asp Glu Ala Asp Tyr Tyr Cys Gln Val Leu Asp Arg Arg Ser Asp His
                85                  90                  95

Trp Leu Phe Gly Gly Gly Thr Lys Leu Thr Val Leu Gly Gln Pro Lys
            100                 105                 110

Ala Ala Pro Ser Val Thr Leu Phe Pro Pro Cys Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Val Ser
    210

<210> SEQ ID NO 27
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27
```

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Gly Thr Tyr Tyr Gly Asn Tyr Phe Glu Tyr Trp
            100                 105                 110

Gly Arg Gly Thr Leu Val Thr Val Ser Ser Ala Ser Thr Lys Gly Pro
        115                 120                 125

Ser Val Cys Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Val Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Cys Arg Glu Glu Met Thr Lys Asn Gln Val
        355                 360                 365

Ser Leu Trp Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
```

```
                420                 425                 430
Met His Glu Ala Leu His Asn His Tyr Thr Gln Lys Ser Leu Ser Leu
            435                 440                 445

Ser Pro Gly
    450

<210> SEQ ID NO 28
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser Tyr Val Leu Thr Gln Pro Pro Ser Val Ser Val Ala Pro Gly Lys
1               5                   10                  15

Thr Ala Arg Ile Thr Cys Gly Gly Asp Asn Ile Gly Gly Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Leu Asp Arg Arg Ser Asp His
                85                  90                  95

Phe Leu Phe Gly Gly Gly Thr Lys Leu Thr Val Leu Gly Gln Pro Lys
            100                 105                 110

Ala Ala Pro Ser Val Thr Leu Phe Pro Pro Cys Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Val Ser
    210

<210> SEQ ID NO 29
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
agctacgtgc tgacgcagcc gccgtcagtg tcagtggccc caggaaagac ggccaggatt    60
acctgtgggg gagacaacat tggaggtaaa agtgttcact ggtaccagca gaagccaggc   120
caggcccctg tgttggtcat ctattatgat agtgaccggc cctcaggcat ccctgagcga   180
ttctctggct ccaactctgg gaacacggcc accctgacca tcagcagggt cgaagccggg   240
```

```
gatgaggccg attattactg tcaggtgttg gatcgtcgta gtgatcattt cctgttcggc      300
ggagggacca agctgaccgt cctaggtcag cccaaggcgg cgccctcggt cactctgttc      360 ccgcccctgct ctgaggagct tcaagccaac aaggccacac tggtgtgtct cataagtgac     420
ttctacccgg gagccgtgac agtggcctgg aaggcagata gcagcccgt caaggcggga      480 gtggagacca ccacaccctc caaacaaagc aacaacaagt acgcggccag cagctacctg     540
agcctgacgc ctgagcagtg gaagtcccac agaagctaca gctgccaggt cacgcatgaa     600
gggagcaccg tggagaagac agtggccccct acagaagtgt ca                       642
```

```
<210> SEQ ID NO 30
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Gly Thr Tyr Tyr Gly Asn Tyr Phe Glu Tyr Trp
            100                 105                 110

Gly Gln Gly Thr Leu Val Thr Val Ser Ser Ala Ser Thr Lys Gly Pro
        115                 120                 125

Ser Val Cys Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Val Asp Lys Thr His Thr Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

| | | | | | | | | | | | |
|---|---|---|---|---|---|---|---|---|---|---|---|
|Val|His|Asn|Ala|Lys|Thr|Lys|Pro|Arg|Glu|Glu|Gln|Tyr|Asn|Ser|Thr|
| |290| | | |295| | | |300| | | | | | |

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Cys Arg Glu Glu Met Thr Lys Asn Gln Val
        355                 360                 365

Ser Leu Trp Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 31
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagagggtcc    300
tatggtacct actacggaaa ctactttgaa tactggggcc agggcaccct ggtcaccgtc    360
tcgagtgcgt cgaccaaagg tccgagcgtg tgcccgctgg caccgagcag caaaagcacc    420
tctggtggca ccgcagcact gggttgtctg gtgaaagatt attttccgga accggttacc    480
gtttcttgga tagcggtgc actgaccagc ggtgttcata cctttccggc agtcctgcag    540
agcagcggtc tgtatagcct gtctagcgtt gttaccgttc cgagcagcag cctgggcacc    600
cagacctata tttgcaatgt gaatcataaa ccgagcaata ccaaagttga taacgcgtt    660 gaaccgaaaa gcgtggacaa aactcacacg tgcccaccgt gcccagcacc tgagttcgag    720
gggggaccgt cagtcttcct cttccccca aaacccaagg acaccctcat gatctcccgg    780
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagccagcat cgagaaaacc   1020
```

-continued

```
atctccaaag ccaaagggca gccccgagaa ccacaggtct acaccctgcc cccatgccgg    1080
gaggagatga ccaagaacca ggtcagcctg tggtgcctgg tcaaaggctt ctatcccagc    1140
gacatcgccg tggagtggga gagcaatggg cagccggaga caactacaa gaccacgcct     1200 cccgtgctgg actccgacgg ctccttcttc ctctatagca agctcaccgt ggacaagagc    1260
aggtggcagc aggggaacgt cttctcatgc tccgtgatgc atgaggctct gcacaaccac    1320
tacacgcaga agagcttaag cctgtctccg ggtaaa                              1356
```

<210> SEQ ID NO 32
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 33
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Arg Val Ser Ser Ser
                20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Leu Pro
                 85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
210                 215

<210> SEQ ID NO 34
<211> LENGTH: 707
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Arg Val Ser Ser Ser
                20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Leu Pro
                 85                  90                  95

Trp Thr Phe Gly Cys Gly Thr Lys Val Glu Ile Lys Gly Gly Gly Gly
            100                 105                 110

Ser Gly Gly Gly Gly Ser Gly Gly Gly Ser Gly Gly Gly Gly Ser
            115                 120                 125

Glu Val Gln Leu Val Glu Ser Gly Gly Gly Leu Val Gln Pro Gly Gly
            130                 135                 140

Ser Leu Arg Leu Ser Cys Ala Ala Ser Gly Phe Thr Phe Ser Arg Tyr
145                 150                 155                 160
```

```
Trp Met Ser Trp Val Arg Gln Ala Pro Gly Lys Cys Leu Glu Trp Val
            165                 170                 175

Ala Asn Ile Lys Gln Asp Gly Ser Glu Lys Tyr Tyr Val Asp Ser Val
        180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Glu Gly Gly Trp Phe Gly Glu Leu Ala Phe Asp Tyr Trp Gly
225                 230                 235                 240

Gln Gly Thr Leu Val Thr Val Ser Ser Gly Gly Gly Ser Gly Gly
            245                 250                 255

Gly Gly Ser Gln Val Gln Leu Gln Glu Ser Gly Pro Gly Leu Val Lys
        260                 265                 270

Pro Ser Gln Thr Leu Ser Leu Thr Cys Ala Val Tyr Gly Gly Ser Phe
        275                 280                 285

Ser Ser Gly Tyr Trp Asn Trp Ile Arg Lys His Pro Gly Lys Gly Leu
    290                 295                 300

Glu Tyr Ile Gly Tyr Ile Ser Tyr Asn Gly Ile Thr Tyr His Asn Pro
305                 310                 315                 320

Ser Leu Lys Ser Arg Ile Thr Ile Asn Arg Asp Thr Ser Lys Asn Gln
            325                 330                 335

Tyr Ser Leu Gln Leu Asn Ser Val Thr Pro Glu Asp Thr Ala Val Tyr
        340                 345                 350

Tyr Cys Ala Arg Tyr Lys Tyr Asp Tyr Asp Gly Gly His Ala Met Asp
        355                 360                 365

Tyr Trp Gly Gln Gly Thr Leu Val Thr Val Ser Ser Ala Ser Thr Lys
    370                 375                 380

Gly Pro Ser Val Phe Pro Leu Ala Pro Cys Ser Arg Ser Thr Ser Glu
385                 390                 395                 400

Ser Thr Ala Ala Leu Gly Cys Leu Val Lys Asp Tyr Phe Pro Glu Pro
            405                 410                 415

Val Thr Val Ser Trp Asn Ser Gly Ala Leu Thr Ser Gly Val His Thr
        420                 425                 430

Phe Pro Ala Val Leu Gln Ser Ser Gly Leu Tyr Ser Leu Ser Ser Val
        435                 440                 445

Val Thr Val Pro Ser Ser Ser Leu Gly Thr Lys Thr Tyr Thr Cys Asn
    450                 455                 460

Val Asp His Lys Pro Ser Asn Thr Lys Val Asp Lys Arg Val Glu Ser
465                 470                 475                 480

Lys Tyr Gly Pro Pro Cys Pro Pro Cys Pro Ala Pro Glu Phe Leu Gly
            485                 490                 495

Gly Pro Ser Val Phe Leu Phe Pro Pro Lys Pro Lys Asp Thr Leu Met
        500                 505                 510

Ile Ser Arg Thr Pro Glu Val Thr Cys Val Val Val Asp Val Ser Gln
        515                 520                 525

Glu Asp Pro Glu Val Gln Phe Asn Trp Tyr Val Asp Gly Val Glu Val
    530                 535                 540

His Asn Ala Lys Thr Lys Pro Arg Glu Glu Gln Phe Asn Ser Thr Tyr
545                 550                 555                 560

Arg Val Val Ser Val Leu Thr Val Leu His Gln Asp Trp Leu Asn Gly
            565                 570                 575
```

```
Lys Glu Tyr Lys Cys Lys Val Ser Asn Lys Gly Leu Pro Ser Ser Ile
                580                 585                 590

Glu Lys Thr Ile Ser Lys Ala Lys Gly Gln Pro Arg Glu Pro Gln Val
            595                 600                 605

Tyr Thr Leu Pro Pro Ser Gln Glu Glu Met Thr Lys Asn Gln Val Ser
        610                 615                 620

Leu Thr Cys Leu Val Lys Gly Phe Tyr Pro Ser Asp Ile Ala Val Glu
625                 630                 635                 640

Trp Glu Ser Asn Gly Gln Pro Glu Asn Asn Tyr Lys Thr Thr Pro Pro
                645                 650                 655

Val Leu Asp Ser Asp Gly Ser Phe Phe Leu Tyr Ser Arg Leu Thr Val
            660                 665                 670

Asp Lys Ser Arg Trp Gln Glu Gly Asn Val Phe Ser Cys Ser Val Met
        675                 680                 685

His Glu Ala Leu His Asn His Tyr Thr Gln Lys Ser Leu Ser Leu Ser
690                 695                 700

Leu Gly Lys
705

<210> SEQ ID NO 35
<211> LENGTH: 707
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220
```

```
Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

Gly Gly Gly Gly Ser Gly Gly Gly Gly Ser Glu Ile Val Leu Thr Gln
    450                 455                 460

Ser Pro Gly Thr Leu Ser Leu Ser Pro Gly Glu Arg Ala Thr Leu Ser
465                 470                 475                 480

Cys Arg Ala Ser Gln Arg Val Ser Ser Ser Tyr Leu Ala Trp Tyr Gln
                485                 490                 495

Gln Lys Pro Gly Gln Ala Pro Arg Leu Leu Ile Tyr Asp Ala Ser Ser
            500                 505                 510

Arg Ala Thr Gly Ile Pro Asp Arg Phe Ser Gly Ser Gly Ser Gly Thr
        515                 520                 525

Asp Phe Thr Leu Thr Ile Ser Arg Leu Glu Pro Glu Asp Phe Ala Val
    530                 535                 540

Tyr Tyr Cys Gln Gln Tyr Gly Ser Leu Pro Trp Thr Phe Gly Cys Gly
545                 550                 555                 560

Thr Lys Val Glu Ile Lys Gly Gly Gly Ser Gly Gly Gly Gly Ser
                565                 570                 575

Gly Gly Gly Gly Ser Gly Gly Gly Ser Glu Val Gln Leu Val Glu
                580                 585                 590

Ser Gly Gly Gly Leu Val Gln Pro Gly Gly Ser Leu Arg Leu Ser Cys
    595                 600                 605

Ala Ala Ser Gly Phe Thr Phe Ser Arg Tyr Trp Met Ser Trp Val Arg
        610                 615                 620

Gln Ala Pro Gly Lys Cys Leu Glu Trp Val Ala Asn Ile Lys Gln Asp
625                 630                 635                 640
```

Gly Ser Glu Lys Tyr Tyr Val Asp Ser Val Lys Gly Arg Phe Thr Ile
                    645                 650                 655

Ser Arg Asp Asn Ala Lys Asn Ser Leu Tyr Leu Gln Met Asn Ser Leu
            660                 665                 670

Arg Ala Glu Asp Thr Ala Val Tyr Tyr Cys Ala Arg Glu Gly Gly Trp
            675                 680                 685

Phe Gly Glu Leu Ala Phe Asp Tyr Trp Gly Gln Gly Thr Leu Val Thr
    690                 695                 700

Val Ser Ser
705

<210> SEQ ID NO 36
<211> LENGTH: 707
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

-continued

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                    325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

Gly Gly Gly Gly Ser Gly Gly Gly Ser Glu Ile Val Leu Thr Gln
450                 455                 460

Ser Pro Gly Thr Leu Ser Leu Ser Pro Gly Glu Arg Ala Thr Leu Ser
465                 470                 475                 480

Cys Arg Ala Ser Gln Arg Val Ser Ser Tyr Leu Ala Trp Tyr Gln
                485                 490                 495

Gln Lys Pro Gly Gln Ala Pro Arg Leu Leu Ile Tyr Asp Ala Ser Ser
            500                 505                 510

Arg Ala Thr Gly Ile Pro Asp Arg Phe Ser Gly Ser Gly Ser Gly Thr
            515                 520                 525

Asp Phe Thr Leu Thr Ile Ser Arg Leu Glu Pro Glu Asp Phe Ala Val
530                 535                 540

Tyr Tyr Cys Gln Gln Tyr Gly Ser Leu Pro Trp Thr Phe Gly Cys Gly
545                 550                 555                 560

Thr Lys Val Glu Ile Lys Gly Gly Gly Ser Gly Gly Gly Gly Ser
                565                 570                 575

Gly Gly Gly Gly Ser Gly Gly Gly Ser Glu Val Gln Leu Val Glu
            580                 585                 590

Ser Gly Gly Gly Leu Val Gln Pro Gly Gly Ser Leu Arg Leu Ser Cys
            595                 600                 605

Ala Ala Ser Gly Phe Thr Phe Ser Arg Tyr Trp Met Ser Trp Val Arg
610                 615                 620

Gln Ala Pro Gly Lys Cys Leu Glu Trp Val Ala Asn Ile Lys Gln Asp
625                 630                 635                 640

Gly Ser Glu Lys Tyr Tyr Val Asp Ser Val Lys Gly Arg Phe Thr Ile
                645                 650                 655

Ser Arg Asp Asn Ala Lys Asn Ser Leu Tyr Leu Gln Met Asn Ser Leu
            660                 665                 670

Arg Ala Glu Asp Thr Ala Val Tyr Tyr Cys Ala Arg Glu Gly Gly Trp
            675                 680                 685

Phe Gly Glu Leu Ala Phe Asp Tyr Trp Gly Gln Gly Thr Leu Val Thr
690                 695                 700

Val Ser Ser
705

<210> SEQ ID NO 37
<211> LENGTH: 718
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gly Gly Ser Gly Gly Gly Gly Ser Glu
385                 390                 395                 400

Ile Val Met Thr Gln Ser Pro Ala Thr Leu Ser Val Ser Pro Gly Glu
                405                 410                 415

Arg Ala Thr Leu Ser Cys Arg Ala Ser Gln Ser Val Ser Ser Tyr Leu
            420                 425                 430

Gly Trp Tyr Gln Gln Lys Pro Gly Gln Ala Pro Arg Leu Leu Ile Tyr
        435                 440                 445

Gly Ala Ser Thr Arg Ala Thr Gly Ile Pro Ala Arg Phe Ser Gly Ser
    450                 455                 460

Gly Ser Gly Thr Glu Phe Thr Leu Thr Ile Ser Ser Leu Gln Ser Glu
465                 470                 475                 480

Asp Phe Ala Val Tyr Tyr Cys Gln Gln Tyr Gln Asn Trp Pro Leu Leu
                485                 490                 495

Thr Phe Gly Cys Gly Thr Lys Leu Glu Ile Lys Gly Gly Gly Gly Ser
            500                 505                 510

Gly Gly Gly Gly Ser Gly Gly Gly Ser Gly Gly Gly Gly Ser Glu
        515                 520                 525

Val Gln Leu Leu Glu Ser Gly Gly Gly Leu Val Gln Pro Gly Gly Ser
    530                 535                 540

Leu Arg Leu Ser Cys Ala Ala Ser Gly Phe Thr Phe Ser Pro Tyr Met
545                 550                 555                 560

Met Gln Trp Val Arg Gln Ala Pro Gly Lys Cys Leu Glu Trp Val Ser
                565                 570                 575

Ser Ile Trp Pro Ser Gly Gly Lys Thr Tyr Tyr Ala Asp Ser Val Lys
            580                 585                 590

Gly Arg Phe Thr Ile Ser Arg Asp Asn Ser Lys Asn Thr Leu Tyr Leu
        595                 600                 605

Gln Met Asn Ser Leu Arg Ala Glu Asp Thr Ala Val Tyr Tyr Cys Ala
    610                 615                 620

Arg Val Arg Arg Gly Gly Ala Thr Asp Tyr Trp Gly Gln Gly Thr Leu
625                 630                 635                 640

Val Thr Val Ser Ser Gly Gly Gly Gly Ser Gly Gly Gly Gly Ser Gly
                645                 650                 655

Gln Pro Glu Asn Asn Tyr Lys Thr Thr Pro Pro Val Leu Asp Ser Asp
            660                 665                 670

Gly Ser Phe Phe Leu Tyr Ser Lys Leu Thr Val Asp Lys Ser Arg Trp
        675                 680                 685

Gln Gln Gly Asn Val Phe Ser Cys Ser Val Met His Glu Ala Leu His
    690                 695                 700

Asn His Tyr Thr Gln Lys Ser Leu Ser Leu Ser Pro Gly Lys
705                 710                 715

<210> SEQ ID NO 38
<211> LENGTH: 716
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 38

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Pro Tyr
            20                  25                  30

Met Met Gln Trp Val Arg Gln Ala Pro Gly Lys Gly Leu Glu Trp Val
        35                  40                  45

Ser Ser Ile Trp Pro Ser Gly Gly Lys Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Arg Gly Gly Ala Thr Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gly Gly Gly Ser Gly Gly Gly Ser Asp Ile Gln Met Thr
385                 390                 395                 400

Gln Ser Pro Ser Thr Leu Ser Ala Ser Val Gly Asp Arg Val Thr Ile
                405                 410                 415
```

```
Thr Cys Arg Ala Ser Gln Ser Ile Ser Ser Trp Leu Ala Trp Tyr Gln
            420                 425                 430

Gln Lys Pro Gly Lys Ala Pro Lys Leu Leu Ile Tyr Lys Ala Ser Ser
            435                 440                 445

Leu Glu Ser Gly Val Pro Ser Arg Phe Ser Gly Ser Gly Ser Gly Thr
450                 455                 460

Glu Phe Thr Leu Thr Ile Ser Ser Leu Gln Pro Asp Phe Ala Thr
465                 470                 475                 480

Tyr Tyr Cys Lys Gln Tyr Ala Asp Tyr Trp Thr Phe Gly Cys Gly Thr
                485                 490                 495

Lys Val Glu Ile Lys Gly Gly Gly Gly Ser Gly Gly Gly Gly Ser Gly
            500                 505                 510

Gly Gly Ser Gly Gly Gly Ser Glu Val Gln Leu Val Glu Ser
            515                 520                 525

Gly Gly Gly Leu Val Gln Pro Gly Gly Ser Leu Arg Leu Ser Cys Ala
530                 535                 540

Ala Ser Gly Phe Thr Phe Ser Ser His Asp Met His Trp Val Arg Gln
545                 550                 555                 560

Ala Thr Gly Lys Cys Leu Glu Trp Val Ser Gly Ile Gly Thr Ala Gly
            565                 570                 575

Asp Thr Tyr Tyr Pro Asp Ser Val Lys Gly Arg Phe Thr Ile Ser Arg
            580                 585                 590

Glu Asn Ala Lys Asn Ser Leu Tyr Leu Gln Met Asn Ser Leu Arg Ala
            595                 600                 605

Gly Asp Thr Ala Val Tyr Tyr Cys Ala Arg Asp Arg Tyr Ser Pro Thr
            610                 615                 620

Gly His Tyr Tyr Gly Met Asp Val Trp Gly Gln Gly Thr Thr Val Thr
625                 630                 635                 640

Val Ser Ser Gly Gly Gly Gly Ser Gly Gly Gly Gly Ser Gly Gln Pro
            645                 650                 655

Glu Asn Asn Tyr Lys Thr Thr Pro Pro Val Leu Asp Ser Asp Gly Ser
            660                 665                 670

Phe Phe Leu Tyr Ser Lys Leu Thr Val Asp Lys Ser Arg Trp Gln Gln
            675                 680                 685

Gly Asn Val Phe Ser Cys Ser Val Met His Glu Ala Leu His Asn His
            690                 695                 700

Tyr Thr Gln Lys Ser Leu Ser Leu Ser Pro Gly Lys
705                 710                 715

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ile Ser Arg Thr Pro
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 40

Ala Lys Gly Gln Pro
1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Gly Gly Gly Ser Gly Gly Gly Gly Ser
1               5                   10

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Gly Gly Gly Ser Gly Gly Gly Gly Ser Gly Gly Gly Gly Ser
1               5                   10                  15

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Gly Gly Gly Ser Gly Gly Gly Gly Ser Gly Gly Gly Gly Ser Gly
1               5                   10                  15

Gly Gly Gly Ser
            20

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Pro Lys Ser Cys Asp Lys Thr His Thr Cys Pro Pro Cys Pro
1               5                   10                  15

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Pro Lys Ser Cys Asp Lys Thr
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Pro Lys Ser Cys Gly Lys Thr
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Pro Lys Ser Cys
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Gly Gly Gly Ser
1               5

<210> SEQ ID NO 49
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Lys His Thr Asn Leu
            20                  25                  30

Tyr Trp Ser Arg His Met Tyr Trp Tyr Gln Gln Lys Pro Gly Gln Ala
        35                  40                  45

Pro Arg Leu Leu Ile Tyr Leu Thr Ser Asn Arg Ala Thr Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Gln Gln Trp
                85                  90                  95

Ser Ser Asn Pro Phe Thr Phe Gly Gln Gly Thr Lys Leu Glu Ile Lys
            100                 105                 110

<210> SEQ ID NO 50
<211> LENGTH: 449
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Tyr Thr Ile Tyr Ser Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Arg Ala Pro Asn Ser Phe Tyr Glu Tyr Tyr Phe Asp Tyr Trp
        100                 105                 110

Gly Gln Gly Thr Thr Val Thr Val Ser Ser Ala Ser Thr Lys Gly Pro
    115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Lys Thr Tyr Thr Cys Asn Val Asp
    195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
        260                 265                 270

Pro Glu Val Gln Phe Asn Trp Tyr Val Asp Gly Val Glu Val His Asn
    275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Gln Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
        420                 425                 430

Ala Leu His Asn His Tyr Thr Gln Lys Ser Leu Ser Leu Ser Leu Gly
            435                 440                 445

Lys

<210> SEQ ID NO 51
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Tyr Thr Ile Tyr Ser Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Pro Asn Ser Phe Tyr Glu Tyr Tyr Phe Asp Tyr Trp
            100                 105                 110

Gly Gln Gly Thr Thr Val Thr Val Ser Ser
        115                 120

<210> SEQ ID NO 52
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Tyr Gly Met
```

```
                    100                 105                 110
Asp Val Trp Gly Gln Gly Thr Thr Val Thr Val Ser Ser
            115                 120                 125

<210> SEQ ID NO 53
<211> LENGTH: 167
<212> TYPE: PRT
<213> ORGANISM: Artificial Sequence
<220> FEATURE:
<223> OTHER INFORMATION: CTLA-4 HC

<400> SEQUENCE: 53

Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro
            20                  25                  30

Gly Lys Gly Leu Glu Trp Val Ala Val Ile Trp Tyr Asp Gly Ser Asn
        35                  40                  45

Lys Tyr Tyr Ala Asp Ser Val Lys Gly Arg Phe Thr Ile Ser Arg Asp
50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Asp Pro Arg Gly Ala Thr Leu
                85                  90                  95

Tyr Tyr Tyr Tyr Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His
                165

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Pro Gly Thr Lys Val Glu Ile Lys
            100                 105
```

<210> SEQ ID NO 55
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 56
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Val Glu Ser Gly Gly Gly Leu Val Gln Pro Gly Arg
1               5                   10                  15

Ser Leu Arg Leu Ser Cys Thr Ala Ser Gly Tyr Thr Phe Pro Asp Tyr
            20                  25                  30

Tyr Met Asn Trp Val Arg Gln Ala Pro Gly Lys Gly Leu Glu Trp Val
        35                  40                  45

Gly Asp Ile Asp Pro Asn Tyr Gly Gly Thr Thr Tyr Asn Ala Ser Val
    50                  55                  60

Lys Gly Arg Phe Thr Ile Ser Val Asp Arg Ser Lys Ser Ile Ala Tyr
65                  70                  75                  80

```
Leu Gln Met Ser Ser Leu Lys Thr Glu Asp Thr Ala Val Tyr Tyr Cys
                 85                  90                  95

Ala Arg Gly Ala Leu Thr Asp Trp Gly Gln Gly Thr Met Val Thr Val
            100                 105                 110

Ser Ser

<210> SEQ ID NO 57
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Ile Gln Leu Thr Gln Ser Pro Ser Ile Leu Ser Ala Ser Val Gly
1               5                   10                  15

Asp Arg Val Thr Ile Thr Cys Arg Ala Ser Ser Val Ser Tyr Ile
            20                  25                  30

Tyr Trp Phe Gln Gln Lys Pro Gly Lys Ala Pro Lys Pro Leu Ile Tyr
            35                  40                  45

Ala Thr Phe Asn Leu Ala Ser Gly Val Pro Ser Arg Phe Ser Gly Ser
    50                  55                  60

Gly Ser Gly Thr Ser Tyr Thr Leu Thr Ile Ser Ser Leu Gln Pro Glu
65                  70                  75                  80

Asp Phe Ala Thr Tyr Tyr Cys Gln Gln Trp Ser Asn Asn Pro Leu Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 58
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Ile Gln Leu Thr Gln Ser Pro Ser Ile Leu Ser Ala Ser Val Gly
1               5                   10                  15

Asp Arg Val Thr Ile Thr Cys Arg Ala Ser Ser Val Ser Tyr Ile
            20                  25                  30
```

Tyr Trp Phe Gln Gln Lys Pro Gly Lys Ala Pro Lys Pro Leu Ile Tyr
            35                  40                  45

Ala Thr Phe Asn Leu Ala Ser Gly Val Pro Ser Arg Phe Ser Gly Ser
 50                  55                  60

Gly Ser Gly Thr Ser Tyr Thr Leu Thr Ile Ser Ser Leu Gln Pro Glu
65                  70                  75                  80

Asp Phe Ala Thr Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 59
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 60
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 61
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Thr Val Leu Thr Gln Pro Pro Ser Val Ser Val Ala Pro Gly Lys
1               5                   10                  15

Thr Ala Ser Ile Ser Cys Gly Gly Asp Asn Ile Gly Gly Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Gln Arg Phe Ser Gly Ser
50                  55                  60

Asn Ser Gly Asn Thr Ala Thr Leu Thr Ile His Arg Val Glu Ala Gly
65                  70                  75                  80

Asp Glu Ala Asp Tyr Tyr Cys Gln Val Leu Asp Arg Arg Ser Asp His
                85                  90                  95

Trp Leu Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 62
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Thr Val Leu Thr Gln Pro Pro Ser Val Ser Val Ala Pro Gly Lys
1               5                   10                  15

Thr Ala Ser Ile Ser Cys Gly Gly Asp Asn Ile Gly Gly Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Gln Arg Phe Ser Gly Ser
50                  55                  60

```
Asn Ser Gly Asn Thr Ala Thr Leu Thr Ile His Arg Val Glu Ala Gly
 65                  70                  75                  80

Asp Glu Ala Asp Tyr Tyr Cys Gln Val Leu Asp Arg Arg Ser Asp His
                 85                  90                  95

Trp Leu Phe Gly Gly Gly Thr Lys Leu Thr Val Leu
            100                 105

<210> SEQ ID NO 63
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ser Tyr Gly Thr Tyr Tyr Gly Asn Tyr Phe Glu Tyr Trp
            100                 105                 110

Gly Arg Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 64
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Gly Thr Tyr Tyr Gly Asn Tyr Phe Glu Tyr Trp
            100                 105                 110

Gly Arg Gly Thr Leu Val Thr Val Ser Ser
        115                 120

<210> SEQ ID NO 65
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Ser Tyr Val Leu Thr Gln Pro Pro Ser Val Ser Val Ala Pro Gly Lys
1               5                   10                  15

Thr Ala Arg Ile Thr Cys Gly Gly Asp Asn Ile Gly Gly Lys Ser Val
            20                  25                  30
```

```
His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Leu Asp Arg Arg Ser Asp His
                 85                  90                  95

Trp Leu Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 66
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ser Tyr Val Leu Thr Gln Pro Pro Ser Val Ser Val Ala Pro Gly Lys
1               5                   10                  15

Thr Ala Arg Ile Thr Cys Gly Gly Asp Asn Ile Gly Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Leu Asp Arg Arg Ser Asp His
                 85                  90                  95

Trp Leu Phe Gly Gly Gly Thr Lys Leu Thr Val Leu
            100                 105

<210> SEQ ID NO 67
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67
```

-continued

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Gly Thr Tyr Tyr Gly Asn Tyr Phe Glu Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
```

```
                        420                 425                 430
Ala Leu His Asn His Tyr Thr Gln Lys Ser Leu Ser Leu Ser Leu Gly
        435                 440                 445

Lys

<210> SEQ ID NO 68
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Gly Thr Tyr Tyr Gly Asn Tyr Phe Glu Tyr Trp
            100                 105                 110

Gly Gln Gly Thr Leu Val Thr Val Ser Ser
        115                 120

<210> SEQ ID NO 69
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser
        115                 120

<210> SEQ ID NO 70
```

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys
            100                 105

<210> SEQ ID NO 71
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 72
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
            85                  90                  95

Thr Phe Gly Gln Gly Thr Lys Val Glu Ile Lys Arg Thr Val Ala Ala

```
              100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210
```

<210> SEQ ID NO 73
<211> LENGTH: 288
<212> TYPE: PRT
<213> ORGANISM: Homo sapiens

<400> SEQUENCE: 73

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255
```

```
Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 74
<211> LENGTH: 176
<212> TYPE: PRT
<213> ORGANISM: Homo sapiens

<400> SEQUENCE: 74

Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
            20                  25                  30

Val Thr Ser Glu His Glu Leu Thr Cys Gln Ala Glu Gly Tyr Pro Lys
        35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Thr Asn Glu Ile Phe Tyr Cys Thr
                85                  90                  95

Phe Arg Arg Leu Asp Pro Glu Glu Asn His Thr Ala Glu Leu Val Ile
            100                 105                 110

Pro Glu Leu Pro Leu Ala His Pro Pro Asn Glu Arg Thr His Leu Val
        115                 120                 125

Ile Leu Gly Ala Ile Leu Leu Cys Leu Gly Val Ala Leu Thr Phe Ile
    130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175

<210> SEQ ID NO 75
<211> LENGTH: 223
<212> TYPE: PRT
<213> ORGANISM: Homo sapiens

<400> SEQUENCE: 75

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125
```

```
Cys Lys Val Glu Leu Met Tyr Pro Pro Tyr Tyr Leu Gly Ile Gly
    130                 135                 140
Asn Gly Thr Gln Ile Tyr Val Ile Asp Pro Glu Pro Cys Pro Asp Ser
145                 150                 155                 160
Asp Phe Leu Leu Trp Ile Leu Ala Ala Val Ser Ser Gly Leu Phe Phe
                165                 170                 175
Tyr Ser Phe Leu Leu Thr Ala Val Ser Leu Ser Lys Met Leu Lys Lys
                180                 185                 190
Arg Ser Pro Leu Thr Thr Gly Val Tyr Val Lys Met Pro Pro Thr Glu
            195                 200                 205
Pro Glu Cys Glu Lys Gln Phe Gln Pro Tyr Phe Ile Pro Ile Asn
    210                 215                 220
```

<210> SEQ ID NO 76
<211> LENGTH: 301
<212> TYPE: PRT
<213> ORGANISM: Homo sapiens

<400> SEQUENCE: 76

```
Met Phe Ser His Leu Pro Phe Asp Cys Val Leu Leu Leu Leu Leu Leu
1                   5                   10                  15
Leu Leu Thr Arg Ser Ser Glu Val Glu Tyr Arg Ala Glu Val Gly Gln
                20                  25                  30
Asn Ala Tyr Leu Pro Cys Phe Tyr Thr Pro Ala Ala Pro Gly Asn Leu
            35                  40                  45
Val Pro Val Cys Trp Gly Lys Gly Ala Cys Pro Val Phe Glu Cys Gly
        50                  55                  60
Asn Val Val Leu Arg Thr Asp Glu Arg Asp Val Asn Tyr Trp Thr Ser
65                  70                  75                  80
Arg Tyr Trp Leu Asn Gly Asp Phe Arg Lys Gly Asp Val Ser Leu Thr
                85                  90                  95
Ile Glu Asn Val Thr Leu Ala Asp Ser Gly Ile Tyr Cys Cys Arg Ile
                100                 105                 110
Gln Ile Pro Gly Ile Met Asn Asp Glu Lys Phe Asn Leu Lys Leu Val
            115                 120                 125
Ile Lys Pro Ala Lys Val Thr Pro Ala Pro Thr Arg Gln Arg Asp Phe
130                 135                 140
Thr Ala Ala Phe Pro Arg Met Leu Thr Thr Arg Gly His Gly Pro Ala
145                 150                 155                 160
Glu Thr Gln Thr Leu Gly Ser Leu Pro Asp Ile Asn Leu Thr Gln Ile
                165                 170                 175
Ser Thr Leu Ala Asn Glu Leu Arg Asp Ser Arg Leu Ala Asn Asp Leu
                180                 185                 190
Arg Asp Ser Gly Ala Thr Ile Arg Ile Gly Ile Tyr Ile Gly Ala Gly
            195                 200                 205
Ile Cys Ala Gly Leu Ala Leu Ala Leu Ile Phe Gly Ala Leu Ile Phe
        210                 215                 220
Lys Trp Tyr Ser His Ser Lys Glu Lys Ile Gln Asn Leu Ser Leu Ile
225                 230                 235                 240
Ser Leu Ala Asn Leu Pro Pro Ser Gly Leu Ala Asn Ala Val Ala Glu
                245                 250                 255
Gly Ile Arg Ser Glu Glu Asn Ile Tyr Thr Ile Glu Glu Asn Val Tyr
                260                 265                 270
Glu Val Glu Glu Pro Asn Glu Tyr Tyr Cys Tyr Val Ser Ser Arg Gln
            275                 280                 285
```

Gln Pro Ser Gln Pro Leu Gly Cys Arg Phe Ala Met Pro
    290                 295                 300

<210> SEQ ID NO 77
<211> LENGTH: 278
<212> TYPE: PRT
<213> ORGANISM: Homo sapiens

<400> SEQUENCE: 77

Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30

Gln Val Arg Gln Gly Ser Gln Ala Thr Leu Val Cys Gln Val Asp Gln
        35                  40                  45

Ala Thr Ala Trp Glu Arg Leu Arg Val Lys Trp Thr Lys Asp Gly Ala
    50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
            100                 105                 110

Trp Ala Ala Val Glu Ile Pro Glu Leu Glu Ala Glu Gly Asn Ile
        115                 120                 125

Thr Arg Leu Phe Val Asp Pro Asp Pro Thr Gln Asn Arg Asn Arg
    130                 135                 140

Ile Ala Ser Phe Pro Gly Phe Leu Phe Val Leu Leu Gly Val Gly Ser
145                 150                 155                 160

Met Gly Val Ala Ala Ile Val Trp Gly Ala Trp Phe Trp Gly Arg Arg
                165                 170                 175

Ser Cys Gln Gln Arg Asp Ser Gly Asn Ala Phe Tyr Ser Asn Val Leu
            180                 185                 190

Tyr Arg Pro Arg Gly Ala Pro Lys Lys Ser Glu Asp Cys Ser Gly Glu
        195                 200                 205

Gly Lys Asp Gln Arg Gly Gln Ser Ile Tyr Ser Thr Ser Phe Pro Gln
    210                 215                 220

Pro Ala Pro Arg Gln Pro His Leu Ala Ser Arg Pro Cys Pro Ser Pro
225                 230                 235                 240

Arg Pro Cys Pro Ser Pro Arg Pro Gly His Pro Val Ser Met Val Arg
                245                 250                 255

Val Ser Pro Arg Pro Ser Pro Thr Gln Gln Pro Arg Pro Lys Gly Phe
            260                 265                 270

Pro Lys Val Gly Glu Glu
        275

<210> SEQ ID NO 78
<211> LENGTH: 277
<212> TYPE: PRT
<213> ORGANISM: Homo sapiens

<400> SEQUENCE: 78

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

```
Gly Asp Thr Tyr Pro Ser Asn Asp Arg Cys Cys His Glu Cys Arg Pro
        35                  40                  45
Gly Asn Gly Met Val Ser Arg Cys Ser Arg Ser Gln Asn Thr Val Cys
 50                  55                  60
Arg Pro Cys Gly Pro Gly Phe Tyr Asn Asp Val Val Ser Ser Lys Pro
 65                  70                  75                  80
Cys Lys Pro Cys Thr Trp Cys Asn Leu Arg Ser Gly Ser Glu Arg Lys
                 85                  90                  95
Gln Leu Cys Thr Ala Thr Gln Asp Thr Val Cys Arg Cys Arg Ala Gly
            100                 105                 110
Thr Gln Pro Leu Asp Ser Tyr Lys Pro Gly Val Asp Cys Ala Pro Cys
        115                 120                 125
Pro Pro Gly His Phe Ser Pro Gly Asp Asn Gln Ala Cys Lys Pro Trp
130                 135                 140
Thr Asn Cys Thr Leu Ala Gly Lys His Thr Leu Gln Pro Ala Ser Asn
145                 150                 155                 160
Ser Ser Asp Ala Ile Cys Glu Asp Arg Asp Pro Pro Ala Thr Gln Pro
                165                 170                 175
Gln Glu Thr Gln Gly Pro Pro Ala Arg Pro Ile Thr Val Gln Pro Thr
            180                 185                 190
Glu Ala Trp Pro Arg Thr Ser Gln Gly Pro Ser Thr Arg Pro Val Glu
        195                 200                 205
Val Pro Gly Gly Arg Ala Val Ala Ala Ile Leu Gly Leu Gly Leu Val
    210                 215                 220
Leu Gly Leu Leu Gly Pro Leu Ala Ile Leu Leu Ala Leu Tyr Leu Leu
225                 230                 235                 240
Arg Arg Asp Gln Arg Leu Pro Pro Asp Ala His Lys Pro Pro Gly Gly
                245                 250                 255
Gly Ser Phe Arg Thr Pro Ile Gln Glu Glu Gln Ala Asp Ala His Ser
            260                 265                 270
Thr Leu Ala Lys Ile
        275

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gly Phe Thr Phe Ser Ser Tyr Ala Met Ser
1               5                   10

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Ala Ile Ser Gly Ser Gly Gly Ser Thr Tyr Tyr Ala Asp Ser Val Lys
1               5                   10                  15
Gly
```

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gly Ser Tyr Gly Thr Tyr Tyr Gly Asn Tyr Phe Glu Tyr
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gly Gly Asp Asn Ile Gly Gly Lys Ser Val His
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Tyr Asp Ser Asp Arg Pro Ser
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Leu Asp Arg Arg Ser Asp His
1               5

<210> SEQ ID NO 85
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ser Tyr Gly Thr Tyr Tyr Gly Asn Tyr Phe Glu Tyr Trp
            100                 105                 110

Gly Arg Gly Thr Leu Val Thr Val Ser Ser
            115                 120
```

```
<210> SEQ ID NO 86
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Thr Val Leu Thr Gln Pro Pro Ser Val Ser Val Ala Pro Gly Lys
 1               5                  10                  15

Thr Ala Ser Ile Ser Cys Gly Gly Asp Asn Ile Gly Gly Lys Ser Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Gln Arg Phe Ser Gly Ser
 50                  55                  60

Asn Ser Gly Asn Thr Ala Thr Leu Thr Ile His Arg Val Glu Ala Gly
 65                  70                  75                  80

Asp Glu Ala Asp Tyr Tyr Cys Gln Val Leu Asp Arg Arg Ser Asp His
                 85                  90                  95

Trp Leu Phe Gly Gly Gly Thr Lys Leu Thr Val Leu
            100                 105
```

```
<210> SEQ ID NO 87
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ser Tyr Gly Thr Tyr Tyr Gly Asn Tyr Phe Glu Tyr Trp
            100                 105                 110

Gly Arg Gly Thr Leu Val Thr Val Ser Ser Ala Ser Thr Lys Gly Pro
            115                 120                 125
```

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 88
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Thr Val Leu Thr Gln Pro Pro Ser Val Ser Val Ala Pro Gly Lys
1               5                   10                  15

Thr Ala Ser Ile Ser Cys Gly Gly Asp Asn Ile Gly Gly Lys Ser Val
            20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Arg Phe Ser Gly Ser
 50                  55                  60

Asn Ser Gly Asn Thr Ala Thr Leu Thr Ile His Arg Val Glu Ala Gly
 65                  70                  75                  80

Asp Glu Ala Asp Tyr Tyr Cys Gln Val Leu Asp Arg Arg Ser Asp His
                 85                  90                  95

Trp Leu Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
            210

<210> SEQ ID NO 89
<211> LENGTH: 712
<212> TYPE: PRT
<213> ORGANISM: Artificial Sequence
<220> FEATURE:
<223> OTHER INFORMATION: BiS3 PD-1(LO115)/TIM3(O13-1) HC

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
            35                  40                  45

Ala Tyr Ile Ser Ser Gly Ser Tyr Thr Ile Tyr Ser Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Ala Pro Asn Ser Phe Tyr Glu Tyr Tyr Phe Asp Tyr Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

```
Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys Gly Gly Gly Ser Gly Gly Gly Ser Glu Val
    450                 455                 460

Gln Leu Leu Glu Ser Gly Gly Leu Val Gln Pro Gly Gly Ser Leu
465                 470                 475                 480

Arg Leu Ser Cys Ala Ala Ser Gly Phe Thr Phe Ser Ser Tyr Ala Met
                485                 490                 495

Ser Trp Val Arg Gln Ala Pro Gly Lys Cys Leu Glu Trp Val Ser Ala
            500                 505                 510

Ile Ser Gly Ser Gly Gly Ser Thr Tyr Tyr Ala Asp Ser Val Lys Gly
        515                 520                 525

Arg Phe Thr Ile Ser Arg Asp Asn Ser Lys Asn Thr Leu Tyr Leu Gln
    530                 535                 540

Met Asn Ser Leu Arg Ala Glu Asp Thr Ala Val Tyr Tyr Cys Ala Arg
545                 550                 555                 560

Gly Ser Tyr Gly Thr Tyr Tyr Gly Asn Tyr Phe Glu Tyr Trp Gly Gln
                565                 570                 575

Gly Thr Leu Val Thr Val Ser Ser Gly Gly Gly Gly Ser Gly Gly Gly
            580                 585                 590

Gly Ser Gly Gly Gly Gly Ser Gly Gly Gly Gly Ser Ser Tyr Val Leu
```

```
                    595                 600                 605

Thr Gln Pro Pro Ser Val Ser Val Ala Pro Gly Lys Thr Ala Arg Ile
    610                 615                 620

Thr Cys Gly Gly Asp Asn Ile Gly Gly Lys Ser Val His Trp Tyr Gln
625                 630                 635                 640

Gln Lys Pro Gly Gln Ala Pro Val Leu Val Ile Tyr Tyr Asp Ser Asp
                645                 650                 655

Arg Pro Ser Gly Ile Pro Glu Arg Phe Ser Gly Ser Asn Ser Gly Asn
                660                 665                 670

Thr Ala Thr Leu Thr Ile Ser Arg Val Glu Ala Gly Asp Glu Ala Asp
                675                 680                 685

Tyr Tyr Cys Gln Val Leu Asp Arg Arg Ser Asp His Phe Leu Phe Gly
690                 695                 700

Cys Gly Thr Lys Leu Thr Val Leu
705                 710

<210> SEQ ID NO 90
<211> LENGTH: 219
<212> TYPE: PRT
<213> ORGANISM: Artificial Sequence
<220> FEATURE:
<223> OTHER INFORMATION: BiS3 PD-1(LO115)/TIM3(O13-1) LC

<400> SEQUENCE: 90

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Lys His Thr Asn Leu
            20                  25                  30

Tyr Trp Ser Arg His Met Tyr Trp Tyr Gln Gln Lys Pro Gly Gln Ala
        35                  40                  45

Pro Arg Leu Leu Ile Tyr Leu Thr Ser Asn Arg Ala Thr Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Gln Gln Trp
                85                  90                  95

Ser Ser Asn Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 91
<211> LENGTH: 722
<212> TYPE: PRT
```

<210> ORGANISM: Artificial Sequence
<220> FEATURE:
<223> OTHER INFORMATION: BiS5 PD-1(L0115)/TIM3(O13-1) HC

<400> SEQUENCE: 91

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Tyr Thr Ile Tyr Ser Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Pro Asn Ser Phe Tyr Glu Tyr Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Phe Glu
225                 230                 235                 240

Gly Gly Pro Ser Val Phe Leu Phe Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gly Gly Gly Ser Gly Gly Gly Gly Ser Glu
```

```
                385                 390                 395                 400
        Val Gln Leu Leu Glu Ser Gly Gly Gly Leu Val Gln Pro Gly Ser
                            405                 410                 415

Leu Arg Leu Ser Cys Ala Ala Ser Gly Phe Thr Phe Ser Ser Tyr Ala
                        420                 425                 430

Met Ser Trp Val Arg Gln Ala Pro Gly Lys Cys Leu Glu Trp Val Ser
                    435                 440                 445

Ala Ile Ser Gly Ser Gly Gly Ser Thr Tyr Tyr Ala Asp Ser Val Lys
                450                 455                 460

Gly Arg Phe Thr Ile Ser Arg Asp Asn Ser Lys Asn Thr Leu Tyr Leu
        465                 470                 475                 480

Gln Met Asn Ser Leu Arg Ala Glu Asp Thr Ala Val Tyr Tyr Cys Ala
                        485                 490                 495

Arg Gly Ser Tyr Gly Thr Tyr Tyr Gly Asn Tyr Phe Glu Tyr Trp Gly
                    500                 505                 510

Gln Gly Thr Leu Val Thr Val Ser Ser Gly Gly Gly Ser Gly Gly
                515                 520                 525

Gly Gly Ser Gly Gly Gly Ser Gly Gly Gly Ser Ser Tyr Val
            530                 535                 540

Leu Thr Gln Pro Pro Ser Val Ser Val Ala Pro Gly Lys Thr Ala Arg
        545                 550                 555                 560

Ile Thr Cys Gly Gly Asp Asn Ile Gly Gly Lys Ser Val His Trp Tyr
                        565                 570                 575

Gln Gln Lys Pro Gly Gln Ala Pro Val Leu Val Ile Tyr Tyr Asp Ser
                    580                 585                 590

Asp Arg Pro Ser Gly Ile Pro Glu Arg Phe Ser Gly Ser Asn Ser Gly
                595                 600                 605

Asn Thr Ala Thr Leu Thr Ile Ser Arg Val Glu Ala Gly Asp Glu Ala
            610                 615                 620

Asp Tyr Tyr Cys Gln Val Leu Asp Arg Arg Ser Asp His Phe Leu Phe
        625                 630                 635                 640

Gly Cys Gly Thr Lys Leu Thr Val Leu Gly Gly Gly Ser Gly Gly
                        645                 650                 655

Gly Gly Ser Gly Gln Pro Glu Asn Asn Tyr Lys Thr Thr Pro Pro Val
                    660                 665                 670

Leu Asp Ser Asp Gly Ser Phe Phe Leu Tyr Ser Lys Leu Thr Val Asp
                675                 680                 685

Lys Ser Arg Trp Gln Gln Gly Asn Val Phe Ser Cys Ser Val Met His
            690                 695                 700

Glu Ala Leu His Asn His Tyr Thr Gln Lys Ser Leu Ser Leu Ser Pro
        705                 710                 715                 720

Gly Lys

<210> SEQ ID NO 92
<211> LENGTH: 219
<212> TYPE: PRT
<213> ORGANISM: Artificial Sequence
<220> FEATURE:
<223> OTHER INFORMATION: BiS5 PD-1(LO115)/TIM3(O13-1) LC

<400> SEQUENCE: 92

Gln Ile Val Leu Thr Gln Ser Pro Ala Thr Leu Ser Leu Ser Pro Gly
        1               5                   10                  15

Glu Arg Ala Thr Leu Ser Cys Ser Ala Ser Ser Lys His Thr Asn Leu
                    20                  25                  30
```

Tyr Trp Ser Arg His Met Tyr Trp Tyr Gln Gln Lys Pro Gly Gln Ala
              35                  40                  45

Pro Arg Leu Leu Ile Tyr Leu Thr Ser Asn Arg Ala Thr Gly Ile Pro
 50                  55                  60

Ala Arg Phe Ser Gly Ser Gly Ser Gly Thr Asp Phe Thr Leu Thr Ile
 65                  70                  75                  80

Ser Ser Leu Glu Pro Glu Asp Phe Ala Val Tyr Tyr Cys Gln Gln Trp
                 85                  90                  95

Ser Ser Asn Pro Phe Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 93
<211> LENGTH: 214
<212> TYPE: PRT
<213> ORGANISM: Artificial Sequence
<220> FEATURE:
<223> OTHER INFORMATION: OX40SLR LCv kappa

<400> SEQUENCE: 93

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Lys Leu His Ser Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Ser Ala Leu Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

-continued

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 94
<211> LENGTH: 720
<212> TYPE: PRT
<213> ORGANISM: Artificial Sequence
<220> FEATURE:
<223> OTHER INFORMATION: BiS5-OX40SLR HC-G1-N434A-PD-L1

<400> SEQUENCE: 94

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Ala Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Glu Gly Gly His Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

```
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gly Gly Ser Gly Gly Gly Ser Glu Val
385                 390                 395                 400

Gln Leu Val Glu Ser Gly Gly Gly Leu Val Gln Pro Gly Gly Ser Leu
                405                 410                 415

Arg Leu Ser Cys Ala Ala Ser Gly Phe Thr Phe Ser Arg Tyr Trp Met
            420                 425                 430

Ser Trp Val Arg Gln Ala Pro Gly Lys Cys Leu Glu Trp Val Ala Asn
        435                 440                 445

Ile Lys Gln Asp Gly Ser Glu Lys Tyr Tyr Val Asp Ser Val Lys Gly
    450                 455                 460

Arg Phe Thr Ile Ser Arg Asp Asn Ala Lys Asn Ser Leu Tyr Leu Gln
465                 470                 475                 480

Met Asn Ser Leu Arg Ala Glu Asp Thr Ala Val Tyr Tyr Cys Ala Arg
                485                 490                 495

Glu Gly Gly Trp Phe Gly Glu Leu Ala Phe Asp Tyr Trp Gly Gln Gly
            500                 505                 510

Thr Leu Val Thr Val Ser Ser Gly Gly Gly Gly Ser Gly Gly Gly Gly
        515                 520                 525

Ser Gly Gly Gly Gly Ser Gly Gly Gly Gly Ser Glu Ile Val Leu Thr
    530                 535                 540

Gln Ser Pro Gly Thr Leu Ser Leu Ser Pro Gly Glu Arg Ala Thr Leu
545                 550                 555                 560

Ser Cys Arg Ala Ser Gln Arg Val Ser Ser Ser Tyr Leu Ala Trp Tyr
                565                 570                 575

Gln Gln Lys Pro Gly Gln Ala Pro Arg Leu Leu Ile Tyr Asp Ala Ser
            580                 585                 590

Ser Arg Ala Thr Gly Ile Pro Asp Arg Phe Ser Gly Ser Gly Ser Gly
        595                 600                 605

Thr Asp Phe Thr Leu Thr Ile Ser Arg Leu Glu Pro Glu Asp Phe Ala
    610                 615                 620

Val Tyr Tyr Cys Gln Gln Tyr Gly Ser Leu Pro Trp Thr Phe Gly Cys
625                 630                 635                 640

Gly Thr Lys Val Glu Ile Lys Gly Gly Gly Ser Gly Gly Gly Gly
                645                 650                 655

Ser Gly Gln Pro Glu Asn Asn Tyr Lys Thr Thr Pro Pro Val Leu Asp
            660                 665                 670

Ser Asp Gly Ser Phe Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Ala His Tyr Thr Gln Lys Ser Leu Ser Leu Ser Pro Gly Lys
705                 710                 715                 720

<210> SEQ ID NO 95
<211> LENGTH: 707
```

```
<212> TYPE: PRT
<213> ORGANISM: Artificial Sequence
<220> FEATURE:
<223> OTHER INFORMATION: BiS2-PD-1- OX40 HC -4P

<400> SEQUENCE: 95
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Gln Thr
130                 135                 140

Leu Ser Leu Thr Cys Ala Val Tyr Gly Gly Ser Phe Ser Ser Gly Tyr
145                 150                 155                 160

Trp Asn Trp Ile Arg Lys His Pro Gly Lys Cys Leu Glu Tyr Ile Gly
            165                 170                 175

Tyr Ile Ser Tyr Asn Gly Ile Thr Tyr His Asn Pro Ser Leu Lys Ser
        180                 185                 190

Arg Ile Thr Ile Asn Arg Asp Thr Ser Lys Asn Gln Tyr Ser Leu Gln
    195                 200                 205

Leu Asn Ser Val Thr Pro Glu Asp Thr Ala Val Tyr Tyr Cys Ala Arg
210                 215                 220

Tyr Lys Tyr Asp Tyr Asp Gly His Ala Met Asp Tyr Trp Gly Gln
225                 230                 235                 240

Gly Thr Leu Val Thr Val Ser Ser Gly Gly Gly Gly Ser Gly Gly Gly
            245                 250                 255

Gly Ser Glu Val Gln Leu Val Glu Ser Gly Gly Gly Leu Val Gln Pro
        260                 265                 270

Gly Gly Ser Leu Arg Leu Ser Cys Ala Ala Ser Gly Phe Thr Phe Ser
    275                 280                 285

Asp Tyr Gly Met His Trp Val Arg Gln Ala Pro Gly Lys Gly Leu Glu
290                 295                 300

Trp Val Ala Tyr Ile Ser Ser Gly Ser Tyr Thr Ile Tyr Ser Ala Asp
305                 310                 315                 320

Ser Val Lys Gly Arg Phe Thr Ile Ser Arg Asp Asn Ala Lys Asn Ser
            325                 330                 335

Leu Tyr Leu Gln Met Asn Ser Leu Arg Ala Glu Asp Thr Ala Val Tyr
        340                 345                 350

Tyr Cys Ala Arg Arg Ala Pro Asn Ser Phe Tyr Glu Tyr Tyr Phe Asp
    355                 360                 365

Tyr Trp Gly Gln Gly Thr Thr Val Thr Val Ser Ser Ala Ser Thr Lys
370                 375                 380

Gly Pro Ser Val Phe Pro Leu Ala Pro Cys Ser Arg Ser Thr Ser Glu
385                 390                 395                 400

Ser Thr Ala Ala Leu Gly Cys Leu Val Lys Asp Tyr Phe Pro Glu Pro
            405                 410                 415

Val Thr Val Ser Trp Asn Ser Gly Ala Leu Thr Ser Gly Val His Thr
        420                 425                 430

Phe Pro Ala Val Leu Gln Ser Ser Gly Leu Tyr Ser Leu Ser Ser Val
    435                 440                 445

Val Thr Val Pro Ser Ser Ser Leu Gly Thr Lys Thr Tyr Thr Cys Asn
450                 455                 460

Val Asp His Lys Pro Ser Asn Thr Lys Val Asp Lys Arg Val Glu Ser
465                 470                 475                 480

Lys Tyr Gly Pro Pro Cys Pro Pro Cys Pro Ala Pro Glu Phe Leu Gly
                485                 490                 495

Gly Pro Ser Val Phe Leu Phe Pro Pro Lys Pro Lys Asp Thr Leu Met
                500                 505                 510

Ile Ser Arg Thr Pro Glu Val Thr Cys Val Val Val Asp Val Ser Gln
            515                 520                 525

Glu Asp Pro Glu Val Gln Phe Asn Trp Tyr Val Asp Gly Val Glu Val
530                 535                 540

His Asn Ala Lys Thr Lys Pro Arg Glu Glu Gln Phe Asn Ser Thr Tyr
545                 550                 555                 560

Arg Val Val Ser Val Leu Thr Val Leu His Gln Asp Trp Leu Asn Gly
                565                 570                 575

Lys Glu Tyr Lys Cys Lys Val Ser Asn Lys Gly Leu Pro Ser Ser Ile
            580                 585                 590

Glu Lys Thr Ile Ser Lys Ala Lys Gly Gln Pro Arg Glu Pro Gln Val
        595                 600                 605

Tyr Thr Leu Pro Pro Ser Gln Glu Glu Met Thr Lys Asn Gln Val Ser
    610                 615                 620

Leu Thr Cys Leu Val Lys Gly Phe Tyr Pro Ser Asp Ile Ala Val Glu
625                 630                 635                 640

Trp Glu Ser Asn Gly Gln Pro Glu Asn Asn Tyr Lys Thr Thr Pro Pro
                645                 650                 655

Val Leu Asp Ser Asp Gly Ser Phe Phe Leu Tyr Ser Arg Leu Thr Val
                660                 665                 670

Asp Lys Ser Arg Trp Gln Glu Gly Asn Val Phe Ser Cys Ser Val Met
            675                 680                 685

His Glu Ala Leu His Asn His Tyr Thr Gln Lys Ser Leu Ser Leu Ser
690                 695                 700

Leu Gly Lys
705

<210> SEQ ID NO 96
<211> LENGTH: 707
<212> TYPE: PRT
<213> ORGANISM: Artificial Sequence
<220> FEATURE:
<223> OTHER INFORMATION: BiS3-OX40 HC-4P-PD-1

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

```
Gly Met His Trp Val Arg Gln Ala Pro Gly Lys Gly Leu Glu Trp Val
         35                  40                  45
Ala Tyr Ile Ser Ser Gly Ser Tyr Thr Ile Tyr Ser Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Arg Ala Pro Asn Ser Phe Tyr Glu Tyr Tyr Phe Asp Tyr Trp
             100                 105                 110
Gly Gln Gly Thr Thr Val Thr Val Ser Ser Ala Ser Thr Lys Gly Pro
         115                 120                 125
Ser Val Phe Pro Leu Ala Pro Cys Ser Arg Ser Thr Ser Glu Ser Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                 165                 170                 175
Ala Val Leu Gln Ser Ser Gly Leu Tyr Ser Leu Ser Ser Val Val Thr
             180                 185                 190
Val Pro Ser Ser Ser Leu Gly Thr Lys Thr Tyr Thr Cys Asn Val Asp
         195                 200                 205
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                 245                 250                 255
Arg Thr Pro Glu Val Thr Cys Val Val Val Asp Val Ser Gln Glu Asp
             260                 265                 270
Pro Glu Val Gln Phe Asn Trp Tyr Val Asp Gly Val Glu Val His Asn
         275                 280                 285
Ala Lys Thr Lys Pro Arg Glu Glu Gln Phe Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                 325                 330                 335
Thr Ile Ser Lys Ala Lys Gly Gln Pro Arg Glu Pro Gln Val Tyr Thr
             340                 345                 350
Leu Pro Pro Ser Gln Glu Glu Met Thr Lys Asn Gln Val Ser Leu Thr
         355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                 405                 410                 415
Ser Arg Trp Gln Glu Gly Asn Val Phe Ser Cys Ser Val Met His Glu
             420                 425                 430
Ala Leu His Asn His Tyr Thr Gln Lys Ser Leu Ser Leu Ser Leu Gly
         435                 440                 445
Lys Gly Gly Gly Gly Ser Gly Gly Gly Gly Ser Asp Ile Gln Met Thr
```

```
                450                 455                 460
Gln Ser Pro Ser Ser Leu Ser Ala Ser Val Gly Asp Arg Val Thr Ile
465                 470                 475                 480

Thr Cys Arg Ala Ser Gln Asp Ile Ser Asn Tyr Leu Asn Trp Tyr Gln
                    485                 490                 495

Gln Lys Pro Gly Lys Ala Pro Lys Leu Leu Ile Tyr Tyr Thr Ser Lys
                500                 505                 510

Leu His Ser Gly Val Pro Ser Arg Phe Ser Gly Ser Gly Ser Gly Thr
                515                 520                 525

Asp Tyr Thr Leu Thr Ile Ser Ser Leu Gln Pro Glu Asp Phe Ala Thr
                530                 535                 540

Tyr Tyr Cys Gln Gln Gly Ser Ala Leu Pro Trp Thr Phe Gly Cys Gly
545                 550                 555                 560

Thr Lys Val Glu Ile Lys Gly Gly Gly Ser Gly Gly Gly Gly Ser
                    565                 570                 575

Gly Gly Gly Gly Ser Gly Gly Gly Ser Gln Val Gln Leu Gln Glu
                580                 585                 590

Ser Gly Pro Gly Leu Val Lys Pro Ser Gln Thr Leu Ser Leu Thr Cys
                595                 600                 605

Ala Val Tyr Gly Gly Ser Phe Ser Ser Gly Tyr Trp Asn Trp Ile Arg
                610                 615                 620

Lys His Pro Gly Lys Cys Leu Glu Tyr Ile Gly Tyr Ile Ser Tyr Asn
625                 630                 635                 640

Gly Ile Thr Tyr His Asn Pro Ser Leu Lys Ser Arg Ile Thr Ile Asn
                    645                 650                 655

Arg Asp Thr Ser Lys Asn Gln Tyr Ser Leu Gln Leu Asn Ser Val Thr
                660                 665                 670

Pro Glu Asp Thr Ala Val Tyr Tyr Cys Ala Arg Tyr Lys Tyr Asp Tyr
                675                 680                 685

Asp Gly Gly His Ala Met Asp Tyr Trp Gly Gln Gly Thr Leu Val Thr
                690                 695                 700

Val Ser Ser
705

<210> SEQ ID NO 97
<211> LENGTH: 219
<212> TYPE: PRT
<213> ORGANISM: Artificial Sequence
<220> FEATURE:
<223> OTHER INFORMATION: PD1 LCv kappa

<400> SEQUENCE: 97

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Lys His Thr Asn Leu
                20                  25                  30

Tyr Trp Ser Arg His Met Tyr Trp Tyr Gln Gln Lys Pro Gly Gln Ala
            35                  40                  45

Pro Arg Leu Leu Ile Tyr Leu Thr Ser Asn Arg Ala Thr Gly Ile Pro
        50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Gln Gln Trp
                85                  90                  95

Ser Ser Asn Pro Phe Thr Phe Gly Gln Gly Thr Lys Leu Glu Ile Lys
```

-continued

```
              100                 105                110
Arg Thr Val Ala Ala Pro Ser Val Phe Ile Phe Pro Pro Ser Asp Glu
        115                 120                125

Gln Leu Lys Ser Gly Thr Ala Ser Val Val Cys Leu Leu Asn Asn Phe
        130                 135                140

Tyr Pro Arg Glu Ala Lys Val Gln Trp Lys Val Asp Asn Ala Leu Gln
145                 150                 155                160

Ser Gly Asn Ser Gln Glu Ser Val Thr Glu Gln Asp Ser Lys Asp Ser
                165                 170                175

Thr Tyr Ser Leu Ser Ser Thr Leu Thr Leu Ser Lys Ala Asp Tyr Glu
        180                 185                190

Lys His Lys Val Tyr Ala Cys Glu Val Thr His Gln Gly Leu Ser Ser
        195                 200                205

Pro Val Thr Lys Ser Phe Asn Arg Gly Glu Cys
        210                 215
```

BISPECIFIC BINDING PROTEINS AND USES THEREOF

CROSS-REFERENCE TO RELATED APPLICATIONS

This application claims priority to and the benefit of U.S. Provisional Application No. 62/332,788 filed May 6, 2016, the disclosure of which is incorporated herein by reference in its entirety.

SEQUENCE LISTING

The present application is being filed along with a Sequence Listing in electronic format. The Sequence Listing is provided as a file entitled IOBS_100_ST25.txt created May 2, 2017, which is 244 kb in size. The information in the electronic format of the sequence listing is incorporated herein by reference in its entirety.

BACKGROUND

Cancer continues to be a major global health burden. Despite progress in the treatment of cancer, there continues to be an unmet medical need for more effective and less toxic therapies, especially for those patients with advanced disease or cancers that are resistant to existing therapeutics.

The role of the immune system, in particular T cell-mediated cytotoxicity, in tumor control is well recognized. There is mounting evidence that T cells control tumor growth and survival in cancer patients, both in early and late stages of the disease. However, tumor-specific T-cell responses are difficult to mount and sustain in cancer patients. The continuing advancement and successes of cancer immunotherapies, which stimulate or enhance innate immune responses against cancer, make such therapeutics an attractive treatment option when compared to therapies that utilize non-specific chemotherapeutics and/or radiation.

A number of molecular targets have been identified for their potential utility as immuno-oncology (IO) therapeutics against cancer. Some molecular targets that are being investigated for their therapeutic potential in the area of immuno-oncology therapy include cytotoxic T lymphocyte antigen-4 (CTLA-4 or CD152), programmed death ligand 1 (PD-L1 or B7-H1 or CD274), Programmed Death-1 (PD-1), OX40 (CD134 or TNFRSF4) and T-cell inhibitory receptor T-cell immunoglobulin and mucin-domain containing-3 (TIM3). While some of these targets have been successfully exploited therapeutically (e.g., PD-1 and CTLA-4), many patients have been unresponsive to the therapeutics that have been developed. And, while a therapeutic regimen that includes higher doses and/or a combination of immunotherapies may be considered, such therapies may be associated with increased risk of side effects, which tend to increase with higher doses and cumulative exposure, and appear to be additive when used with combination immunotherapies. Some common side effects include hypophysitis, thyroiditis, adrenal insufficiency, enterocolitis, dermatitis, pneumonitis, hepatitis, pancreatitis, motor and sensory neuropathies, and arthritis. Furthermore, as immunotherapeutics are typically associated with high costs, a therapy that includes a combination of immunotherapeutics can be cost-prohibitive to patients.

As such, there remains a need to continue to identify candidate targets for IO therapeutics, develop new therapeutics to the existing targets, and to develop therapeutic strategies that avoid disadvantages of immunotherapies that are currently in use, including the lack of patient response and the increased risk of side effects involved with combination treatment. IO therapeutics (e.g., binding proteins) that are bispecific for a combination of target molecules, particularly those that exhibit greater binding affinity for the target molecules when compared to the binding affinity for a combination of individual monospecific binding proteins, represent a class of particularly desirable molecules for therapeutic potential.

SUMMARY OF THE INVENTION

The invention provides bispecific molecules or proteins that bind two epitopes (e.g., a first and a second epitope) and that are bivalent for binding to each of the first and second epitopes. The invention also provides methods of inducing an immune response in a subject as well as methods for treating or preventing cancer in a subject (e.g., a human subject) by administering the proteins, nucleic acid molecules and/or compositions to the subject.

In one aspect, the invention provides a protein, containing: a first binding domain (BD1) that binds to a first epitope, a second binding domain (BD2) that binds to a second epitope, and an Fc region having $C_H2$ and $C_H3$ domain; where the Fc region includes BD2 at a solvent exposed loop in the $C_H2$ domain, the $C_H3$ domain, or at the interface of the $C_H2$ and $C_H3$ domains; and where the protein is bivalent for binding to each of the first and second epitopes.

In another aspect, the invention provides a composition containing a protein or antibody according to any aspect herein and a pharmaceutically acceptable carrier.

In another aspect, the invention provides a method of treating or preventing cancer in a subject, the method involving administering the protein or antibody according to any aspect herein to the subject (e.g., a human subject). In various embodiments, the cancer is one or more of ovarian cancer, breast cancer, colorectal cancer, prostate cancer, cervical cancer, uterine cancer, testicular cancer, bladder cancer, head and neck cancer, melanoma, pancreatic cancer, renal cell carcinoma, and lung cancer.

In another aspect, the invention provides a method of inducing an immune response in a subject, the method involving administering the protein or antibody according to any aspect herein to the subject (e.g., a human subject).

In another aspect, the invention provides a nucleic acid molecule having a nucleotide sequence encoding a protein or an antibody according to any aspect herein.

In another aspect, the invention provides a vector containing a nucleic acid molecule according to any aspect herein.

In another aspect, the invention provides a host cell containing a vector according to any aspect herein.

In one aspect, the invention provides a bispecific binding protein that binds to PD-1 and CTLA-4 having a first peptide having the amino acid sequence of SEQ ID NO:1, and a second peptide having the amino acid sequence of SEQ ID NO:2.

In another aspect, the invention provides a bispecific binding protein that binds to PD-1 and CTLA-4 having a first peptide having the amino acid sequence of SEQ ID NO:3, and a second peptide having the amino acid sequence of SEQ ID NO:4.

In another aspect, the invention provides a bispecific binding protein that binds to PD-1 and CTLA-4 having, a first peptide having the amino acid sequence of SEQ ID NO:5, and a second peptide having the amino acid sequence of SEQ ID NO:6.

In one aspect, the invention provides a bispecific binding protein that binds to PD-1 and CTLA-4 having a first heavy chain having the amino acid sequence of SEQ ID NO: 9, a first light chain having the amino acid sequence of SEQ ID NO: 7, a second heavy chain having the amino acid sequence of SEQ ID NO: 12, and a second light chain having the amino acid sequence of SEQ ID NO: 4.

In one aspect, the invention provides a bispecific binding protein that binds to PD-L1 and CTLA-4 having a first peptide having the amino acid sequence of SEQ ID NO:14 and a second peptide having the amino acid sequence of SEQ ID NO:15.

In another aspect, the invention provides a bispecific binding protein that binds to PD-L1 and CTLA-4 having a first peptide having the amino acid sequence of SEQ ID NO:16, and a second peptide having the amino acid sequence of SEQ ID NO:17.

In another aspect, the invention provides a bispecific binding protein that binds to PD-L1 and CTLA-4 having a first peptide having the amino acid sequence of SEQ ID NO:18, and a second peptide having the amino acid sequence of SEQ ID NO:19.

In one aspect, the invention provides a bispecific binding protein that binds to PD-1 and TIM3 having a first peptide having the amino acid sequence of SEQ ID NO:22, and a second peptide having the amino acid sequence of SEQ ID NO:23.

In another aspect, the invention provides a bispecific binding protein that binds to PD-1 and TIM3 having a first peptide having the amino acid sequence of SEQ ID NO:24 or SEQ ID NO:91, and a second peptide having the amino acid sequence of SEQ ID NO:23 or SEQ ID NO: 92.

In one aspect, the invention provides a bispecific binding protein that binds to PD-1 and TIM3 having a first heavy chain having the amino acid sequence of SEQ ID NO:9, a first light chain having the amino acid sequence of SEQ ID NO: 7, a second heavy chain having the amino acid sequence of SEQ ID NO:27 or SEQ ID NO: 30, and a second light chain having the amino acid sequence of SEQ ID NO: 26 or SEQ ID NO: 28.

In one aspect, the invention provides a bispecific binding protein that binds to OX40 and PD-L1 having a first peptide having the amino acid sequence of SEQ ID NO:34, and a second peptide having the amino acid sequence of SEQ ID NO:32.

In another aspect, the invention provides a bispecific binding protein that binds to OX40 and PD-L1 having a first peptide having the amino acid sequence of SEQ ID NO:35, and a second peptide having the amino acid sequence of SEQ ID NO:32.

In another aspect, the invention provides a bispecific binding protein that binds to OX40 and PD-L1 having a first peptide having the amino acid sequence of SEQ ID NO:36 or SEQ ID NO:94, and a second peptide having the amino acid sequence of SEQ ID NO:32 or SEQ ID NO:93.

In one aspect, the invention provides an antibody or antigen binding fragment thereof that binds to TIM3 having a heavy chain having CDR1, CDR2, and CDR3 and a light chain having CDR1, CDR2, and CDR3, wherein the heavy chain CDR1 comprises SEQ ID NO:88, the heavy chain CDR2 comprises SEQ ID NO:80, the heavy chain CDR3 comprises SEQ ID NO:81, and the light chain CDR1 comprises SEQ ID NO:82, the light chain CDR2 comprises SEQ ID NO:83, the light chain CDR3 comprises SEQ ID NO:84.

In other aspects, the invention provides a composition having a bispecific binding protein and a pharmaceutically acceptable carrier; a nucleic acid molecule having a nucleotide sequence encoding a bispecific binding protein; methods of treating or preventing cancer in a subject, by administering a bispecific binding protein; and methods of enhancing an immune response in a subject, by administering a bispecific binding protein.

In various embodiments of any aspect delineated herein, the Fc region comprises BD2 at a solvent exposed loop in the amino acid sequence in the $C_H2$ domain, the $C_H3$ domain, or at the interface of the $C_H2$ and $C_H3$ domain.

In various embodiments of any aspect delineated herein, the solvent exposed loop includes an amino acid sequence from the $C_H2$ domain. In particular embodiments, the solvent exposed loop includes the amino acid sequence ISRTP (SEQ ID NO: 39).

In various embodiments of any aspect delineated herein, the solvent exposed loop includes an amino acid sequence from the $C_H3$ domain. In particular embodiments, the solvent exposed loop includes the amino acid sequence SNG.

In various embodiments of any aspect delineated herein, the solvent exposed loop includes an amino acid sequence from the interface of the $C_H2$ domain and the $C_H3$ domain. In particular embodiments, the protein of claim 7, where the solvent exposed loop comprises the amino acid sequence AKGQP (SEQ ID NO: 40).

In various embodiments of any aspect delineated herein, BD2 is or includes a single-chain variable fragment (scFv).

In various embodiments of any aspect delineated herein, BD1 is or includes a binding domain that is one or more of an Fab domain, an scFv, a single domain antibody, and an antibody variable domain. In particular embodiments, BD1 includes a Fab domain.

In various embodiments of any aspect delineated herein, the Fab domain is connected to the Fc region via an antibody hinge region. In certain embodiments, the Fc region is or includes a domain that is one or more of an Fc region from an IgG1, IgG2, IgG3, IgG4, IgA, IgM, IgE, or IgD. In particular embodiments, the Fc region comprises a variant Fc region. In some embodiments, the Fc region is aglycosylated, deglycosylated, and/or is afucosylated or has reduced fucosylation.

In various embodiments of any aspect delineated herein, the protein further includes a protein linker L1 between BD2 and the Fc region. In various embodiments of any aspect delineated herein, the protein further includes a first protein linker, L1, and a second protein linker, L2, between BD2 and the Fc region. In various embodiments of any aspect delineated herein, BD2 is associated with the Fc region via a protein linker L1. In various embodiments of any aspect delineated herein, BD2 is associated with the Fc region via two protein linkers, L1 and L2. In certain embodiments, L1 and L2 are independently selected from $(G_4S)_2$ (SEQ ID NO:41), $(G_4S)_3$, (SEQ ID NO:42), and $(G_4S)_4$ (SEQ ID NO:43).

In various embodiments of any aspect delineated herein, the protein includes a chimeric heavy chain having the following polypeptide domains, from N-terminus to C-terminus: $V_H1$-$C_H1$-$C_H2$ (N-term)-BD2-$C_H2$ (C-term)-$C_H3$; and BD1 includes a Fab domain; where $V_H1$ includes a heavy chain variable domain of the Fab domain and $C_H1$ includes the heavy chain constant domain 1 of the Fab.

In various embodiments of any aspect delineated herein, the protein includes a chimeric heavy chain having the following polypeptide domains, from N-terminus to C-terminus: $V_H1$-$C_H1$-$C_H2$-BD2-$C_H3$; and BD1 includes a Fab domain; where $V_H1$ comprises a heavy chain variable domain of the Fab domain and $C_H1$ includes the heavy chain constant domain 1 of the Fab.

In various embodiments of any aspect delineated herein, the protein includes a chimeric heavy chain having the following polypeptide domains, from N-terminus to C-terminus: $V_H1$-$C_H1$-$C_H2$-$C_H3$(N-term)-BD2-$C_H3$(C-term); and BD1 includes a Fab domain; where $V_H1$ includes a heavy chain variable domain of the Fab domain, and $C_H1$ includes the heavy chain constant domain 1 of the Fab.

In various embodiments of any aspect delineated herein, BD2 is or includes an scFv. In particular embodiments, the scFv includes, from N-terminus to C-terminus: $V_H2$-polypeptide linker-$V_L2$ or $V_L2$-polypeptide linker-$V_H2$; where $V_H2$ includes the heavy chain variable domain of the scFv and $V_L2$ includes the light chain variable domain of the scFv.

In various embodiments of any aspect delineated herein, the protein further includes a protein linker L1 between BD2 and the Fc region. In various embodiments of any aspect delineated herein, the protein further includes a first protein linker, L1, and a second protein linker, L2, between BD2 and the Fc region.

In various embodiments of any aspect delineated herein, the BD2 is associated via a linker (L1) to the $C_H2$ domain, the $C_H2$ domain, or the interface of the $C_H2$ and $C_H3$ domains of the Fc region.

In various embodiments of any aspect delineated herein, the BD2 is associated via two protein linkers, L1 and L2 to the $C_H2$ domain, the $C_H3$ domain, or the interface of the $C_H2$ and $C_H3$ domains of the Fc region. In various embodiments, L1 and L2 are independently selected from protein linkers having a length of 1-25 amino acids. In particular embodiments, L1 and L2 are independently selected from $(G_4S)_2$ (SEQ ID NO:41), $(G_4S)_3$, (SEQ ID NO:42), and $(G_4S)_4$ (SEQ ID NO:43).

In various embodiments of any aspect delineated herein, the first and second epitopes are different. In various embodiments of any aspect delineated herein, the first and second epitopes are the same.

BRIEF DESCRIPTION OF THE DRAWINGS

For the purpose of illustrating the disclosure, there are depicted in the drawings certain aspects of the disclosure. However, the disclosure is not limited to the precise arrangements and instrumentalities of the aspects depicted in the drawings.

FIGS. 1A-1F depict a general schematic diagram of certain exemplary proteins described herein. The CH2 and CH3 regions are illustrated in FIGS. 1A-1C using PyMOL and identify solvent exposed surface loop regions as spheres. FIG. 1A depicts the loop in the CH2 region; FIG. 1B depicts the loop in the CH2-CH3 interface; and FIG. 1C depicts the loop in the CH3 region. Exemplary constructs are illustrated in FIGS. 1D-1F that include representative BD1 and BD2 domains as Fab and scFv domains, respectively. FIG. 1D depicts BD1 attached at the hinge region and BD2 attached at solvent exposed loops in the CH2 region. FIG. 1E depicts BD1 attached at the hinge region and BD2 attached at solvent exposed loops in the CH2-CH3 interface. FIG. 1F depicts BD1 attached at the hinge region and BD2 attached at solvent exposed loops in the CH3 region.

FIGS. 2A-2C provide an expanded view of the solvent accessible loop sequences in CH2, at the CH2-CH3 interface, and in CH3 as described herein. Examples of constructs incorporating a BD2 (scFv) are included in each of FIGS. 2A-2C. FIG. 2A illustrates the representative loop sequence ISRTP (SEQ ID NO:39) identified in the CH2 loop upstream of the CH2-CH3 interface. FIG. 2B illustrates the representative loop sequence AKGQP (SEQ ID NO:40) in the CH2-CH3 interface. FIG. 2C illustrates the representative loop sequence SNG in the CH3 region downstream of the CH2-CH3 interface.

FIGS. 6A-D shows that PD-1/CTLA-4 bispecific binding proteins inhibit the PD-1 and CTLA-4 pathways in reporter gene assays. FIG. 6A depicts T-cell activation via PD-1 blockade. FIG. 6B depicts T-cell activation via CTLA-4 blockade. FIG. 6C shows the results of the PD-1 reporter assay. FIG. 6D shows the results of the CTLA-4 reporter assay.

FIG. 10A is a schematic of the assay (n=4 donors; 2 independent experiments).

FIG. 16A-B shows T cell dependent antibody response (TDAR) in cynomolgus monkeys dosed with PD-1/CTLA-4 DuetMab (MEDI5752) and PD-1/CTLA-4 BiS5Ab (MEDI8500).

FIG. 17 shows a model system to study PD-1/CTLA-4 bispecific molecules in which stable CHO cells express diverse levels of human PD-1 and/or CTLA-4.

FIGS. 21A-D show that PD-1/CTLA-4 DuetMab saturates CTLA-4 on CHO cells expressing excess PD-1 at ~250-fold lower concentrations compared to a combination of monoclonal antibodies.

FIGS. 22A-F show that PD-1/CTLA-4 DuetMab saturates CTLA-4 on CHO cells expressing excess PD-1 at ~500-fold lower concentrations compared to cells expressing only CTLA-4.

FIGS. 23A-B shows PD-1/CTLA-4 DuetMab preferentially binds in cis to PD-1 and CTLA-4 on the surface of same cell. Treme in FIG. 23B is a CTLA-4 mAb.

FIGS. 24A-D show binding and internalization of PD-1/CTLA-4 DuetMab and parental monoclonal antibodies to cultured T cells. PD-1/CTLA-4 DuetMab has internalization properties of tremelimumab.

FIG. 25A shows a schematic of the internalization assay. FIG. 25B shows that PD-1/CTLA-4 DuetMab takes on internalization properties of tremelimumab in stable CHO cells expressing 10-fold excess PD-1.

FIGS. 28A-28C provide a summary of the cell killing activity of monospecific TIM3 and bispecific PD-1_TIM3PD-1 bispecific constructs in a cell killing assay. FIG. 28A shows brightfield images of cocultured wells at 18 hr. Combination of anti-TIM-3+anti-PD1 or the TIM-3/PD-1 bispecific formats enhance tumor cell death and increase T cell activation as assessed by reduction of adherent cells and enhanced blasting (clumping) of T cells. FIG. 28B shows assessment of viability dye uptake by tumor cells after 18 hr co-culture with melanoma specific CD8+ T cells. FIG. 28C shows IFNγ secretion after 18 hr co-culture. The bispecific constructs generally demonstrate better killing activity, with the DuetMab format exhibiting the most robust killing activity.

FIG. 29 demonstrates the concurrent binding of a PD-1/TIM3 DuetMab construct having a TIM3 arm sequence that is an affinity mature variant of clone 62.

FIG. 30 shows binding of PD-1/TIM3 bispecific antibodies, including BiS3, BiS5, and DuetMab, to CHO cells overexpressing human TIM3 or human PD1. PD-1 and TIM3 expression data are shown in the inset.

FIGS. 34A-C show the results of a PD-1 reporter assay (dual cell system) using PD-1/TIM3 bispecific antibodies, including BiS3, BiS5, and DuetMab, All bispecific formats demonstrate similar activity as parental LO115 IgG1 (compilation of 3-5 independent experiments/3 biological replicates per treatment).

FIGS. 40A-F shows binding of the bispecific constructs that target PD-L1 and OX40 to CHO cells expressing human or cynomolgus OX40 and PD-L1/B7H1.

FIGS. 41A-B shows binding of the bispecific constructs that target PD-L1 and OX40 to Jurkat OX40 reporter cells, NCI H358, CHOK1 B7H1(PD-L1)/OKT3 cells, and HEK CD32a cells, measured by flow cytometry (HyperCyt).

FIGS. 43A-B shows the results of an OX40 reporter assay in HEK CD32a cells using OX40/PD-L1 bispecific molecules.

FIGS. 44A-B shows the results of an OX40 reporter assay in CHOK PD-L1 overexpressing cells using OX40/PD-L1 bispecific molecules.

FIGS. 45A-B shows PD-L1 mediated OX40 agonism with tumor cells using OX40/PD-L1 bispecific molecules.

FIGS. 46A-D shows results indicating no agonism was detected with NCI H358 PD-L1 KO cells using OX40/PD-L1 bispecific molecules in controls for the OX40/tumor cell assay.

FIG. 48A shows a schematic of the Treg suppression assay experiment to test the OX40/PD-L1 bispecific molecules. FIGS. 48B-C show the Treg suppression based on binding of the bispecific molecule.

FIGS. 51A-B shows the design of a mixed leukocyte reaction (MLR) assay experiment to test OX40/PD-L1 bispecific molecules.

FIGS. 53A-B shows that BiS2 and BiS5 OX40/PD-L1 bispecific molecules mediate antibody-dependent cell-mediated cytotoxicity (ADCC) of natural killer (NK) cells against PD-L1 or OX40 expressing CHO cells.

FIG. 65A depicts a schematic of an OX40 reporter assay. FIG. 65B shows the results of the OX40 reporter assay using PD1 LO115 mAb, OX40 mAb, a control mAb and PD1 (LO115)/OX40 BiS2 mAb.

FIG. 73A illustrates the effect of pH on thermal stability of BiS4. FIG. 73B illustrates the effect of pH on thermal stability of BiS5. FIG. 73C depicts a representative curve-fitted DSC thermogram for BiS4 with $T_{onset}$, $T_m1$, $T_m2$, and $T_m3$. FIG. 73D depicts a representative curve-fitted DSC thermograms for BiS5 with $T_{onset}$, $T_m1$, $T_m2$, and $T_m3$. FIG. 73E depicts a plot representing the effect of pH on $T_{onset}$, $T_m1$, $T_m2$, and $T_m3$ for BiS4 and BiS5 formats.

FIG. 74A provides an overlay plot of SEC chromatograms of BiS4 and BiS5 before and after thermal stress, the solid lines correspond to BiS4 and BiS5 samples at time zero (no stress) and dotted lines correspond to BiS4 and BiS5 samples incubated at 40° C. for 4 week (stressed). FIG. 74B provides a bar chart representing the effect of pH 7.5 on different species (monomer, fragments, and aggregates) of BiS4 and BiS5 as measured on day zero and after 4 weeks at 40° C.

FIG. 75A shows the percentage of monomer remaining, as measured by HP-SEC over a period of 4 weeks. FIG. 75B shows the percentage of fragmentation, as measured by HP-SEC over a period of 4 weeks. FIG. 75C shows the percentage of aggregation, as measured by HP-SEC over a period of 4 weeks. The data presented is from single vial analysis.

FIG. 76A shows the effect of different pH conditions on the rate of monomer loss. at 40° C. FIG. 76B shows the effect of different pH conditions on the rate of fragmentation at 40° C. FIG. 76C shows the effect of different pH conditions on the rate of aggregation at 40° C.

FIG. 77A shows that at pH 7.5 and 40° C. (at time=0), neither molecule exhibits appreciable fragmentation. FIG. 77B shows that under the same conditions as FIG. 77A, but after 2 weeks storage at 40° C., appreciable fragmentation is observed for BiS4 and minimal fragmentation for BiS5.

DETAILED DESCRIPTION

Figure 1A:
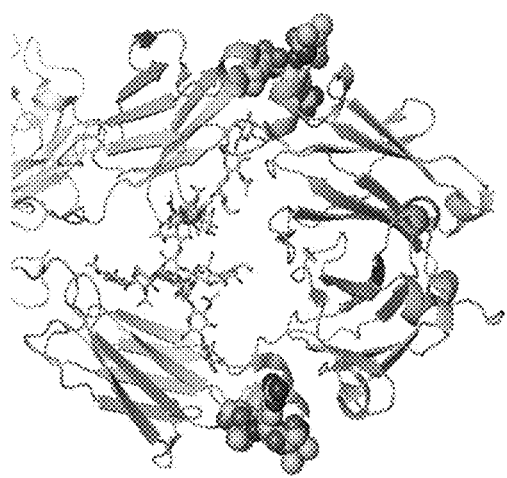

Before continuing to describe the present disclosure in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The numbering of amino acids in the variable domain, complementarity determining region (CDRs) and framework regions (FR), of an antibody follow, unless otherwise indicated, the Kabat definition as set forth in Kabat et al. Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insertion (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence. Maximal alignment of framework residues frequently requires the insertion of "spacer" residues in the numbering system, to be used for the Fv region. In addition, the identity of certain individual residues at any given Kabat site number may vary from antibody chain to antibody chain due to interspecies or allelic divergence.

As used herein, the terms "antibody" and "antibodies", also known as immunoglobulins, encompass monoclonal antibodies (including full-length monoclonal antibodies), polyclonal antibodies, multispecific antibodies formed from at least two different epitope binding fragments (e.g., multispecific antibodies, e.g., PCT publication WO2009018386, PCT Application No. PCT/US2012/045229, incorporated herein by reference in its entirety), BiSAbs, human antibodies, humanized antibodies, camelised antibodies, single-chain Fvs (scFv), single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain at least one antigen-binding site. Antibodies also include peptide fusions with antibodies or portions thereof such as a protein fused to an Fc domain. Immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)). Antibodies may be derived from any mammal, including, but not limited to, humans, monkeys, pigs, horses, rabbits, dogs, cats, mice, etc., or other animals such as birds (e.g. chickens).

CTLA-4

Cytotoxic T-lymphocyte-associated protein 4 (CTLA-4) is expressed on activated T cells and serves as a co-inhibitor to keep T-cell responses in check following CD28-mediated T cell activation. CTLA-4 is believed to regulate the amplitude of the early activation of naïve and memory T cells following TCR engagement and to be part of a central inhibitory pathway that affects both antitumor immunity and autoimmunity. CTLA-4 is expressed exclusively on T cells, and the expression of its ligands CD80 (B7.1) and CD86 (B7.2), is largely restricted to antigen-presenting cells, T cells, and other immune mediating cells. Antagonistic anti-CTLA-4 antibodies that block the CTLA-4 signaling pathway have been reported to enhance T-cell activation. One such antibody, ipilimumab, was approved by the FDA in 2011 for the treatment of metastatic melanoma. The use of anti-CTLA-4 antibodies to treat infections and tumors and up-modulate an adaptive immune response has been proposed (see, U.S. Pat. Nos. 6,682,736; 7,109,003; 7,132,281; 7,411,057; 7,824,679; 8,143,379 7,807,797; 8,491,895; 8,883,984; and US Publication No. 20150104409, incorporated herein by reference in their entireties).

PD-L1

Programmed Death Ligand 1 (PD-L1) is also part of a complex system of receptors and ligands that are involved in controlling T-cell activation. In normal tissue, PD-L1 is expressed on T cells, B cells, dendritic cells, macrophages, mesenchymal stem cells, bone marrow-derived mast cells, as well as various non-hematopoietic cells. Its normal function is to regulate the balance between T-cell activation and tolerance through interaction with its two receptors: programmed death 1 (also known as PD-1 or CD279) and CD80 (also known as B7-1 or B7.1). PD-L1 is also expressed by tumors and acts at multiple sites to help tumors evade detection and elimination by the host immune system. PD-L1 is expressed in a broad range of cancers with a high frequency. In some cancers, expression of PD-L1 has been associated with reduced survival and unfavorable prognosis. Antibodies that block the interaction between PD-L1 and its receptors are able to relieve PD-L1-dependent immunosuppressive effects and enhance the cytotoxic activity of antitumor T cells in vitro. Durvalumab is a human monoclonal antibody directed against human PD-L1 that is capable of blocking the binding of PD-L1 to both the PD-1 and CD80 receptors. The use of anti-PD-L1 antibodies to treat infections and tumors and enhance an adaptive immune response has been proposed (see, U.S. Pat. Nos. 8,779,108 and 9,493,565 incorporated herein by reference in their entirety).

PD-1

Programmed Death-1 ("PD-1") is an approximately 31 kD type I membrane protein member of the extended CD28/CTLA-4 family of T cell regulators (see, Ishida, Y. et al. (1992) Induced Expression Of PD-1, A Novel Member Of The Immunoglobulin Gene Superfamily, Upon Programmed Cell Death," EMBO J. 11:3887-3895.

PD-1 is expressed on activated T cells, B cells, and monocytes (Agata, Y. et al. (1996) "Expression of the PD-1 Antigen on the Surface of Stimulated Mouse T and B Lymphocytes," Int. Immunol. 8(5):765-772; Martin-Orozco, N. et al. (2007) "Inhibitory Costimulation and Anti-Tumor Immunity," Semin. Cancer Biol. 17(4):288-298). PD-1 is a receptor responsible for down-regulation of the immune system following activation by binding of PDL-1 or PDL-2 (Martin-Orozco, N. et al. (2007) "Inhibitory Costimulation and Anti-Tumor Immunity," Semin. Cancer Biol. 17(4):288-298) and functions as a cell death inducer (Ishida, Y. et al. (1992) "Induced Expression of PD-1, A Novel Member of The Immunoglobulin Gene Superfamily, Upon Programmed Cell Death," EMBO J. 11: 3887-3895; Subudhi, S. K. et al. (2005) "The Balance of Immune Responses: Costimulation Verse Coinhibition," J. Molec. Med. 83: 193-202). This process is exploited in many tumours via the over-expression of PD-L1, leading to a suppressed immune response.

PD-1 is a well-validated target for immune mediated therapy in oncology, with positive results from clinical trials in the treatment of melanoma and non-small cell lung cancers (NSCLC), among others. Antagonistic inhibition of the PD-1/PD-L-1 interaction increases T-cell activation, enhancing recognition and elimination of tumour cells by the host immune system. The use of anti-PD-1 antibodies to treat infections and tumors and enhance an adaptive immune response has been proposed (see, U.S. Pat. Nos. 7,521,051; 7,563,869; 7,595,048).

OX40

OX40 (CD134; TNFRSF4) is a tumor necrosis factor receptor found primarily on activated CD4$^+$ and CD8$^+$ T cells, regulatory T (Treg) cells and natural killer (NK) cells (Croft et al., 2009, *Immunol Rev.* 229:173-91). OX40 has one known endogenous ligand, OX40 ligand (OX40L; CD152; TNFSF4), which exists in a trimeric form and can cluster OX40, resulting in potent cell signaling events within T cells. Id. Signaling through OX40 on activated CD4$^+$ and CD8$^+$ T cells leads to enhanced cytokine production, granzyme and perforin release, and expansion of effector and memory T cell pools (Jensen et al., 2010, *Semin Oncol.* 37:524-32). In addition, OX40 signaling on Treg cells inhibits expansion of Tregs, shuts down the induction of Tregs and blocks Treg-suppressive function (Voo et al., 2013, *J Immunol.* 191:3641-50; Vu et al., 2007, *Blood.* 110:2501-10).

Immunohistochemistry studies and early flow cytometry analyses showed that OX40 is expressed on T cells infiltrating a broad range of human cancers (Baruah et al., 2011, *Immunobiology* 217:668-675; Curti et al, 2013, *Cancer Res.* 73:7189-98; Ladanyi et al, 2004, *Clin Cancer Res.* 10:521-30; Petty et al, 2002, *Am J Surg.* 183:512-8; Ramstad et al, 2000, *Am J Surg.* 179:400-6; Sarff et al, 2008, *Am J Surg.* 195:621-5; discussion 625; Vetto et al, 1997, *Am J Surg.* 174:258-65). While not wishing to be bound by theory, OX40 expression on tumor-infiltrating lymphocytes correlates with longer survival in several human cancers, suggesting that OX40 signals can play a role in establishing an antitumor immune response (Ladanyi et al., 2004, *Clin Cancer Res.* 10:521-30; Petty et al., 2002, *Am J Surg.* 183:512-8).

In a variety of nonclinical mouse tumor models, agonists of OX40, including antibodies and OX40 ligand fusion proteins, have been used successfully with promising results (Kjaergaard et al., 2000, *Cancer Res.* 60:5514-21; Ndhlovu et al., 2001, *J Immunol.* 167:2991-9; Weinberg et al., 2000, *J Immunol.* 164:2160-9). Co-stimulating T cells through OX40 promoted anti-tumor activity that in some cases was durable, providing long-lasting protection against subsequent tumor challenge (Weinberg et al., 2000, *J Immunol.* 164:2160-9). Treg-cell inhibition and co-stimulation of effector T cells were shown to be necessary for tumor growth inhibition of OX40 agonists (Piconese et al., 2008, *J Exp Med.* 205:825-39). Many strategies and technologies have been explored to enhance the anti-tumor effect of OX40 agonist therapy through combinations with vaccines, chemotherapy, radiotherapy, and immunotherapy (Jensen et al., 2010, *Semin Oncol.* 37:524-32; Melero et al., 2013, *Clin Cancer Res.* 19:997-1008). The use of anti-OX40 antibodies to treat infections and tumors and up-modulate an adaptive immune response has been proposed (see, US Publication No. 20160137740, incorporated herein by reference in its entirety).

TIM3

The T-cell inhibitory receptor Tim-3 (T-cell immunoglobulin and mucin-domain containing-3) plays a role in regulating antitumor immunity as it is expressed on IFN-gamma producing CD4+ helper 1 (Th1) and CD8+ T cytotoxic1 (Tc1) T cells. It was initially identified as a T-cell inhibitory receptor, acting as an immune checkpoint receptor that functions specifically to limit the duration and magnitude of Th1 and Tc1 T-cell responses. Further research has identified that the Tim-3 pathway may cooperate with the PD-1 pathway to promote the development of a severe dysfunctional phenotype in CD8+ T cells in cancer. It has also been expressed in regulatory T cells (Treg) in certain cancers. In view of the involvement the TIM3 pathway in key immune cell populations that are immunosuppressed in some cancers, it represents an attractive candidate for immuno-oncology therapy. See, Anderson, A. C., *Cancer Immunol Res.*, (2014) 2:393-398; and Ferris, R. L., et al., *J Immunol.* (2014) 193:1525-1530.

A. Bispecific Binding Proteins

Adding multiple binding sites to a molecule having specificity for a single binding domain can greatly enhance the capabilities (e.g. therapeutic, diagnostic, etc) of the molecule. For example, a bispecific antibody may bind to more than one region of the same target biomolecule, conferring greater specificity than a mono-specific polypeptide that binds to only one epitope on a target. Alternately, a bispecific antibody may bind to multiple target biomolecules, such as targets that are present in a complex, or targets for which sequestering and/or clustering is desired. In a third scenario, the same bispecific antibody may perform distinct functions at any given time, depending on the localization and/or expression of its target molecules.

Described herein are novel binding proteins. One such configuration of these novel binding proteins is referred to as "DuetMab." DuetMab has the following basic structure: an Fc region having a modified heavy chain, wherein the CH1 region of the modified heavy chain has a substitution of a native cysteine to a non-cysteine amino acid, and a substitution of a native non-cysteine amino acid to a cysteine amino acid; a modified corresponding light chain, where the CL region of the modified light chain also has a substitution of a native cysteine to a non-cysteine amino acid, and a substitution of a native non-cysteine amino acid to a cysteine amino acid; a second Fc region having a second heavy chain; and second corresponding modified light chain, where the modified heavy chain is directly linked to the corresponding modified light chain, and on a separate target binding arm, the second heavy chain is directly linked to the second corresponding light chain, and where the substituted cysteine of the modified heavy chain, resulting from the substitution of the native non-cysteine amino acid to the cysteine amino acid, and the substituted cysteine of the modified corresponding light chain, resulting from the substitution of the native non-cysteine amino acid to the cysteine amino acid, can form a disulphide bond. Disclosure related to DuetMab can found e.g., in U.S. Pat. No. 9,527,927, incorporated herein by reference in its entirety.

Additional exemplary configurations of these novel binding proteins are referred to as "BiSAb" or "BiSAbs". Schematic representations of exemplary BiSAbs, as well as specific examples of particular BiSAbs are provided herein. More generally, a BiSAb is a polypeptide containing two binding units, each of which binds to an epitope (e.g., binding unit 1 binds to a first epitope and binding unit 2 binds to a second epitope). The basic BiSAb is bivalent for binding to each of the two epitopes (e.g., the polypeptide comprises two binding unit 1's ("BD1" or "BU1") and two binding unit 2's ("BD2" or "BU2")). Thus, where the binding unit 1 and 2 bind different epitopes, the BiSAb has the multi-specificity of a conventional bispecific antibody and the bivalency of a conventional antibody molecule. In embodiments where binding unit 1 and 2 bind the same epitope the BiSAb has the monospecificity of a conventional antibody but is tetravalent. In addition to binding units, BiSAbs also include linker polypeptides and an Fc portion. The disclosure relates to a broad set of bispecific binding proteins, such as the BiSAb and proteins comprising a BiSAb core, that target molecules that modulate immune response. Generally, the novel binding protein platforms and exemplary bispecific binding proteins (BiSAbs) described herein comprise binding units/domains, linker polypeptides and an Fc portion. The disclosure also provides nucleic acid molecules encoding such BiSAbs as well as vectors and host cells that include such nucleic acids and which may be used in methods of producing and using such BiSAbs. BiSAbs, binding proteins comprising a BiSAb core, and the various portions of BiSAbs are described in greater detail herein.

In some aspects a BiSAb can comprise two heavy-light chain pairs derived from a specific binding protein (i.e., antibody), wherein the heavy and light chains each comprise a variable region (e.g. VL and VH), which together form a first binding unit, and wherein the heavy chains each further comprises a second binding unit (e.g. an scFv domain attached to Fc or Fab). Where the first and second binding units bind different epitopes each heavy-light chain pair is bispecific and the two pairs together are bivalent for each epitope. Where the first and second binding units bind the same epitope each heavy-light chain pair is monospecific and the two pairs together are tetravalent for the epitope. In some aspects, the two heavy-light chain pairs are identical. In some aspects, the two heavy-light chain pairs are not identical.

In specific embodiments, the domains of the BiSAbs may be based on known immunoglobulin domains. Immunoglobulin molecules such as monoclonal antibodies (mAbs) are widely used as diagnostic and therapeutic agents, and methods for engineering the binding fragments of mAbs are well-known in the art. Monoclonal antibodies, like all immunoglobulin molecules, are made up of heavy chain and light chain peptide subunits, which each include variable and constant domains that confer binding specificity (variable domain) and isotype (constant domain).

The BiSAbs disclosed herein may have a similar overall structure to a conventional antibody, but are distinguishable by the presence of an additional binding unit that is attached at a location within the Fab domain, attached at a location away from the Fab domain and within the Hinge or Fc regions (e.g., within the CH2, CH3, or CH4 regions, or at the interface of such regions such as the CH2-CH3 interface). Thus, unlike conventional antibodies that are bivalent for binding to a single epitope, BiSAbs are bivalent for binding to two epitopes. However, as described herein, BiSAbs may still maintain numerous desirable properties of conventional antibodies, such as ability to bind FcRn and ability to bind C1q and Fcγ receptors (e.g., indicative of ability to mediate antibody and complement dependent cytotoxicity).

Binding domains described herein can comprise antigen binding fragments containing only portions of a mAb molecule, such as Fab, F(ab')$_2$, Fab', scFv, di-scFv, sdAb fragments, as these fragments have found use as diagnostic or therapeutic agents. In addition, specific residues in the variable domains can be altered to improve binding specificity and/or stability of antibodies and antibody fragments. Other residues not directly involved in antigen binding can be replaced in order to "humanize" regions of non-human antibodies and reduce immunogenicity of the mAb.

Although BiSAbs differ from conventional antibodies, for example, they are bivalent for binding to two different epitopes (or tetravalent for binding to a single epitope) many of the portions of BiSAbs are derived from or analogous to portions of conventional antibodies. Any mAb domains and/or fragments known in the art may be used in the BiSAbs described herein. In particular, the BiSAb may comprise Fab and/or scFv fragments, or variants thereof. Exemplary, non-limiting variants of scFv include but are not limited to tandem di-scFvs, tandem tri-scFvs, diabodies, and tri(a)bodies.

The disclosure relates generally to novel binding proteins, of which BiSAbs are an illustrative example. Additional examples are binding proteins comprising a BiSAb core as well as one or more additional binding units and/or binding proteins comprising an extended BiSAb core. It should be understood that whenever BiSAbs or features of BiSAbs are described herein, such description applies generally to the novel binding proteins of the disclosure, regardless of whether such binding proteins include two binding units or more than two binding units. Accordingly, the term BiSAb is exemplary of binding proteins described herein and, where context permits, any such reference to BiSAb may also be used to describe binding proteins comprising a BiSAb core.

Novel BiSAb Structural Platform.

Figure 1B:
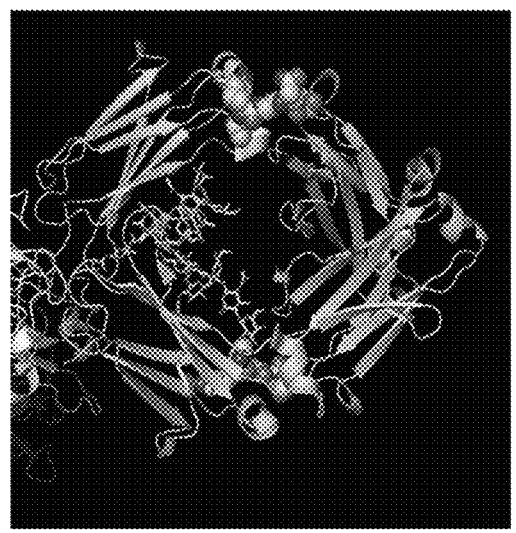
Figure 1C:
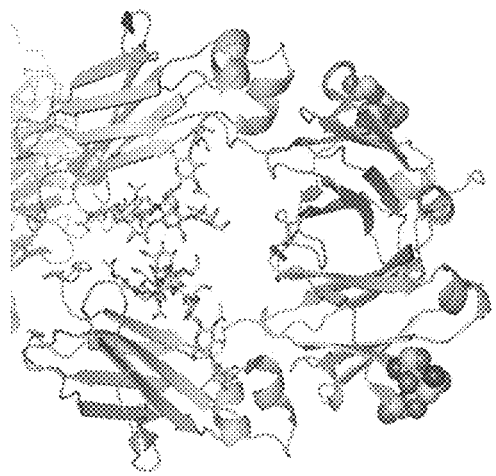
Figure 2A:
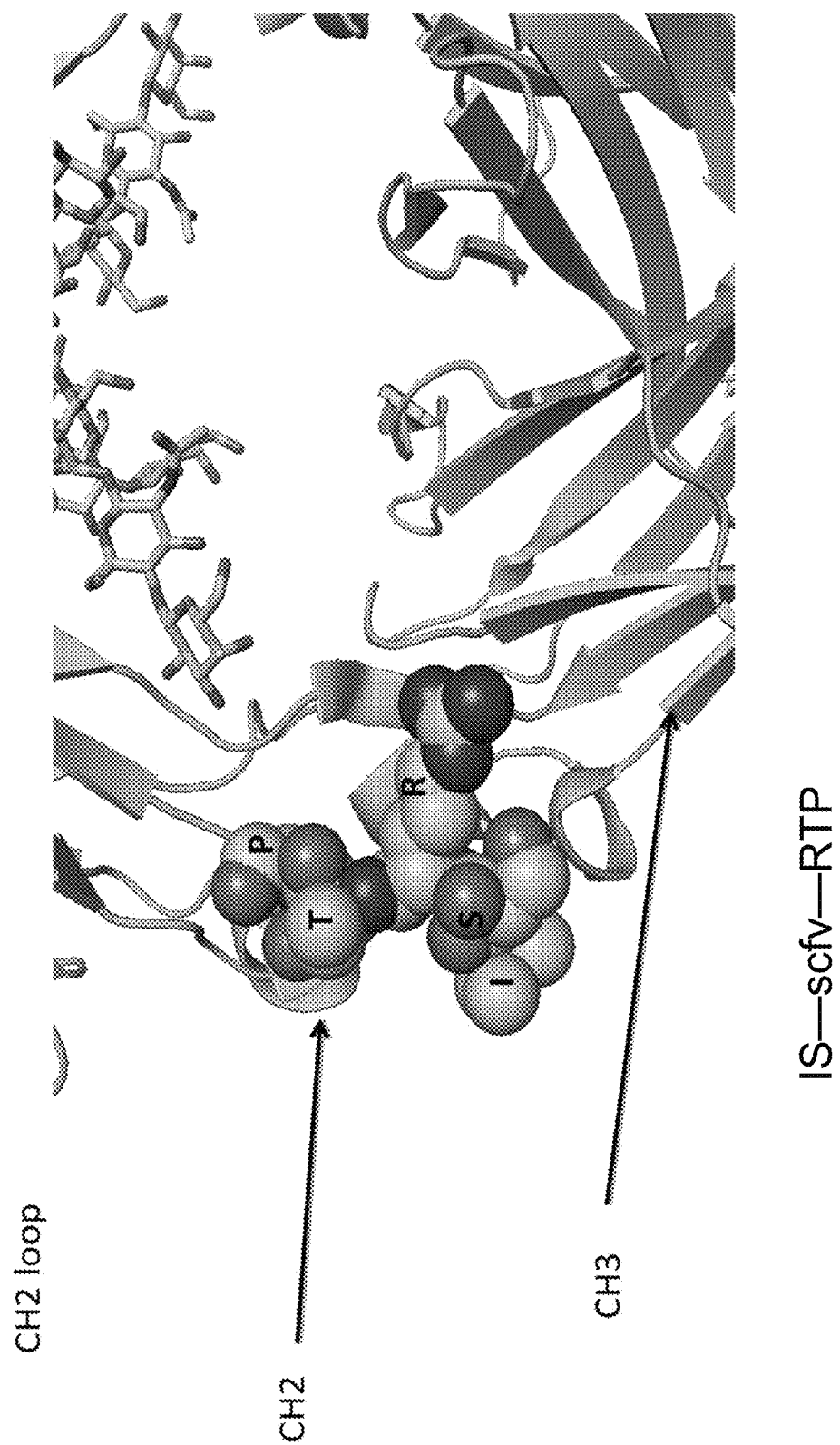
Figure 2B:
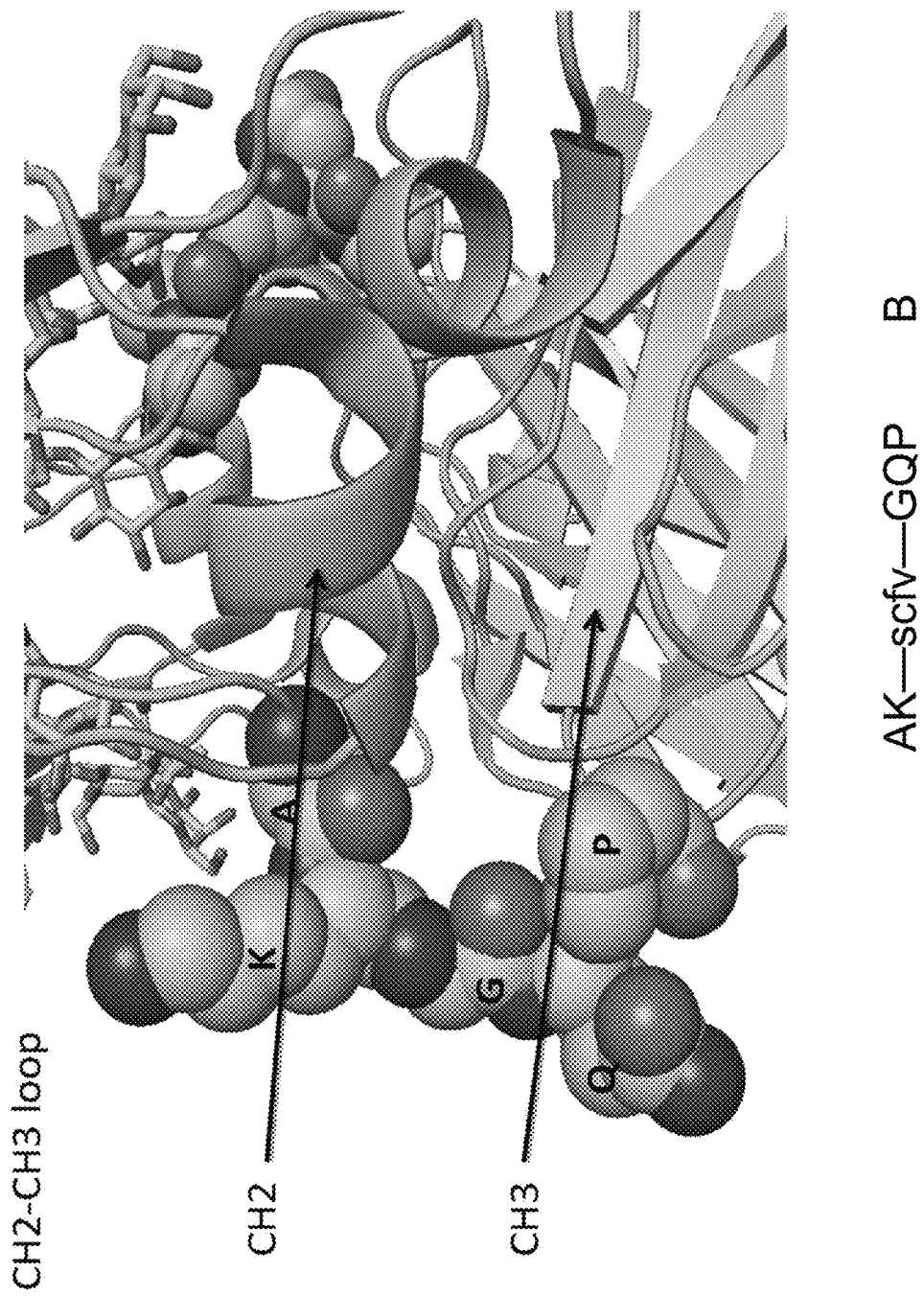

In one aspect the disclosure provides BiSAb binding proteins having a structural platform comprising domains that are generally illustrated by the schematic diagrams in FIGS. 1A-1F. These diagrams are illustrative and thus insertion between additional residues is also within the scope of the disclosed binding proteins. FIGS. 1A-1C depict the Fc region of an antibody at the CH2-CH3 interface of an IgG1 that was modeled using PyMOL, and illustrates several exemplary BiSAbs of the disclosure. Three surface exposed loops were identified at or near the CH2-CH3 interface that were likely able to withstand the insertion of a second binding moiety (e.g., an scFv) without compromising the structural integrity or stability of the IgG or second binding moiety. FIG. 1A is a schematic diagram of one such representative loop ISRTP (SEQ ID NO:39) identified in the CH2 region near at the CH2-CH3 interface. FIG. 1D also shows a representative construct IS-scFv-RTP, wherein a scFv is inserted between S and R of the ISRTP loop. FIG. 1B is a schematic diagram of the representative loop AKGQP (SEQ ID NO:40) identified at the CH2-CH3 interface. FIG. 1E shows a representative construct AK-scfv-GQP, wherein a scFv is inserted between K and G of the AKGQP loop. FIG. 1C is a schematic diagram of the representative loop SNG identified in the CH3 region downstream of the CH2-CH3 interface. FIG. 1F also shows the representative construct S-scfv-NG, wherein a scFv is inserted between S and N of the SNG loop. Examples herein provide illustration of constructs oriented as SN-scFv-G, wherein a scFv is inserted between N and G of the SNG loop.

Thus, one aspect of the disclosure relates to a BiSAb that comprises two identical heavy-light chain pairs, wherein each heavy-light chain pair is bispecific and the two identical pairs are together bivalent for each epitope. Each heavy-light chain pair comprises a binding domain (BD) that can comprise a Fab domain that binds a first epitope (binding unit 1), a second binding domain (BD2) that binds a second epitope (or binding unit 2 that may be, for example, an scFv) and an Fc region. In some embodiments the second binding domain may be associated with the Fab domain. In some embodiments the Fc region of the BiSAb may be associated with the second binding domain (BD2) that binds a second epitope (binding unit 2; depicted as an scFv in FIGS. 1D-1F).

In some embodiments the disclosure provides for a BiSAb having a general platform structure that comprises two chimeric heavy chains, each comprising a heavy chain variable region (VH1), a heavy chain constant region (CH1), a hinge or polypeptide linker region, an Fc region comprising a CH2 domain and a CH3 domain, wherein a second binding domain (BD2), optionally flanked on one or both sides by a polypeptide linker (L1 and/or L2) is associated with solvent exposed loops in the Fc region in the sequence of (i) the CH2 region, (ii) the interface of the CH2 and CH3 region, or (iii) the CH3 region. The BiSAb of this aspect of the disclosure also comprises two conventional antibody light chains, each comprising a light chain variable region (VL1) and light chain constant region (CL), which forms part of the first binding domain (BD1). The binding domain (BD2) of the particular BiSAb illustrated in FIGS. 1D-1F is an scFv.

FIGS. 1D-1F provide a useful schematic representation of a BiSAb, which may also be referred to herein as a BiSAb "core". The polypeptide chain, as shown in FIG. 1D, comprises a heavy chain having: a VH1 domain, a CH1 domain, a hinge/linker, a partial N-terminal CH2 domain, an optional linker (referred to herein as L1 or a first polypeptide linker), binding unit 2 (such as VL2 and VH2 of an scFv), another optional linker (e.g., L2 or a second polypeptide linker), the remaining C-terminal CH2 domain, and a CH3 domain. Because this heavy chain may include BD2 having alternative binding proteins and/or traditional light chain regions, it is referred to herein as a chimeric heavy chain. A BiSAb comprises two such chimeric heavy chains, and these may be the same or different. Note that the variable heavy chain domain (VH) for binding unit 1 is referred to as VH1. In certain aspects, this is a variable heavy chain of a Fab that binds to a first epitope. Similarly, the variable light chain domain (VL) for binding unit 1 is referred to as VL1. In certain aspects, this is a variable light chain of a Fab that binds to a first epitope. In contrast, the domains for binding unit two are denoted with the number "2", such as VH2 and VL2 for aspects in which binding unit 2 is an scFv that binds to a second epitope.

Similarly, the polypeptide chain, as shown in FIG. 1E, comprises a heavy chain having: a VH1 domain, a CH1 domain, a hinge/linker, a CH2 domain, an optional linker (referred to herein as L1 or a first polypeptide linker), binding unit 2 (such as VL2 and VH2 of an scFv), another optional linker (e.g., L2 or a second polypeptide linker), and a CH3 domain. In this embodiment the BiSAb comprises a second binding domain, illustrated as scFv associated with the Fc at the sequence at the interface of the CH2 and CH3 regions.

The polypeptide chain, as shown in FIG. 1F, comprises a heavy chain having: a VH1 domain, a CH1 domain, a hinge/linker, a CH2 domain, a partial CH3 domain, an optional linker (referred to herein as L1 or a first polypeptide linker), binding unit 2 (such as VL2 and VH2 of an scFv), another optional linker (e.g., L2 or a second polypeptide linker), the CH3 domain.

In these embodiments the BiSAbs typically include a typical or modified antibody hinge region in the chimeric heavy chain sequences. Non-limiting examples of amino acid sequences that contain a hinge region include: EPKSCDKTHTCPPCP (SEQ ID NO:44); EPKSCDKT (SEQ ID NO:45); EPKSCGKT (SEQ ID NO:46); EPKSC (SEQ ID NO:47).

Having described the general format for the aspects relating to the particular structural platform for certain BiSAb molecules disclosed herein, the various portions and exemplary functional properties of the disclosed BiSAbs are described in greater detail below. In other embodiments, the disclosure contemplates and provides other BiSAb binding proteins that comprise alternative structural formats and arrangements which are described briefly herein as well as in other disclosures (see, e.g., US Publication No. 20090155275 and U.S. Pat. No. 9,580,509) each of which are incorporated herein by reference.

1. Binding Units

BiSAbs of the disclosure comprise at least two binding units or binding domains (binding unit/domain 1 and binding unit/domain 2). In certain aspects each binding unit binds to a different epitope, either different epitopes located on the same target molecule or epitopes on different targets. Because each binding unit of a BiSAb is present as a pair (there are two binding unit 1s and two binding unit 2s) BiSAbs exhibit bivalent binding to each epitope. It will be understood from the teachings herein, that where each binding unit binds the same epitope a BiSAb will exhibit tetravalent binding to the epitope.

In certain aspects, the first binding unit is a Fab fragment, for example, a Fab fragment of a conventional monoclonal antibody or a recombinantly produced antigen binding fragment comprising a variable light chain (VL1), a constant light chain (CL), a variable heavy chain (VH1), and a constant heavy chain portion (CH1). Optionally, the light and heavy chains of the Fab may be interconnected via one or more disulfide linkages such as, for example, via a suitable antibody hinge region. The Fab binds to a first epitope.

In certain aspects, the Fab is derived from or based on the sequence of a conventional monoclonal antibody, such as a conventional murine, humanized, or human antibody. In certain aspects, BiSAb containing the Fab derived from or based on the sequence of a conventional monoclonal antibody retains one or more functional activities of the conventional antibody (e.g., retains at least 80% or more (80%, 85%, 90%, 95%, 97%, 98%, 99% or 100%) of a functional activity). For example, in certain aspects, the BiSAb containing such a Fab retains one or more of the affinity for antigen, inhibitory activity, immune system modulation activity, activation or induction of an immune response, and/or cell (e.g., cancer cell) killing activity of the conventional antibody.

In certain aspects, BiSAbs of the disclosure comprise binding unit 2 and binding unit 2 comprises a binding domain that binds a second epitope. The binding unit 2 (or binding domain 2 (BD2)) may be associated with the BiSAb using any suitable strategy. As used herein a BD2 that is "associated" with the BiSAb (e.g., within the Fc region in some embodiments, within the Fab region in other embodiments) means that the two molecules have an interaction between them such that the BD2 retains orientation for target binding and association with the Fc portion or with the Fab portion of the BiSAb structure. Examples of such interactions include covalent bonding via an amino acid linkers, covalent bonding through recombinant expression of BD2 within the Fab region, within the hinge region, or within the Fc region at the CH2, CH3, or interface of CH2 and CH3, or the CH4 region, and non-covalent interactions such as van der Waals and hydrogen bonding interactions within those same regions. Non-limiting examples of binding domains (or "BDs" or "binding units") falling within the scope of the disclosure include antibody variable regions, antibody fragments, scFvs, single chain diabodies, or other binding domains known in the art. Binding domains also include bispecific single chain diabodies, or single chain diabodies designed to bind two distinct epitopes In one aspect, epitope binding domains useful in the construction of multispecific epitope binding domains of the disclosure are exemplified in US20100298541 and US20130079280 which are hereby incorporated by reference for all purposes.

In certain aspects, the BiSAb can comprise a binding domain that includes an scFv. Thus, in certain aspects, binding unit 2 comprises an scFv. It is to be understood that an scFv encompasses a polypeptide chain comprising a variable heavy chain domain (VH) linked to a variable light chain domain (VL) via a flexible polypeptide linker. FIGS. 1D-1F show a schematic of an exemplary BiSAb, wherein the BD (here, depicted as binding unit 2) is an scFv having domains as described herein that may be designated as VL2 and VH2. In some aspects the polypeptide linker between VH2 and VL2 comprises a protease cleavage site. The VH and VL domains of the scFv may be derived from the same or from different antibodies. In some aspects, a VH or VL of the scFv may comprise one or more CDRs which bind to a target of interest, while the remainder of the VH or VL domain is derived from a different antibody or is synthetic. In some aspects, the scFv comprises at least one CDR of an antibody, e.g., an antibody known in the art to bind to a target of interest. In some aspects, the scFv comprises at least two CDRs of a given antibody. In some aspects, the scFv comprises at least three CDRs of a given antibody. In some aspects, the scFv comprises at least four CDRs of a given antibody. In some aspects, the scFv comprises at least five CDRs of a given antibody. In some aspects, the scFv comprises at least six CDRs of a given antibody.

In certain aspects, the BD may comprise a ligand binding domain of a receptor or a receptor binding domain of a ligand. In some aspects the BD comprises a sequence that has binding affinity for one or more epitopes on a target selected from the group consisting of CTLA-4, PD-1, PD-L1, OX40, and TIM3, as described above. In some embodiments the binding domain exhibits specific binding activity for a target selected from the group consisting of CTLA-4, PD-1, PD-L1, OX40, and TIM3. The BiSAbs disclosed herein can comprise any combination of binding domains that have binding affinity or specific binding activity for the molecular targets disclosed herein. For example the BiSAbs disclosed herein may comprise a combination of binding domains that allow for bispecific binding to targets including; CTLA-4 and PD-1; CTLA-4 and PD-L1; CTLA-4 and TIM3; PD-1 and PD-L1; PD-L1 and OX40; PD-1 and TIM3; PD-L1 and TIM3; and TIM3. BiSAbs that include binding domains that bind particular target combinations are illustrated in the Examples and include the non-limiting combinations of PD-1/CTLA-4; PD-L1/CTLA-4; PD-1/OX40; PD-L1/OX40; and PD-1/TIM3.

In some further embodiments, the BiSAbs exhibit a binding activity (e.g., binding affinity and/or binding specificity) for at least one of the target molecules that is greater the binding activity of the parental monospecific binding sequence used to generate the BiSAb. In similar embodiments, the BiSAbs can exhibit a binding activity (e.g., binding affinity and/or binding specificity) for both of the target molecules that is greater than the binding activity of both of the parental monospecific binding sequences used to generate the BiSAbs. In yet a further embodiment, the BiSAbs can exhibit a binding activity (e.g., binding affinity and/or binding specificity) for both of the target molecules that is greater than the binding activity for the combination of the parental monospecific binding sequences used to generate the BiSAbs. The enhancement of the binding properties of the BiSAbs relative to the parental monospecific binding sequences, either alone or in combination, provide unexpected advantages relative to the use of monospecific therapeutics that target the same molecules, even when used in combination.

In some embodiments the disclosure relates an antibody, or antigen binding fragment thereof, that binds to a target selected from the group consisting of CTLA-4, PD-1, PD-L1, OX40, and TIM3. In such embodiments the antibody, or antigen binding fragment thereof, may comprise a heavy chain sequence and a light chain sequence, or a portion of a heavy chain sequence and a light chain sequence that comprises the CDR1, CDR2, and CDR3 sequences of the heavy and the light chain sequences. In other embodiments the antibody, or antigen binding fragment thereof, may comprise a heavy chain variable (HCv) region sequence and a light chain variable (LCv) region sequence, or a portion of a HCv and a LCv that comprises the CDR1, CDR2, and CDR3 sequences of the heavy and the light chain sequences. In yet other embodiments the antibody, or antigen binding fragment thereof, may comprise the CDR1, CDR2, and CDR3 sequences of the heavy and the light chain sequences. In some embodiments the antibody may be a chimeric, a humanized, or a human antibody. In some embodiments the antibody may be a polyclonal or a monoclonal antibody. In further embodiments, the antibody is a monoclonal antibody.

In some embodiments, domains that comprise all or a portion of an antigen binding region of such "parental" antibodies as discussed above may be used to generate the bispecific binding proteins (BiSAbs) that are disclosed herein. The non-limiting embodiments that are illustrated in the Examples provide a description relating to how antibody sequences may be identified and combined to produce a BiSAb that exhibits bispecific binding to a combination of molecular targets.

Several methodologies can be used alone or in combination to improve the stability of a BiSAb comprising an scFv molecule. One potential methodology that can be used, alone or in combination with one or more of the other methodologies described herein, is engineered the length and/or composition of the linker connecting the scFv domains to stabilize the scFv portion.

Another potential methodology that can be used is to introduce at least two amino acid substitutions (also referred to as modifications or mutations) into the VH and/or VL domains of the scFv so as to promote disulfide bond formation (see for example Brinkmann et al., 1993, PNAS, 90:7538-42; Zhu et al., 1997, Prot. Sci. 6:781-8; Reiter et al., 1994, Biochem. 33:5451-9; Reiter et al., 1996, Nature 14: 1239-45; Luo et al., 1995, J. Biochem. 118:825-31; Young et al., 1995, FEBS Let. 377:135-9; Glockshuber et al., 1990, Biochem. 29:1362-7). This method can be used alone or in combination with one or more of the other methodologies described herein.

In certain aspects, one or more mutations can be introduced into each of the VH and VL domains of the scFv to promote interchain disulfide bond formation between the VH and VL domains upon expression of a BiSAb comprising an scFv. In another aspect, the two mutations are introduced in the same domain of the chain. In a certain aspect, the two mutations are introduced in different chains. In certain aspects, multiple complementary mutations are introduced to promote formation of multiple disulfide bonds or other stabilizing interactions. In certain aspects, a cysteine is introduced to promote the disulfide bond formation. Exemplary amino acids that may be mutated to cysteine include amino acids 43, 44, 45, 46, 47, 103, 104, 105, and 106 of VH2 and amino acids 42, 43, 44, 45, 46, 98, 99, 100, and 101 of VL2. The foregoing numbering is based on Kabat numbering identifying the position relative only to the VH2 and VL2 of the scFv (and not relative to the position of the amino acid in the full length sequence of the BiSAb or SEQ ID NOs provided herein). Exemplary combinations of amino acid positions which may be mutated to cysteine residues include: VH44-VL100, VH105-VL43, VH105-VL42, VH44-VL101, VH106-VL43, VH104-VL43, VH44-VL99, VH45-VL98, VH46-VL98, VH103-VL43, VH103-VL44, and VH103-VL45. In some aspects, amino acid 44 of VH and amino acid 100 of VL are mutated to cysteines.

Another method that can be used, alone or in combination with one or more of the other methods described herein, is selecting the order of the domains of the scFv. In certain aspects, the orientation of the VH domain relative to the VL domain is optimized for stability. In certain aspects, the scFv is in the VH-linker-VL orientation. In certain aspects, the scFv is in the VL-linker-VH orientation. In embodiments relating to the novel BiSAb format disclosed herein, the orientation of the domains in the scFv can determine how the scFv associates with the Fc portion of the BiSAb. While this is described in more detail below in the context of polypeptide linkers. Briefly, however, given that the BD (e.g., an scFv) is interconnected to the CH2, CH3, or at the interface of CH2 and CH3 by optional polypeptide linkers (L1) and (L2), the order of domains determines which portion of the scFv is interconnected to L1 and which portion of the scFv is interconnected to L2.

A further method that can be used, alone or in combination with the other methods described herein, is to introduce one or more stabilizing mutations by mutating one or more surface residues of the scFv. In some aspects, one, two, three, four, five, six, or more than six residues are mutated in one or both of the VH and/or VL domain of the scFv. In certain aspects, changes are made in only the VH domain of the scFv. In certain aspects, changes are made in only the VL domain of the scFv. In certain aspects, changes are made in both the VH and VL domains of the scFv. The same number of changes may be made in each domain or a different number of changes may be made in each domain. In certain aspects, one or more of the changes is a conservative amino acid substitution from the residue present in the unmodified, parent scFv. In other aspects, one or more of the changes is a non-conservative amino acid substitution from the residue present in the unmodified, parent scFv. When multiple substitutions are made, either in one or both of the VH or VL domains of the scFv, each substitution is independently a conservative or a non-conservative substitution. In certain aspects, all of the substitutions are conservative substitutions. In certain aspects, all of the substitutions are non-conservative. In certain aspects, at least one of the substitutions is conservative. In certain aspects, at least one or the substitutions is non-conservative.

Yet another method that can be used, on its own or in combination with other methods, is to introduce one or more amino acid substitutions by mutating one or more residues present in the VH and/or VL domain of the scFv to match the most frequent residue at said particular position of a consensus sequence of VH and/or VL domain of known antibodies. In certain aspects, substitutions are introduced at one, two, three, four, five, six, or more than six positions in one or both of the VH domain and/or the VL domain of the scFv. The same number of changes may be made in each domain or a different number of changes may be made in each domain. In certain aspects, one or more of the changes in sequence match that of a given consensus is a conservative amino acid substitution from the residue present in the unmodified VH and/or VL sequence. In other aspects, one or more of the changes represent a non-conservative amino acid substitution from the residue present in the unmodified VH and/or VL sequence. When multiple substitutions are made, either in one or both of the VH or VL domain of the scFv, each substitution is independently a conservative or a non-conservative substitution. In certain aspects, all of the substitutions are conservative substitutions. In certain aspects, all of the substitutions are non-conservative substitutions. In certain aspects, at least one of the substitutions is conservative. In certain aspects, at least one or the substitutions is non-conservative.

It should be noted that any of the modifications described as useful for modifying or stabilizing the scFv portion can be applied to modify the Fab portion. For example, the variable domains of the Fab portion of a BiSAb can be modified to improve stability, antigen binding and the like. Moreover, either the Fab or scFv portion can be modified to reduce immunogenicity.

In certain aspects, binding unit 2 (the BD) is an scFv, for example, an scFv derived from a conventional monoclonal antibody comprising a variable light chain (VL2) and a variable heavy chain (VH2) interconnected by a flexible linker, such as a glycine-serine linker. Optionally, the variable light and variable heavy chains of the scFv may be further interconnected via one or more disulfide linkages, and as described above, may include one or more mutations or variations. The scFv binds to a second epitope. In certain aspects the second epitope is different from the first epitope bound by binding unit 1. In other aspects the second epitope is the same as the first epitope bound by binding unit 1. In certain aspects, the scFv is derived from or based on the sequence of a conventional monoclonal antibody, such as a conventional murine, humanized or human antibody. In certain aspects, BiSAb containing the scFv derived from or based on the sequence of a conventional monoclonal antibody retains one or more functional activities of the conventional antibody (e.g., retains at least 80% or more (80%, 85%, 90%, 95%, 97%, 98%, 99% or 100%) of a functional activity). For example, in certain aspects, the BiSAb containing such an scFv retains one or more of the affinity for antigen, inhibitory activity, or cell killing activity of the conventional antibody.

In certain aspects a BiSAb comprises any of the binding unit 1s and binding unit 2s described herein, including any combination of a binding unit 1 and a binding unit 2. For example, in certain aspects, the disclosure provides a polypeptide comprising a Fab that binds to a particular target (e.g., that binds to an epitope on a particular target), such as a Fab comprising a particular amino acid sequence or encoded by a particular nucleotide sequence and/or an scFv that binds to a particular target (e.g., that binds to an epitope on a particular target), such as an scFv comprising a particular amino acid sequence or encoded by a particular nucleotide sequence.

As described in detail above, binding unit 1 and binding unit 2 may be associated with the BiSAb via covalent bonding via a linker polypeptide 1 (L1, L2). Generally, the linkage is via the chimeric heavy chain of the BiSAb, such that the interconnection is via the heavy chain $C_H2$ domain, the heavy chain $C_H3$ domain, or at the interface of the heavy chain $C_H2$ domain and $C_H3$ domain or, in some embodiments, within the hinge region or Fab domain. L1 and L2 can vary in length and sequence independently from each other, and exemplary configurations are described herein. The disclosure contemplates BiSAbs comprising any combination of binding units and linker polypeptides, including any combination of the specific binding units that bind desired target(s) and specific L1 and L2 polypeptide linkers described herein.

2. Fc Region

As used herein, "Fc region" encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes such as IgA, IgD, IgE and IgM. The Fc region may be a native sequence Fc region or an altered Fc region. The Fc region of an immunoglobulin generally comprises two constant domains, a $C_H2$ domain and a $C_H3$ domain, and optionally comprises a $C_H4$ domain. BiSAbs of the disclosure include an Fc region comprising a $C_H2$ domain and a $C_H3$ domain.

a. Altered Fc Regions

Altered Fc regions (also referred to herein as "variant Fc regions") may be used to alter the effector function and/or half-life of a BiSAb of the disclosure. One or more alterations may be made in the Fc region in order to change functional and/or pharmacokinetic properties of molecules. Such alterations may result in a decrease or increase of C1q binding and complement dependent cytotoxicity (CDC) or of FcγR binding, for IgG, and antibody-dependent cellular cytotoxicity (ADCC), or antibody dependent cell-mediated phagocytosis (ADCP). The present disclosure encompasses BiSAbs wherein changes have been made to fine tune the effector function, either by enhancing or diminishing function or providing a desired effector function. Accordingly, in one aspect of the disclosure, the BiSAbs comprise a variant Fc region (i.e., Fc regions that have been altered as discussed below). BiSAbs comprising a variant Fc region are also referred to here as "Fc variant BiSAbs." As used herein "native" refers to the unmodified parental sequence and the BiSAb comprising a native Fc region is herein referred to as a "native Fc BiSAb". Fc variant BiSAbs can be generated by numerous methods well known to one skilled in the art. Non-limiting examples include, isolating antibody coding regions (e.g., from hybridoma) and making one or more desired substitutions in the Fc region. Alternatively, the antigen-binding portion (e.g., variable regions) of a BiSAb may be subcloned into a vector encoding a variant Fc region. In one aspect, the variant Fc region exhibits a similar level of inducing effector function as compared to the native Fc region. In another aspect, the variant Fc region exhibits a higher induction of effector function as compared to the native Fc. In another aspect, the variant Fc region exhibits lower induction of effector function as compared to the native Fc. Some specific aspects of variant Fc regions are detailed infra. Methods for measuring effector function are well known in the art.

In general, the effector function is modified through changes in the Fc region, including but not limited to, amino acid substitutions, amino acid additions, amino acid deletions and changes in post translational modifications to Fc amino acids (e.g. glycosylation). The methods described below may be used to fine tune the effector function of a BiSAb of the disclosure, a ratio of the binding properties of the Fc region for the FcR (e.g., affinity and specificity), resulting in a BiSAb with the desired properties.

It is understood that the Fc region as used herein includes the polypeptides comprising the constant region of an antibody molecule, excluding the first constant region immunoglobulin domain. Thus Fc refers to the last two constant region immunoglobulin domains of IgA, IgD, and IgG, and the last three constant region immunoglobulin domains of IgE and IgM, and, optionally, all or a portion of the flexible hinge N-terminal to these domains. For IgA and IgM, Fc may include the J chain. For IgG, Fc comprises immunoglobulin domains Cgamma2 and Cgamma3 (Cγ2 and Cγ3) and optionally a portion of the lower hinge between Cgamma1 (Cγ1) and Cgamma2 (Cγ2). Although the boundaries of the Fc region may vary, as used herein the human IgG heavy chain Fc region comprises residues A231 to its carboxyl-terminus, wherein the numbering is according to the EU index as set forth in Kabat. Fc may refer to this region in isolation, or this region in the context of an antibody, antibody fragment, or Fc fusion protein. Polymorphisms have been observed at a number of different Fc positions, including but not limited to positions 270, 272, 312, 315, 356, and 358 of IgG1 as numbered by the EU index, and thus slight differences between the presented sequence and sequences in the prior art may exist.

In one aspect, the present disclosure encompasses Fc variant BiSAbs which have altered binding properties for an Fc ligand (e.g., an Fc receptor, C1q) relative to a native Fc BiSAb. Examples of binding properties include but are not limited to, binding specificity, equilibrium dissociation constant ($K_d$), dissociation and association rates ($k_{off}$ and $k_{on}$ respectively), binding affinity and/or avidity. It is known in the art that the equilibrium dissociation constant ($K_d$) is defined as $k_{off}/k_{on}$. In certain aspects, a BiSAb comprising an Fc variant region with a low $K_d$ may be more desirable than a BiSAb with a high $K_d$. However, in some instances the value of the $k_{on}$ or $k_{off}$ may be more relevant than the value of the $K_d$. One skilled in the art can determine which kinetic parameter is most important for a given application. For example, a modification that reduces binding to one or more positive regulator (e.g., FcγRIIIA) and/or enhanced binding to an inhibitory Fc receptor (e.g., FcγRIIB) would be suitable for reducing ADCC activity. Accordingly, the ratio of binding affinities (e.g., the ratio of equilibrium dissociation constants ($K_d$)) for different receptors can indicate if the ADCC activity of an Fc variant BiSAb of the disclosure is enhanced or decreased. Additionally, a modification that reduces binding to C1q would be suitable for reducing or eliminating CDC activity.

In one aspect, Fc variant BiSAbs exhibit altered binding affinity for one or more Fc receptors including, but not limited to FcRn, FcγRI (CD64) including isoforms FcγRIA, FcγRIB, and FcγRIC; FcγRII (CD32 including isoforms FcγRIIA, FcγRIIB, and FcγRIIC); and FcγRIII (CD16, including isoforms FcγRIIIA and FcγRIIIB) as compared to a native Fc BiSAb.

In certain aspects, an Fc variant BiSAb has increased affinity for an Fc ligand. In other aspects, an Fc variant BiSAb has decreased affinity for an Fc ligand relative to a native Fc BiSAb.

In a specific aspect, an Fc variant BiSAb has enhanced binding to the Fc receptor FcγRIIIA In another specific aspect, an Fc variant BiSAb has enhanced binding to the Fc receptor FcγRIIB In a further specific aspect, an Fc variant BiSAb has enhanced binding to both the Fc receptors FcγRIIIA and FcγRIIB In certain aspects, Fc variant BiSAbs that have enhanced binding to FcγRIIIA do not have a concomitant increase in binding the FcγRIIB receptor as compared to a native Fc BiSAb. In a specific aspect, an Fc variant BiSAb has reduced binding to the Fc receptor FcγRIIIA In a further specific aspect, an Fc variant BiSAb has reduced binding to the Fc receptor FcγRIIB In another specific aspect, and Fc variant BiSAb has enhanced binding to the Fc receptor FcRn. In still another specific aspect, an Fc variant BiSAb exhibiting altered affinity for FcγRIIIA and/or FcγRIIB has enhanced binding to the Fc receptor FcRn. In yet another specific aspect, an Fc variant BiSAb exhibiting altered affinity for FcγRIIIA and/or FcγRIIB has altered binding to C1q relative to a native Fc BiSAb.

In another aspect, Fc variant BiSAbs exhibit increased or decreased affinities to C1q relative to a native Fc BiSAb. In still another specific aspect, an Fc variant BiSAb exhibiting altered affinity for C1q has enhanced binding to the Fc receptor FcRn. In yet another specific aspect, an Fc variant BiSAb exhibiting altered affinity for C1q has altered binding to FcγRIIIA and/or FcγRIIB relative to a native Fc BiSAb.

It is recognized that antibodies are capable of directing the attack and destruction of targeted antigen through multiple processes collectively known in the art as antibody effector functions. One of these processes, known as "antibody-dependent cell-mediated cytotoxicity" or "ADCC" refers to a form of cytotoxicity in which secreted Ig bound onto Fc gamma receptors (FcγRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are required for such killing. Lysis of the target cell is extracellular, requires direct cell-to-cell contact, and does not involve complement. Another process encompassed by the term effector function is complement-dependent cytotoxicity (hereinafter referred to as "CDC") which refers to a biochemical event of antibody-mediated target cell destruction by the complement system. The complement system is a complex system of proteins found in normal blood plasma that combines with antibodies to destroy pathogenic bacteria and other foreign cells. Still another process encompassed by the term effector function is antibody dependent cell-mediated phagocytosis (ADCP) which refers to a cell-mediated reaction wherein nonspecific cytotoxic cells that express one or more effector ligands recognize bound antibody on a target cell and subsequently cause phagocytosis of the target cell.

It is contemplated that Fc variant BiSAbs are characterized by in vitro functional assays for determining one or more FcγR mediated effector cell functions. In certain aspects, Fc variant BiSAbs have similar binding properties and effector cell functions in in vivo models (such as those described and disclosed herein) as those in in vitro based assays. However, the present disclosure does not exclude Fc variant BiSAbs that do not exhibit the desired phenotype in in vitro based assays but do exhibit the desired phenotype in vivo.

The serum half-life of proteins comprising Fc regions may be increased by increasing the binding affinity of the Fc region for FcRn. The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body (or other mammal) or a specific compartment thereof, for example, as measured in serum, i.e., circulating half-life, or in other tissues. Half-life may vary from one immunoglobulin or class of immunoglobulin to another. In general, an increase in antibody (or BiSAb) half-life results in an increase in mean residence time (MRT) in circulation for the BiSAb administered.

The increase in half-life allows for the reduction in amount of drug given to a patient as well as reducing the frequency of administration. To increase the serum half-life of a BiSAb, one may incorporate a salvage receptor binding epitope into the BiSAb (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. Alternatively, BiSAbs of the disclosure with increased half-lives may be generated by modifying amino acid residues identified as involved in the interaction between the Fc and the FcRn receptor (see, for examples, U.S. Pat. Nos. 6,821,505 and 7,083,784). In addition, the half-life of BiSAbs of the disclosure may be increased by conjugation to PEG or albumin by techniques widely utilized in the art.

It is contemplated that either insertion of additional binding domains into the Fc region as described here and/or subsequent binding by antigen may affect Fc activity. For instance, binding antigen may increase or decrease binding affinity and activity for FcgRs, C1q, and FcRn. This would create an antigen-dependent switch to modulate various antibody-dependent processes. In one aspect, antigen binding may decrease interaction with FcRn, allowing a free BiSAb to interact with FcRn and have a normal half-life, but allow rapid clearance/cellular internalization of BiSAb-Ag complexes. Further, this could allow BD2-antigen mediated interactions to have an effect on the clearance of antigens bound by BD1. In an additional aspect, the BiSAb could comprise the Fc region directly inserted to BD2 (Fc-BD2).

Figure 8:
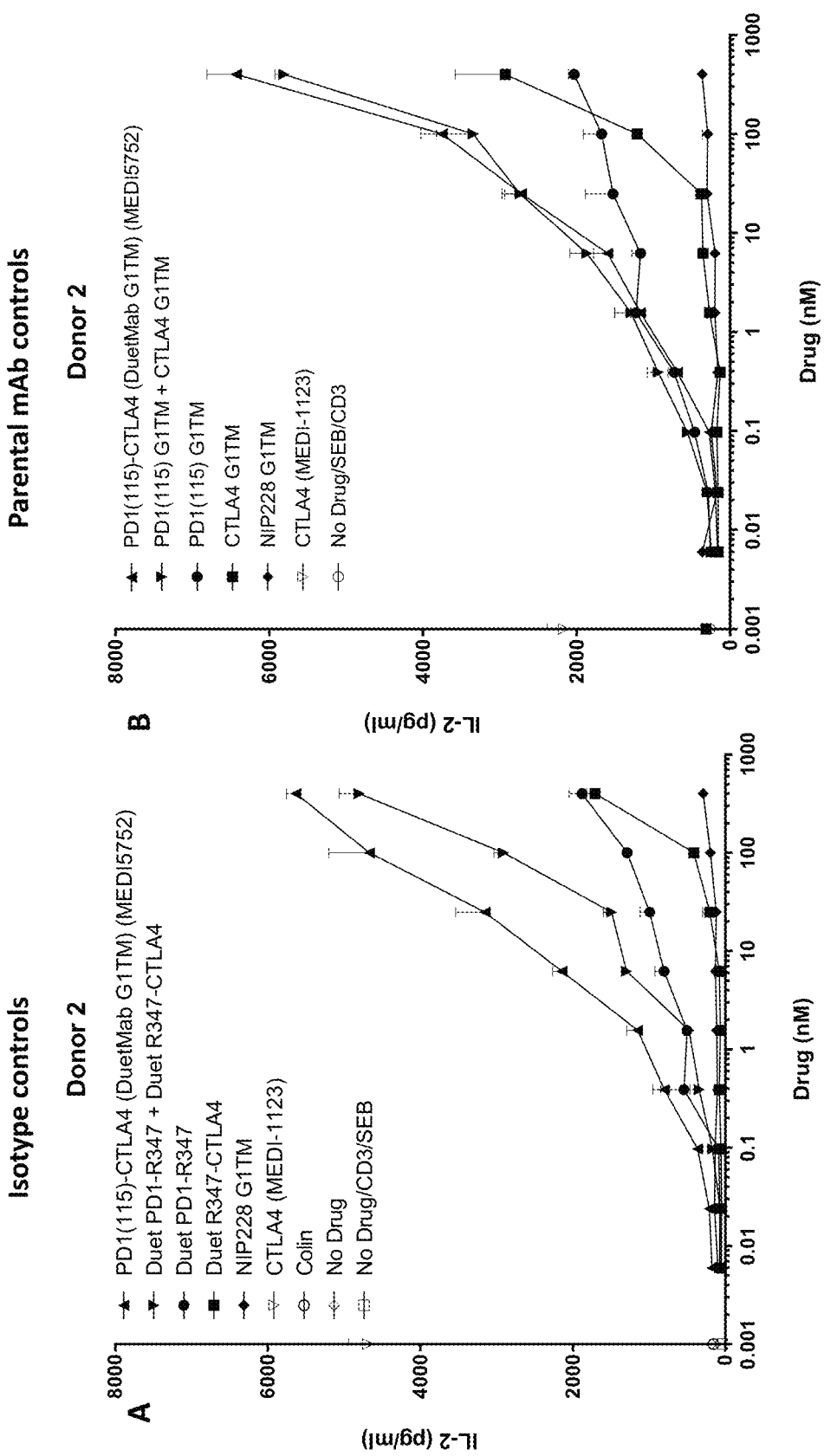
FIGS. 8A-B show the activity of PD-1/CTLA-4 DuetMab in SEB assays compared to isotype and parental mAb controls.
Figure 9:
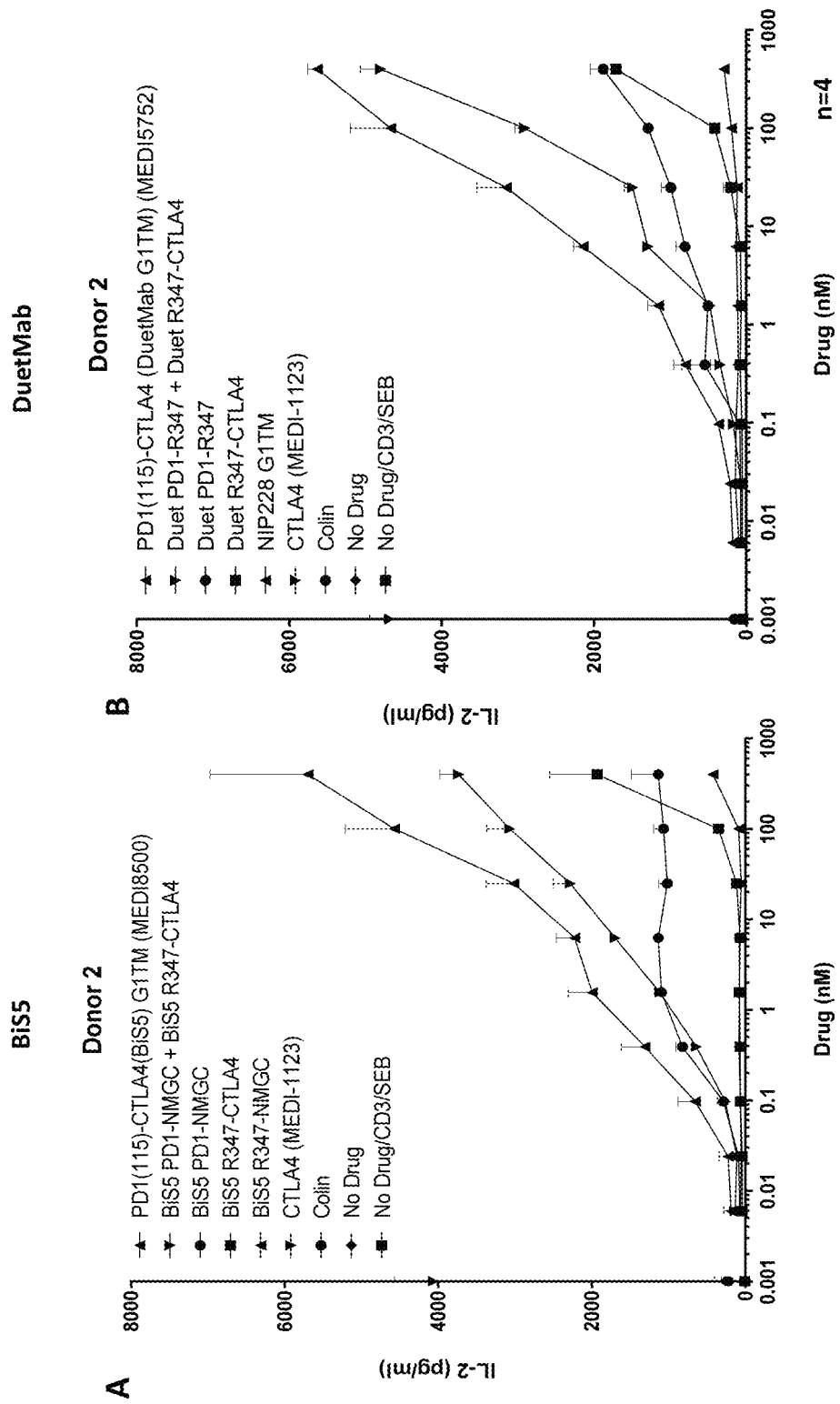
FIGS. 9A-B show activity of PD-1/CTLA-4 BiS5Ab compared to PD-1/CTLA-4 DuetMab in SEB assays.
Figure 12:
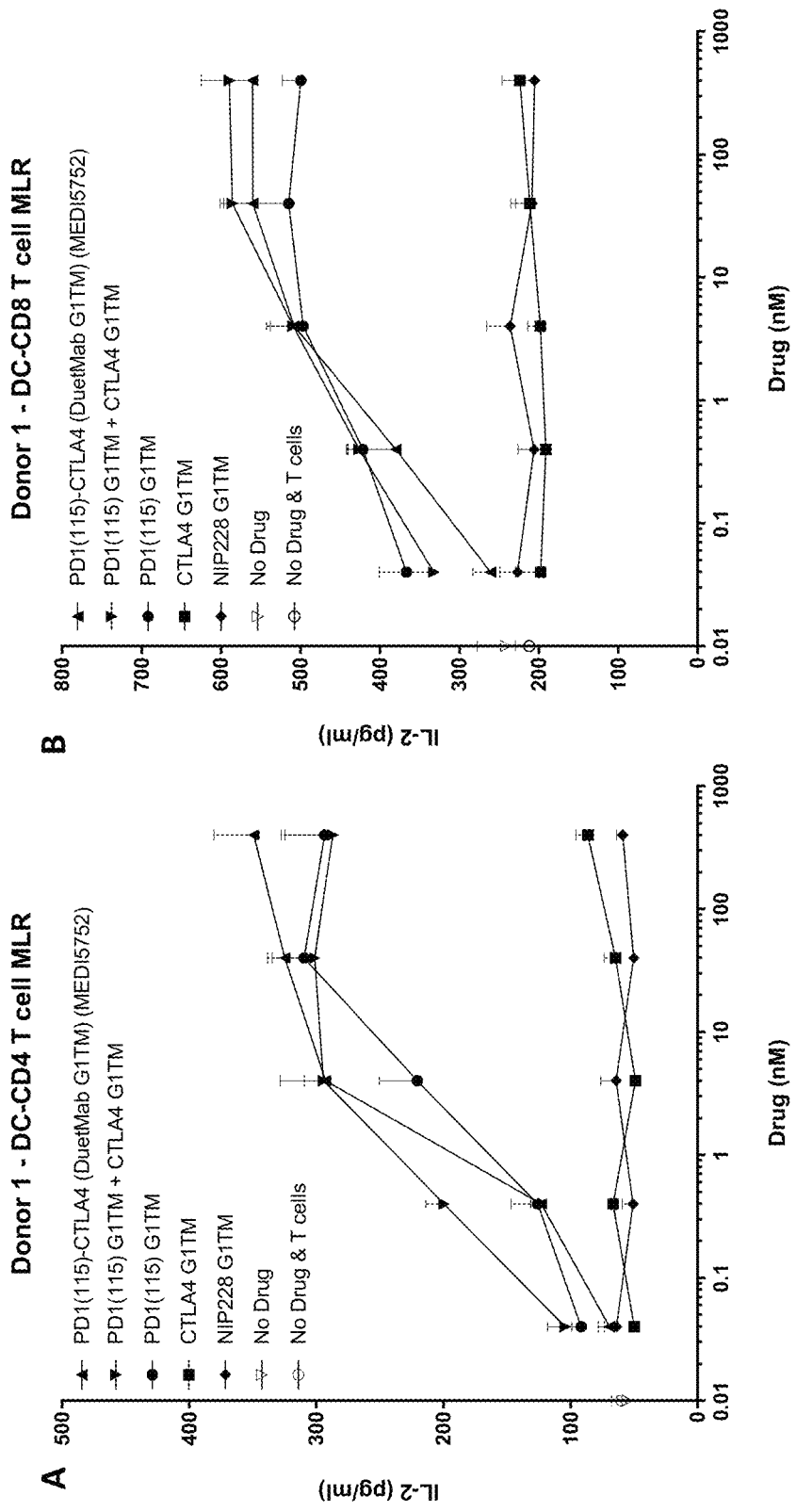
FIG. 12A-D show the activity of PD-1/CTLA-4 DuetMab in MLR assays compared to parental mAb controls (n=2 donors; 1 experiment).
Figure 12:
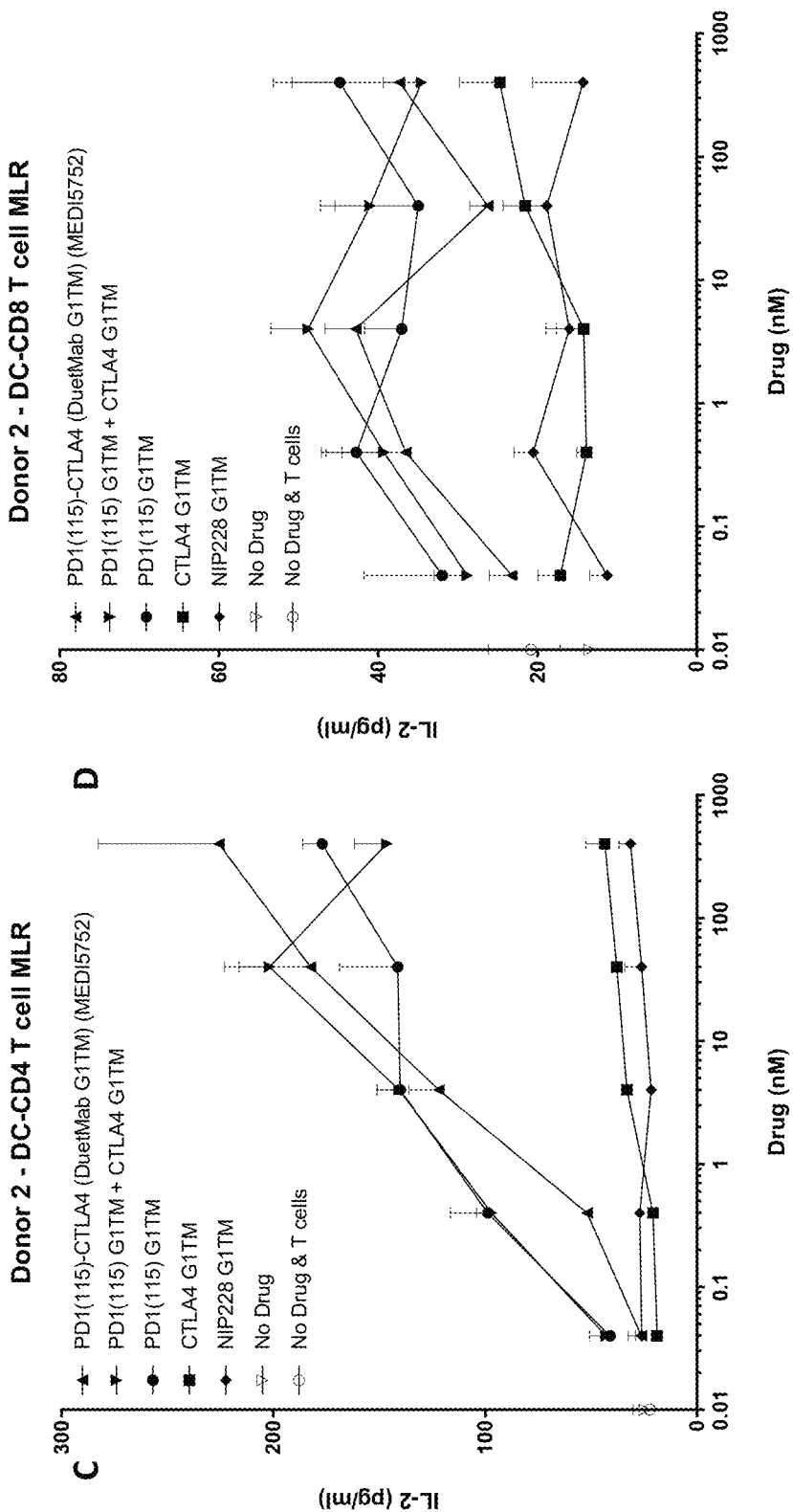
Figure 13:
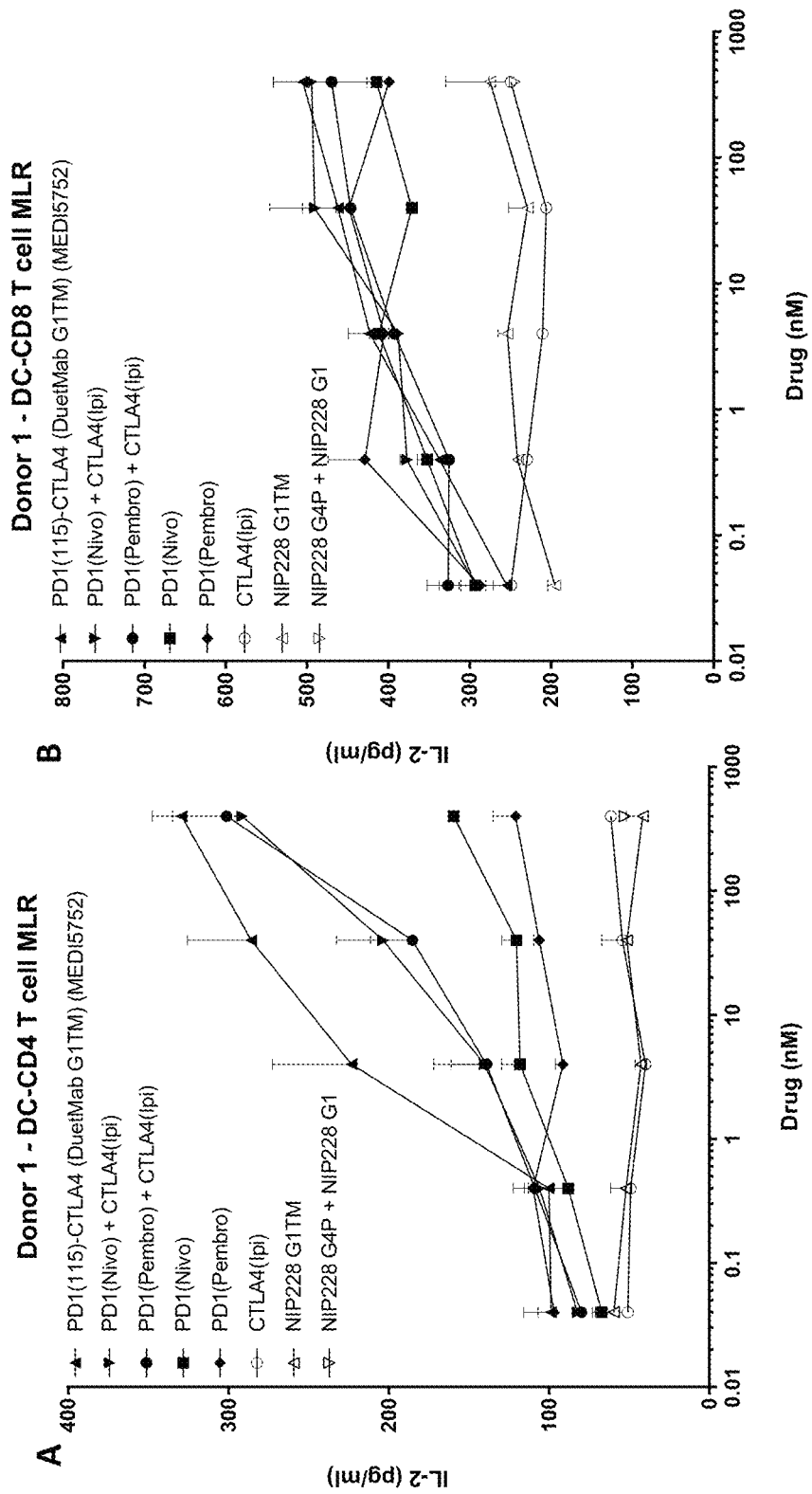
FIGS. 13A-D shows the activity of PD-1/CTLA-4 DuetMab in MLR assays compared to competitor antibodies (n=2 donors; 1 experiment).
Figure 13:
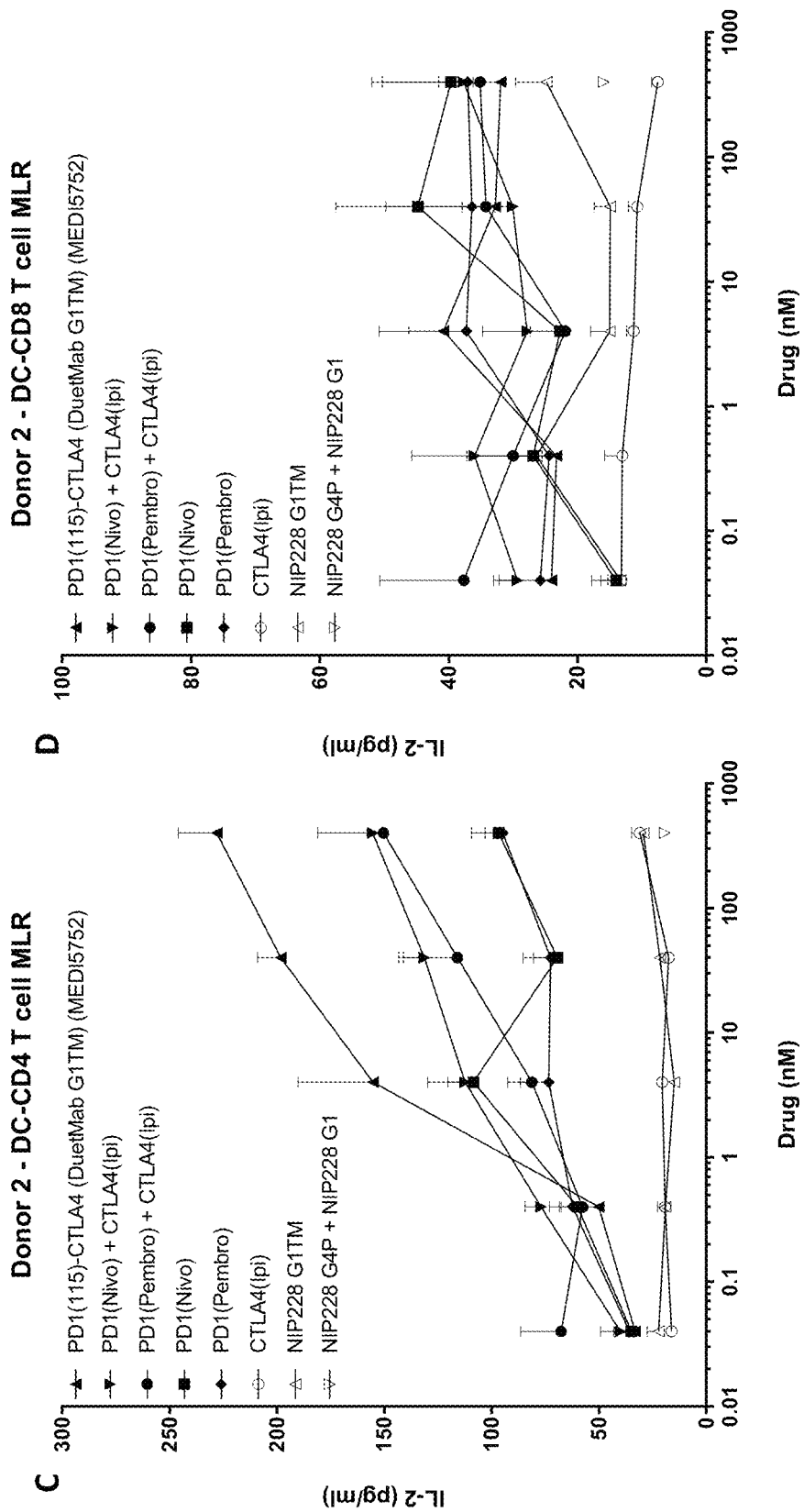

In one aspect, the present disclosure provides Fc variants, wherein the Fc region comprises a modification (e.g., amino acid substitutions, amino acid insertions, amino acid deletions) at one or more positions selected from the group consisting of 221, 225, 228, 234, 235, 236, 237, 238, 239, 240, 241, 243, 244, 245, 247, 250, 251, 252, 254, 255, 256, 257, 262, 263, 264, 265, 266, 267, 268, 269, 279, 280, 284, 292, 296, 297, 298, 299, 305, 308, 313, 316, 318, 320, 322, 325, 326, 327, 328, 329, 330, 331, 332, 333, 334, 339, 341, 343, 370, 373, 378, 392, 416, 419, 421, 428, 433, 434, 435, 436, 440, and 443 as numbered by the EU index as set forth in Kabat. Optionally, the Fc region may comprise a modification at additional and/or alternative positions known to one skilled in the art (see, e.g., U.S. Pat. Nos. 5,624,821; 6,277,375; 6,737,056; 7,083,784; 7,317,091; 7,217,797; 7,276,585; 7,355,008). Additional, useful amino acid positions and specific substitutions are exemplified in Tables 2, and 6-10 of U.S. Pat. No. 6,737,056; the tables presented in FIG. 41 of US 2006/024298; the tables presented in FIGS. 5, 12, and 15 of US 2006/235208; the tables presented in FIGS. 8, 9 and 10 of US 2006/0173170 and the tables presented in FIGS. 8-10, 13 and 14 of WO 09/058492.

In a specific aspect, the present disclosure provides an Fc variant, wherein the Fc region comprises at least one substitution selected from the group consisting of 221K, 221Y, 225E, 225K, 225W, 228P, 234D, 234E, 234N, 234Q, 234T, 234H, 234Y, 234I, 234V, 234F, 235A, 235D, 235R, 235P, 235S, 235N, 235Q, 235T, 235H, 235Y, 235I, 235V, 235E, 235F, 236E, 237L, 237M, 237P, 239D, 239E, 239N, 239Q, 239F, 239T, 239H, 239Y, 240I, 240A, 240T, 240M, 241W, 241L, 241Y, 241E, 241R. 243W, 243L 243Y, 243R, 243Q, 244H, 245A, 247L, 247V, 247G, 250E, 250Q, 251F, 252L, 252Y, 254S, 254T, 255L, 256E, 256F, 256M, 257C, 257M, 257N, 262I, 262A, 262T, 262E, 263I, 263A, 263T, 263M, 264L, 264I, 264W, 264T, 264R, 264F, 264M, 264Y, 264E, 265A, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 296G, 297S, 297D, 297E, 298A, 298H, 298I, 298T, 298F, 299I, 299L, 299A, 299S, 299V, 299H, 299F, 299E, 305I, 308F 313F, 316D, 318A, 318S, 320A, 320S, 322A, 322S, 325Q, 325L, 325I, 325D, 325E, 325A, 325T, 325V, 325H, 326A, 326D, 326E, 326G, 326M, 326V, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 333A, 333D, 333G, 333Q, 333S, 333V, 334A, 334E, 334H, 334L, 334M, 334Q, 334V, 334Y, 339T, 370E, 370N, 378D, 392T, 396L, 416G, 419H, 421K, 428L, 428F, 433K, 433L, 434A, 424F, 434W, 434Y, 436H, 440Y and 443W as numbered by the EU index as set forth in Kabat. Optionally, the Fc region may comprise additional and/or alternative amino acid substitutions known to one skilled in the art including, but not limited to, those exemplified in Tables 2, and 6-10 of U.S. Pat. No. 6,737,056; the tables presented in FIG. 41 of US 2006/024298; the tables presented in FIGS. 5, 12, and 15 of US 2006/235208; the tables presented in FIGS. 8, 9 and 10 of US 2006/0173170 and the tables presented in FIGS. 8, 9 and 10 of US20090041770, all of which are incorporated herein by reference.

In a specific aspect, the disclosure provides an Fc variant BiSAb, wherein the Fc region comprises at least one modification (e.g., amino acid substitutions, amino acid insertions, amino acid deletions) at one or more positions selected from the group consisting of 228, 234, 235 and 331 as numbered by the EU index as set forth in Kabat. In one aspect, the modification is at least one substitution selected from the group consisting of 228P, 234F, 235E, 235F, 235Y, and 331S as numbered by the EU index as set forth in Kabat.

In another specific aspect, the present disclosure provides an Fc variant BiSAb, wherein the Fc region is an IgG4 Fc region and comprises at least one modification at one or more positions selected from the group consisting of 228 and 235 as numbered by the EU index as set forth in Kabat. In still another specific aspect, the Fc region is an IgG4 Fc region and the non-naturally occurring amino acids are selected from the group consisting of 228P, 235E and 235Y as numbered by the EU index as set forth in Kabat.

In another specific aspect, the present disclosure provides an Fc variant BiSAb, wherein the Fc region comprises at least one non-naturally occurring amino acid at one or more positions selected from the group consisting of 239, 330 and 332 as numbered by the EU index as set forth in Kabat. In one aspect, the modification is at least one substitution selected from the group consisting of 239D, 330L, 330Y, and 332E as numbered by the EU index as set forth in Kabat. See, U.S. Pat. No. 7,317,091, incorporated herein by referenced in its entirety.

In a specific aspect, the present disclosure provides an Fc variant BiSAb, wherein the Fc region comprises at least one non-naturally occurring amino acid at one or more positions selected from the group consisting of 252, 254, and 256 as numbered by the EU index as set forth in Kabat. In one aspect, the modification is at least one substitution selected from the group consisting of 252Y, 254T and 256E as numbered by the EU index as set forth in Kabat. See, U.S. Pat. No. 7,083,784, incorporated herein by reference in its entirety.

In certain aspects, the present disclosure provides an Fc variant BiSAb, wherein the Fc region comprises a non-naturally occurring amino acid at position 428 as numbered by the EU index as set forth in Kabat. In one aspect, the modification at position 428 is selected from the group consisting of 428T, 428L, 428F, and 428S as numbered by the EU index as set forth in Kabat. See, U.S. Pat. No. 7,670,600, incorporated herein by reference in its entirety. In another aspect, an Fc variant BiSAb may further comprises a non-naturally occurring amino acid at position 434 as numbered by the EU index as set forth in Kabat. In one aspect, the modification at position 434 is selected from the group consisting of 434A, 434S, and 434F as numbered by the EU index as set forth in Kabat. In other aspects, the present disclosure provides an Fc variant BiSAb, wherein the Fc region comprises a non-naturally occurring amino acid at positions 428 and 434 as numbered by the EU index as set forth in Kabat. In a specific aspect, the Fc region comprises 428L, 434S. See, U.S. Pat. No. 8,088,376.

In certain aspects, the effector functions elicited by IgG antibodies strongly depend on the carbohydrate moiety linked to the Fc region of the protein (Claudia Ferrara et al., 2006, Biotechnology and Bioengineering 93:851-861). Thus, glycosylation of the Fc region can be modified to increase or decrease effector function (see for examples, Umana et al, 1999, Nat. Biotechnol 17:176-180; Davies et al., 2001, Biotechnol Bioeng 74:288-294; Shields et al, 2002, J Biol Chem 277:26733-26740; Shinkawa et al., 2003, J Biol Chem 278:3466-3473; U.S. Pat. Nos. 6,602,684; 6,946,292; 7,064,191; 7,214,775; 7,393,683; 7,425,446; 7,504,256; POTELLIGENT™ technology (Biowa, Inc. Princeton, N.J.); GLYCOMAB™ glycosylation engineering technology (GLYCART biotechnology AG, Zurich, Switzerland)). Accordingly, in one aspect the Fc regions of BiSAbs of the disclosure comprise altered glycosylation of amino acid residues. In another aspect, the altered glycosylation of the amino acid residues results in lowered effector function. In another aspect, the altered glycosylation of the amino acid residues results in increased effector function. In a specific aspect, the Fc region has reduced fucosylation. In another aspect, the Fc region is afucosylated (see for examples, U.S. Patent Application Publication No. 2005/0226867). In one aspect, these BiSAbs with increased effector function, specifically ADCC, are generated in host cells (e.g., CHO cells, Lemna minor) engineered to produce highly defucosylated polypeptide with over 100-fold higher ADCC compared to polypeptide produced by the parental cells (Mori et al., 2004, Biotechnol Bioeng 88:901-908; Cox et al., 2006, Nat Biotechnol., 24:1591-7).

Addition of sialic acid to the oligosaccharides on IgG molecules can enhance their anti-inflammatory activity and alter their cytotoxicity (Keneko et al., Science, 2006, 313: 670-673; Scallon et al., Mol. Immuno. 2007 March; 44(7): 1524-34). The studies referenced above demonstrate that IgG molecules with increased sialylation have anti-inflammatory properties whereas IgG molecules with reduced sialylation have increased immunostimulatory properties (e.g., increase ADCC activity). Therefore, a BiSAb can be modified with an appropriate sialylation profile for a particular application (US Publication No. 2009/0004179 and International Publication No. WO 2007/005786).

In one aspect, the Fc regions of BiSAbs of the disclosure comprise an altered sialylation profile compared to the native Fc region. In one aspect, the Fc regions of BiSAbs of the disclosure comprise an increased sialylation profile compared to the native Fc region. In another aspect, the Fc regions of BiSAbs of the disclosure comprise a decreased sialylation profile compared to the native Fc region.

In one aspect, the Fc variants of the present disclosure may be combined with other known Fc variants such as those disclosed in Ghetie et al., 1997, Nat Biotech. 15:637-40; Duncan et al, 1988, Nature 332:563-564; Lund et al., 1991, J. Immunol 147:2657-2662; Lund et al, 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:4963-4969; Armour et al., 1999, Eur J Immunol 29:2613-2624; Idusogie et al, 2000, J Immunol 164:4178-4184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 7,122,637; 7,183,387; 7,332,581; 7,335,742; 7,371,826; 6,821,505; 6,180,377; 7,317,091; 7,355,008. Other modifications and/or substitutions and/or additions and/or deletions of the Fc domain will be readily apparent to one skilled in the art.

It is notable that polypeptides presented in the BiSAb format comprising a native Fc retain the ability to bind FcRn and C1q and to mediate ADCC, as shown in the examples. Thus, in certain aspects, a BiSAb retains the ability to bind FcRn and/or C1q and/or one or more Fcgamma receptors (FcγRs). For example, in certain aspects, a BiSAb retains at least 70%, 75%, 80%, 85%, 90%, 95%, 96%, 97%, 98%, 99%, or 100% of the ability to bind FcRn and/or C1q and/or one or more FcγRs, as compared to a conventional antibody that binds to one of the epitopes to which the BiSAb binds. In certain aspects, a BiSAb is generated from the binding domains of one or two conventional antibodies, and the comparison of activity is made to one or both of those conventional antibodies.

Altered Fc regions may also be used to generate heavy chain heterodimers, resulting in BiSAbs comprising two different heavy-light chain pairs. To facilitate the formation of heterodimers the interface between a pair of Fc regions is engineered to maximize the percentage of heterodimers which are recovered from recombinant cell culture. In certain aspects, the interface comprises at least a part of the CH3 domain. In this method, a "protrusion" is generated by replacing one or more, small amino acid side chains from the interface of the first antibody molecule with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers. CH3 modifications include, for example, Y407V/T366S/L368A on one heavy chain and T366W on the other heavy chain; S354C/T366W on one heavy chain and Y349C/Y407V/T366S/L368A on the other heavy chain. Additional modifications resulting in a protrusion on one chain and a cavity on the other are described in U.S. Pat. No. 7,183,076; US 2014/0348839; and Merchant et al., 1998, Nat. Biotech 16:677-681. Some non-limiting examples of modifications that can result in a protrusion-cavity arrangement are presented in Table 1a. Other modifications which may be used to generate heterodimers include but are not limited to those which alter the charge polarity across the Fc dimer interface such that co-expression of electrostatically matched Fc regions results in heterodimerization. Modifications which alter the charge polarity include, but are not limited to, those presented in Table 1b below (also see, US20090182127; Gunasekaran et al., 2010, JBC 285:19637-46). In addition, Davis et al. (2010, Prot. Eng. Design & Selection 23:195-202) describe a heterodimeric Fc platform using strand-exchanged engineered domain (SEED) CH3 regions which are derivatives of human IgG and IgA CH3 domains (also, see WO 2007/110205).

TABLE 1a

CH3 modifications for heterodimerization (protrusion-cavity)

| Modification(s) in one heavy chain | Modification(s) in other heavy chain |
|---|---|
| T366Y | Y407T |
| T366W | Y407A |
| T366Y | Y407T |
| T394W | F405A |
| T366Y/F405A | T394W/Y407T |
| T366W/F405W | T394S/Y407A |
| F405W | T394S |
| D399C | K392C |
| T366W | T366S/L368A/Y407V |
| T366W/D399C | T366S/L368A/K392C/Y407V |
| T366W/K392C | T366S/D399C/L368A/Y407V |
| S354C/T366W | Y349C/T366S//L368A/Y407V |
| Y349C/T366W | S354C/T366S//L368A/Y407V |
| E356C/T366W | Y349C/T366S//L368A/Y407V |
| Y349C/T366W | E356C/T366S//L368A/Y407V |
| E357C/T366W | Y349C/T366S//L368A/Y407V |
| Y349C/T366W | E357C/T366S//L368A/Y407V |

TABLE 1b

CH3 modifications for heterodimerization

| Modification(s) in one heavy chain | Modification(s) in other heavy chain |
| --- | --- |
| K370E/D399K/K439D | D356K/E357K/K409D |
| K409D | D399K |
| K409E | D399K |
| K409E | D399R |
| K409D | D399R |
| D339K | E356K |
| D399K/E356K | K409D/K392D |
| D399K/E356K | K409D/K439D |
| D399K/E357K | K409D/K370D |
| D399K/E356K/E357K | K409D/K392D/K370D |
| D399K/E357K | K409D/K392D |
| K392D/K409D | D399K |
| K409D/K360D | D399K |

A person skilled in the art would understand that in some aspects, an Fc Fusion protein can form dimers due to the homodimeric nature of molecules comprising an Fc region. In some aspects the Fc regions of a binding protein (e.g., BiSAb) may be differentially engineered with mutations to: promote and/or maintain heterodimerization (e.g., chimeric mutations, complementary mutations, dock and lock mutations, knobs into holes mutations, strand-exchange engineered domain (SEED) mutations, etc., see for example, U.S. Pat. No. 7,183,076; Merchant et al. (1998) Nat. Biotech 16:677-681; Ridgway et al. (1996) Protein Engineering 9:617-621; Davis et al. (2010) Prot. Eng. Design & Selection 23:195-202; WO 2007/110205; WO 2007/147901; Gunasekaran et al. (2010) JBC 285:19637-46, all incorporated herein by reference). Accordingly, a binding protein can be engineered to form a heterodimer comprising for example a first binding protein, binding domain, or BiSAb fused to a first Fc region or fragment thereof, and a second (i.e., different) binding protein, binding domain, or BiSAb fused to a second Fc region or fragment, wherein the first and second Fc regions, or fragments thereof have been engineered to heterodimerize.

3. Glycosylation

In addition to the ability of glycosylation to alter the effector function of polypeptides, modified glycosylation in the variable region can alter the affinity of the antibody (or BiSAb) for a target antigen. In one aspect, the glycosylation pattern in the variable region of the present BiSAbs is modified. For example, an aglycosylated BiSAb can be made (i.e., the BiSAb lacks glycosylation). Glycosylation can be altered to, for example, increase the affinity of the BiSAb for a target antigen. Such carbohydrate modifications can be accomplished by, for example, altering one or more sites of glycosylation within the BiSAb sequence. For example, one or more amino acid substitutions can be made that result in elimination of one or more variable region framework glycosylation sites to thereby eliminate glycosylation at that site. Such aglycosylation may increase the affinity of the BiSAb for antigen. Such an approach is described in further detail in U.S. Pat. Nos. 5,714,350 and 6,350,861. One or more amino acid substitutions can also be made that result in elimination of a glycosylation site present in the Fc region (e.g., Asparagine 297 of IgG). Furthermore, aglycosylated BiSAbs may be produced in bacterial cells which lack the necessary glycosylation machinery.

4. Polypeptide Linkers

Linkers may be used to join domains/regions of the BiSAb chimeric heavy chain into a contiguous molecule. As described herein, a BiSAb may include one, two, or more linker polypeptides, (e.g., L1 and L2). Additionally, a BiSAb may include additional linkers, such as a flexible linker interconnecting the variable heavy and light chains of an scFv. Additionally, a BiSAb may include additional linkers, such as a flexible linker interconnecting the variable heavy and light chains of an scFv and other linkers that connect other binding units to the BiSAb core structure.

An exemplary, non-limiting example of a linker is a polypeptide chain comprising at least 4 residues. Portions of such linkers may be flexible, hydrophilic and have little or no secondary structure of their own (linker portions or flexible linker portions). Linkers of at least 4 amino acids may be used to join domains and/or regions that are positioned near to one another after the molecule has assembled. Longer or shorter linkers may also be used. Thus, linkers may be approximately 1, 2, 3, 4, 5, 6, 7, 8, 9, 10, 11, 12, 13, 14, 15, 16, 17, 18, 19, 20, 25, 30, 35, 40, 45, or approximately 50 residues in length. When multiple linkers are used to interconnect portions of the molecule, the linkers may be the same or different (e.g., the same or different length and/or amino acid sequence).

Linkers may be cleavable linkers, which contain at least one bond that can be selectively cleaved by a cleavage reagent. Cleavable linkers may be used to facilitate removal of all or a portion of the linker sequence. Linkers may be engineered to contain protease cleavage sites, so that cleavage occurs in the middle of the linker or in at least one end of the linker. For example, thrombin sites may be engineered at each of the two flanking ends of a linker. Depending on the type of linker used, cleavage may also be mediated by agents such as TCEP, TFA, and DTT. Linkers may be designed so that cleavage reagents remove all residues from the linker from the cleavage product. Other exemplary non-limiting linkers include prodrug linkers whose bonds can be selectively cleaved under in vivo conditions, for example, in the presence of endogenous enzymes or other endogenous factors, or simply in aqueous fluids present in the body or in cells of the body. When BiSAbs contain more than one polypeptide linker, each of the linkers may be different, or at least one of the linkers may be different from the others. In some aspects a BiSAb comprises a cleavable linker. In a specific aspect, the BiSAb comprises an scFv, wherein the scFv comprises a cleavable linker between VH2 and VL2.

The linker(s) facilitate formation of the desired structure. Linkers may comprise (Gly-Ser)$_n$ residues, with some Glu or Lys residues dispersed throughout to increase solubility. Alternatively or additionally linkers may not comprise any Serine residues, such linkers may be preferable where the linker is subject to O-linked glycosylation. In some aspects, linkers may contain cysteine residues, for example, if dimerization of linkers is used to bring the domains of the BiSAb into their properly folded configuration. In some aspects, the BiSAb comprises at least two polypeptide linkers that join domains of the polypeptide. In other aspects, the BiSAb comprises at least three polypeptide linkers. In other aspects the BiSAb comprises four or more polypeptide linkers.

In some aspects, the polypeptide linker comprises a portion of an Fc moiety. For example, in some aspects, the polypeptide linker can comprise a portion of immunoglobulin hinge domain of an IgG1, IgG2, IgG3, and/or IgG4 antibody. In some aspects, the polypeptide linker comprises a portion of a mutated immunoglobulin hinge domain of an IgG1, IgG2, IgG3 and/or IgG4. In some aspects, the polypeptide linker comprises at least 5, 7, 8, or 15 amino acid residues of an immunoglobulin hinge region/domain of an IgG1, IgG2, IgG3, and/or IgG4 antibody. In some aspects, the polypeptide linker comprises at least 5, 7, 8, or 15 amino acid residues of a modified immunoglobulin hinge region/domain of an IgG1, IgG2, IgG3, and/or IgG4 antibody.

The polypeptide linker may comprise all, or a portion of a hinge region that naturally comprises three cysteines. In certain aspects, the selected hinge region is truncated or otherwise altered or substituted relative to the complete and/or naturally-occurring hinge region such that only one or two of the cysteine residues remain. Similarly, in certain other aspects, the polypeptide linker may comprise a mutated or otherwise altered portion of a hinge region in which the number of cysteine residues is reduced by amino acid substitution or deletion, for example a mutated or otherwise altered hinge region containing zero, one or two cysteine residues as described herein.

A mutated or otherwise altered hinge domain may thus be derived or constructed from (or using) a wild-type immunoglobulin hinge domain that contains one or more cysteine residues. In certain aspects, a mutated or otherwise altered portion of a hinge region may contain zero or only one cysteine residue, wherein the mutated or otherwise altered hinge region is or has been derived from a wild type immunoglobulin hinge region that contains, respectively, one or more or two or more cysteine residues. In the mutated or otherwise altered portion of a hinge region, the cysteine residues of the wild-type immunoglobulin hinge region are preferably deleted or substituted with amino acids that are incapable of forming a disulfide bond. In some aspects, a mutated or otherwise altered portion of a hinge region is or has been derived from a human IgG wild-type hinge region, which may include any of the four human IgG isotype subclasses, IgG1, IgG2, IgG3 or IgG4.

In some aspects, the polypeptide linker comprises a portion of a hinge region comprising the cysteine residue that forms a disulfide bond with an immunoglobulin light chain (EU residue 220). In some aspects, the polypeptide linker comprises an altered portion of a hinge region comprising an amino acid substitution at EU residue C220. In some aspects, the polypeptide linker comprises the amino acid substitution C220V.

In some aspects, the polypeptide linker comprises an amino acid substitution that prevents hinge-related spontaneous self-cleavage. In some aspects, the polypeptide linker comprises an amino acid substitution at position at EU position D221. In some aspects, the polypeptide linker comprises the amino acid substitution D221G. In some aspects, the polypeptide linker lacks the amino acid D221.

As discussed above, some embodiments include one or more polypeptide linkers that comprise or consist of a gly-ser linker. As used herein, the term "gly-ser linker" refers to a peptide that consists of glycine and serine residues. An exemplary gly-ser linker comprises an amino acid sequence of the formula (Gly$_4$Ser)n, wherein n is a positive integer (e.g., 1, 2, 3, 4, 5, 6, 7, 8, 9 or 10). Some preferred and non-limiting examples of a gly-ser linker includes (Gly$_4$Ser)$_2$, (SEQ ID NO:41) and (Gly$_4$Ser)$_4$, (SEQ ID NO:42) as well as (Gly$_4$Ser)$_3$ (SEQ ID NO:43). In yet other aspects, two or more gly-ser linkers are incorporated in series in a polypeptide linker. In some aspects, the polypeptide linker comprises at least a portion of a hinge region (e.g., derived from an IgG1, IgG2, IgG3, or IgG4 molecule) and a series of gly-ser amino acid residues (e.g., a gly-ser linker such as (Gly$_4$Ser)n, where n is 2, 3, or 4).

In certain aspects, linkers (e.g., L1 and/or L2 and/or L3, etc.) include both a hinge portion and a linker portion, such as a linker portion comprising a gly-ser linker. In other aspects, L1 and/or L2 include only a hinge portion or only a linker portion, such as a gly-ser linker. In other aspects, L1 and L2 include a gly-ser linker portion. In certain aspects, the gly-ser linker within a BiSAb is the same length, whereas in other aspects, the gly-ser linker portion within a BiSAb (e.g., L1 and L2) are different lengths. When a BiSAb comprises an scFv, the heavy and light chains of the scFv may be connected to the BiSAb (e.g., BD1, Fab, Fc, etc.) by a flexible linker. This flexible linker generally does not include a hinge portion, but rather, is a gly-ser linker or other flexible linker. The length and amino acid sequence of a flexible linker interconnecting domains of an scFv may be readily selected and optimized (e.g., (Gly$_4$Ser)n, (SEQ ID NO:48) where n is 2, 3, or 4 or more).

Regardless of the polypeptide linker used to interconnect various binding units and domains (e.g., between binding domains/units (e.g., Fab-scFv), or binding domain/unit to Fc (e.g., scFv via L1 and L2), the BiSAb may optionally comprise additional polypeptide linkers. The lengths and sequence of such additional polypeptide linkers are independently selected. For example, the BiSAb may further comprise a flexible polypeptide linker interconnecting the variable heavy and light chains of a scFv. This flexible polypeptide linker may comprise a gly-ser linker. Generally, this linker does not include a hinge portion.

It is contemplated here that varying the length of the linkers flanking BD2 can impact on the orientation of the BD2 antigen binding site and spacing relative to the rest of the BiSAb molecule. For example, a short N-terminal linker and long C-terminal linker may create an orientation where the binding site is conformed in one direction, while a long N-terminal and short C-terminal linker may impart an opposite conformational orientation. Accordingly, linker length may be modulated in order to orient the BD2 antigen binding site and have important impacts on creating or avoiding steric effects between BD1 and BD2 and/or BD2 and other entities that bind the antibody molecule in the Fc or other domains.

5. Specific Configuration of BiSAbs

As discussed above, one aspect of the disclosure relates to a BiSAb structural arrangement (platform) that comprises two heavy-light chain pairs (illustrated in FIGS. 1A-1F). In some embodiments of this aspect, the polypeptide sequence of the BiSAb chimeric heavy chain may comprise a polypeptide sequence comprising an antibody heavy chain variable domain (VH1), a polypeptide sequence comprising an antibody heavy chain constant domain 1 (CH1), a portion of the Fc domain, a polypeptide sequence comprising a first polypeptide linker (L1), a polypeptide sequence comprising a binding domain (BD2), a polypeptide sequence comprising a second polypeptide linker (L2), and a polypeptide sequence comprising the remainder of the Fc domain. In some aspects, the Fc domain comprises a $C_H2$ domain and a $C_H3$ domain. Thus, certain embodiments provide a BiSAb chimeric heavy chain that may comprise polypeptide sequences in the following orientation from N-terminus to C-terminus: VH1-$C_H$1-$C_H$2 (N-term)-L1-BD2-L2-$C_H$2 (C-term)-$C_H$3; VH1-$C_H$1-$C_H$2-L1-BD2-L2-$C_H$3; and VH1-$C_H$1-$C_H$2-$C_H$3 (N-term)-L1-BD2-L2-$C_H$3 (C-term). The polypeptide sequence of the BiSAb light chain may comprise a light chain variable domain (VL1) and a light chain constant domain (CL). Thus, a BiSAb light chain may comprise polypeptide sequence in the following orientation from N-terminus to C-terminus: VL1-CL. Note that VH1, VL1, and CL are used to denote portions of "binding unit 1" (BD1) that binds a first epitope. BD2 is used to denote portions of "binding unit 2" that binds a second epitope.

In the aspects where the binding domain is an scFv, the BiSAb chimeric heavy chain may comprise a polypeptide sequence comprising an antibody heavy chain variable domain (VH1), a polypeptide sequence comprising an antibody heavy chain constant domain 1 (CH1), a polypeptide sequence comprising a first polypeptide linker (L1), a polypeptide sequence comprising an antibody light chain variable domain (VL2), a polypeptide sequence comprising a flexible linker, a polypeptide sequence comprising an antibody heavy chain variable domain (VH2), a polypeptide sequence comprising a second polypeptide linker (L2), and a polypeptide sequence comprising an antibody Fc domain. Thus, the chimeric heavy chain of a BiSAb comprising an scFv as the BD2 may comprise a polypeptide sequences in the following orientation from N-terminus to C-terminus: VH1-CH1-CH2(N-term)-L1-VL2-L3-VH2-L2-CH2(C-term)-CH3; VH1-CH1-CH2-L1-VL2-L3-VH2-L2-CH3; VH1-CH1-CH2-CH3(N-term)-L1-VL2-L3-VH2-L2-CH3 (C-term); VH1-CH1-CH2(N-term)-L1-VH2-L3-VL2-L2-CH2(C-term)-CH3; VH1-CH1-CH2-L1-VH2-L3-VL2-L2-CH3; and VH1-CH1-CH2-CH3(N-term)-L1-VH2-L3-VL2-L2-CH3(C-term).

The chimeric heavy chain is a polypeptide chain comprising an amino acid sequence (e.g., the amino acid sequence of each of the polypeptide domains). The chimeric heavy chain is a polypeptide chain comprising an amino acid sequence (e.g., the amino acid sequence of each of the polypeptide domains). Note that VH1, VL1, and CL are used to denote portions of binding unit 1, with VH1 and VL1 denoting that portion that binds the first epitope. VH2 and VL2 is used to denote portions of binding unit 2 that bind the second epitope. In certain aspects, additional scFv binding domains are present at the N-terminal and/or C-terminal ends of the polypeptides that make up the BiSAb core (wherein the BiSAb core further comprises binding unit (BD) 3 and/or 4 and/or 5). In certain aspects, more than one scFv binding domains are present within the BiSAb core. Each additional scFv comprises an antibody heavy chain variable region denoted as VH3, VH4, VH5, and a corresponding antibody light chain variable region denoted as VL3, VL4, VL5.

6. Labels, Conjugates and Moieties

In certain features, drugs and other molecules may be targeted to BiSAb via site-specific conjugation. For example, BiSAbs may comprise cysteine engineered domains (including cysteine(s) engineered into a binding unit and/or Fc domain), which result in free thiol groups for conjugation reactions. In certain aspects, a BiSAb is engineered to incorporate specific conjugation sites. In some aspects, the present disclosure provides an Fc variant BiSAb, wherein the Fc region comprises an amino acid substitution at one or more of positions 239, 282, 289, 297, 312, 324, 330, 335, 337, 339, 356, 359, 361, 383, 384, 398, 400, 440, 422, and 442, as numbered by the EU index. In some aspects, the Fc region comprises substitutions at one or more of the following groups of positions: a) 289 and 440; b) 330 and 440; c) 339 and 440; d) 359 and 440; e) 289 and 359; f) 330 and 359; g) 339 and 359; h) 289 and 339; i) 330 and 339; j) 289 and 330; k) 339 and 442; l) 289, 339, and 442; m) 289, 330, and 339; n) 330, 339, and 442; and o) 289, 330, and 442. In other aspects, the present disclosure provides a BiSAb, wherein the CH1 domain of the Fab arm comprises a substitution at one or more of positions 131, 132, 134, 135, 136 and 139, as numbered by the EU index. In one aspect the substitution comprises a substitution to an amino acid chosen from cysteine, lysine, tyrosine, histidine, selenocysteine, and selenomethionine. In a specific aspect, the substitution is a cysteine. Methods for generating stable cysteine engineered antibodies are described in U.S. Pat. No. 7,855,275, U.S. 20110033378 and US20120213705, the contents of which are incorporated herein by reference in their entirety.

7. Exemplary Targets

While the aspects and embodiments relating to the various DuetMab and BiSAb platform(s) described herein can be generated to bind to any desired target or targets, the BiSAbs disclosed herein preferably target specific pairs of target molecules (e.g., binding unit 1 binds one of the targets and binding unit 2 binds the other target). As discussed above and as exemplified in the illustrative Examples below, the antibodies, DuetMabs and BiSAbs disclosed herein are targeted to a molecule that modulates an immune response in a recipient subject, or in immune cells in culture. In some embodiments the binding domain exhibits specific binding activity for a target selected from the group consisting of CTLA-4, PD-1, PD-L1, OX40, and TIM3. The DuetMabs and BiSAbs can comprise a combination of different binding domains in various orders and orientations, where the domains have binding affinity for, or bind specifically to the targets disclosed herein. For example the DuetMabs and BiSAbs disclosed herein may comprise a combination of binding domains that allow for bispecific binding to targets including; CTLA-4 and PD-1; CTLA-4 and PD-L1; and CTLA-4; CTLA-4 and TIM3; PD-1 and PD-L1; PD-L1 and OX40; PD-1 and TIM3; PD-L1 and TIM3. DuetMabs and BiSAbs that include binding domains that bind particular target combinations are illustrated in the Examples and include the non-limiting combinations of PD-1/CTLA-4; PD-L1/CTLA-4; PD-1/TIM3; and PD-L1/OX40. In certain embodiments, the BiSAbs have enhanced binding properties relative to the binding properties of the combined individual monospecific binding proteins that are used to generate the BiSAbs.

In certain aspects, a DuetMab or BiSAb of the disclosure binds two different epitopes on the same target (e.g., binding unit 1 binds a first epitope on a target and binding unit 2 binds a second epitope on the same target).

In some aspects, the multimeric nature of the DuetMabs or BiSAbs of the disclosure confers the ability to target labels or therapeutics to a specific cell type or molecular target. For example, one functional domain in a DuetMab or BiSAb may bind to a target at the surface of a cell, while another functional domain in the same DuetMab or BiSAb binds to a hapten or labeling agent useful for detection. Similarly, one functional domain may bind to a cellular target while a second functional domain binds to a toxin. Because both binding reactions are mediated through a single molecule, the toxin may be placed in the proximity of the cellular target, where it affects a cytotoxic function.

B. Nucleic Acid Molecules Encoding BiSAbs

The present disclosure provides nucleic acid molecules that encode BiSAbs. One aspect of the disclosure provides nucleic acid molecules encoding any of the BiSAbs of the disclosure. A nucleic acid molecule may encode a heavy chain and/or light chain of any of the BiSAb molecules that are disclosed herein, as well as any of the individual binding domains (e.g., scFvs) that are disclosed herein. One of skill in the art will appreciate that such polynucleotide molecules may vary in nucleotide sequence given nucleic acid codon degeneracy as well as codon frequency for particular organisms, as is generally known in the art.

C. Vectors and Host Cells for Producing BiSAbs and Subsequent Purification

The disclosure relates to methods for producing BiSAbs. In certain aspects, recombinant nucleic acid molecules that encode all or a portion of the BiSAbs disclosed herein may be operably linked to one or more regulatory nucleotide sequences in an expression construct. The nucleic acid sequences encoding the BiSAb light and chimeric heavy chains can be cloned in the same expression vector in any orientation (e.g., light chain in front of the heavy chain or vice versa) or can be cloned in two different vectors. If expression is carried out using one vector, the two coding genes can have their own genetic elements (e.g., promoter, RBS, leader, stop, polyA, etc) or they can be cloned with one single set of genetic elements, but connected with a cistron element. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome.

In certain aspects, the expression vector contains a selectable marker gene to allow the selection of transformed host cells. Selectable marker genes are well known in the art and will vary with the host cell used. In certain aspects, this disclosure relates to an expression vector comprising a nucleotide sequence encoding a polypeptide and operably linked to at least one regulatory sequence. Regulatory sequences are art-recognized and are selected to direct expression of the encoded polypeptide. Accordingly, the term regulatory sequence includes promoters, enhancers, and other expression control elements. Exemplary, non-limiting regulatory sequences are described in Goeddel; *Gene Expression Technology: Methods in Enzymology*, Academic Press, San Diego, Calif. (1990). It should be understood that the design of the expression vector may depend on such factors as the choice of the host cell to be transformed and/or the type of protein desired to be expressed. Moreover, the copy number of the particular vector, the ability to control that copy number and the expression of any other protein encoded by the vector, such as antibiotic markers, should also be considered.

The disclosure further pertains to methods of producing a BiSAb of the disclosure. For example, a host cell transfected with one or more than one expression vector encoding a BiSAb (e.g., a single vector encoding the chimeric heavy and the light chain or two vectors, one encoding the chimeric heavy chain and one encoding the light chain) can be cultured under appropriate conditions to allow expression of the polypeptide to occur. The BiSAb may be secreted and isolated from a mixture of cells and medium containing the polypeptide. Alternatively, the BiSAb may be retained in the cytoplasm or in a membrane fraction and the cells harvested, lysed and the protein isolated. A cell culture includes host cells, media and other byproducts. Suitable media for cell culture are well known in the art. BiSAbs can be isolated from cell culture medium, host cells, or both using techniques known in the art for purifying proteins, including ion-exchange chromatography, gel filtration chromatography, ultrafiltration, electrophoresis, and immunoaffinity purification. In certain aspects, the BiSAb is made as a fusion protein containing a domain which facilitates its purification.

A recombinant nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. In certain aspects, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Ban virus (pHEBo, pREP-derived and p205) can be used for transient expression of proteins in eukaryotic cells. The various methods employed in the preparation of the plasmids and in the transformation of host organisms are known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Once a molecule has been produced, it may be purified by any method known in the art for purification of a protein, an immunoglobulin molecule or other multimeric molecules using techniques such as, for example, chromatography (e.g., ion exchange, affinity, particularly by affinity for the specific antigens Protein A or Protein G, and sizing column chromatography), centrifugation, differential solubility, or by any other standard technique for the purification of proteins. Further, the molecules disclosed herein may be fused to heterologous polypeptide sequences (e.g., affinity tags) as are routinely employed to facilitate purification.

Regardless of how a BiSAb is generated and purified, binding assays, for example, dual ELISA assays, may be performed (before and/or after purification) to confirm functional binding activity of the BiSAb. Such binding assays are generally known in the art.

D. Pharmaceutical Formulations

In certain aspects, the disclosure provides pharmaceutical compositions. Such pharmaceutical compositions may be compositions comprising a nucleic acid molecule that encodes a BiSAb. Such pharmaceutical compositions may also be compositions comprising a DuetMabs, a BiSAb, a combination of DuetMabs, or a combination of BiSAbs, and a pharmaceutically acceptable excipient. In certain aspects, the pharmaceutical compositions of the disclosure are used as a medicament.

E. Uses

As discussed herein the DuetMabs and BiSAbs may be used to bind targets associated with cancer and cell proliferative diseases or disorders that may be responsive to an immunotherapy, for example, by inhibiting an immunosuppressive activity and/or by inducing an immune response that is associated with the target molecule(s). For example, aberrant signalling and/or inhibited immune response may contribute to unwanted cell proliferation and cancer. Accordingly, DuetMabs. BiSAbs and the antibodies disclosed herein may be used to treat unwanted cell proliferation and/or cancer associated with an inhibited, reduced, or insufficient immune response targeted against the cancer. In particular, the tumor growth curve of a tumor and/or the volume of a tumor may be reduced by administration of a DuetMab of BiSAb that induces and/or stimulates an immune response in a subject, such as, for example a human patient suffering from a cancer.

Thus, the disclosure also relates to various methods that comprise administration of the binding proteins disclosed herein to a subject in need thereof. In one aspect, the disclosure relates to a method for inducing an immune response in a subject having, or at risk of developing, a cancer comprising administration of a binding protein disclosed herein to the subject. In some embodiments, the method activates an immune response against the cancer in the subject. In some embodiments, the method enhances an immune response against the cancer in the subject. In some embodiments, the method activates an immune response pathway that is inhibited in the subject, wherein the activation increases an immune response that targets the cancer in the subject. In some embodiments the method enhances an immune response pathway that targets the cancer in the subject.

In another aspect, the disclosure relates to a method for treating cancer in a subject in need thereof comprising administering a binding protein disclosed herein to the subject. In one embodiment the method of treating cancer comprises stopping or slowing the growth of the cancer in the subject. In one embodiment the method of treating cancer comprises stopping or slowing the metastasis of the cancer to other areas in the subject. In one embodiment the method of treating cancer comprises killing cancer cells in the subject. In one embodiment the method of treating cancer comprises halting the proliferation and/or the spread of cancer cells in the subject.

In various embodiments of the above aspects, the methods relate to treating a subject for a tumor disease and/or a cancer disease. In embodiments the cancer is selected from the group of cancers that are susceptible to an immune response induced in the subject. In some embodiments, the cancer is one or more of an ovarian cancer, breast cancer, colorectal cancer, prostate cancer, cervical cancer, uterine cancer, testicular cancer, bladder cancer, head and neck cancer, melanoma, pancreatic cancer, renal cell carcinoma, or lung cancer. In some embodiments the cancer is selected from digestive or gastro-intestinal cancers (e.g., anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric cancer; hepatocellular cancer (e.g., hepatocellular carcinoma) including adult (primary) hepatocellular cancer and childhood hepatocellular cancer; pancreatic cancer including childhood pancreatic cancer; sarcoma, rhabdomyo sarcoma; islet cell pancreatic cancer; rectal cancer; and small intestine cancer); lung cancer (e.g., non-small cell lung cancer (NSCLC) and small cell lung cancer (SCLC)); head and neck cancer (e.g., lip and oral cavity cancer; oral cancer including childhood oral cancer; hypopharyngeal cancer; laryngeal cancer including childhood laryngeal cancer; metastatic squamous neck cancer with occult primary; mouth cancer; nasal cavity and paranasal sinus cancer; nasopharyngeal cancer including childhood nasopharyngeal cancer; oropharyngeal cancer; parathyroid cancer; pharyngeal cancer; salivary gland cancer including childhood salivary gland cancer; throat cancer; and thyroid cancer); ovarian and breast cancer.

In the above methods, the amount of binding protein that is administered to the subject is effective to induce an immune response, increase an immune response, stop or slow the growth of cancer, stop or slow the metastasis of cancer, kill cancer cells, and/or slow or stop the proliferation and/or spread of cancer cells in the subject.

In embodiments of the above methods, the binding protein comprises a DuetmAb or BiSAb as disclosed herein. In some embodiments of the above methods, the binding protein comprises an antibody, or an antigen-binding fragment thereof, as disclosed herein.

As used herein, the term "subject" is intended to include human and non-human animals, particularly mammals. Examples of subjects include human subjects for example a human patient having a disorder, e.g., a disorder described herein, such as cancer, or a normal subject. A "non-human animal" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.). In particular embodiments, the subject is a human patient.

"Treatment" or "treat" refers to both therapeutic treatment and prophylactic or preventative measures. Those subjects in need of treatment include those already with the disorder as well as those prone to have the disorder or those in which the disorder is to be prevented. When used with reference to a disease or a subject in need of treatment the terms accordingly include, but are not limited to, halting or slowing of disease progression, remission of disease, prophylaxis of symptoms, reduction in disease and/or symptom severity, or reduction in disease length as compared to an untreated subject. In embodiments, the methods of treatment can abate one or more clinical indications of the particular disease being treated.

The Examples that follow are provided to illustrate particular aspects and embodiments of the disclosure provided above and should not be interpreted as limiting to the scope of the description or to the appended claimed subject matter.

EXAMPLES

Materials and Methods
Immune Response Modulation Assay
A cytomegalovirus (CMV) antigen recall assay was used to evaluate the potential immune response induced by certain of the immunotherapeutic molecules described herein.
Reagents for the assay include:
CMV reactive frozen peripheral blood mononuclear cells (PBMC);
AIM V® Medium (Life Technologies, cat#12055-091);

phosphate buffered saline (PBS, Life technologies, cat#20012-043);

PepTivator®, CMVpp65 peptide pool, (Miltenyi Biotec, cat#130-093-438, 50 µg/ml);

Ovalbumin, (Thermo scientific cat#77120, 1 mg/ml);

Costar, 96 well plate non-TC treated (Corning, cat#3788); and an immunotherapeutic molecule.

General Assay Protocol:

The day before the assay was performed frozen PBMCs were thawed in warm AIM V medium. The cells were washed twice in Costar 96 round well plate. The concentration of cells was adjusted to a concentration of $1\times10^6$ cells/mL.

Aliquots (100 µL) of cells were dispensed in individual wells, leaving the outside columns and rows of the plate empty. The cells were allowed to rest overnight.

The following day, 100 µL of AIMV medium containing 2× PepTivator CMV peptide pool (0.1 µg/ml-0.05 µg/ml final) and 2× immunotherapeutic molecule were added to the wells.

After 72 hours, 25 µL of supernatant from each well was transferred to a pre-blocked and washed MSD plates (anti-human IFN gamma). After addition of standards, plates were incubated for 2 hours at room temperature. After the incubation period, the MSD plates were washed three times. Following the washing, 25 µL of SULFO-TAG detection antibody was added and allowed to react for 1 hour at room temperature. The plates were washed again and 150 µL of 2λ MSD read buffer was added before readings were taken.

Staphylococcal Enterotoxin A/B (SEA/SEB) Assay Protocol

Reagents used in either the SEB or SEA assay protocol to determine the effect of the DuetMabs or BiSAbs on IL-2 immune response include:

Leukocyte cones (NHSBT code NC24; from Addenbrookes Hospital);

50 ml Falcon tubes (BD 352070);

Ficoll-Paque PLUS (GE Healthcare 17-1440-02);

Anti-CD3 (clone OKT3; 1 mg/ml; eBioscience; cat no:16-0037-85);

Ammonium chloride solution (Stemcell Technologies 07850);

Staphylococcal enterotoxin A (SEA; Sigma, S-9399) or Staphylococcal enterotoxin B (SEB; Sigma, S-4881) stock solutions at 1 mg/ml stored at −20° C.;

Culture media (all from Life Technologies): RPMI1640 with glutamax (61870) supplemented with 10% v/v heat inactivated FCS (90005M) and 100 U/ml penicillin+100 ug/ml streptomycin (15140-122);

V-bottomed plate (Greiner BioOne 651201);

96-well flat-bottom plates (Corning Costar 7107).

Reagents for the IL-2 DELFIA ELISA include:

FLUONUNC Maxisorp ELISA plates (Nunc 437958);

Europium-labelled streptavidin, SA-Eu (Perkin-Elmer 1244-360);

DELFIA® assay buffer (Perkin-Elmer, #4002-0010);

DELFIA® enhancement solution (Perkin-Elmer 4001-0010); at RT prior to use;

Assay diluent: DELFIA wash buffer (0.05% Tween-20, 20 mM Tris, 150 mM NaCl; pH 7.2-7.4) supplemented with 0.1% BSA, sterile filtered;

Milk powder (Marvel; Premier Foods);

Sample Diluent (RPMI1640+10% FCS+1% Penicillin/Streptomycin as above);

PBS (ThermoFisher 14190235);

PBS-Tween (0.01% Tween-20 in PBS);

Human IL-2 ELISA kit (Duoset DY202, R&D Systems);

Biotek plate washer (EL406) with automated plate loader (Biostack).

General Assay Protocol

Figure 90:
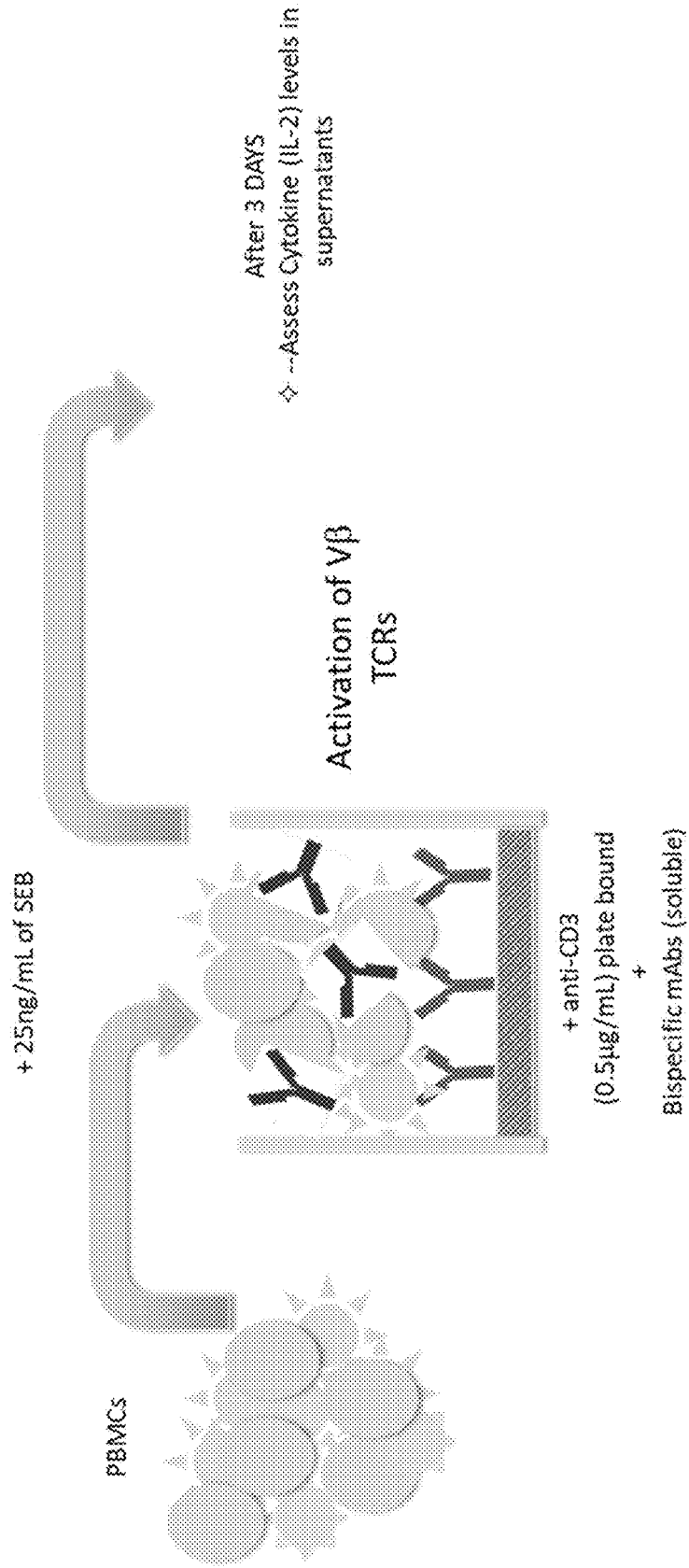
FIG. 90 depicts the SEB assay format.

PBMCs were isolated from human blood leukocyte cones (NHS Blood and Transplant Service code NC24) using density gradient centrifugation (Ficoll-Paque PLUS; GE Healthcare), then red blood cells were lysed in ammounium chloride solution (Stemcell Technologies). Anti-human CD3 (clone OKT3 at 0.5 ug/ml in PBS; eBioscience) was coated in flat-bottomed 96 well plates (Corning Costar 7107) for 2 hrs at 37° C. Then, $0.2\times10^6$ cells were added, per well, of the PBMC in culture media (RPMI1640-Glutamax supplemented with 10% v/v heat inactivated bovine serum and 100 U/100 ug per ml Steptomycin/Penicillin (respectively) (Life Technologies). PBMC were further stimulated by addition of Staphylococcal Enterotoxin A or B (SEB; Sigma Aldrich) within a range of 0.0088-0.1 ug/mL, and candidate DuetMabs or BiSAbs were added to the final tested concentrations. Following 3 days culture at 37° C. and 5% $CO_2$ supernatants were removed from cells and IL-2 secretion determined using commercial ELISA according to manufacturer's instructions (R&D Systems Duoset product code DY202). See FIG. 90.

Mixed Leukocyte Reaction (MLR) Assay Protocol (Fresh Blood)

The MLR cell-based assay was also used to provide in vitro correlation of T cell function in response to the DuetMabs and BiSAbs disclosed herein. Reagents used in performing the MLR assay from fresh blood samples include:

8 mL CPT Heparin tubes;

AIM-V Medium (serum free) Gibco #12055-091, no additives;

50 ml conical tubes;

2 ml cryopreservation vials;

ACK lysing Buffer (Gibco # A10492-01);

96 well tissue culture treated U-bottom plates BD falcon #3077;

PHA (Roche) 1 mg/ml (10 ug/mL final concentration), as a positive control;

General Assay Protocol

PBMCs were prepared from blood samples drawn into CPT Heparin tubes. The tubes are centrifuged for 20 min at 2700 rpm without the brake at 25° C. The top layer of serum is aspirated. The remaining material was gently pipetted, and everything above CPT tube plug was collected and placed into 50 ml conical tubes. To the cells was added AIM-V medium to wash the cells (3 times at 1500 rpm, with the brake on, at 25° C. for 5 minutes). Any remaining red blood cells were lysed using red blood cell lysing buffer (e.g., about 5 min. with about 3 ml buffer). The remaining cells were washed twice with AIM-V medium (1500 rpm, break on, at 25° C. for 5 minutes). If needed, the pellets were consolidated into a single tube and resuspended in AIM-V medium, and a cell count was made.

To perform the MLR assay, the cells were plated into 96 well plates at 200,000 cells per donor per well in AIM-V medium, 50 ul per donor (total of 400,000/100 ul). The candidate molecules were added (4×) 50 ul per well diluted in Serum Free AIM-V Medium. After 72 hrs., the plates were imaged and 30 ul of supernatant was removed for human TH1/TH2 (MSD) cytokine assay.

Human TH1/TH2 MSD 10-plex Protocol

This assay was used to determine amounts of cytokines present in culture supernatants in response to the administration of the DuetMabs and BiSAbs disclosed herein. To perform the assay, blocker agent was prepared by dissolving 200 mg of blocker B into 20 ml PBS per plate. 150 ul dissolved blocker was added to each well. The plate was sealed and shaken for 2 hrs at room temperature or overnight at 4° C. The wells were washed 3× with PBST buffer. A calibrator was prepared by diluting frozen calibrator blend 10 ul into 1 ml of diluent, and was further serially diluted 4 fold. To separate wells was added 25 ul of calibrator (standard) and 25 ul samples. The wells were incubated for 2 hrs, at room temperature with shaking. Following incubation, the wells were washed 3× with PBST.

Detection antibody is prepared and diluted to the necessary concentration, and was added to each well. Following a 2 hr. incubation at room temperature with shaking, the wells were washed (3×) in PBST. Prior to reading on the MSD machine, read buffer was added to each well.

Tumor Specific Killing Assay Protocol

The human CD8+ T cell line (JR6C12) with reactivity against human gp100$_{209-217}$ peptide was kindly provided by Dr. Steven Rosenberg (National Cancer Institute, Bethesda, Md.). JR6C12 cells were co-cultured with a CFSE (Cell-Trace CFSE proliferation kit, ThermoFisher) labeled human melanoma line (Mel624) for 18 hours at 37 C at a 1:1 ratio (20,000 JR6C12+20,000 Mel624) in a 96 well flat bottom plate. The candidate molecules were added at time 0 of the co-culture at a concentration of 69 nM. After 18 hrs, wells were visualized by bright field microscopy. Supernatants were collected for MSD analysis and adherent cells were trypsinized and washed (2×) in PBS prior to viability staining (Zombie UV Fixable Viability kit, Biolegend). Viability dye uptake of CFSE labeled cells was assessed by flow cytometry on a LSRFortessa (BD).

Example 1. Identification of Candidate Fc Locations for Binding Domain Attachment Using the open-source software PyMOL molecular visualization system, antibody structure was investigated in the CH2 and CH3 regions as well as at or near the CH2-CH3 interface in order to identify candidate regions, such as exposed surface loops, for binding domain attachment. Such regions would accommodate for insertion of a second binding domain (e.g., an scFv) without compromising the structural integrity or stability of the IgG or the second binding domain itself. From the analysis, three regions were identified (represented as spheres in FIGS. 1A-1C). FIGS. 1D, 1E, and 1F depict embodiments of the binding proteins, showing attachment of a second binding domain (with an scFv for purposes of illustration) in each of the loops identified in FIGS. 1A, 1B, and 1C, respectively.

FIG. 2A provides a more detailed schematic diagram of the amino acid sequence of one of the identified representative loops identified in the CH2 region near the CH2-CH3 interface and comprising the sequence ISRTP (SEQ ID NO:39). A binding domain may be inserted within this amino acid sequence to generate any number of representative constructs such as, for example, inserting scFv domains as illustrated in the Examples (e.g., I-scFv-SRTP, IS-scFv-RTP, ISR-scFv-TP, or ISRT-scFv-P scFV-ISRTP, and ISRTP-scFV, where the "-scFv-" identifies the point in the native loop sequence to which the binding domain may be associated. FIG. 2B is a similar schematic diagram that is representative of the loop identified in the CH2-CH3 interface and comprising the amino acid sequence AKGQP (SEQ ID NO:40). Representative constructs described herein can include a binding domain (such as, for example, a scFv domain) attached to this loop sequence as described herein, including A-scFv-KGQP, AK-scFv-GQP, AKG-scFv-QP, AKGQ-scFv-P, scFV-AKGQ, AKGQ-scFV, where the "-scFv-" identifies the point in the native loop sequence to which the binding domain may be associated. FIG. 2C provides a schematic diagram of the representative loop identified downstream of the CH2-CH3 interface, within the CH3 region and comprising the amino acid sequence SNG. The representative constructs for this loop sequence, discussed in terms of the illustrative embodiments for the other two loop regions above, include scFV-SNG, S-scFv-NG SN-scFv-G, and SNG-scFV.

Example 2. Generation and Characterization of a Series of Parental Antibodies and Bispecific Binding Proteins Including Combination of Binding Units A series of monoclonal antibodies were developed and characterized. Using combinations of antigen-binding sequences (e.g., CDRs, HCv, LCv, HC, LC) derived from these "parental" antibodies a series of bispecific binding proteins were generated, and shown to have bispecific binding activity for the combined target antigens. The bispecific binding proteins were designed to have the particular structural platform motif which is disclosed herein (i.e., "BiS5").

Parental antibody sequences are described in the following Tables:

TABLE 2a

Parental antibody sequences

| Description/ Target | Sequence |
|---|---|
| PD-1 | |
| PD-1 LC | QIVLTQSPATLSLSPGERATLSCSASSKHTNLYWSRHMYWYQQKPGQAPRLLI YLTSNRATGIPARFSGSGSGTDFTLTISSLEPEDFAVYYCQQWSSNPFTFGQGT KLEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKS FNRGEC (SEQ ID NO: 23) |
| PD-1 LCv | QIVLTQSPATLSLSPGERATLSCSASSKHTNLYWSRHMYWYQQKPGQAPRLLI YLTSNRATGIPARFSGSGSGTDFTLTISSLEPEDFAVYYCQQWSSNPFTFGQGT KLEIK (SEQ ID NO: 49) |
| PD-1 HC | EVQLVESGGGLVQPGGSLRLSCAASGFTFSDYGMHWVRQAPGKGLEWVAYI SSGSYTIYSADSVKGRFTISRDNAKNSLYLQMNSLRAEDTAVYYCARRAPNSF YEYYFDYWGQGTTVTVSSASTKGPSVFPLAPCSRSTSESTAALGCLVKDYFPE |

TABLE 2a-continued

Parental antibody sequences

| Description/Target | Sequence |
|---|---|
| | PVTVSWNSGALTSGVHTFPAVLQSSGLYSLSSVVTVPSSSLGTKTYTCNVDHK PSNTKVDKRVESKYGPPCPPCPAPEFLGGPSVFLFPPKPKDTLMISRTPEVTCV VVDVSQEDPEVQFNWYVDGVEVHNAKTKPREEQFNSTYRVVSVLTVLHQD WLNGKEYKCKVSNKGLPSSIEKTISKAKGQPREPQVYTLPPSQEEMTKNQVSL TCLVKGFYPSDIAVEWESNGQPENNYKTTPPVLDSDGSFFLYSRLTVDKSRW QEGNVFSCSVMHEALHNHYTQKSLSLSLGK (SEQ ID NO: 50) |
| PD-1 HCv | EVQLVESGGGLVQPGGSLRLSCAASGFTFSDYGMHWVRQAPGKGLEWVAYI SSGSYTIYSADSVKGRFTISRDNAKNSLYLQMNSLRAEDTAVYYCARRAPNSF YEYYFDYWGQGTTVTVSS (SEQ ID NO: 51) |

CTLA-4

| CTLA-4 HCv | QVQLVESGGGVVQPGRSLRLSCAASGFTFSSYGMHWVRQAPGKGLEWVAVI WYDGSNKYYADSVKGRFTISRDNSKNTLYLQMNSLRAEDTAVYYCARDPRG ATLYYYYYGMDVWGQGTTVTVSS (SEQ ID NO: 52) |
|---|---|
| CTLA-4 HC | GVVQPGRSLRLSCAASGFTFSSYGMHWVRQAPGKGLEWVAVIWYDGSNKY YADSVKGRFTISRDNSKNTLYLQMNSLRAEDTAVYYCARDPRGATLYYYYY GMDVWGQGTTVTVSSASTKGPSVFPLAPCSRSTSESTAALGCLVKDYFPEPVT VSWNSGALTSGVH (SEQ ID NO: 53) |
| CTLA-4 LCv | DIQMTQSPSSLSASVGDRVTITCRASQSINSYLDWYQQKPGKAPKLLIYAASSL QSGVPSRFSGSGSGTDFTLTISSLQPEDFATYYCQQYYSTPFTFGPGTKVEIK (SEQ ID NO: 54) |
| CTLA-4 LC | DIQMTQSPSSLSASVGDRVTITCRASQSINSYLDWYQQKPGKAPKLLIYAASSL QSGVPSRFSGSGSGTDFTLTISSLQPEDFATYYCQQYYSTPFTFGPGTKVEIKRT VAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC (SEQ ID NO: 55) |

PD-L1

| PD-L1 (AMP714) HCv | EVQLVESGGGLVQPGRSLRLSCTASGYTFPDYYMNWVRQAPGKGLEWVGDI DPNYGGTTYNASVKGRFTISVDRSKSIAYLQMSSLKTEDTAVYYCARGALTD WGQGTMVTVSS (SEQ ID NO: 56) |
|---|---|
| PD-L1 (AMP714) LC | QIQLTQSPSILSASVGDRVTITCRASSSVSYIYWFQQKPGKAPKPLIYATFNLAS GVPSRFSGSGSGTSYTLTISSLQPEDFATYYCQQWSNNPLTFGQGTKVEIKRTV AAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 57) |
| PD-L1 (AMP714) LCv | QIQLTQSPSILSASVGDRVTITCRASSSVSYIYWFQQKPGKAPKPLIYATFNLAS GVPSRFSGSGSGTSYTLTISSLQPEDFATYYCQQWSNNPLTFGQGTKVEIK (SEQ ID NO: 58) |
| PD-L1 (MEDI4736) HCv | EVQLVESGGGLVQPGGSLRLSCAASGFTFSRYWMSWVRQAPGKGLEWVANI KQDGSEKYYVDSVKGRFTISRDNAKNSLYLQMNSLRAEDTAVYYCAREGGW FGELAFDYWGQGTLVTVSS (SEQ ID NO: 59) |
| PD-L1 (MEDI4736) LC | EIVLTQSPGTLSLSPGERATLSCRASQRVSSSYLAWYQQKPGQAPRLLIYDASS RATGIPDRFSGSGSGTDFTLTISRLEPEDFAVYYCQQYGSLPWTFGQGTKVEIK RTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC (SEQ ID NO: 33) |
| PD-L1 (MEDI4736) LCv | EIVLTQSPGTLSLSPGERATLSCRASQRVSSSYLAWYQQKPGQAPRLLIYDASS RATGIPDRFSGSGSGTDFTLTISRLEPEDFAVYYCQQYGSLPWTFGQGTKVEIK (SEQ ID NO: 60) |

TIM3

| TIM3 (WT) #62 LC | QTVLTQPPSVSVAPGKTASISCGGDNIGGKSVHWYQQKPGQAPVLVIYYDSD RPSGIPQRFSGSNSGNTATLTIHRVEAGDEADYYCQVLDRRSDHWLFGGGTK LTVLGQPKAAPSVTLFPPSSEELQANKATLVCLISDFYPGAVTVAWKADSSPV KAGVETTTPSKQSNNKYAASSYLSLTPEQWKSHRSYSCQVTHEGSTVEKTVA PTECS (SEQ ID NO: 61) |
|---|---|
| TIM3 (WT) #62 LCv | QTVLTQPPSVSVAPGKTASISCGGDNIGGKSVHWYQQKPGQAPVLVIYYDSD RPSGIPQRFSGSNSGNTATLTIHRVEAGDEADYYCQVLDRRSDHWLFGGGTK LTVL (SEQ ID NO: 62) |

TABLE 2a-continued

Parental antibody sequences

| Description/ Target | Sequence |
|---|---|
| TIM3 (WT) #62 HC | EVQLLESGGGLVQPGGSLRLSCAAS<u>GFTFSSYAMS</u>WVRQAPGKGLEWVS<u>AIS</u><br><u>GSGGSTYYADSVKG</u>RFTISRDNSKNTLYLQMNSLRAEDTAVYYCAR<u>GSYGT</u><br><u>YYGNYFEY</u>WGRGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCNVDH<br>KPSNTKVDKRVESKYGPPCPPCPAPEFLGGPSVFLFPPKPKDTLMISRTPEVTC<br>VVVDVSQEDPEVQFNWYVDGVEVHNAKTKPREEQFNSTYRVVSVLTVLHQD<br>WLNGKEYKCKVSNKGLPSSIEKTISKAKGQPREPQVYTLPPSQEEMTKNQVSL<br>TCLVKGFYPSDIAVEWESNGQPENNYKTTPPVLDSDGSFFLYSRLTVDKSRW<br>QEGNVFSCSVMHEALHNHYTQKSLSLSLGK (SEQ ID NO: 63) |
| TIM3 (WT) #62 HCv | EVQLLESGGGLVQPGGSLRLSCAAS<u>GFTFSSYAMS</u>WVRQAPGKGLEWVS<u>AIS</u><br><u>GSGGSTYYADSVKG</u>RFTISRDNSKNTLYLQMNSLRAEDTAVYYCAR<u>GSYGT</u><br><u>YYGNYFEY</u>WGRGTLVTVSS (SEQ ID NO: 64) |
| TIM3 (germlined) #62 LC | SYVLTQPPSVSVAPGKTARITC<u>GGDNIGGKSVH</u>WYQQKPGQAPVLVIY<u>YDSD</u><br><u>RPS</u>GIPERFSGSNSGNTATLTISRVEAGDEADYYC<u>QVLDRRSDH</u>WLFGGGTKL<br>TVLGQPKAAPSVTLFPPSSEELQANKATLVCLISDFYPGAVTVAWKADSSPVK<br>AGVETTTPSKQSNNKYAASSYLSLTPEQWKSHRSYSCQVTHEGSTVEKTVAP<br>TECS (SEQ ID NO: 65) |
| TIM3 (germlined) #62 LCv | SYVLTQPPSVSVAPGKTARITC<u>GGDNIGGKSVH</u>WYQQKPGQAPVLVIY<u>YDSD</u><br><u>RPS</u>GIPERFSGSNSGNTATLTISRVEAGDEADYYC<u>QVLDRRSDH</u>WLFGGGTKL<br>TVL (SEQ ID NO: 66) |
| TIM3 (germlined) #62 HC | EVQLLESGGGLVQPGGSLRLSCAAS<u>GFTFSSYAMS</u>WVRQAPGKGLEWVS<u>AIS</u><br><u>GSGGSTYYADSVKG</u>RFTISRDNSKNTLYLQMNSLRAEDTAVYYCAR<u>GSYGT</u><br><u>YYGNYFEY</u>WGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCNVDH<br>KPSNTKVDKRVESKYGPPCPPCPAPEFLGGPSVFLFPPKPKDTLMISRTPEVTC<br>VVVDVSQEDPEVQFNWYVDGVEVHNAKTKPREEQFNSTYRVVSVLTVLHQD<br>WLNGKEYKCKVSNKGLPSSIEKTISKAKGQPREPQVYTLPPSQEEMTKNQVSL<br>TCLVKGFYPSDIAVEWESNGQPENNYKTTPPVLDSDGSFFLYSRLTVDKSRW<br>QEGNVFSCSVMHEALHNHYTQKSLSLSLGK (SEQ ID NO: 67) |
| TIM3 (germlined) #62 HCv | EVQLLESGGGLVQPGGSLRLSCAAS<u>GFTFSSYAMS</u>WVRQAPGKGLEWVS<u>AIS</u><br><u>GSGGSTYYADSVKG</u>RFTISRDNSKNTLYLQMNSLRAEDTAVYYCAR<u>GSYGT</u><br>YYGNYFEYWGQGTLVTVSS (SEQ ID NO: 68) |
| OX40 | |
| OX40 HCv | QVQLQESGPGLVKPSQTLSLTCAVYGGSFS<u>SGYWN</u>WIRKHPGKGLEYIG<u>YISY</u><br><u>NGITYHNPSLKS</u>RITINRDTSKNQYSLQLNSVTPEDTAVYYCAR<u>YKYDYDGG</u><br><u>HAMDY</u>WGQGTLVTVSS (SEQ ID NO: 69) |
| OX40 LCv | DIQMTQSPSSLSASVGDRVTITC<u>RASQDISNYLN</u>WYQQKPGKAPKLLIY<u>YTSK</u><br><u>LHS</u>GVPSRFSGS GSGTDYTLTISSLQPEDFATYYC<u>QQGSALPWT</u>FGQGTKVEIK<br>(SEQ ID NO: 70) |
| OX40 HC | QVQLQESGPGLVKPSQTLSLTCAVYGGSFSSGYWNWIRKHPGKGLEYIGYISY<br>NGITYHNPSLKSRITINRDTSKNQYSLQLNSVTPEDTAVYYCARYKYDYDGG<br>HAMDYWGQGTLVTVSSASTKGPSVFPLAPSSKSTSGGTAALGCLVKDYFPEP<br>VTVSWNSGALTSGVHTFPAVLQSSGLYSLSSVVTVPSSSLGTQTYICNVNHKP<br>SNTKVDKRVEPKSCDKTHTCPPCPAPELLGGPSVFLFPPKPKDTLMISRTPEVT<br>CVVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSREEMTKNQ<br>VSLTCLVKGFYPSDIAVEWESNGQPENNYKTTPPVLDSDGSFFLYSKLTVDKS<br>RWQQGNVFSCSVMHEALHNHYTQKSLSLSPGK (SEQ ID NO: 71) |
| OX40 LC | DIQMTQSPSSLSASVGDRVTITCRASQDISNYLNWYQQKPGKAPKLLIYYTSK<br>LHSGVPSRFSGSGSGTDYTLTISSLQPEDFATYYCQQGSALPWTFGQGTKVEIK<br>RTVAAPSVFIFPPSDEQLKSGTASVVCLLNNFYPREAKVQWKVDNALQSGNS<br>QESVTEQDSKDSTYSLSSTLTLSKADYEKHKVYACEVTHQGLSSPVTKSFNRG<br>EC (SEQ ID NO: 72) |

TABLE 2b

Antigen sequences

| Description/Target | Sequence |
|---|---|
| PD-1 human | MQIPQAPWPVVWAVLQLGWRPGWFLDSPDRPWNPPTFSPALLVVTEGDNAT FTCSFSNTSESFVLNWYRMSPSNQTDKLAAFPEDRSQPGQDCRFRVTQLPNGR DFHMSVVRARRNDSGTYLCGAISLAPKAQIKESLRAELRVTERRAEVPTAHPS PSPRPAGQFQTLVVGVVGGLLGSLVLLVWVLAVICSRAARGTIGARRTGQPL KEDPSAVPVFSVDYGELDFQWREKTPEPPVPCVPEQTEYATIVFPSGMGTSSP ARRGSADGPRSAQPLRPEDGHCSWPL (SEQ ID NO: 73) |
| PD-L1 human | MRIFAVFIFMTYWHLLNAPYNKINQRILVVDPVTSEHELTCQAEGYPKAEVIW TSSDHQVLSGKTTTTNSKREEKLFNVTSTLRINTTTNEIFYCTFRRLDPEENHT AELVIPELPLAHPPNERTHLVILGAILLCLGVALTFIFRLRKGRMMDVKKCGIQ DTNSKKQSDTHLEET (SEQ ID NO: 74) |
| CTLA-4 human | MACLGFQRHKAQLNLATRTWPCTLLFFLLFIPVFCKAMHVAQPAVVLASSRG IASFVCEYASPGKATEVRVTVLRQADSQVTEVCAATYMMGNELTFLDDSICT GTSSGNQVNLTIQGLRAMDTGLYICKVELMYPPPYYLGIGNGTQIYVIDPEPCP DSDFLLWILAAVSSGLFFYSFLLTAVSLSKMLKKRSPLTTGVYVKMPPTEPEC EKQFQPYFIPIN (SEQ ID NO: 75) |
| TIM3 human | MFSHLPFDCVLLLLLLLLTRSSEVEYRAEVGQNAYLPCFYTPAAPGNLVPVC WGKGACPVFECGNVVLRTDERDVNYWTSRYWLNGDFRKGDVSLTIENVTL ADSGIYCCRIQIPGIMNDEKFNLKLVIKPAKVTPAPTRQRDFTAAFPRMLTTRG HGPAETQTLGSLPDINLTQISTLANELRDSRLANDLRDSGATIRIGIYIGAGICA GLALALIFGALIFKWYSHSKEKIQNLSLISLANLPPSGLANAVAEGIRSEENIYTI EENVYEVEEPNEYYCYVSSRQQPSQPLGCRFAMP (SEQ ID NO: 76) |
| OX40 human | MCVGARRLGRGPCAALLLLGLGLSTVTGLHCVGDTYPSNDRCCHECRPGNG MVSRCSRSQNTVCRPCGPGFYNDVVSSKPCKPCTWCNLRSGSERKQLCTATQ DTVCRCRAGTQPLDSYKPGVDCAPCPPGHFSPGDNQACKPWTNCTLAGKHT LQPASNSSDAICEDRDPPATQPQETQGPPARPITVQPTEAWPRTSQGPSTRPVE VPGGRAVAAILGLGLVLGLLGPLAILLALYLLRRDQRLPPDAHKPPGGGSFRT PIQEEQADAHSTLAKI (SEQ ID NO: 78) |

Example 2(a) PD-1/CTLA-4 Bispecific Binding Proteins

Figure 4:
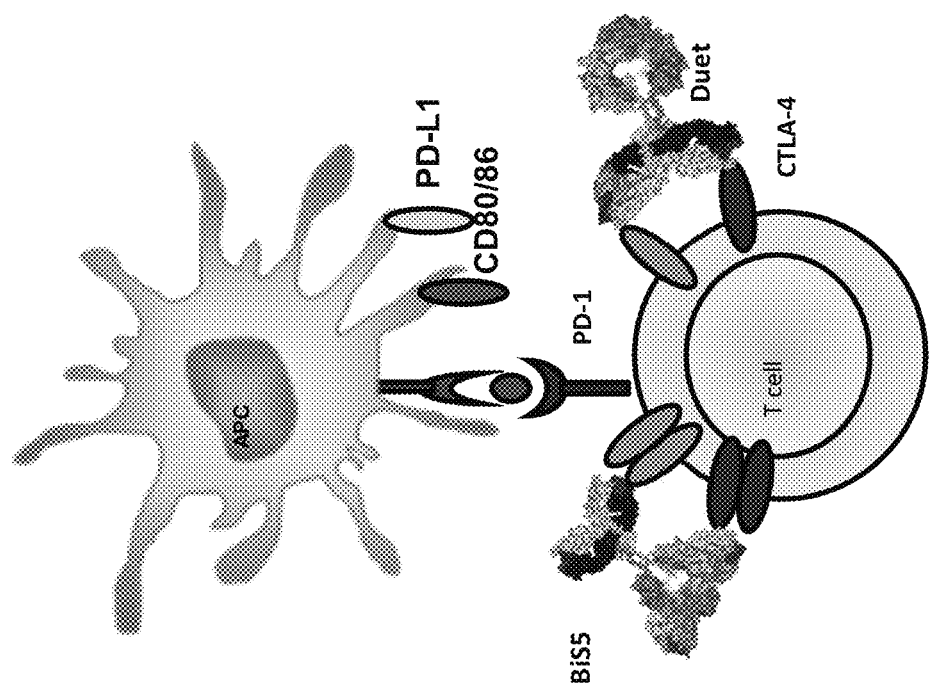
FIG. 4 shows a schematic of the proposed mechanism for the PD-1/CTLA-4 blockade.

Without being bound by theory, there is a strong clinical and preclinical rationale for the combination of PD-1 and CTLA-4 blockade. Thus, it would be desirable to maximize the risk/benefit ratio of PD-1 and CTLA-4 combination (FIG. 4).

The following bispecific binding proteins that bind PD-1 and CTLA-4 were created using the parental sequences identified above in Table 2. Proteins identified as Bis2, Bis3, and Bis5 were generated with the sequences identified below and were assessed for concurrent antigen binding activity using the Octet binding assay as discussed below.

TABLE 3

BIS constructs for PD-1/CTLA-4

| Description | Sequence |
|---|---|
| Bis2 PD-1/CTLA-4 HC | DIQMTQSPSSLSASVGDRVTITCRASQSINSYLDWYQQKPGKAPKLLIY AASSLQSGVPSRFSGSGSGTDFTLTISSLQPEDFATYYCQQYYSTPFTFG CGTKVEIKGGGGSGGGGSGGGGSGGGGSQVQLVESGGGVVQPGRSLR LSCAASGFTFSSYGMHWVRQAPGKCLEWVAVIWYDGSNKYYADSVK GRFTISRDNSKNTLYLQMNSLRAEDTAVYYCARDPRGATLYYYYGM DVWGQGTTVTVSSGGGGSGGGGSEVQLVESGGGLVQPGGSLRLSCAA SGFTFSDYGMHWVRQAPGKGLEWVAYISSGSYTIYSADSVKGRFTISR DNAKNSLYLQMNSLRAEDTAVYYCARRAPNSFYEYYFDYWGQGTTV TVSSASTKGPSVFPLAPCSRSTSESTAALGCLVKDYFPEPVTVSWNSGA LTSGVHTFPAVLQSSGLYSLSSVVTVPSSSLGTKTYTCNVDHKPSNTKV DKRVESKYGPPCPPCPAPEFLGGPSVFLFPPKPKDTLMISRTPEVTCVVV DVSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLY SRLTVDKSRWQEGNVFSCSVMHEALHNHYTQKSLSLSLGK (SEQ ID NO: 1) |
| Bis2 PD-1/CTLA-4 LC | QIVLTQSPATLSLSPGERATLSCSASSKHTNLYWSRHMYWYQQKPGQA PRLLIYLTSNRATGIPARFSGSGSGTDFTLTISSLEPEDFAVYYCQQWSS NPFTFGQGTKLEIKRTVAAPSVFIFPPSDEQLKSGTASVVCLLNNFYPRE AKVQWKVDNALQSGNSQESVTEQDSKDSTYSLSSTLTLSKADYEKHK VYACEVTHQGLSSPVTKSFNRGEC (SEQ ID NO: 2) |

TABLE 3-continued

BIS constructs for PD-1/CTLA-4

| Description | Sequence |
|---|---|
| Bis3 PD-1/CTLA-4 HC | EVQLVESGGGLVQPGGSLRLSCAASGFTFSDYGMHWVRQAPGKGLE WVAYISSGSYTIYSADSVKGRFTISRDNAKNSLYLQMNSLRAEDTAVY YCARRAPNSFYEYYFDYWGQGTTVTVSSASTKGPSVFPLAPCSRSTSES TAALGCLVKDYFPEPVTVSWNSGALTSGVHTFPAVLQSSGLYSLSSVV TVPSSSLGTKTYTCNVDHKPSNTKVDKRVESKYGPPCPPCPAPEFLGGP SVFLFPPKPKDTLMISRTPEVTCVVVDVSQEDPEVQFNWYVDGVEVHN AKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHE ALHNHYTQKSLSLSLGKGGGGSGGGGSDIQMTQSPSSLSASVGDRVTI TCRASQSINSYLDWYQQKPGKAPKLLIYAASSLQSGVPSRFSGSGSGTD FTLTISSLQPEDFATYYCQQYYSTPFTFGCGTKVEIKGGGGSGGGGSGG GGSGGGGSQVQLVESGGGVVQPGRSLRLSCAASGFTFSSYGMHWVRQ APGKCLEWVAVIWYDGSNKYYADSVKGRFTISRDNSKNTLYLQMNSL RAEDTAVYYCARDPRGATLYYYYGMDVWGQGTTVTVSS (SEQ ID NO: 3) |
| Bis3 PD-1/CTLA-4 LC | QIVLTQSPATLSLSPGERATLSCSASSKHTNLYWSRHMYWYQQKPGQA PRLLIYLTSNRATGIPARFSGSGSGTDFTLTISSLEPEDFAVYYCQQWSS NPFTFGQGTKLEIKRTVAAPSVFIFPPSDEQLKSGTASVVCLLNNFYPRE AKVQWKVDNALQSGNSQESVTEQDSKDSTYSLSSTLTLSKADYEKHK VYACEVTHQGLSSPVTKSFNRGEC (SEQ ID NO: 4) |
| Bis5 PD-1/CTLA-4 HC | EVQLVESGGGLVQPGGSLRLSCAASGFTFSDYGMHWVRQAPGKGLE WVAYISSGSYTIYSADSVKGRFTISRDNAKNSLYLQMNSLRAEDTAVY YCARRAPNSFYEYYFDYWGQGTTVTVSSASTKGPSVFPLAPCSRSTSES TAALGCLVKDYFPEPVTVSWNSGALTSGVHTFPAVLQSSGLYSLSSVV TVPSSSLGTKTYTCNVDHKPSNTKVDKRVESKYGPPCPPCPAPEFLGGP SVFLFPPKPKDTLMISRTPEVTCVVVDVSQEDPEVQFNWYVDGVEVHN AKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWES NGGGGSGGGGSDIQMTQSPSSLSASVGDRVTITCRASQSINSYLDWYQ QKPGKAPKLLIYAASSLQSGVPSRFSGSGSGTDFTLTISSLQPEDFATYY CQQYYSTPFTFGCGTKVEIKGGGGSGGGGSGGGGSGGGGSQVQLVES GGGVVQPGRSLRLSCAASGFTFSSYGMHWVRQAPGKCLEWVAVIWY DGSNKYYADSVKGRFTISRDNSKNTLYLQMNSLRAEDTAVYYCARDP RGATLYYYYGMDVWGQGTTVTVSSGGGGSGGGGSGQPENNYKTTP PVLDSDGSFFLYSRLTVDKSRWQEGNVFSCSVMHEALHNHYTQKSLSL SLGK (SEQ ID NO: 5) |
| Bis5 PD-1/CTLA-4 LC | QIVLTQSPATLSLSPGERATLSCSASSKHTNLYWSRHMYWYQQKPGQA PRLLIYLTSNRATGIPARFSGSGSGTDFTLTISSLEPEDFAVYYCQQWSS NPFTFGQGTKLEIKRTVAAPSVFIFPPSDEQLKSGTASVVCLLNNFYPRE AKVQWKVDNALQSGNSQESVTEQDSKDSTYSLSSTLTLSKADYEKHK VYACEVTHQGLSSPVTKSFNRGEC (SEQ ID NO: 6) |

Octet Binding Assay (BiS2, BiS3, and BiS5)

To evaluate binding of the bispecific binding molecules disclosed herein, an Octet QK equipped with Ni-NTA biosensor tips and 10× kinetics buffer were used (ForteBio, Menlo Park, Calif.). For this particular series of bispecific binding proteins, His-tagged PD-L1-Fc, his-tagged PD-1-Fc and CTLA-4-Fc (human recombinant proteins) were purchased from R&D Systems (Minneapolis, Minn.). All binding assays were performed at 25° C.

Figure 3:
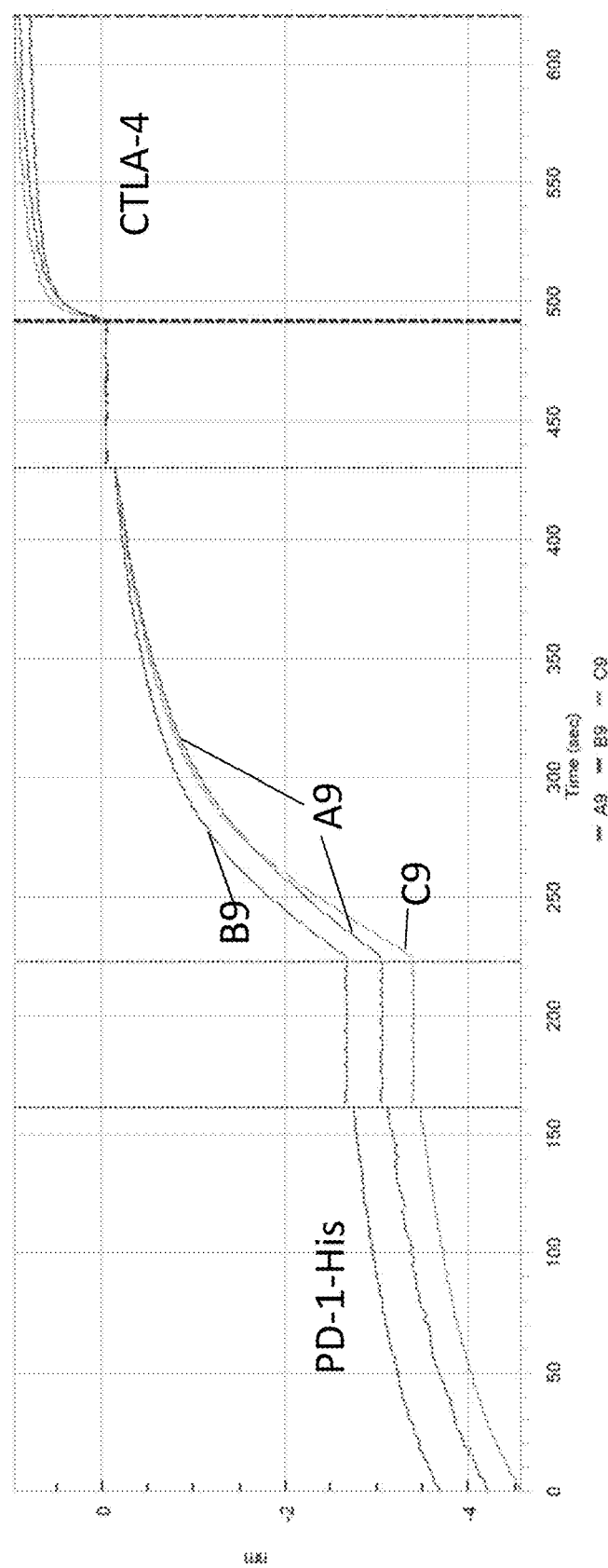
FIG. 3 demonstrates the concurrent binding of the BiS2, BiS3, and BiS5 constructs that target PD-1 and CTLA-4. Trace A9 shows BiS2 PD-1/CTLA-4, trace B9 shows Bis3 PD-1/CTLA-4, and trace C9 shows Bis5 PD-1/CTLA-4.

Sample plates were agitated at 1000 rpm prior to analysis. The Ni-NTA biosensor tips were pre-wetted for 5 min. in 1× kinetic buffer. The 1× kinetic buffer also served as the running buffer for baseline determination and as the dilution buffer for antigens and bispecific antibodies. Ni-NTA biosensor tips were dipped into 100 nM his-tagged PD-L1-Fc (see, (b), below) or his-tagged PD-1-Fc for antigen capture for about 1 min. The antigen-coated biosensor tips were each dipped into 10 μg/ml bispecific antibodies for ~5 minutes and then moved into a column of wells containing 100 nM CTLA-4-Fc antigen for 2 minutes. The binding results are shown in FIG. 3.

A bispecific binding protein in DuetMab format that binds PD-1 and CTLA-4 was created using the parental sequences identified above in Table 2. The PD-1/CTLA-4 DuetMab was generated with the sequences in Table 4 below and was assessed as discussed below, including in comparison with PD-1/CTLA-4 Bis5.

TABLE 4

DuetMab constructs for PD-1/CTLA-4

| Description | Sequence |
|---|---|
| DuetMab PD-1 (L0115) LC | QIVLTQSPATLSLSPGERATLSC*SASSKHTNLYWSRHMYWY*QQKPGQA PRLLIY*LTSNRAT*GIPARFSGSGSGTDFTLTISSLEPEDFAVYYC*QQWSS NP*FTFGQGTKLEIKRTVAAPSVFIFPPSDEQLKSGTASVVCLLNNFYPRE |

TABLE 4-continued

DuetMab constructs for PD-1/CTLA-4

| Description | Sequence |
|---|---|
| Amino acid | AKVQWKVDNALQSGNSQESVTEQDSKDSTYSLSSTLTLSKADYEKHK<br>VYACEVTHQGLSSPVTKSFNRGEC (SEQ ID NO: 7) |
| DuetMab<br>PD-1(LO115)<br>LC<br>Nucleic acid | CAGATCGTGCTGACCCAGTCCCCTGCCACCCTGTCCCTGAGCCCTGG<br>CGAGAGAGCCACCCTGAGCTGCTCCGCCTCCTCCAAGCACACCAAC<br>CTGTACTGGTCCCGGCACATGTACTGGTATCAGCAGAAGCCCGGCC<br>AGGCCCCTCGGCTGCTGATCTACCTGACCTCTAACCGGGCCACCGG<br>CATCCCTGCCAGATTCTCCGGCTCTGGCTCCGGCACCGACTTCACCC<br>TGACCATCTCCAGCCTGGAACCCGAGGACTTCGCCGTGTACTACTG<br>CCAGCAGTGGTCCTCCAACCCCTTCACCTTCGGCCAGGGCACCAAG<br>CTGGAAATCAAGCGTACGGTGGCTGCACCATCTGTCTTCATCTTCCC<br>GCCATCTGATGAGCAGTTGAAATCTGGAACTGCCTCTGTTGTGTGCC<br>TGCTGAATAACTTCTATCCCAGAGAGGCCAAAGTACAGTGGAAGGT<br>GGATAACGCCCTCCAATCGGGTAACTCCCAGGAGAGTGTCACAGAG<br>CAGGACAGCAAGGACAGCACCTACAGCCTCAGCAGCACCCTGACG<br>CTGAGCAAAGCAGACTACGAGAAACACAAAGTCTACGCCTGCGAA<br>GTCACCCATCAGGGCCTGAGCTCGCCCGTCACAAAGAGCTTCAACA<br>GGGGAGAGTGT (SEQ ID NO: 8) |
| DuetMab<br>PD-1 (LO115)<br>HC<br>Amino acid | EVQLVESGGGLVQPGGSLRLSCAAS*GFTFSDYGMH*WVRQAPGKGLE<br>WVA*YISSGSYTIYSADSVKG*RFTISRDNAKNSLYLQMNSLRAEDTAVYY<br>CAR*RAPNSFYEYYFDY*WGQGTTVTVSSASTKGPSVFPLAPSSKSTSGGT<br>AALGCLVKDYFPEPVTVSWNSGALTSGVHTFPAVLQSSGLYSLSSVVT<br>VPSSSLGTQTYICNVNHKPSNTKVDKRVEPKSCDKTHTCPPCPAPEFEG<br>GPSVFLFPPKPKDTLMISRTPEVTCVVVDVSHEDPEVKFNWYVDGVEV<br>HNAKTKPREEQYNSTYRVVSVLTVLHQDWLNGKEYKCKVSNKALPA<br>SIEKTISKAKGQPREPQVCTLPPSREEMTKNQVSLSCAVKGFYPSDIAVE<br>WESNGQPENNYKTTPPVLDSDGSFFLVSKLTVDKSRWQQGNVFSCSV<br>MHEALHNHYTQKSLSLSPGK (SEQ ID NO: 9) |
| DuetMab<br>PD-1 (LO115)<br>HC<br>Nucleic acid | GAGGTGCAGCTGGTGGAATCCGGCGGAGGACTGGTGCAGCCTGGC<br>GGCTCCCTGAGACTGTCTTGCGCCGCCTCCGGCTTCACATTCTCCGA<br>CTACGGCATGCACTGGGTCCGACAGGCCCCTGGAAAGGGCCTGGAA<br>TGGGTGGCCTACATCTCCTCCGGCTCCTACACCATCTACTCCGCCGA<br>CTCCGTGAAGGGCCGGTTCACCATCTCCCGGGACAACGCCAAGAAC<br>TCCCTGTACCTGCAGATGAACTCCCTGCGGGCCGAGGACACAGCCG<br>TGTACTACTGTGCCAGACGGGCCCCTAACTCCTTCTACGAGTACTAC<br>TTCGACTACTGGGGCCAGGGCACCACCGTGACCGTGTCCTCTGCTA<br>GCACCAAAGGTCCGAGCGTTTTTCCGCTGGCACCGAGCAGCAAAAG<br>CACCTCTGGTGGCACCGCAGCACTGGGTTGTCTGGTGAAAGATTAT<br>TTTCCGGAACCGGTTACCGTTTCTTGGAATAGCGGTGCACTGACCAG<br>CGGTGTTCATACCTTTCCGGCAGTTCTGCAGAGCAGCGGTCTGTATA<br>GCCTGTCTAGCGTTGTTACCGTTCCGAGCAGCAGCCTGGGCACCCA<br>GACCTATATTTGCAATGTGAATCATAAACCGAGCAATACAAAAGTT<br>GATAAACGCGTTGAACCGAAAAGCTGTGACAAAACTCACACGTGCC<br>CACCGTGCCCAGCACCTGAGTTCGGAGGGGGACCGTCAGTCTTCCT<br>CTTCCCCCCAAAACCCAAGGACACCCTCATGATCTCCCGGACCCCT<br>GAGGTCACATGCGTGGTGGTGGACGTGAGCCACGAAGACCCTGAG<br>GTCAAGTTCAACTGGTACGTGGACGGCGTGGAGGTGCATAATGCCA<br>AGACAAAGCCGCGGGAGGAGCAGTACAACAGCACGTACCGTGTGG<br>TCAGCGTCCTCACCGTCCTGCACCAGGACTGGCTGAATGGCAAGGA<br>GTACAAGTGCAAGGTCTCCAACAAAGCCCTCCCAGCCAGATCGAGA<br>AAACCATCTCCAAAGCCAAAGGGCAGCCCCGAGAACCACAGGTCT<br>GCACCCTGCCCCCATCCCGGGAGGAGATGACCAAGAACCAGGTCA<br>GCCTGAGCTGCGCGGTCAAAGGCTTCTATCCCAGCGACATCGCCGT<br>GGAGTGGGAGAGCAATGGGCAGCCGGAGAACAACTACAAGACCAC<br>GCCTCCCGTGCTGGACTCCGACGGCTCCTTCTTCCTCGTTAGCAAGC<br>TCACCGTGGACAAGAGCAGGTGGCAGCAGGGGAACGTCTTCTCATG<br>CTCCGTGATGCATGAGGCTCTGCACAACCACTACACGCAGAAGAGC<br>CTCTCCCTGTCTCCGGGTAAA (SEQ ID NO: 10) |
| DuetMab<br>CTLA-4<br>LC<br>Amino acid | DIQMTQSPSSLSASVGDRVTITC*RASQSINSYLD*WYQQKPGKAPKLLIY<br>*AASSLQS*GVPSRFSGSGSGTDFTLTISSLQPEDFATYYC*QQYYSTP*FTFGP<br>GTKVEIKGQPKAAPSVTLFPPCSEELQANKATLVCLISDFYPGAVTVAW<br>KADSSPVKAGVETTTPSKQSNNKYAASSYLSLTPEQWKSHRSYSCQVT<br>HEGSTVEKTVAPTEVS (SEQ ID NO: 4) |
| DuetMab<br>CTLA-4<br>LC<br>Nucleic acid | GACATCCAGATGACCCAGTCTCCATCCTCCCTGTCTGCATCTGTAGG<br>AGACAGAGTCACCATCACTTGCCGGGCAAGTCAGAGCATTAACAGC<br>TATTTAGATTGGTATCAGCAGAAACCAGGGAAAGCCCCTAAACTCC<br>TGATCTATGCTGCATCCAGTTTGCAAAGTGGGGTCCCATCAAGGTTC<br>AGTGGCAGTGGATCTGGGACAGATTTCACTCTCACCATCAGCAGTC |

TABLE 4-continued

DuetMab constructs for PD-1/CTLA-4

| Description | Sequence |
|---|---|
| | TGCAACCTGAAGATTTTGCAACTTACTACTGTCAACAGTATTACAGT<br>ACTCCATTCACTTTCGGCCCTGGGACCAAAGTGGAAATCAAAGGTC<br>AGCCCAAGGCGGCCCCCTCGGTCACTCTGTTCCCGCCCTGCTCTGAG<br>GAGCTTCAAGCCAACAAGGCCACACTGGTGTGTCTCATAAGTGACT<br>TCTACCCGGGAGCCGTGACAGTGGCCTGGAAGGCAGATAGCAGCCC<br>CGTCAAGGCGGGAGTGGAGACCACCACACCCTCCAAACAAAGCAA<br>CAACAAGTACGCGGCCAGCAGCTACCTGAGCCTGACGCCTGAGCAG<br>TGGAAGTCCCACAGAAGCTACAGCTGCCAGGTCACGCATGAAGGG<br>AGCACCGTGGAGAAGACAGTGGCCCCTACAGAAGTGTCA (SEQ ID<br>NO: 11) |
| DuetMab<br>CTLA-4<br>HC<br>Amino acid | QVQLVESGGGVVQPGRSLRLSCAAS*GFTFSSYGMH*WVRQAPGKGLE<br>WVA*VIWYDGSNKYYADSVKG*RFTISRDNSKNTLYLQMNSLRAEDTAV<br>YYCAR*DPRGATLYYYYGMDV*WGQGTTVTVSSASTKGPSVCPLAPSSK<br>STSGGTAALGCLVKDYFPEPVTVSWNSGALTSGVHTFPAVLQSSGLYS<br>LSSVVTVPSSSLGTQTYICNVNHKPSNTKVDKRVEPKSVDKTHTCPPCP<br>APEFEGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPASIEKTISKAKGQPREPQVYTLPPCREEMTKNQVSLWCLVKGF<br>YPSDIAVEWESNGQPENNYKTTPPVLDSDGSFFLYSKLTVDKSRWQQG<br>NVFSCSVMHEALHNHYTQKSLSLSPGK (SEQ ID NO: 12) |
| DuetMab<br>CTLA-4<br>HC<br>Nucleic acid | CAGGTGCAGCTGGTGGAGTCTGGGGGAGGCGTGGTCCAGCCTGGGA<br>GGTCCCTGAGACTCTCCTGTGCAGCGTCTGGATTCACCTTCAGTAGC<br>TATGGCATGCACTGGGTCCGCCAGGCTCCAGGCAAGGGGCTGGAGT<br>GGGTGGCAGTTATATGGTATGATGGAAGTAATAAATACTATGCAGA<br>CTCCGTGAAGGGCCGATTCACCATCTCCAGAGACAATTCCAAGAAC<br>ACGCTGTATCTGCAAATGAACAGCCTGAGAGCCGAGGACACGGCTG<br>TGTATTACTGTGCGAGAGATCCGAGGGGAGCTACCCTTTACTACTA<br>CTACTACGGTATGGACGTCTGGGGCCAAGGGACCACGGTCACCGTC<br>TCCTCAGCGTCGACCAAAGGTCCGAGCGTGTGCCCGCTGGCACCGA<br>GCAGCAAAAGCACCTCTGGTGGCACCGCAGCACTGGGTTGTCTGGT<br>GAAAGATTATTTTCCGGAACCGGTTACCGTTTCTTGGAATAGCGGTG<br>CACTGACCAGCGGTGTTCATACCTTTCCGGCAGTCCTGCAGAGCAG<br>CGGTCTGTATAGCCTGTCTAGCGTTGTTACCGTTCCGAGCAGCAGCC<br>TGGGCACCCAGACCTATATTTGCAATGTGAATCATAAACCGAGCAA<br>TACCAAAGTTGATAAACGCGTTGAACCGAAAAGCGTGGACAAAACT<br>CACACGTGCCCACCGTGCCCAGCACCTGAGTTCGAGGGGGGACCGT<br>CAGTCTTCCTCTTCCCCCCAAAACCCAAGGACACCCTCATGATCTCC<br>CGGACCCCTGAGGTCACATGCGTGGTGGTGGACGTGAGCCACGAAG<br>ACCCTGAGGTCAAGTTCAACTGGTACGTGGACGGCGTGGAGGTGCA<br>TAATGCCAAGACAAAGCCGCGGGAGGAGCAGTACAACAGCACGTA<br>CCGTGTGGTCAGCGTCCTCACCGTCCTGCACCAGGACTGGCTGAAT<br>GGCAAGGAGTACAAGTGCAAGGTCTCCAACAAAGCCCTCCCAGCCa<br>gCATCGAGAAAACCATCTCCAAAGCCAAAGGGCAGCCCCGAGAACC<br>ACAGGTCTACACCCTGCCCCCATGCCGGGAGGAGATGACCAAGAAC<br>CAGGTCAGCCTGTGGTGCCTGGTCAAAGGCTTCTATCCCAGCGACA<br>TCGCCGTGGAGTGGGAGAGCAATGGGCAGCCGGAGAACAACTACA<br>AGACCACGCCTCCCGTGCTGGACTCCGACGGCTCCTTCTTCCTCTAT<br>AGCAAGCTCACCGTGGACAAGAGCAGGTGGCAGCAGGGGAACGTC<br>TTCTCATGCTCCGTGATGCATGAGGCTCTGCACAACCACTACACGCA<br>GAAGAGCTTAAGCCTGTCTCCGGGTAAA (SEQ ID NO: 13) |

Octet Binding Assay (DuetMab)

Figure 5:
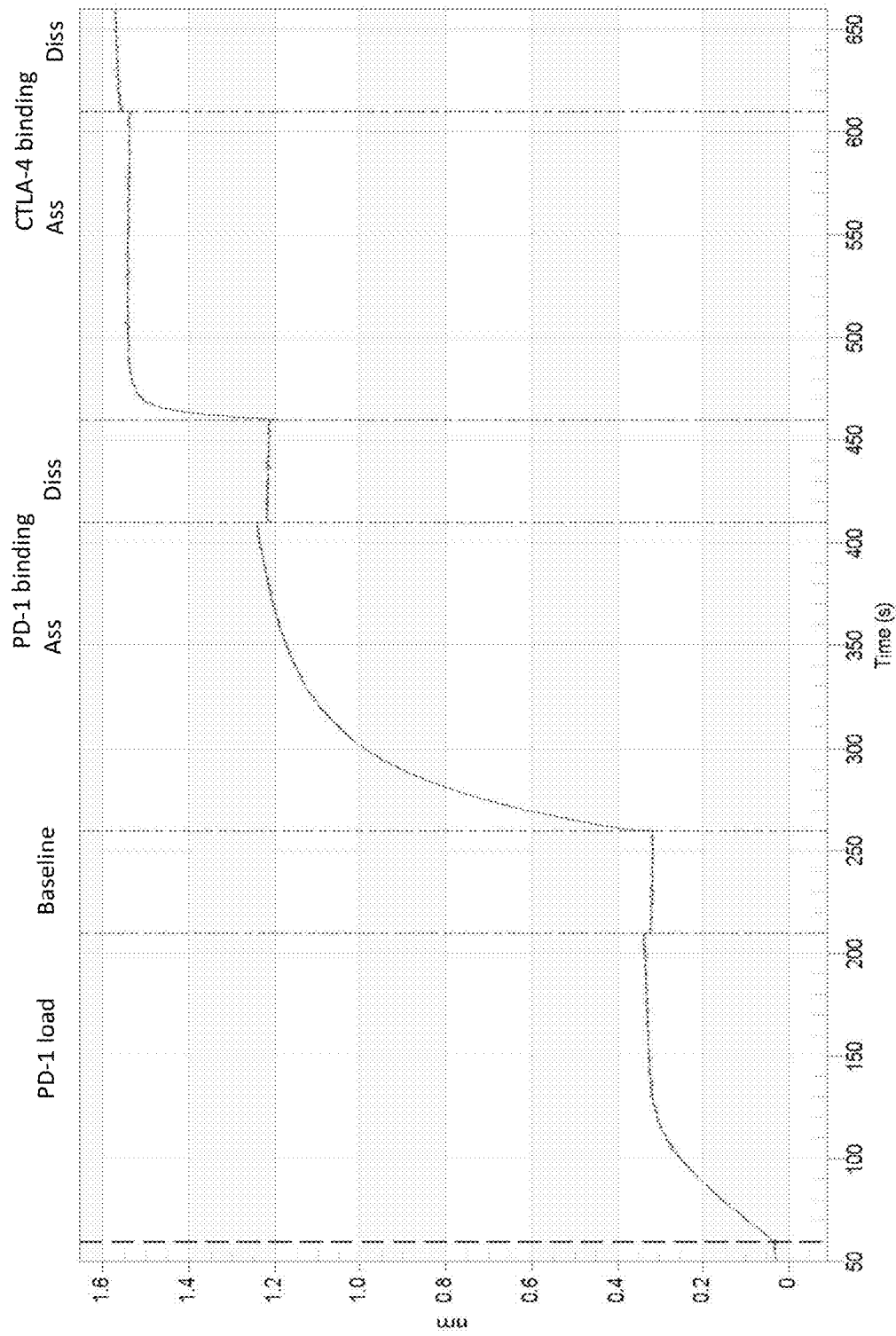
FIG. 5 shows the results of an octet binding assay which demonstrates the concurrent binding of a DuetMab construct that targets PD-1 and CTLA-4.
Figure 6C:
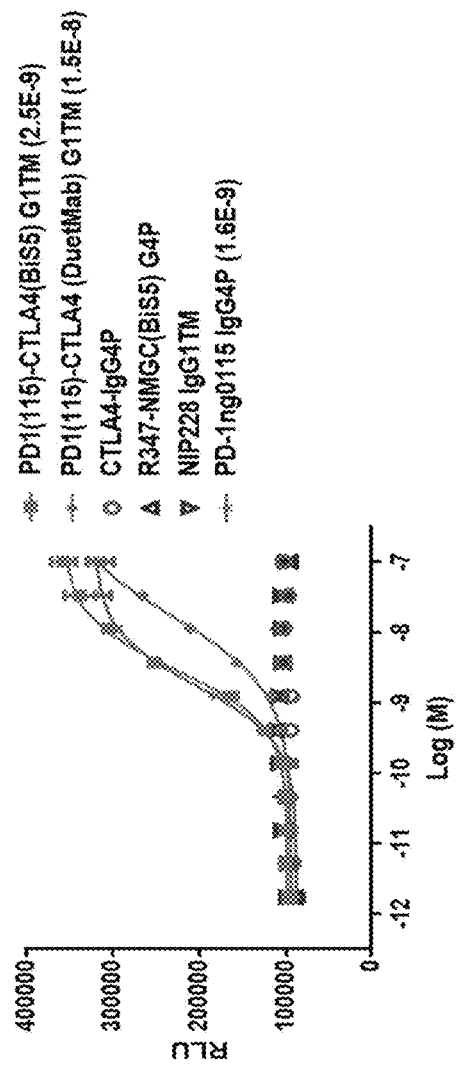
Figure 6D:
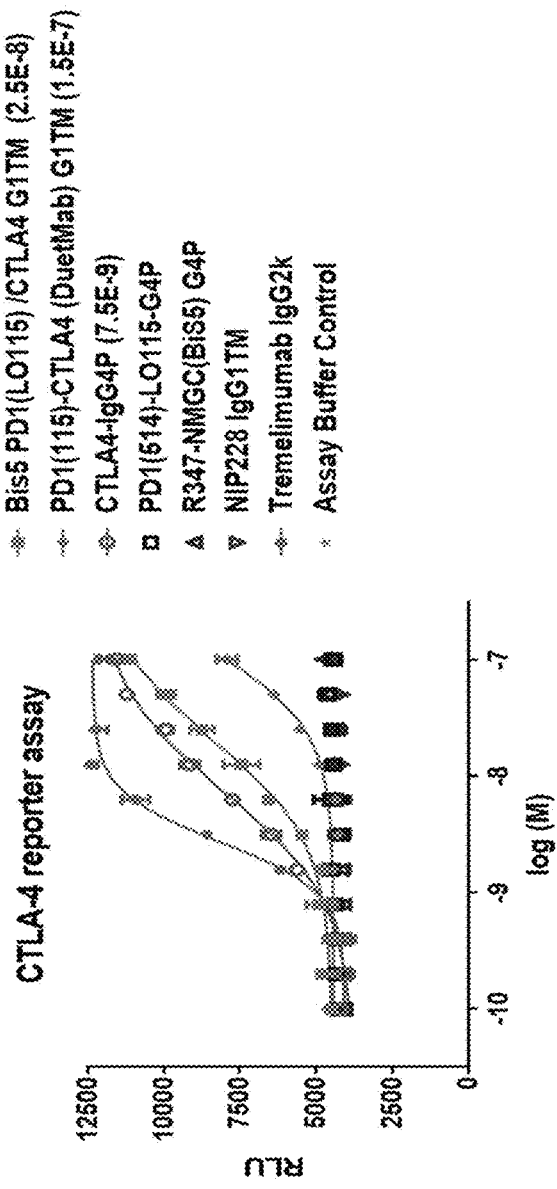

Concurrent binding studies to two distinctive antigens were performed by Octet analysis. Biotinylated human PD-1 was loaded on Streptavidin sensors followed by sequential interactions first with DuetMab PD-1/CTLA-4 and then with soluble CTLA-4 antigen. Streptavidin (SA) biosensors (ForteBio) were used to capture biotinylated human PD-1 at 5 μg/ml in PBS pH 7.2, 3 mg/ml BSA, 0.05% (v/v) Tween 20 (assay buffer). Following a washing step the loaded biosensors were subjected for successive association and dissociation interactions first with sample wells carrying the DuetMab PD-1/CTLA-4 bispecific antibody at 133 nM and then with wells carrying human CTLA-4 antigen at 200 nM. The binding results are shown in FIG. 5.

Intrinsic kinetics of the PD-1/CTLA-4 DuetMab bispecific antibody was also assessed via BiaCore. Binding experiments were carried out using a BIAcore T200 instrument (BIAcore). To capture the antibody, mouse anti-huIgG-Fab was immobilized on a CM5 chip to a target response of 2000 RU. 100 nM of the DuetMab or mAbs were flowed at 20 μL/min for 5 min to achieve approximately 100 response units of captured antibody. Antigen were then injected serially at a flow rate of 50 μl/min for 5 min. Kinetic parameters ($k_{on}$ and $k_{off}$) and dissociation constant (KD) were calculated from a non-linear fit using BIAevaluation 4.1 software. The binding results are shown in Table 5.

TABLE 5

BiaCore data for PD-1/CTLA-4

| | Capture Surface | PD1 | CTLA4 | kon ($\times E + 5\ M^{-1}s^{-1}$) | koff ($\times E - 4\ s^{-1}$) | $K_D$ (nM) | $Chi^2$ |
|---|---|---|---|---|---|---|---|
| Anti-PD-1 (LO115) IgG | mu-anti-huIgG | hu | | 3.02 | 2.37 | 0.79 | 0.08 |
| | mu-anti-huIgG | cyno | | 3.46 | 2.38 | 0.69 | 0.06 |
| | mu-anti-huIgG | mu | | 1.49 | 665 | 447 | 0.13 |
| Anti-CTLA-4 IgG | mu-anti-huIgG | | hu | 6.33 | 3.04 | 0.48 | 0.27 |
| | mu-anti-huIgG | | cyno | 11.47 | 6.74 | 0.59 | 0.47 |
| PD-1/CTLA-4 DuetMab | mu-anti-huIgG | hu | | 2.95 | 2.36 | 0.81 | 0.03 |
| | mu-anti-huIgG | cyno | | 4.90 | 2.15 | 0.44 | 0.03 |
| | mu-anti-huIgG | mu | | 1.40 | 693 | 496 | 0.12 |
| | mu-anti-huIgG | | hu | 6.84 | 4.21 | 0.42 | 0.08 |
| | mu-anti-huIgG | | cyno | 11.43 | 6.34 | 0.55 | 0.18 |

Reporter Gene Assays

Results from reporter gene assays show that PD-1/CTLA-4 bispecific binding proteins inhibited the PD-1 and CTLA-4 pathways (FIG. 6A-D). The BiS5 binding protein retained PD-1 potency compared to parent but had ~3 fold reduced potency compared to anti-CTLA-4 IgGs. The DuetMab antibody had a ~9 fold reduction in PD-1 potency and ~16 fold reduction for CTLA-4 (compared to IgG4P). There is a need in the art for a molecule that has reduced CTLA-4 targeting but retains functional activity (e.g., as shown below in the SEB assay). The PD-1/CTLA-4 bispecific binding proteins thus have the potential to provide a safety benefit to patients.

Staphylococcal Enterotoxin B (SEB) Assay

Figure 7:
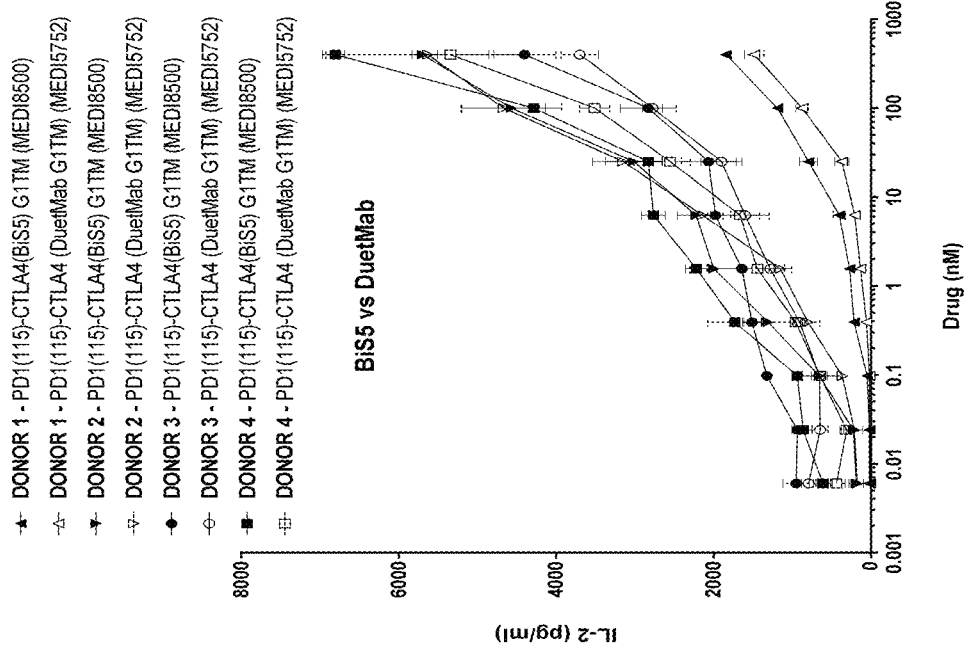
FIG. 7 shows the results of a SEB assay showing that PD-1/CTLA-4 DuetMab and BiS5Ab have equivalent activity in the Staphylococcal enterotoxin B (SEB) assay.

Results from an SEB assay show that DuetMab and BiS5Ab had equivalent activity in SEB primary immune cell assays (FIG. 7), and DuetMab showed greater activity compared to DummyDuet control arms (FIG. 8A). DuetMab showed approximately equivalent activity to the combination of parent molecules, and greater activity compared to LO115 or the CTLA-4 antibody MEDI1123 (tremelimumab) (FIG. 8B). Finally, BiS5 and DuetMab showed greater activity compared to a combination of new isotype controls (FIGS. 9A-B). Data were obtained from four donors across two independent experiments, and these particular assays required the use of IFNγ.

Mixed Leukocyte Reaction (MLR) Assay

Figure 10A:
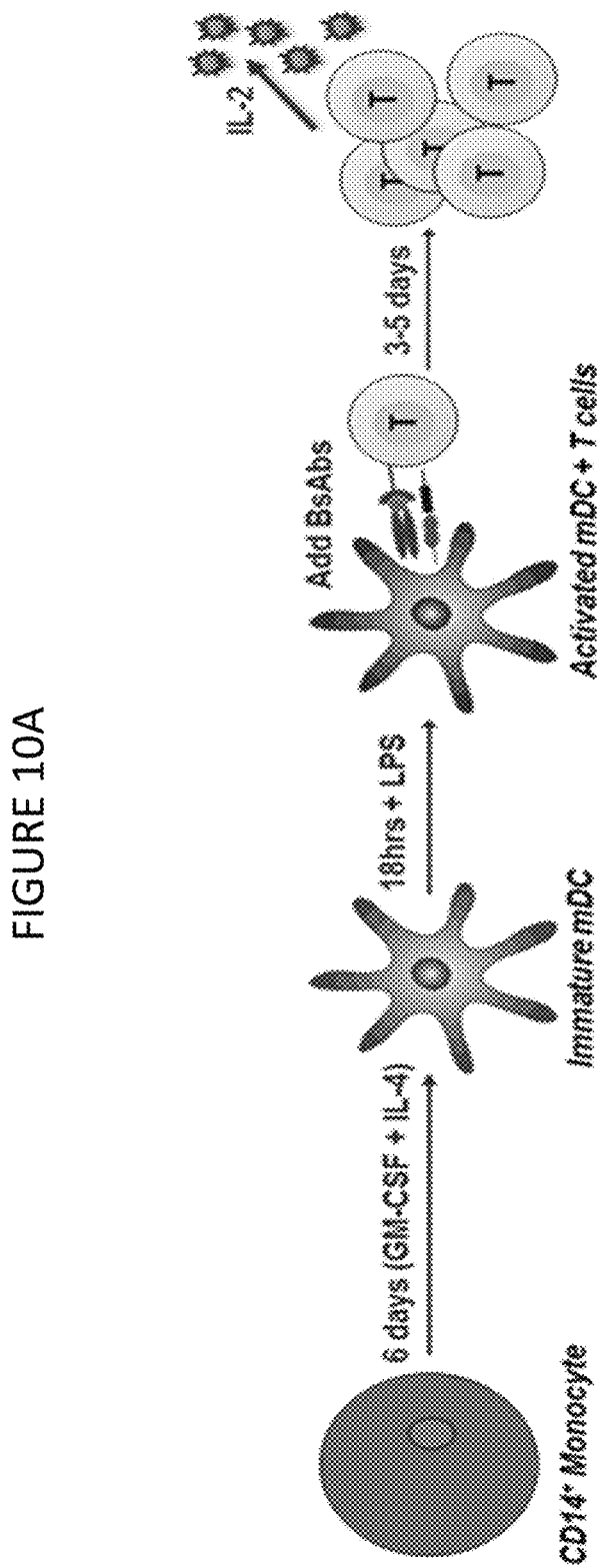
FIGS. 10A-C show that PD-1/CTLA-4 DuetMab and BiS5Ab have equivalent activity in the mixed lymphocyte reaction (MLR) assay.
Figure 10:
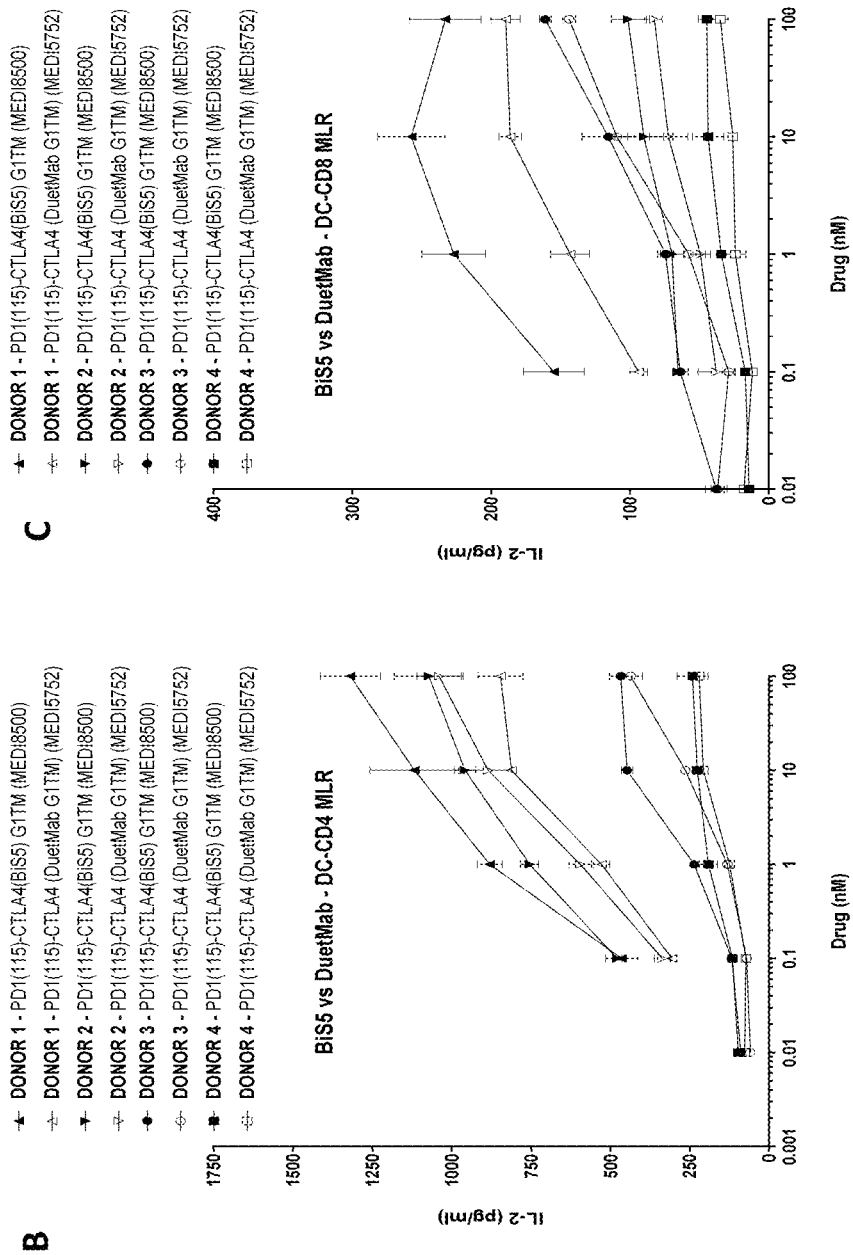
Figure 11:
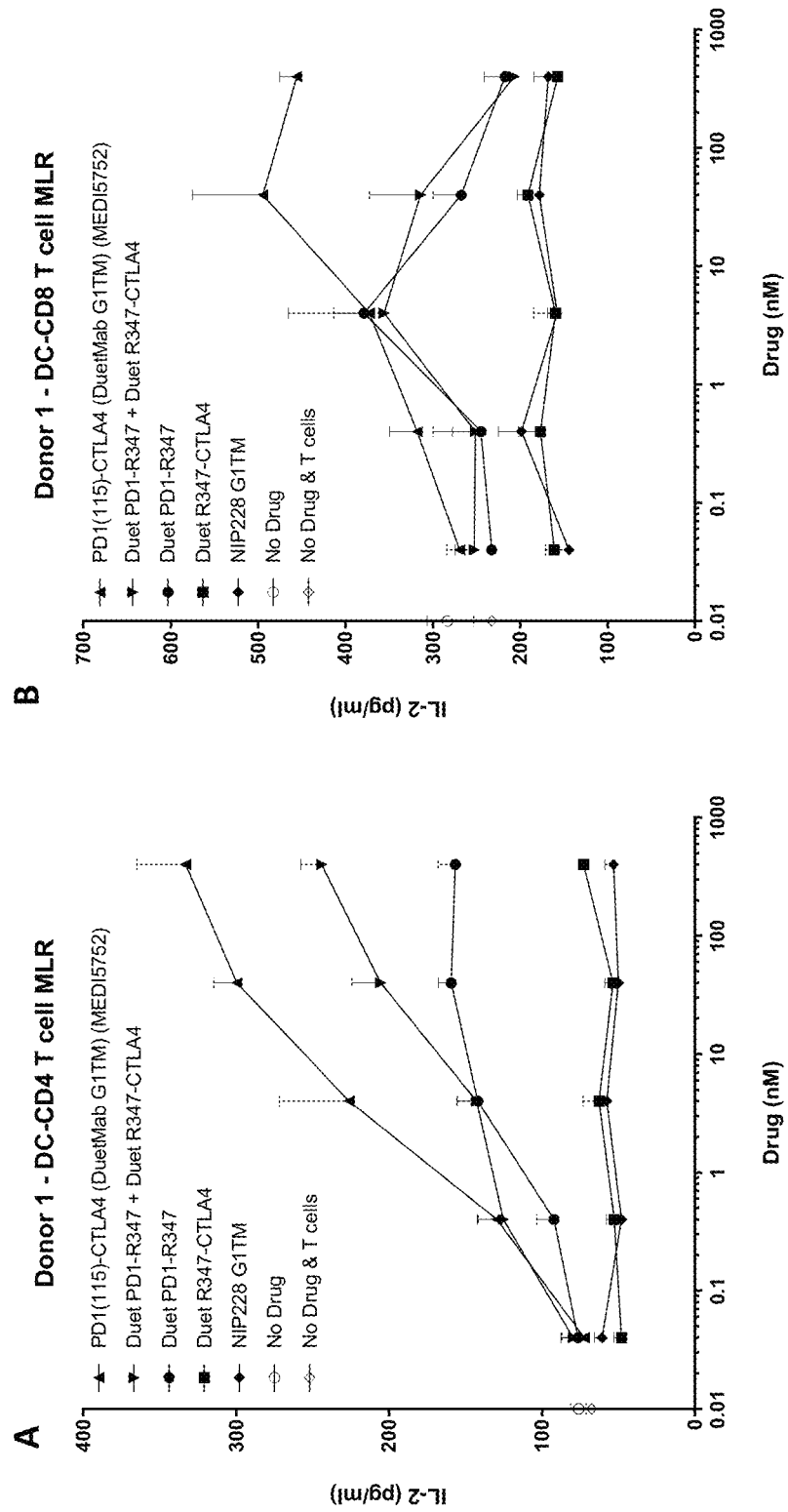
FIGS. 11A-D show the activity of PD-1/CTLA-4 DuetMab in MLR assays compared to isotype controls (n=2 donors; 1 experiment).
Figure 11:
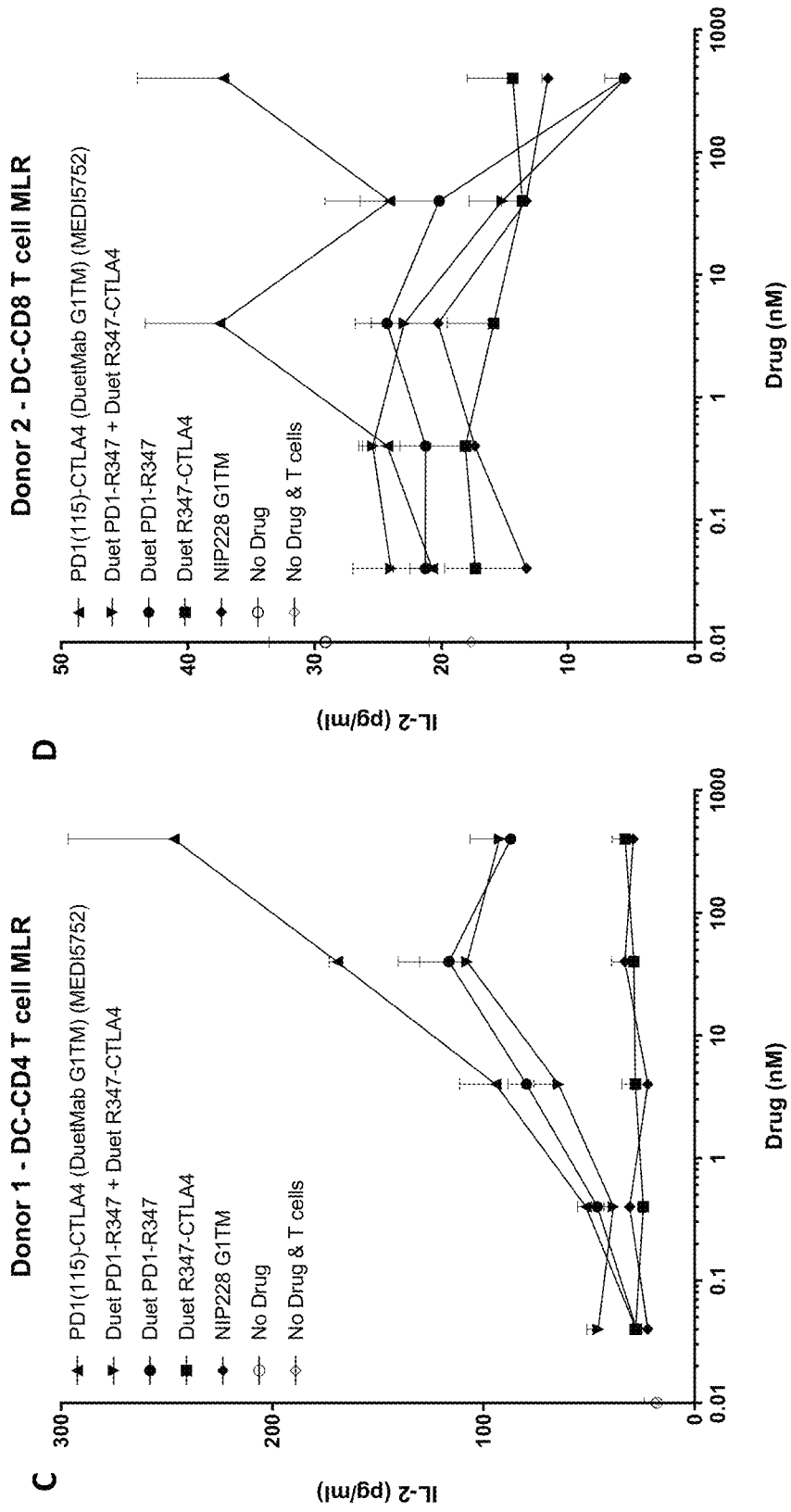

MLR assays were performed to test the PD-1/CTLA-4 bispecific molecules. PD-1/CTLA-4 DuetMab and BiS5Ab had equivalent activity in the mixed lymphocyte reaction (MLR) assay (FIGS. 10A-C). PD-1/CTLA-4 DuetMab had greater activity compared to the combination of Dummy-Duet/isotype control arms. (FIGS. 11A-D). PD-1/CTLA-4 DuetMab had about equivalent activity compared to the combination of parental antibody controls (FIGS. 12A-D). Finally, PD-1/CTLA-4 DuetMab had about equivalent activity compared to the competitor PD-1/CTLA-4 combination and had greater activity than anti-PD-1 alone (e.g., pembrolizumab and nivolumab) (FIGS. 13A-D).

Pharmacokinetic and Pharmacodynamic (PK/PD) Studies

Figure 14:
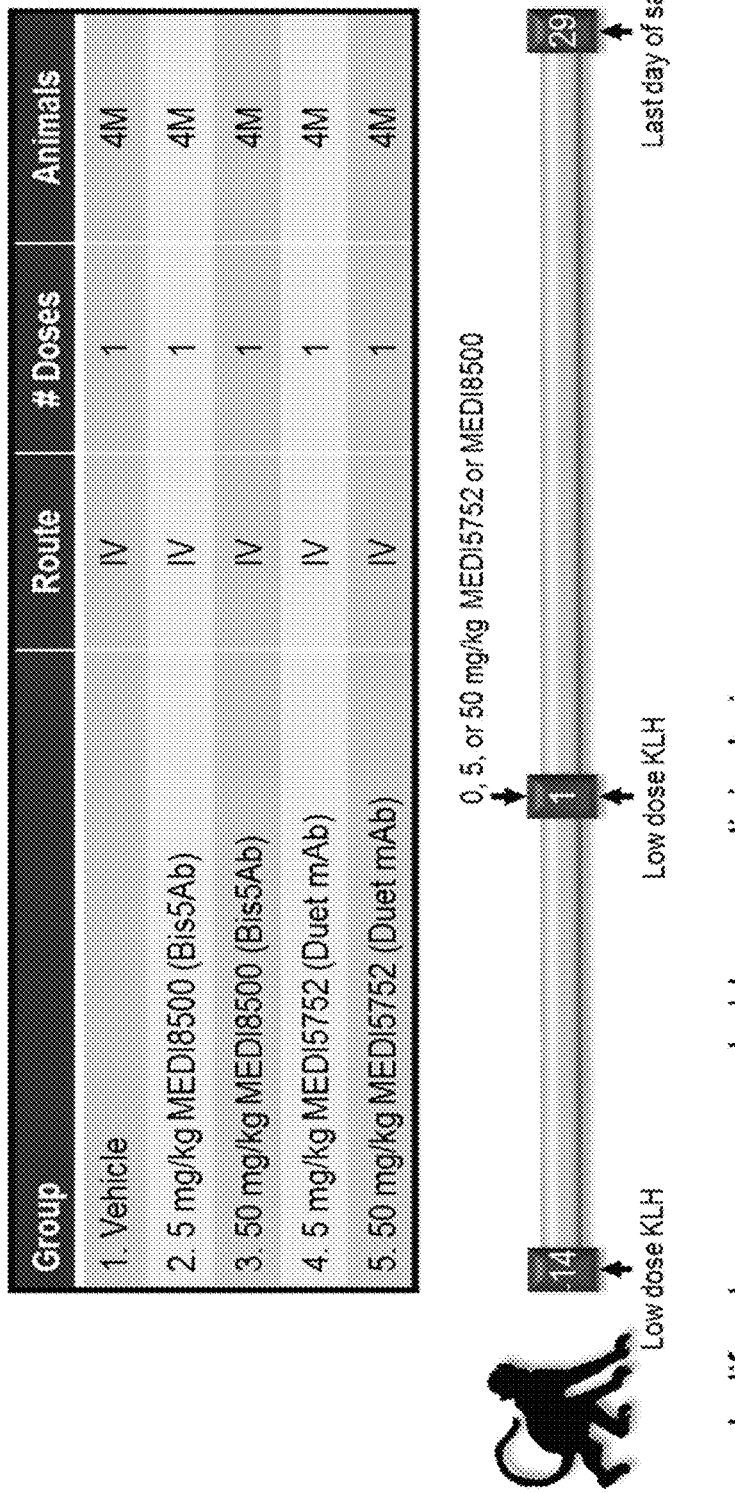
FIG. 14 shows the study design for a single dose pharmacokinetic/pharmacodynamic (PK/PD) study in cynomolgus monkeys.
Figure 15:
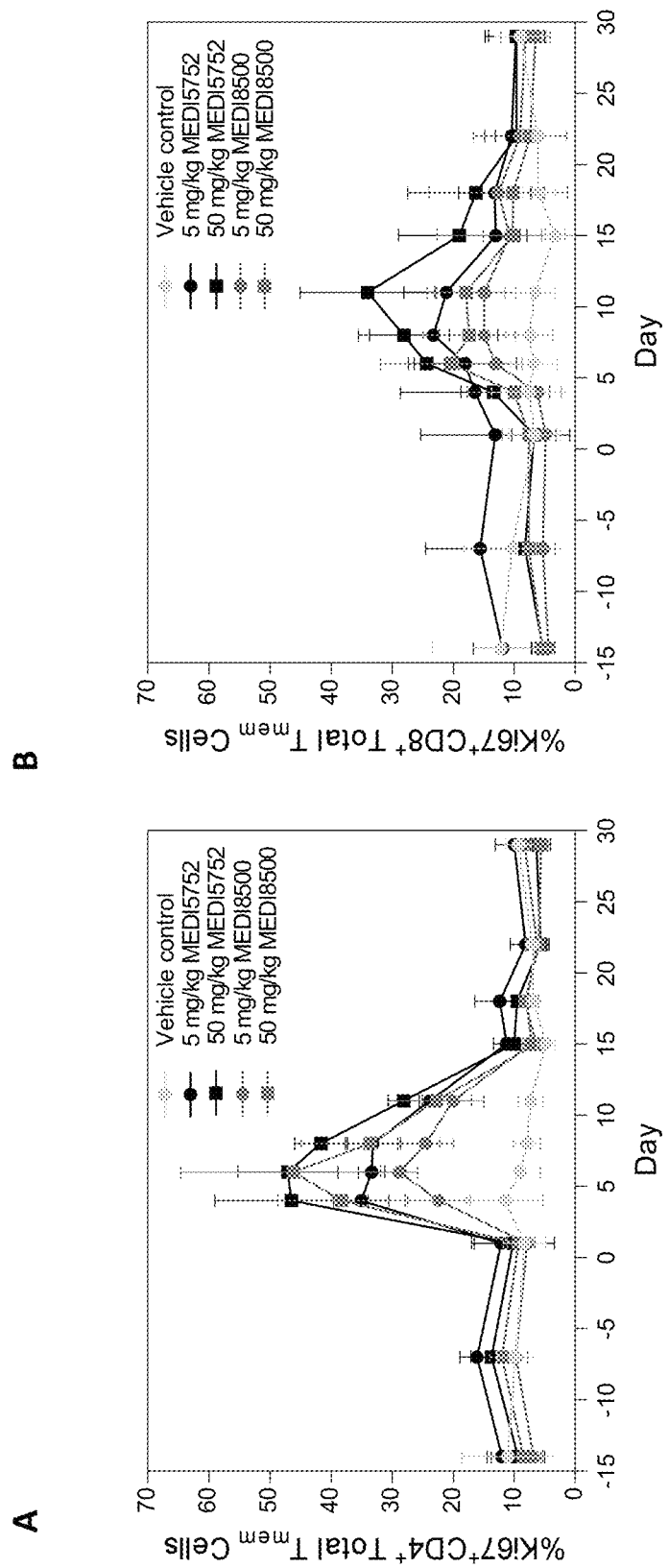
FIGS. 15A-B show that PD-1/CTLA-4 DuetMab showed clear pharmacodynamics (PD) in cynomolgus monkeys.

A study was performed to examine single dose pharmacokinetics/pharmacodynamics (PK/PD) in cynomolgus monkeys. The study design is shown in FIG. 14. DuetMab showed clear pharmacodynamics (PD) in cynomolgus monkeys, and robust PD responses were observed for both molecules (FIGS. 15A-B). Thus confirming the viability of the PD-1/CTLA-4 bispecific binding protein in an in vivo setting, T Cell Dependent Antibody Response (TDAR)

Cynomolgus monkeys were dosed intravenously (saphenous or cephalic vein) with the indicated dose (0.5, 5, 50 mg/kg) of DuetMab or BiS5 bispecific molecules. Keyhole limpet hemocyanin (KLH) protein was reconstituted with the appropriate amount of sterile water for injection under sterile conditions. Low dose KLH solution was administered subcutaneously on each animal's back on two occasions (Day 1 and Day 29). Blood samples for further analysis were obtained from all animals. Evaluation of KLH-specific IgM and IgG antibody titers were performed. Anti-KLH antibodies in monkey serum were detected using ELISA.

T cell dependent antibody response (TDAR) was seen in cynomolgus monkeys dosed with PD-1/CTLA-4 DuetMab (FIG. 16A) and PD-1/CTLA-4 BiS5Ab (FIG. 16B).

CHO Cells Expressing Diverse Levels of Human PD-1 and/or CTLA-4

Figure 18:
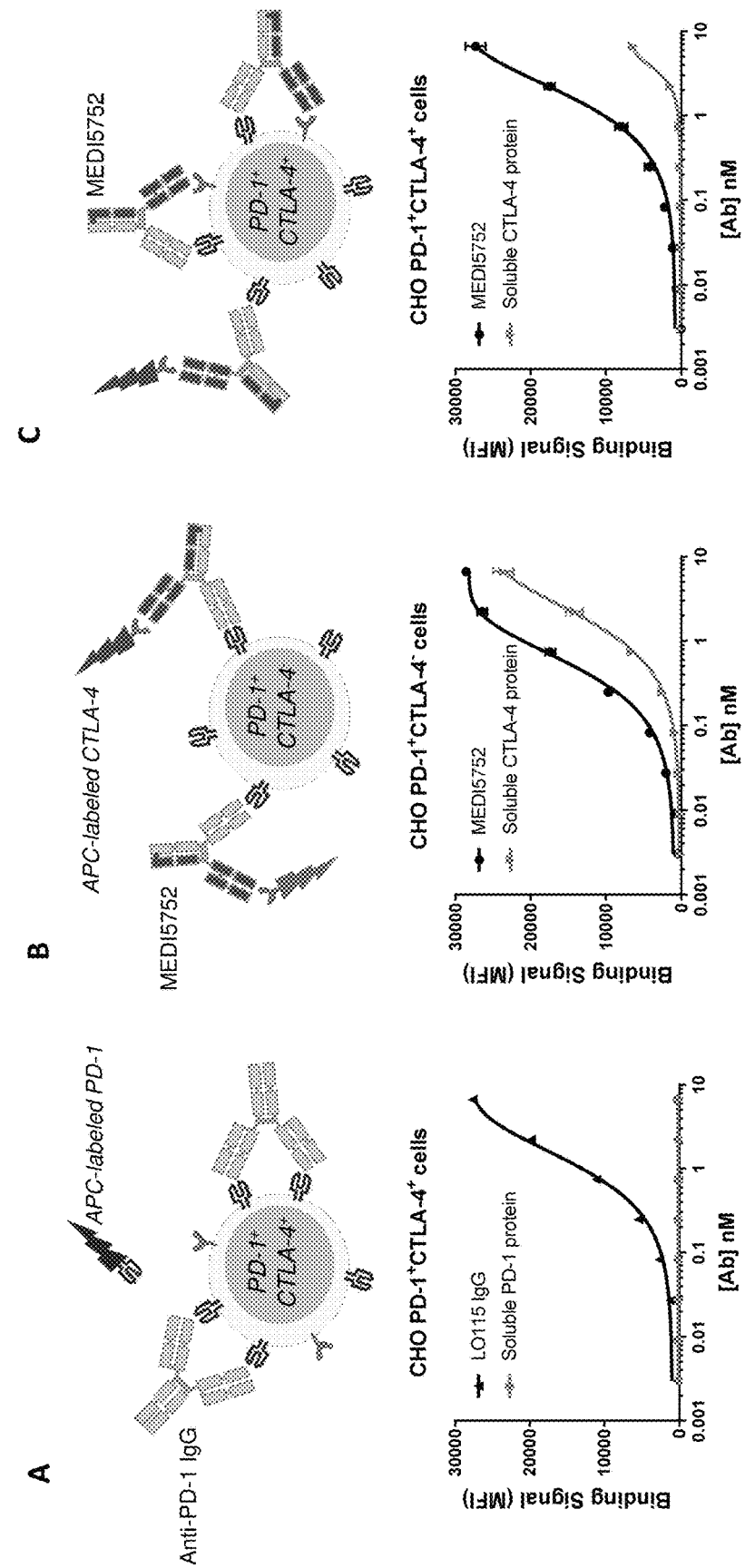
FIGS. 18A-C show that PD-1/CTLA-4 DuetMab concurrently binds PD-1 and CTLA-4 on the surface of the same cell.

A model system was developed to study PD-1/CTLA-4 bispecific molecules using stable CHO cells expressing diverse levels of human PD-1 and/or CTLA-4 (FIG. 17). Free antigen binding-arms on cell-bound DuetMab were detected by flow-cytometry using fluorescently-labeled soluble PD-1 and CTLA-4 proteins. The results of this assay show that PD-1/CTLA-4 DuetMab concurrently binds PD-1 and CTLA-4 on the surface of the same cell (FIGS. 18A-C).

Figure 19B:
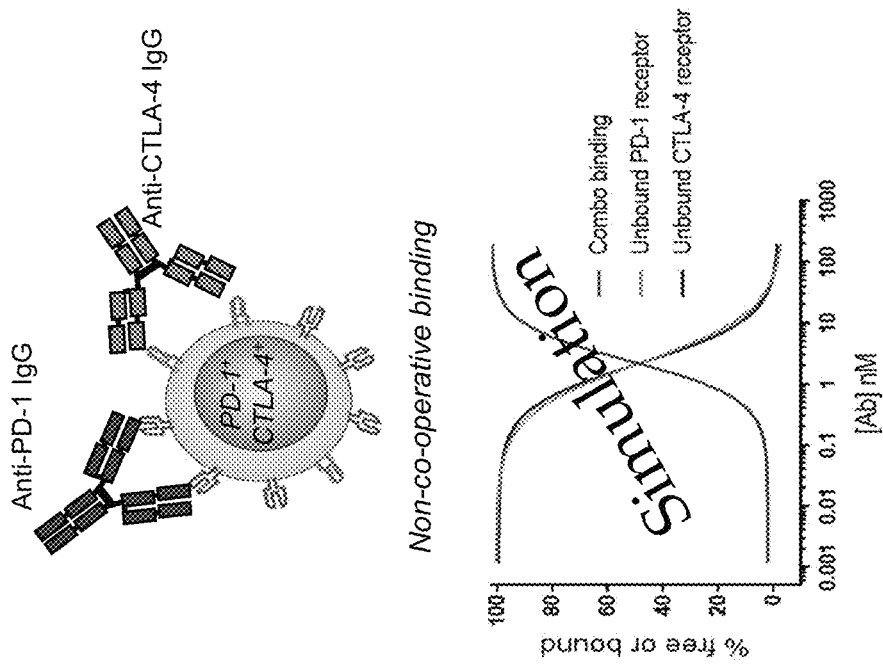
FIGS. 19A-C show an experiment to determine whether co-operative binding differentiates over a combination of anti-PD-1 and anti-CTLA-4 antibodies in the saturation of CTLA-4 on cells expressing excess PD-1.
Figure 19A:
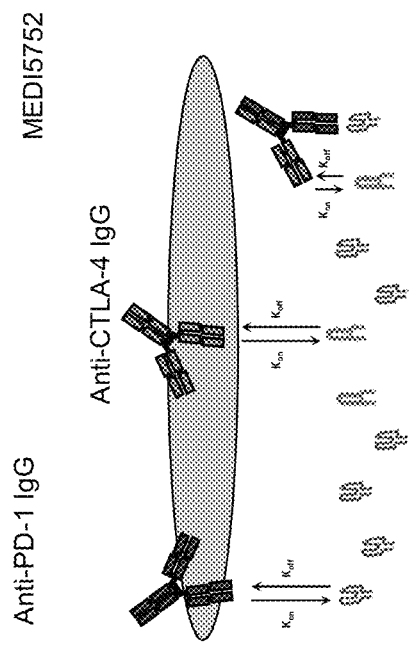
Figure 19C:
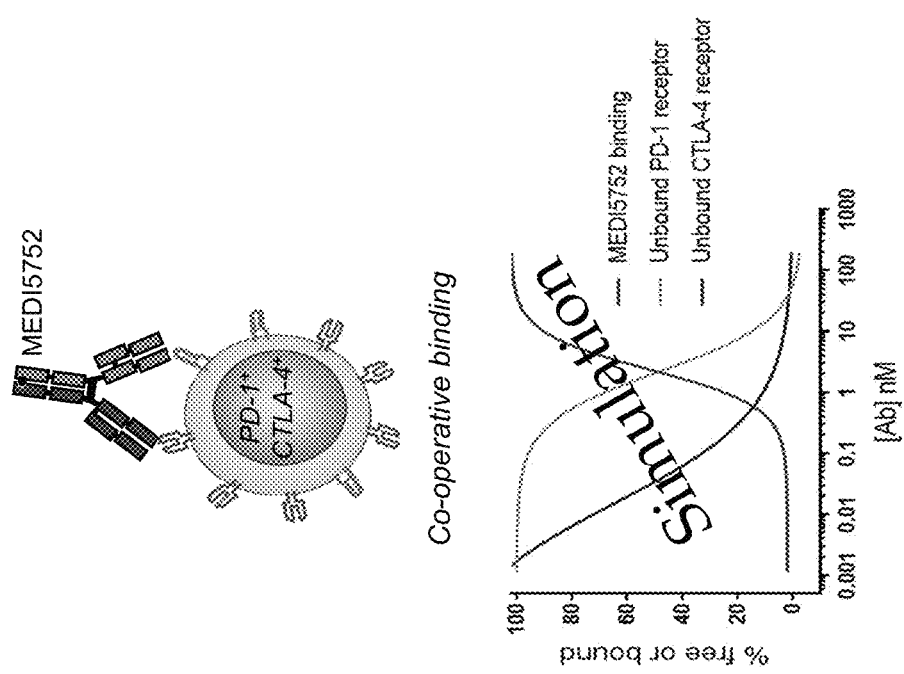
Figure 20B:
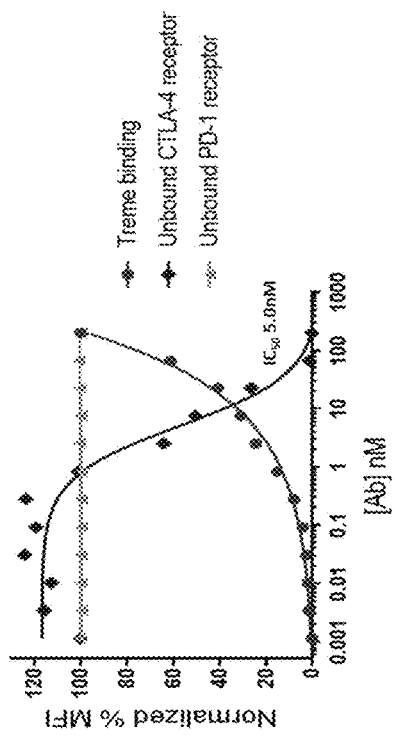
FIGS. 20A-D show that PD-1 and CTLA-4 parental monoclonal antibodies bind and occupy their target receptor without a measurable effect on the untargeted receptor.
Figure 20D:
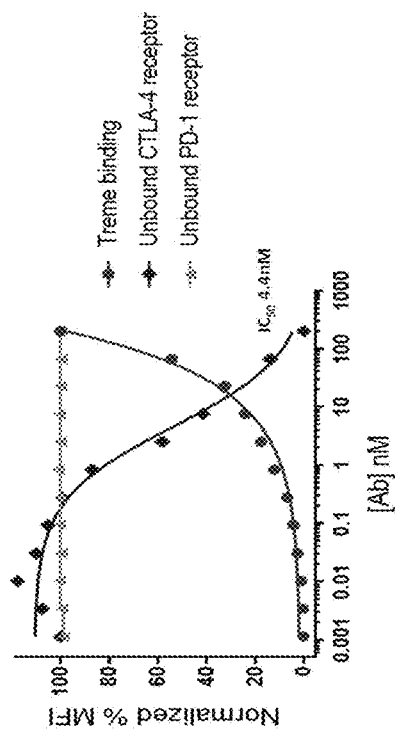
Figure 20A:
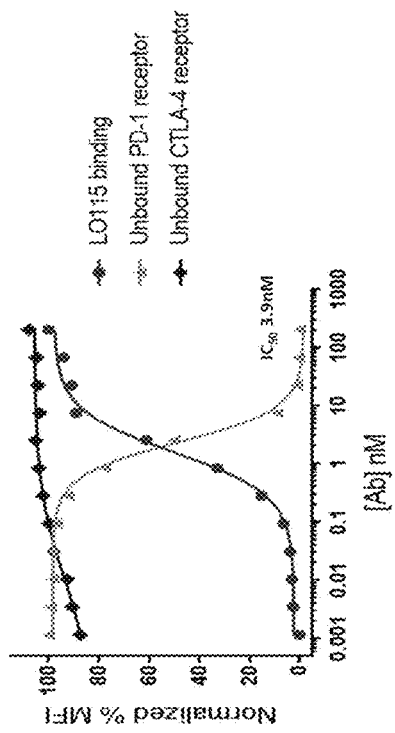
Figure 20C:
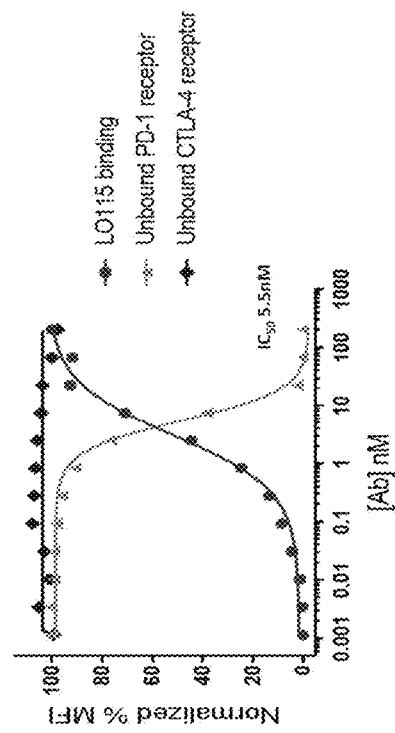
Figure 24D:
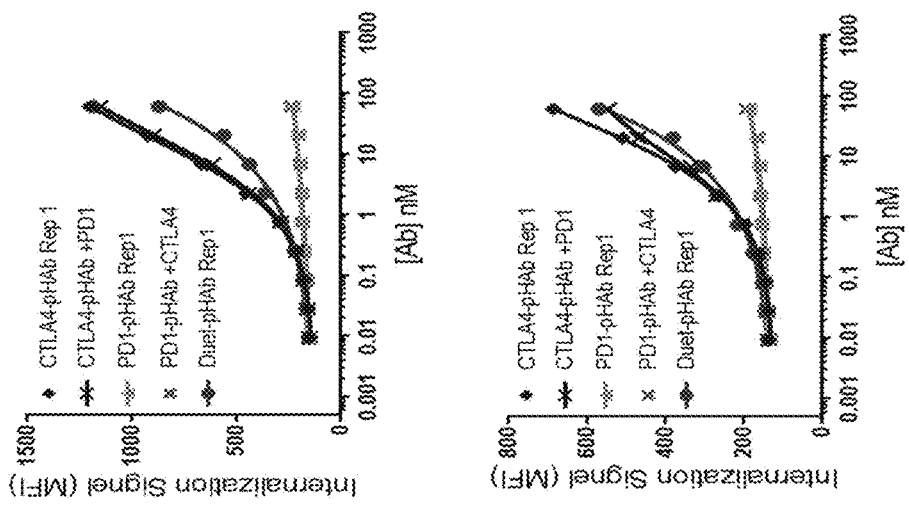

CTLA-4 is continually endocytosed into clathrin-coated pits, resulting in only a small fraction of the receptor expressed at the cell surface at any given time. Recycling of cell-surface CTLA-4 is rapid, with more than 80% of surface CTLA-4 being internalized within 5 minutes. Thus, an experiment was performed to address whether co-operative binding differentiates PD-1/CTLA-4 DuetMab over a combination of anti-PD-1 and anti-CTLA-4 antibodies in the saturation of CTLA-4 on cells expressing excess PD-1 (FIGS. 19A-C). Receptor occupancy of each target antigen was determined independently using labeled anti-PD-1 and anti-CTLA-4 mAbs.

It was found that parental monoclonal antibodies bound and occupied their target receptor without a measurable effect on the untargeted receptor (FIGS. 20A-D). PD-1/CTLA-4 DuetMab saturated CTLA-4 on CHO cells expressing excess PD-1 at ~250-fold lower concentrations compared to a combination of the monoclonal antibodies (FIGS. 21A-D). PD-1/CTLA-4 DuetMab saturated CTLA-4 on CHO cells expressing excess PD-1 at ~500-fold lower concentrations compared to cells expressing only CTLA-4 (FIGS. 22A-F). The PD-1/CTLA-4 DuetMab preferentially bound in cis to PD-1 and CTLA-4 on the surface of the same cell, as determined by quantitation of doublet formation within total pre-mixed CHO population (FIGS. 23A-B). However, PD-1/CTLA-4 DuetMab can also bind in trans to single-expressing cells. PD-1/CTLA-4 DuetMab took on internalization properties of the parent anti-CTLA-4 antibody, tremelimumab (FIGS. 24A-D). Without being bound by theory, the effect shown by this molecule has the potential to induce downregulation of PD-1. The internalization properties of PD-1/CTLA-4 DuetMab were also seen in stable CHO cells expressing 10-fold excess PD-1 (FIG. 25B).

Example 2(b) PD-L1/CTLA-4 Bispecific Binding Proteins

Figure 26:
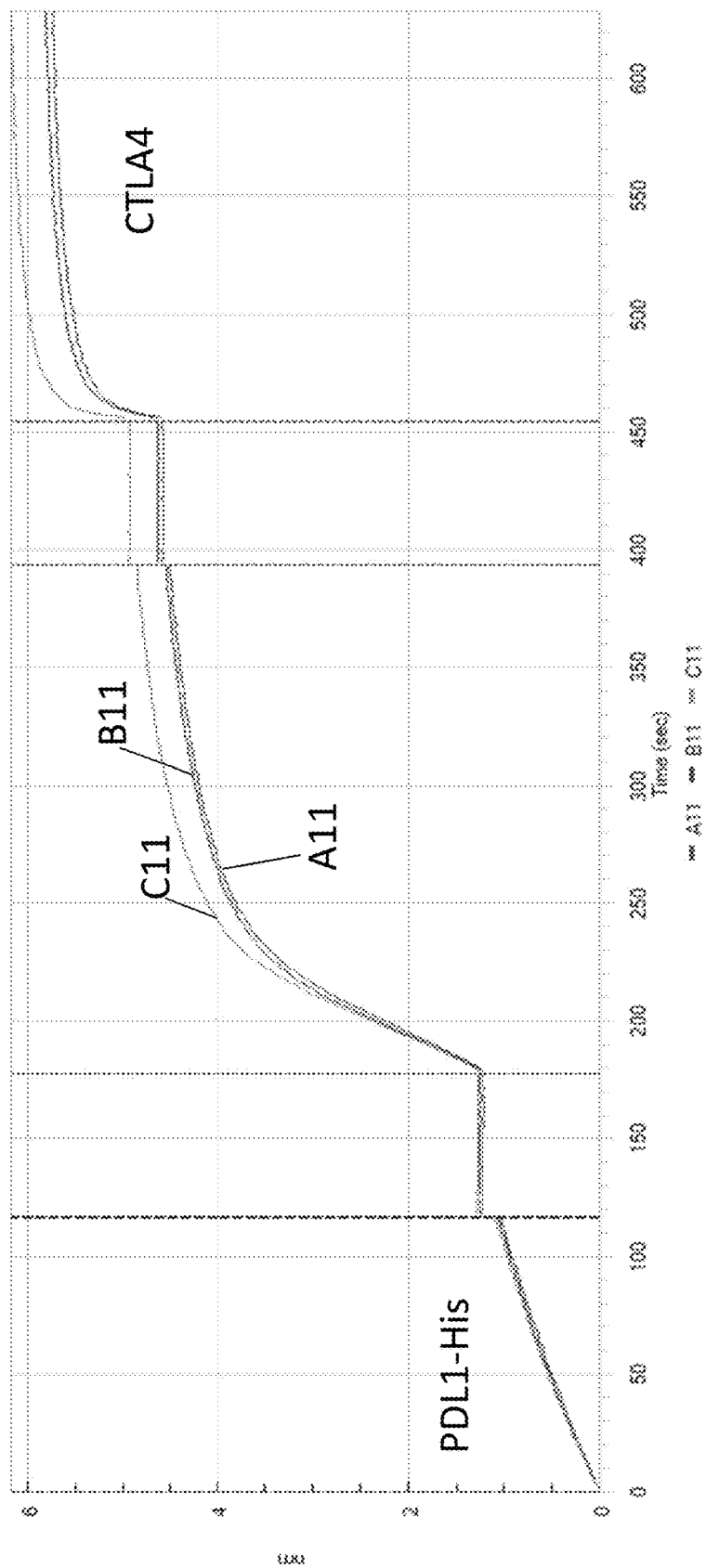
FIG. 26 demonstrates the concurrent binding of the BiS2, BiS3, and BiS5 constructs that target PD-L1 and CTLA-4. Trace A11 shows Bis2 PD-L1CTLA-4, trace B11 shows Bis3 PD-L1/CTLA-4, and trace C11 shows Bis5 PD-L1/CTLA-4.

The following bispecific binding proteins that bind PD-L1 and CTLA-4 were created using the parental sequences identified above in Table 2. Proteins identified as Bis2, Bis3, and Bis5 were generated with the sequences in Table 6 below and sequences identified below were assessed for concurrent antigen binding activity using the Octet binding assay as described above in section 2(a) (FIG. 26)

TABLE 6

| BIS constructs for PD-L1/CTLA-4 | |
|---|---|
| Description | Sequence |
| Bis2 PD-L1/CTLA-4 HC | DIQMTQSPSSLSASVGDRVTITCRASQSINSYLDWYQQKPGKAPKLLIY AASSLQSGVPSRFSGSGSGTDFTLTISSLQPEDFATYYCQQYYSTPFTFG CGTKVEIKGGGGSGGGGSGGGGSGGGGSQVQLVESGGGVVQPGRSLR LSCAASGFTFSSYGMHWVRQAPGKCLEWVAVIWYDGSNKYYADSVK GRFTISRDNSKNTLYLQMNSLRAEDTAVYYCARDPRGATLYYYYGM DVWGQGTTVTVSSGGGGSGGGGSEVQLVESGGGLVQPGGSLRLSCAA SGFTFSRYWMSWVRQAPGKGLEWVANIKQDGSEKYYVDSVKGRFTIS RDNAKNSLYLQMNSLRAEDTAVYYCAREGGWFGELAFDYWGQGTLV TVSSASTKGPSVFPLAPCSRSTSESTAALGCLVKDYFPEPVTVSWNSGA LTSGVHTFPAVLQSSGLYSLSSVVTVPSSSLGTKTYTCNVDHKPSNTKV DKRVESKYGPPCPPCPAPEFLGGPSVFLFPPKPKDTLMISRTPEVTCVVV DVSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLY SRLTVDKSRWQEGNVFSCSVMHEALHNHYTQKSLSLSLGK (SEQ ID NO: 14) |
| Bis2 PD-L1/CTLA-4 LC | EIVLTQSPGTLSLSPGERATLSCRASQRVSSSYLAWYQQKPGQAPRLLI YDASSRATGIPDRFSGSGSGTDFTLTISRLEPEDFAVYYCQQYGSLPWT FGQGTKVEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC (SEQ ID NO: 15) |
| Bis3 PD-L1/CTLA-4 HC | EVQLVESGGGLVQPGGSLRLSCAASGFTFSRYWMSWVRQAPGKGLE WVANIKQDGSEKYYVDSVKGRFTISRDNAKNSLYLQMNSLRAEDTAV YYCAREGGWFGELAFDYWGQGTLVTVSSASTKGPSVFPLAPCSRSTSE STAALGCLVKDYFPEPVTVSWNSGALTSGVHTFPAVLQSSGLYSLSSV VTVPSSSLGTKTYTCNVDHKPSNTKVDKRVESKYGPPCPPCPAPEFLG GPSVFLFPPKPKDTLMISRTPEVTCVVVDVSQEDPEVQFNWYVDGVEV HNAKTKPREEQFNSTYRVVSVLTVLHQDWLNGKEYKCKVSNKGLPSS IEKTISKAKGQPREPQVYTLPPSQEEMTKNQVSLTCLVKGFYPSDIAVE WESNGQPENNYKTTPPVLDSDGSFFLYSRLTVDKSRWQEGNVFSCSV MHEALHNHYTQKSLSLSLGKGGGGSGGGGSDIQMTQSPSSLSASVGD RVTITCRASQSINSYLDWYQQKPGKAPKLLIYAASSLQSGVPSRFSGSG SGTDFTLTISSLQPEDFATYYCQQYYSTPFTFGCGTKVEIKGGGGSGGG GSGGGGSGGGGSQVQLVESGGGVVQPGRSLRLSCAASGFTFSSYGMH WVRQAPGKCLEWVAVIWYDGSNKYYADSVKGRFTISRDNSKNTLYL QMNSLRAEDTAVYYCARDPRGATLYYYYGMDVWGQGTTVTVSS (SEQ ID NO: 16) |
| Bis3 PD-L1/CTLA-4 LC | EIVLTQSPGTLSLSPGERATLSCRASQRVSSSYLAWYQQKPGQAPRLLI YDASSRATGIPDRFSGSGSGTDFTLTISRLEPEDFAVYYCQQYGSLPWT FGQGTKVEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC (SEQ ID NO: 17) |
| Bis5 PD-L1/CTLA-4 HC | EVQLVESGGGLVQPGGSLRLSCAASGFTFSRYWMSWVRQAPGKGLE WVANIKQDGSEKYYVDSVKGRFTISRDNAKNSLYLQMNSLRAEDTAV YYCAREGGWFGELAFDYWGQGTLVTVSSASTKGPSVFPLAPCSRSTSE STAALGCLVKDYFPEPVTVSWNSGALTSGVHTFPAVLQSSGLYSLSSV VTVPSSSLGTKTYTCNVDHKPSNTKVDKRVESKYGPPCPPCPAPEFLG GPSVFLFPPKPKDTLMISRTPEVTCVVVDVSQEDPEVQFNWYVDGVEV HNAKTKPREEQFNSTYRVVSVLTVLHQDWLNGKEYKCKVSNKGLPSS IEKTISKAKGQPREPQVYTLPPSQEEMTKNQVSLTCLVKGFYPSDIAVE WESNGGGGSGGGGSDIQMTQSPSSLSASVGDRVTITCRASQSINSYLD WYQQKPGKAPKLLIYAASSLQSGVPSRFSGSGSGTDFTLTISSLQPEDF ATYYCQQYYSTPFTFGCGTKVEIKGGGGSGGGGSGGGGSGGGGSQVQ LVESGGGVVQPGRSLRLSCAASGFTFSSYGMHWVRQAPGKCLEWVA VIWYDGSNKYYADSVKGRFTISRDNSKNTLYLQMNSLRAEDTAVYYC ARDPRGATLYYYYGMDVWGQGTTVTVSSGGGGSGGGGSGQPENNY |

TABLE 6-continued

BIS constructs for PD-L1/CTLA-4

| Description | Sequence |
| --- | --- |
| | KTTPPVLDSDGSFFLYSRLTVDKSRWQEGNVFSCSVMHEALHNHYTQ KSLSLSLGK (SEQ ID NO: 18) |
| Bis5 PD-L1/CTLA-4 LC | EIVLTQSPGTLSLSPGERATLSCRASQRVSSSYLAWYQQKPGQAPRLLI YDASSRATGIPDRFSGSGSGTDFTLTISRLEPEDFAVYYCQQYGSLPWT FGQGTKVEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC (SEQ ID NO: 19) |

Example 2(c) PD-1/TIM3 Bispecific Binding Proteins

Figure 27A:
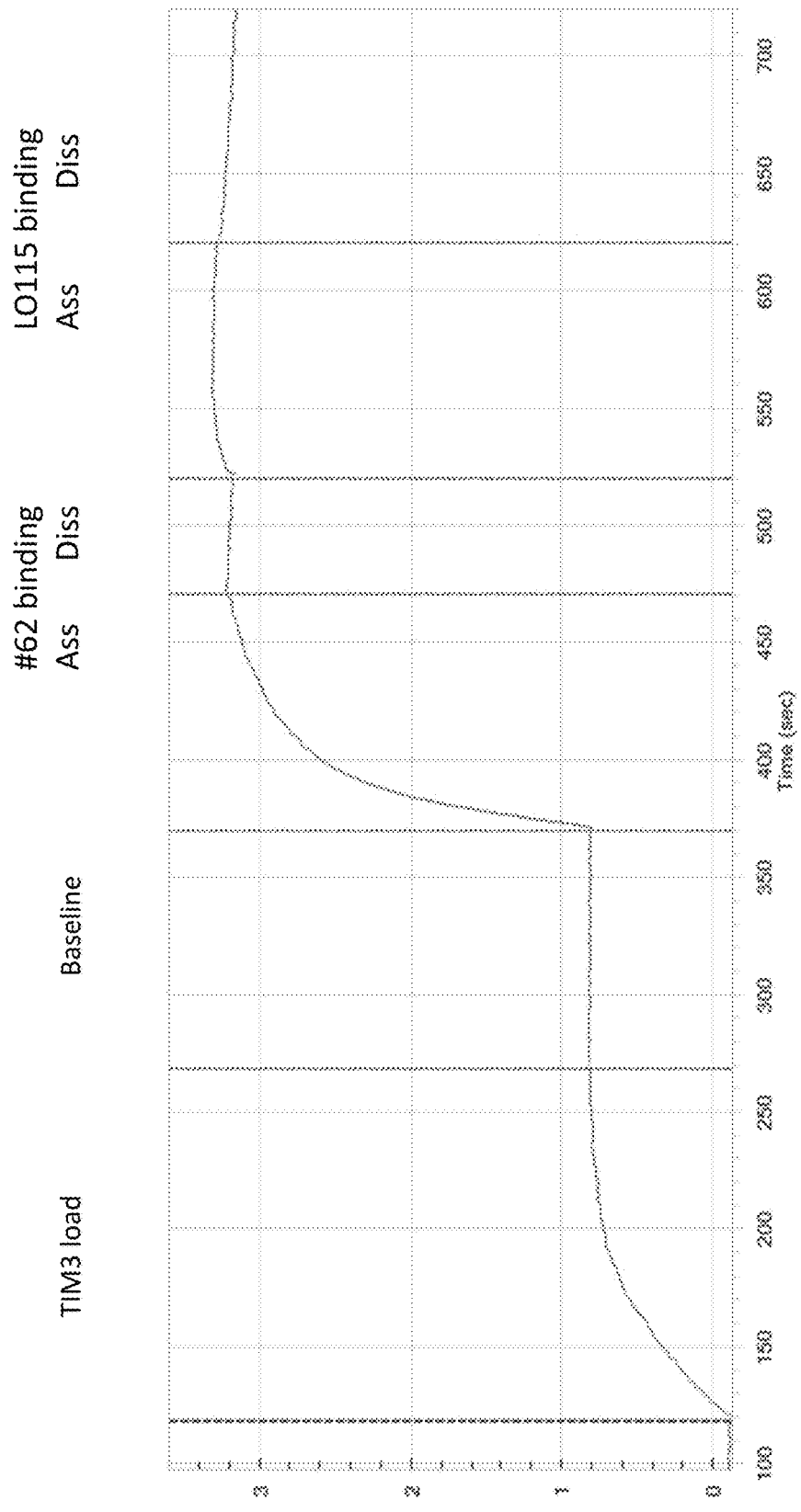
FIG. 27A demonstrates the concurrent binding of the BiS3 construct that targets PD-1 and TIM3 (clone 62, wild type).
Figure 27B:
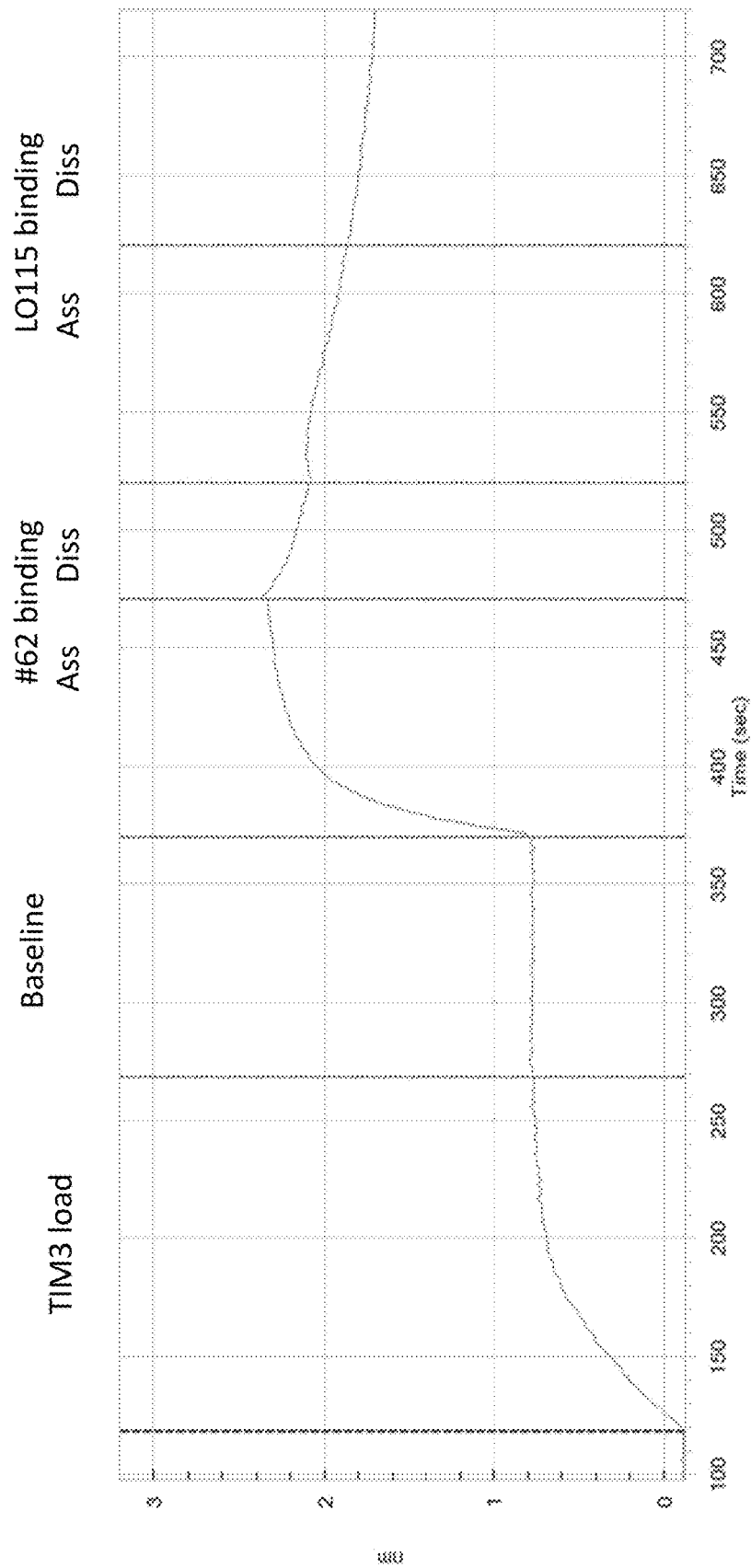
FIG. 27B demonstrates the concurrent binding of a DuetMab construct that targets PD-1 and TIM3 (clone 62, wild type).

The following bispecific binding proteins (Table 7) that bind PD-1 and TIM3 were created using the parental sequences identified above in Table 2. Proteins identified as Bis3, Bis5, and DuetMab were generated with the sequences identified below and were assessed for concurrent binding studies by Octet analysis. Briefly, streptavidin (SA) biosensors (ForteBio) were used to capture biotinylated human TIM3-IgV domain at 2 µg/ml in PBS pH 7.2, 3 mg/ml BSA, 0.05% (v/v) Tween 20 (assay buffer). Following a washing step the loaded biosensors were subjected for successive association and dissociation interactions first with sample wells carrying the bispecific antibodies at 200 nM and then with wells carrying PD-1 antigen at 200 nM. Biotinylated human TIM3-IgV domain was loaded on Streptavidin sensors followed by sequential interactions first with bispecific molecules and then with PD-1 antigen. The binding results are shown in FIGS. 27A-27B.

TABLE 7

BIS constructs for PD-1/TIM3

| Description | Sequence |
| --- | --- |
| TIM3 WT #62 scFv | EVQLLESGGGLVQPGGSLRLSCAASGFTFSSYAMSWVRQAPGKCLEW VSAISGSGGSTYYADSVKGRFTISRDNSKNTLYLQMNSLRAEDTAVYY CARGSYGTYYGNYFEYWGRGTLVTVSSGGGGSGGGGSGGGGSGGGG SQTVLTQPPSVSVAPGKTASISCGGDNIGGKSVHWYQQKPGQAPVLVI YYDSDRPSGIPQRFSGSNSGNTATLTIHRVEAGDEADYYCQVLDRRSD HWLFGCGTKLTVL (SEQ ID NO: 20) |
| PD-1 Heavy chain + TIM3 (WT #62) scFv | EVQLVESGGGLVQPGGSLRLSCAASGFTFSDYGMHWVRQAPGKGLE WVAYISSGSYTIYSADSVKGRFTISRDNAKNSLYLQMNSLRAEDTAVY YCARRAPNSFYEYYFDYWGQGTTVTVSSASTKGPSVFPLAPCSRSTSES TAALGCLVKDYFPEPVTVSWNSGALTSGVHTFPAVLQSSGLYSLSSVV TVPSSSLGTKTYTCNVDHKPSNTKVDKRVESKYGPPCPPCPAPEFLGGP SVFLFPPKPKDTLMISRTPEVTCVVVDVSQEDPEVQFNWYVDGVEVHN AKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHE ALHNHYTQKSLSLSLGKGGGGSGGGGSEVQLLESGGGLVQPGGSLRLS CAASGFTFSSYAMSWVRQAPGKCLEWVSAISGSGGSTYYADSVKGRF TISRDNSKNTLYLQMNSLRAEDTAVYYCARGSYGTYYGNYFEYWGRG TLVTVSSGGGGSGGGGSGGGGSGGGGSQTVLTQPPSVSVAPGKTASIS CGGDNIGGKSVHWYQQKPGQAPVLVIYYDSDRPSGIPQRFSGSNSGNT ATLTIHRVEAGDEADYYCQVLDRRSDHWLFGCGTKLTVL (SEQ ID NO: 21) |
| BiS5 PD-1 Heavy chain + TIM3 (WT #62) scFv | EVQLVESGGGLVQPGGSLRLSCAASGFTFSDYGMHWVRQAPGKGLE WVAYISSGSYTIYSADSVKGRFTISRDNAKNSLYLQMNSLRAEDTAVY YCARRAPNSFYEYYFDYWGQGTTVTVSSASTKGPSVFPLAPCSRSTSES TAALGCLVKDYFPEPVTVSWNSGALTSGVHTFPAVLQSSGLYSLSSVV TVPSSSLGTKTYTCNVDHKPSNTKVDKRVESKYGPPCPPCPAPEFLGGP SVFLFPPKPKDTLMISRTPEVTCVVVDVSQEDPEVQFNWYVDGVEVHN AKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWES NGGGGSGGGGSEVQLLESGGGLVQPGGSLRLSCAASGFTFSSYAMSW VRQAPGKCLEWVSAISGSGGSTYYADSVKGRFTISRDNSKNTLYLQMN SLRAEDTAVYYCARGSYGTYYGNYFEYWGRGTLVTVSSGGGGSGGG GSGGGGSGGGGSQTVLTQPPSVSVAPGKTASISCGGDNIGGKSVHWYQ QKPGQAPVLVIYYDSDRPSGIPQRFSGSNSGNTATLTIHRVEAGDEADY YCQVLDRRSDHWLFGCGTKLTVLGGGGSGGGGSGQPENNYKTTPPVL DSDGSFFLYSRLTVDKSRWQEGNVFSCSVMHEALHNHYTQKSLSLSLG K (SEQ ID NO: 22) |
| BiS5 PD-1 LC | QIVLTQSPATLSLSPGERATLSCSASSKHTNLYWSRHMYWYQQKPGQA PRLLIYLTSNRATGIPARFSGSGSGTDFTLTISSLEPEDFAVYYCQQWSS |

TABLE 7-continued

BIS constructs for PD-1/TIM3

| Description | Sequence |
|---|---|
| | NPFTFGQGTKLEIKRTVAAPSVFIFPPSDEQLKSGTASVVCLLNNFYPRE<br>AKVQWKVDNALQSGNSQESVTEQDSKDSTYSLSSTLTLSKADYEKHK<br>VYACEVTHQGLSSPVTKSFNRGEC (SEQ ID NO: 23) |
| BiS3<br>PD-1 Heavy<br>chain + TIM3 (WT<br>#62) scFv | EVQLVESGGGLVQPGGSLRLSCAASGFTFSDYGMHWVRQAPGKGLE<br>WVAYISSGSYTIYSADSVKGRFTISRDNAKNSLYLQMNSLRAEDTAVY<br>YCARRAPNSFYEYYFDYWGQGTTVTVSSASTKGPSVFPLAPCSRSTSES<br>TAALGCLVKDYFPEPVTVSWNSGALTSGVHTFPAVLQSSGLYSLSSVV<br>TVPSSSLGTKTYTCNVDHKPSNTKVDKRVESKYGPPCPPCPAPEFLGGP<br>SVFLFPPKPKDTLMISRTPEVTCVVVDVSQEDPEVQFNWYVDGVEVHN<br>AKTKPREEQFNSTYRVVSVLTVLHQDWLNGKEYKCKVSNKGLPSSIEK<br>TISKAKGQPREPQVYTLPPSQEEMTKNQVSLTCLVKGFYPSDIAVEWES<br>NGQPENNYKTTPPVLDSDGSFFLYSRLTVDKSRWQEGNVFSCSVMHE<br>ALHNHYTQKSLSLSLGKGGGGSGGGGSEVQLLESGGGLVQPGGSLRLS<br>CAASGFTFSSYAMSWVRQAPGKCLEWVSAISGSGGSTYYADSVKGRF<br>TISRDNSKNTLYLQMNSLRAEDTAVYYCARGSYGTYYGNYFEYWGRG<br>TLVTVSSGGGGSGGGGSGGGGSGGGGSQTVLTQPPSVSVAPGKTASIS<br>CGGDNIGGKSVHWYQQKPGQAPVLVIYYDSDRPSGIPQRFSGSNSGNT<br>ATLTIHRVEAGDEADYYCQVLDRRSDHWLFGCGTKLTVL<br>(SEQ ID NO: 24) |
| BiS3<br>PD-1 LC | QIVLTQSPATLSLSPGERATLSCSASSKHTNLYWSRHMYWYQQKPGQA<br>PRLLIYLTSNRATGIPARFSGSGSGTDFTLTISSLEPEDFAVYYCQQWSS<br>NPFTFGQGTKLEIKRTVAAPSVFIFPPSDEQLKSGTASVVCLLNNFYPRE<br>AKVQWKVDNALQSGNSQESVTEQDSKDSTYSLSSTLTLSKADYEKHK<br>VYACEVTHQGLSSPVTKSFNRGEC (SEQ ID NO: 23) |
| DuetMab<br>PD-1 Heavy chain | EVQLVESGGGLVQPGGSLRLSCAASGFTFSDYGMHWVRQAPGKGLE<br>WVAYISSGSYTIYSADSVKGRFTISRDNAKNSLYLQMNSLRAEDTAVY<br>YCARRAPNSFYEYYFDYWGQGTTVTVSSASTKGPSVFPLAPSSKSTSG<br>GTAALGCLVKDYFPEPVTVSWNSGALTSGVHTFPAVLQSSGLYSLSSV<br>VTVPSSSLGTQTYICNVNHKPSNTKVDKRVEPKSCDKTHTCPPCPAPEF<br>EGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKAL<br>PAPIEKTISKAKGQPREPQVCTLPPSREEMTKNQVSLSCAVKGFYPSDIA<br>VEWESNGQPENNYKTTPPVLDSDGSFFLVSKLTVDKSRWQQGNVFSC<br>SVMHEALHNHYTQKSLSLSPGK (SEQ ID NO: 25) |
| DuetMab<br>TIM3<br>LC | QTVLTQPPSVSVAPGKTASISCGGDNIGGKSVHWYQQKPGQAPVLVIY<br>YDSDRPSGIPQRFSGSNSGNTATLTIHRVEAGDEADYYCQVLDRRSDH<br>WLFGGGTKLTVLGQPKAAPSVTLFPPCSEELQANKATLVCLISDFYPGA<br>VTVAWKADSSPVKAGVETTTPSKQSNNKYAASSYLSLTPEQWKSHRS<br>YSCQVTHEGSTVEKTVAPTEVS (SEQ ID NO: 26) |
| DuetMab<br>TIM3 HC<br>Knob | EVQLLESGGGLVQPGGSLRLSCAASGFTFSSYAMSWVRQAPGKGLEW<br>VSAISGSGGSTYYADSVKGRFTISRDNSKNTLYLQMNSLRAEDTAVYY<br>CARGSYGTYYGNYFEYWGRGTLVTVSSASTKGPSVCPLAPSSKSTSGG<br>TAALGCLVKDYFPEPVTVSWNSGALTSGVHTFPAVLQSSGLYSLSSVV<br>TVPSSSLGTQTYICNVNHKPSNTKVDKRVEPKSVDKTHTCPPCPAPELL<br>GGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALP<br>APIEKTISKAKGQPREPQVYTLPPCREEMTKNQVSLWCLVKGFYPSDIA<br>VEWESNGQPENNYKTTPPVLDSDGSFFLYSKLTVDKSRWQQGNVFSC<br>SVMHEALHNHYTQKSLSLSPG (SEQ ID NO: 27) |

Tumor-specific Killing Activity Assay

Rosenberg Clone-melanoma Killing Assay.

The general cell killing activity of the TIM3/PD-1 bispecific binding molecules and the parental TIM3 antibody were tested using the Rosenberg Clone: JR6C12 and Melanoma cell line: Mel324.

General Assay Protocol

JR6C12 cells functioned as effectors, and are a human CD8+ T cell line expanded from a melanoma patient and specific for gp100-melanoma antigen. To assess therapeutic potential, the Mel624 tumor cells were fluorescently labeled and added with the effectors (JR6C12) and candidate antibody that binds TIM3 and or PD-1. Cells were cocultured for 16 hours. The multiple panels in FIG. 28A provide a visual representation that the addition of TIM3 62 either in combination with anti-PD1 or as PD-1/TIM3 bispecific molecules (as described in Table 7) enhance T cell activation and tumor killing.

Furthermore, as shown in FIGS. 28B-28C, PD-1/TIM3 bispecific molecules demonstrate the greatest tumor killing potency relative to anti-TIM3, anti-PD-1 or isotype control monotherapy as assessed by (b) tumor cell viability dye uptake and (c) IFN-gamma secretion.

In addition to clone 62, another bispecific binding protein that binds PD-1 and TIM3 in DuetMab format was created using the parental sequences identified above in Table 2. The PD-1/TIM3 DuetMab was generated with the sequences in Table 8 below. The sequence of the TIM3 arm was obtained from 013-1, which is an affinity mature variant of clone 62 and the sequence of the anti-PD-1 arm was obtained from LO115, which is identical to the PD-1 arm used for the PD-1/CTLA-4 DuetMab bispecific antibody described above. The PD-1(LO115)/TIM3(013-1) bispecific antibody was assessed as discussed below, including in comparison with PD-1/TIM3 BiS3 and BiS5.

TABLE 8

| | DuetMab construct for PD-1/TIM3 |
|---|---|
| Description | Sequence |
| DuetMab PD-1 (LO115) LC Amino acid | QIVLTQSPATLSLSPGERATLSCSASSKHTNLYWSRHMYWYQQKPGQA PRLLIYLTSNRATGIPARFSGSGSGTDFTLTISSLEPEDFAVYYCQQWSS NPFTFGQGTKLEIKRTVAAPSVFIFPPSDEQLKSGTASVVCLLNNFYPRE AKVQWKVDNALQSGNSQESVTEQDSKDSTYSLSSTLTLSKADYEKHK VYACEVTHQGLSSPVTKSFNRGEC (SEQ ID NO: 7) |
| DuetMab PD-1 (LO115) LC Nucleic acid | CAGATCGTGCTGACCCAGTCCCCTGCCACCCTGTCCCTGAGCCCTGG CGAGAGAGCCACCCTGAGCTGCTCCGCCTCCTCCAAGCACACCAAC CTGTACTGGTCCCGGCACATGTACTGGTATCAGCAGAAGCCCGGCC AGGCCCCTCGGCTGCTGATCTACCTGACCTCTAACCGGGCCACCGG CATCCCTGCCAGATTCTCCGGCTCTGGCTCCGGCACCGACTTCACCC TGACCATCTCCAGCCTGGAACCCGAGGACTTCGCCGTGTACTACTG CCAGCAGTGGTCCTCCAACCCCTTCACCTTCGGCCAGGGCACCAAG CTGGAAATCAAGCGTACGGTGGCTGCACCATCTGTCTTCATCTTCCC GCCATCTGATGAGCAGTTGAAATCTGGAACTGCCTCTGTTGTGTGCC TGCTGAATAACTTCTATCCCAGAGAGGCCAAAGTACAGTGGAAGGT GGATAACGCCCTCCAATCGGGTAACTCCCAGGAGAGTGTCACAGAG CAGGACAGCAAGGACAGCACCTACAGCCTCAGCAGCACCCTGACG CTGAGCAAAGCAGACTACGAGAAACACAAAGTCTACGCCTGCGAA GTCACCCATCAGGGCCTGAGCTCGCCCGTCACAAAGAGCTTCAACA GGGGAGAGTGT (SEQ ID NO: 8) |
| DuetMab PD-1 (LO115) HC Amino acid | EVQLVESGGGLVQPGGSLRLSCAASGFTFSDYGMHWVRQAPGKGLE WVAYISSGSYTIYSADSVKGRFTISRDNAKNSLYLQMNSLRAEDTAVY YCARRAPNSFYEYYFDYWGQGTTVTVSSASTKGPSVFPLAPSSKSTSG GTAALGCLVKDYFPEPVTVSWNSGALTSGVHTFPAVLQSSGLYSLSSV VTVPSSSLGTQTYICNVNHKPSNTKVDKRVEPKSCDKTHTCPPCPAPEF EGGPSVFLFPPKPKDTLMISRTPEVTCVVVDVSHEDPEVKFNWYVDGV EVHNAKTKPREEQYNSTYRVVSVLTVLHQDWLNGKEYKCKVSNKAL PASIEKTISKAKGQPREPQVCTLPPSREEMTKNQVSLSCAVKGFYPSDIA VEWESNGQPENNYKTTPPVLDSDGSFFLVSKLTVDKSRWQQGNVFSC SVMHEALHNHYTQKSLSLSPGK (SEQ ID NO: 9) |
| DuetMab PD-1 (LO115) HC Nucleic-acid | GAGGTGCAGCTGGTGGAATCCGGCGGAGGACTGGTGCAGCCTGGC GGCTCCCTGAGACTGTCTTGCGCCGCCTCCGGCTTCACATTCTCCGA CTACGGCATGCACTGGGTCCGACAGGCCCCTGGAAAGGGCCTGGAA TGGGTGGCCTACATCTCCTCCGGCTCCTACACCATCTACTCCGCCGA CTCCGTGAAGGGCCGGTTCACCATCTCCCGGGACAACGCCAAGAAC TCCCTGTACCTGCAGATGAACTCCCTGCGGGCCGAGGACACAGCCG TGTACTACTGTGCCAGACGGGCCCCTAACTCCTTCTACGAGTACTAC TTCGACTACTGGGGCCAGGGCACCACCGTGACCGTGTCCTCTGCTA GCACCAAAGGTCGAGCGTTTTTCCGCTGGCACCGAGCAGCAAAG CACCTCTGGTGGCACCGCAGCACTGGGTTGTCTGGTGAAAGATTAT TTTCCGGAACCGGTTACCGTTTCTTGGAATAGCGGTGCACTGACCAG CGGTGTTCATACCTTTCCGGCAGTTCTGCAGAGCAGCGGTCTGTATA GCCTGTCTAGCGTTGTTACCGTTCCGAGCAGCAGCCTGGGCACCCA GACCTATATTTGCAATGTGAATCATAAACCGAGCAATACAAAAGTT GATAAACGCGTTGAACCGAAAGCTGTGACAAAACTCACACGTGCC CACCGTGCCCAGCACCTGAGTTCGAGGGGGACCGTCAGTCTTCCT CTTCCCCCAAAACCCAAGGACACCCTCATGATCTCCCGGACCCCT GAGGTCACATGCGTGGTGGTGGACGTGAGCCACGAAGACCCTGAG GTCAAGTTCAACTGGTACGTGGACGGCGTGGAGGTGCATAATGCCA AGACAAAGCCGCGGGAGGAGCAGTACAACAGCACGTACCGTGTGG TCAGCGTCCTCACCGTCCTGCACCAGGACTGGCTGAATGGCAAGGA GTACAAGTGCAAGGTCTCCAACAAAGCCCTCCCAGCCAGCATCGAG AAAACCATCTCCAAAGCCAAGGGGCAGCCCCGAGAACCACAGGTC TGCACCCTGCCCCCATCCCGGGAGGAGATGACCAAGAACCAGGTCA GCCTGAGCTGCGCGGTCAAAGGCTTCTATCCCAGCGACATCGCCGT GGAGTGGGAGAGCAATGGGCAGCCGGAGAACAACTACAAGACCAC GCCTCCCGTGCTGGACTCCGACGGCTCCTTCTTCCTCGTTAGCAAGC TCACCGTGGACAAGAGCAGGTGGCAGCAGGGGAACGTCTTCTCATG CTCCGTGATGCATGAGGCTCTGCACAACCACTACACGCAGAAGAGC CTCTCCCTGTCTCCGGGTAAA (SEQ ID NO: 10) |
| DuetMab TIM3 (O13-1) LC Amino acid | SYVLTQPPSVSVAPGKTARITCGGDNIGGKSVHWYQQKPGQAPVLVIY YDSDRPSGIPERFSGSNSGNTATLTISRVEAGDEADYYCQVLDRRSDHF LFGGGTKLTVLGQPKAAPSVTLFPPCSEELQANKATLVCLISDFYPGAV TVAWKADSSPVKAGVETTTPSKQSNNKYAASSYLSLTPEQWKSHRSY SCQVTHEGSTVEKTVAPTEVS (SEQ ID NO: 28) |
| DuetMab TIM3 (O13-1) LC Nucleic acid | AGCTACGTGCTGACGCAGCCGCCGTCAGTGTCAGTGGCCCCAGGAA AGACGGCCAGGATTACCTGTGGGGGAGACAACATTGGAGGTAAAA GTGTTCACTGGTACCAGCAGAAGCCAGGCCAGGCCCCTGTGTTGGT CATCTATTATGATAGTGACCGGCCCTCAGGCATCCCTGAGCGATTCT CTGGCTCCAACTCTGGGAACACGGCCACCCTGACCATCAGCAGGGT CGAAGCCGGGGATGAGGCCGATTATTACTGTCAGGTGTTGGATCGT |

TABLE 8-continued

DuetMab construct for PD-1/TIM3

| Description | Sequence |
|---|---|
| | CGTAGTGATCATTTCCTGTTCGGCGGAGGGACCAAGCTGACCGTCC<br>TAGGTCAGCCCAAGGCGGCGCCCTCGGTCACTCTGTTCCCGCCCTG<br>CTCTGAGGAGCTTCAAGCCAACAAGGCCACACTGGTGTGTCTCATA<br>AGTGACTTCTACCCGGGAGCCGTGACAGTGGCCTGGAAGGCAGATA<br>GCAGCCCCGTCAAGGCGGGAGTGGAGACCACCACACCCTCCAAAC<br>AAAGCAACAACAAGTACGCGGCCAGCAGCTACCTGAGCCTGACGC<br>CTGAGCAGTGGAAGTCCCACAGAAGCTACAGCTGCCAGGTCACGCA<br>TGAAGGGAGCACCGTGGAGAAGACAGTGGCCCCTACAGAAGTGTC<br>A (SEQ ID NO: 29) |
| DuetMab TIM3 (O13-1) HC Amino acid | EVQLLESGGGLVQPGGSLRLSCAASGFTFSSYAMSWVRQAPGKGLEW<br>VSAISGSGGSTYYADSVKGRFTISRDNSKNTLYLQMNSLRAEDTAVYY<br>CARGSYGTYYGNYFEYWGQGTLVTVSSASTKGPSVCPLAPSSKSTSGG<br>TAALGCLVKDYFPEPVTVSWNSGALTSGVHTFPAVLQSSGLYSLSSVV<br>TVPSSSLGTQTYICNVNHKPSNTKVDKRVEPKSVDKTHTCPPCPAPEFE<br>GGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALP<br>ASIEKTISKAKGQPREPQVYTLPPCREEMTKNQVSLWCLVKGFYPSDIA<br>VEWESNGQPENNYKTTPPVLDSDGSFFLYSKLTVDKSRWQQGNVFSC<br>SVMHEALHNHYTQKSLSLSPGK (SEQ ID NO: 30) |
| BiS3 PD-1 (LO115)/TIM3 (O13-1) HC Amino acid | EVQLVESGGGLVQPGGSLRLSCAASGFTFSDYGMHWVRQAPGKGLE<br>WVAYISSGSYTIYSADSVKGRFTISRDNAKNSLYLQMNSLRAEDTAVY<br>YCARRAPNSFYEYYFDYWGQGTTVTVSSASTKGPSVFPLAPSSKSTSG<br>GTAALGCLVKDYFPEPVTVSWNSGALTSGVHTFPAVLQSSGLYSLSSV<br>VTVPSSSLGTQTYICNVNHKPSNTKVDKRVEPKSCDKTHTCPPCPAPEF<br>EGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKAL<br>PASIEKTISKAKGQPREPQVYTLPPSREEMTKNQVSLTCLVKGFYPSDIA<br>VEWESNGQPENNYKTTPPVLDSDGSFFLYSKLTVDKSRWQQGNVFSC<br>SVMHEALHNHYTQKSLSLSPGKGGGGSGGGGSEVQLLESGGGLVQPG<br>GSLRLSCAASGFTFSSYAMSWVRQAPGKCLEWVSAISGSGGSTYYADS<br>VKGRFTISRDNSKNTLYLQMNSLRAEDTAVYYCARGSYGTYYGNYFE<br>YWGQGTLVTVSSGGGGSGGGGSGGGGSSYVLTQPPSVSVAPG<br>KTARITCGGDNIGGKSVHWYQQKPGQAPVLVIYYDSDRPSGIPERFSGS<br>NSGNTATLTISRVEAGDEADYYCQVLDRRSDHFLFGCGTKLTVL<br>(SEQ ID NO: 89) |
| BiS3 PD-1 (LO115)/TIM3 (O13-1) LC Amino acid | QIVLTQSPATLSLSPGERATLSCSASSKHTNLYWSRHMYWYQQKPGQA<br>PRLLIYLTSNRATGIPARFSGSGSGTDFTLTISSLEPEDFAVYYCQQWSS<br>NPFTFGQGTKLEIKRTVAAPSVFIFPPSDEQLKSGTASVVCLLNNFYPRE<br>AKVQWKVDNALQSGNSQESVTEQDSKDSTYSLSSTLTLSKADYEKHK<br>VYACEVTHQGLSSPVTKSFNRGEC (SEQ ID NO: 90) |
| BiS5 PD-1 (LO115)/TIM3 (O13-1) HC Amino acid | EVQLVESGGGLVQPGGSLRLSCAASGFTFSDYGMHWVRQAPGKGLE<br>WVAYISSGSYTIYSADSVKGRFTISRDNAKNSLYLQMNSLRAEDTAVY<br>YCARRAPNSFYEYYFDYWGQGTTVTVSSASTKGPSVFPLAPSSKSTSG<br>GTAALGCLVKDYFPEPVTVSWNSGALTSGVHTFPAVLQSSGLYSLSSV<br>VTVPSSSLGTQTYICNVNHKPSNTKVDKRVEPKSCDKTHTCPPCPAPEF<br>EGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKAL<br>PASIEKTISKAKGQPREPQVYTLPPSREEMTKNQVSLTCLVKGFYPSDIA<br>VEWESNGGGGSGGGGSEVQLLESGGGLVQPGGSLRLSCAASGFTFSSY<br>AMSWVRQAPGKCLEWVSAISGSGGSTYYADSVKGRFTISRDNSKNTL<br>YLQMNSLRAEDTAVYYCARGSYGTYYGNYFEYWGQGTLVTVSSGGG<br>GSGGGGSGGGGSGGGGSSYVLTQPPSVSVAPGKTARITCGGDNIGGKS<br>VHWYQQKPGQAPVLVIYYDSDRPSGIPERFSGSNSGNTATLTISRVEAG<br>DEADYYCQVLDRRSDHFLFGCGTKLTVLGGGGSGGGGSGQPENNYKT<br>TPPVLDSDGSFFLYSKLTVDKSRWQQGNVFSCSVMHEALHNHYTQKS<br>LSLSPGK (SEQ ID NO: 91) |
| BiS5 PD-1 (LO115)/TIM3 (O13-1) LC Amino acid | QIVLTQSPATLSLSPGERATLSCSASSKHTNLYWSRHMYWYQQKPGQA<br>PRLLIYLTSNRATGIPARFSGSGSGTDFTLTISSLEPEDFAVYYCQQWSS<br>NPFTFGQGTKLEIKRTVAAPSVFIFPPSDEQLKSGTASVVCLLNNFYPRE<br>AKVQWKVDNALQSGNSQESVTEQDSKDSTYSLSSTLTLSKADYEKHK<br>VYACEVTHQGLSSPVTKSFNRGEC (SEQ ID NO: 92) |
| DuetMab TIM3 (O13-1) HC- Nucleic acid | GAGGTGCAGCTGTTGGAGTCTGGGGGAGGCTTGGTACAGCCTGGGG<br>GGTCCCTGAGACTCTCCTGTGCAGCCTCTGGATTCACCTTTAGCAGC<br>TATGCCATGAGCTGGGTCCGCCAGGCTCCAGGGAAGGGGCTGGAGT<br>GGGTCTCAGCTATTAGTGGTAGTGGTGGTAGCACATACTACGCAGA<br>CTCCGTGAAGGGCCGGTTCACCATCTCCAGAGACAATTCCAAGAAC<br>ACGCTGTATCTGCAAATGAACAGCCTGAGAGCCGAGGACACGGCCG<br>TGTATTACTGTGCGAGAGGGTCCTATGGTACCTACTACGGAAACTA<br>CTTTGAATACTGGGGCCAGGGCACCCTGGTCACCGTCTCGAGTGCG<br>TCGACCAAAGGTCCGAGCGTGTGCCCGCTGGCACCGAGCAGCAAAA |

TABLE 8-continued

DuetMab construct for PD-1/TIM3

| Description | Sequence |
|---|---|
| | GCACCTCTGGTGGCACCGCAGCACTGGGTTGTCTGGTGAAAGATTA<br>TTTTCCGGAACCGGTTACCGTTTCTTGGAATAGCGGTGCACTGACCA<br>GCGGTGTTCATACCTTTCCGGCAGTCCTGCAGAGCAGCGGTCTGTAT<br>AGCCTGTCTAGCGTTGTTACCGTTCCGAGCAGCAGCCTGGGCACCC<br>AGACCTATATTTGCAATGTGAATCATAAACCGAGCAATACCAAAGT<br>TGATAAACGCGTTGAACCGAAAAGCGTGGACAAAACTCACACGTGC<br>CCACCGTGCCCAGCACCTGAGTTCGAGGGGGGACCGTCAGTCTTCC<br>TCTTCCCCCCAAAACCCAAGGACACCCTCATGATCTCCCGGACCCCT<br>GAGGTCACATGCGTGGTGGTGGACGTGAGCCACGAAGACCCTGAG<br>GTCAAGTTCAACTGGTACGTGGACGGCGTGGAGGTGCATAATGCCA<br>AGACAAAGCCGCGGGAGGAGCAGTACAACAGCACGTACCGTGTGG<br>TCAGCGTCCTCACCGTCCTGCACCAGGACTGGCTGAATGGCAAGGA<br>GTACAAGTGCAAGGTCTCCAACAAAGCCCTCCCAGCCAGCATCGAG<br>AAAACCATCTCCAAAGCCAAAGGGCAGCCCCGAGAACCACAGGTC<br>TACACCCTGCCCCCATGCCGGGAGGAGATGACCAAGAACCAGGTCA<br>GCCTGTGGTGCCTGGTCAAAGGCTTCTATCCCAGCGACATCGCCGT<br>GGAGTGGGAGAGCAATGGGCAGCCGGAGAACAACTACAAGACCAC<br>GCCTCCCGTGCTGGACTCCGACGGCTCCTTCTTCCTCTATAGCAAGC<br>TCACCGTGGACAAGAGCAGGTGGCAGCAGGGGAACGTCTTCTCATG<br>CTCCGTGATGCATGAGGCTCTGCACAACCACTACACGCAGAAGAGC<br>TTAAGCCTGTCTCCGGGTAAA (SEQ ID NO: 31) |

Octet Binding Assay (DuetMab, TIM3 Arm Affinity Mature Variant)

Concurrent binding studies to two distinctive antigens, PD-1 and TIM3, were performed by Octet analysis. Biotinylated human TIM3 was loaded on Streptavidin sensors followed by sequential interactions first with PD-1/TIM3 DuetMab and then with soluble PD-1 antigen. Streptavidin (SA) biosensors (ForteBio) were used to capture biotinylated human TIM3 at 5 µg/ml in PBS pH 7.2, 3 mg/ml BSA, 0.05% (v/v) Tween 20 (assay buffer). Following a washing step the loaded biosensors were subjected for successive association and dissociation interactions first with sample wells carrying DuetMab PD-1/CTLA-4 bispecific antibody having the TIM3 arm (O13-1), which is the affinity mature variant of clone 62 TIM3 antibody, was loaded at 200 nM and then with wells carrying human PD-1 antigen at 200 nM. The binding results are shown in FIG. 29.

Intrinsic kinetics of the PD-1/TIM3 DuetMab bispecific antibody was also assessed via BiaCore. Binding experiments were carried out using a BIAcore T200 instrument (BIAcore). To capture the antibody, mouse anti-huIgG-Fab was immobilized on a CM5 chip to a target response of 2000 RU. 100 nM of the DuetMab or mAbs were flowed at 20 µL/min for 5 min to achieve approximately 100 response units of captured antibody. Antigen were then injected serially at a flow rate of 50 µl/min for 5 min. Kinetic parameters ($k_{on}$ and $k_{off}$) and dissociation constant (KD) were calculated from a non-linear fit using BIAevaluation 4.1 software. The binding results are shown in Table 9.

TABLE 9

BiaCore data for PD-1/TIM3

| capture | TIM3 | ka ($M^{-1}s^{-1}$) | kd ($s^{-1}$) | $K_D$ (nM) | capture | PD-1 | ka ($M^{-1}s^{-1}$) | kd ($s^{-1}$) | $K_D$ (nM) |
|---|---|---|---|---|---|---|---|---|---|
| O13-1 IgG1-TM | Human | 1.88E+06 | 7.52E−03 | 4.01 | LO115 IgG1-TM | Human | 3.02E+05 | 2.37E−04 | 0.79 |
| DuetMab | Human | 1.96E+06 | 8.13E−03 | 4.15 | DuetMab | Human | 2.95E+05 | 2.36E−04 | 0.69 |
| O13-1 IgG1-TM | Cyno | 2.79E+06 | 7.18E−02 | 25.69 | LO115 IgG1-TM | Cyno | 3.46E+05 | 2.38E−04 | 0.81 |
| DuetMab | Cyno | 2.98E+06 | 7.61E−02 | 25.57 | DuetMab | Cyno | 4.90E+05 | 2.15E−04 | 0.44 |

Figure 31:
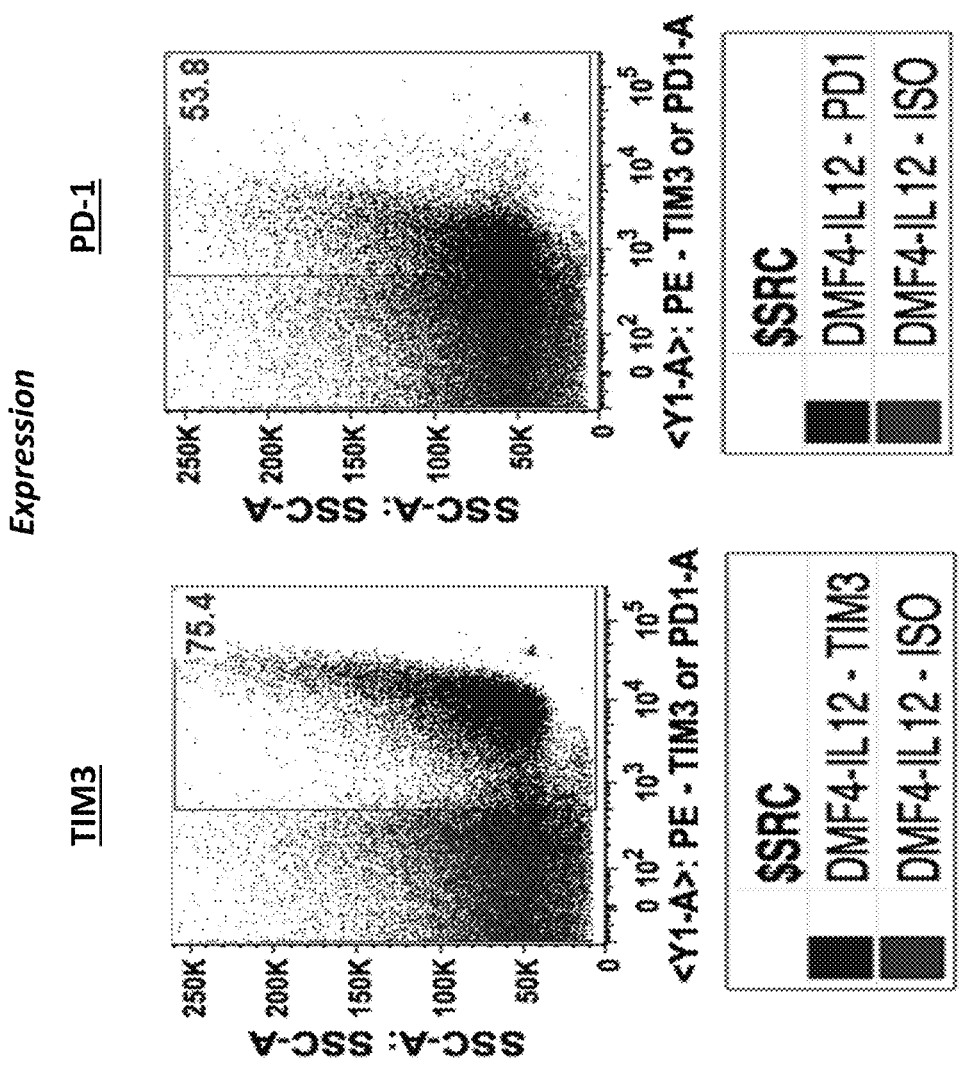
FIG. 31 shows TIM3 and PD-1 expression data on activated T cell clone (DMF4).

PD-1/TIM3 bispecific antibodies, including BiS3, BiS5, and DuetMab, bound to CHO cells overexpressing human TIM3 or human PD-1 (FIG. 30 and Table 25), PD-1 and TIM3 expression (DMF4) are shown in FIG. 31.

TABLE 25

| | anti-TIM3 LOO131 | anti-PD1 LO115 | Duetmab | Bis3 | Bis5 | Nip228 Hu IgG1TM |
|---|---|---|---|---|---|---|
| EC50 | 0.003968 | NA | 0.1036 | 0.02853 | 0.01603 | NA |
| R square | 0.9951 | 0.9792 | 0.9982 | 0.9964 | 0.9954 | 0.9804 |

CMV Ag Recall Assay

Figure 32A:
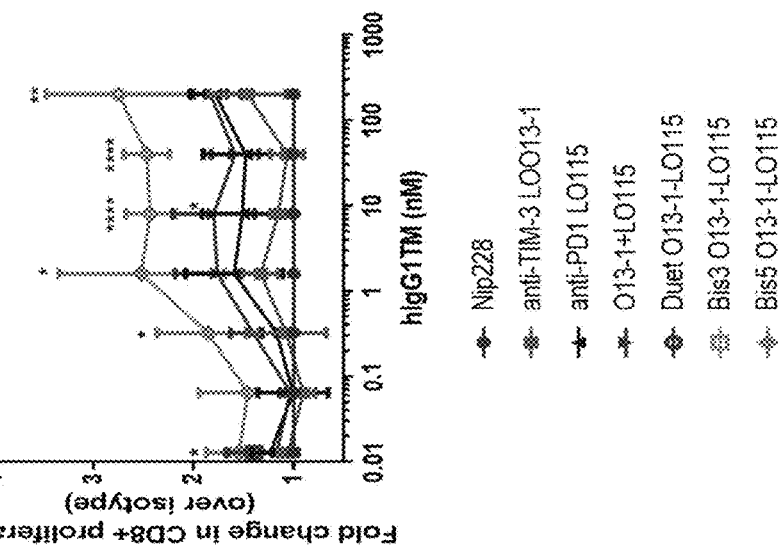
FIGS. 32A-C depict the results from a CMV antigen recall assay showing that PD-1/TIM3 bispecific antibodies, including BiS3, BiS5, and DuetMab, demonstrate enhanced activity compared to isotype treatment (3 donors (1-2 replicates per treatment/per donor), 1 experiment).
Figure 32B:
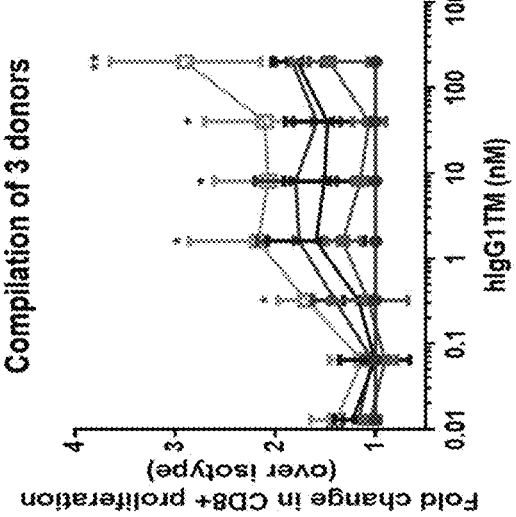
Figure 32C:
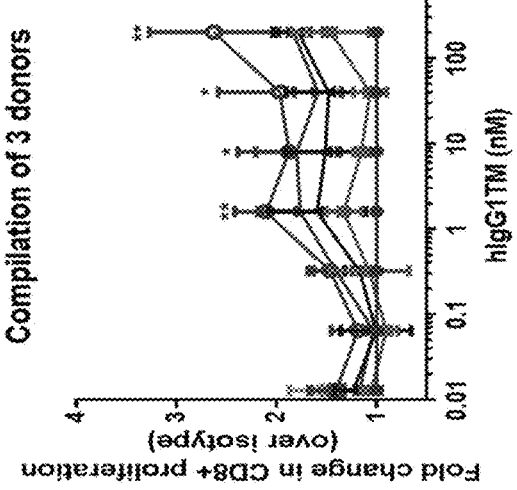
Figure 33A:
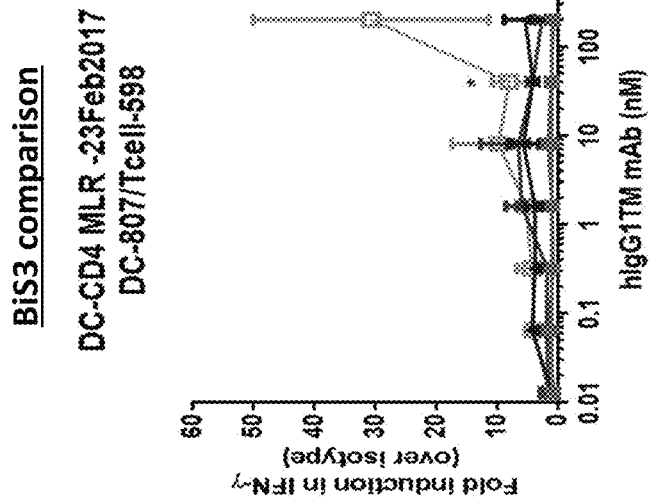
FIGS. 33A-D show that PD-1/TIM3 bispecific antibodies, including BiS3, BiS5, and DuetMab, enhanced interferon (IFNγ) at concentrations above 8 nM in the mixed lymphocyte reaction (MLR) assay (2-4 replicate wells per treatment/1 donor pair/1 of 2 independent experiments).
Figure 33B:
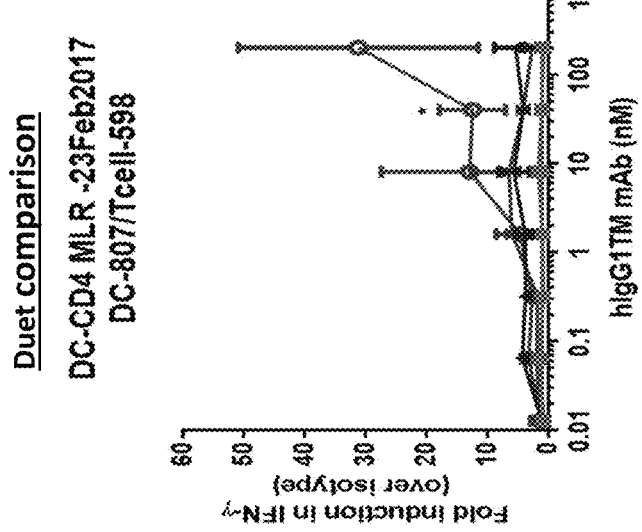
Figure 33D:
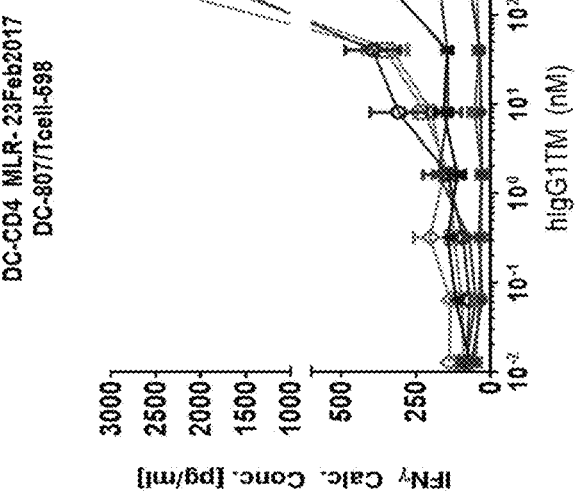
Figure 33C:
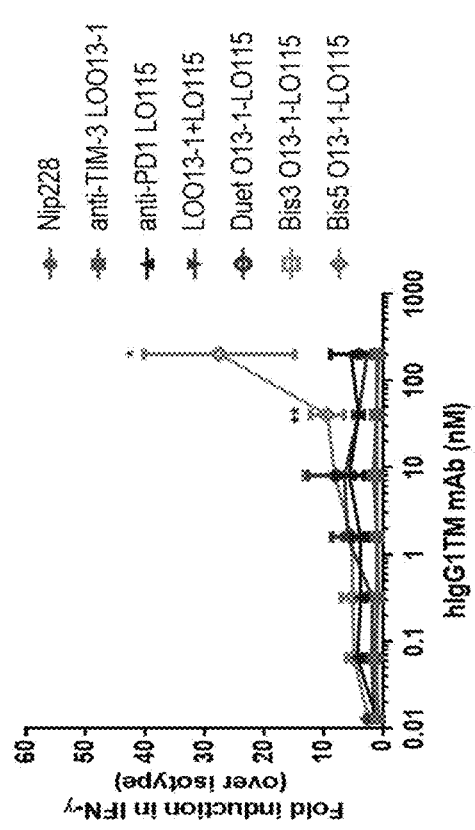

PD-1/TIM3 bispecific antibodies, including BiS3, BiS5, and DuetMab, enhanced CD8+ T cell proliferation in a CMV antigen recall assay compared to isotype treatment (FIGS. 32A-C).

Mixed Leukocyte Reaction (MLR) Assay

PD-1/TIM3 bispecific antibodies, including BiS3, BiS5, and DuetMab, enhanced interferon (IFNγ) secretion in the mixed lymphocyte reaction (MLR) assay, with activity trending above mono- and combination therapy (FIGS. 33A-D).

PD-1/TIM3 bispecific antibodies, including BiS3, BiS5, and DuetMab, demonstrated similar activity as parental LO115 IgG1 in a jurkat NFκB reporter line that predominantly expresses PD-1 (87% PD-1 single positive) (FIGS. 34A-C).

In summary, three bispecific formats (DuetMab, Bis3, and Bis5) were generated for PD-1/TIM-3. All bispecific formats show in vitro functionality equivalent to or better than anti-PD-1, suggesting these molecules may provide superior advantage to current immuno-oncology strategies.

Example 2(d) OX40/PD-L1 Bispecific Binding Proteins

The following bispecific binding proteins that bind PD-L1 and OX40 were created using the parental sequences identified above in Table 2. Proteins identified as Bis2, Bis3, and Bis5 were generated with the sequences in Table 10 below and were assessed for concurrent antigen binding activity using the Octet binding assay as discussed below.

TABLE 10

BIS constructs for OX40/PD-L1

| Description | Sequence |
|---|---|
| OX40 LCv kappa | DIQMTQSPSSLSASVGDRVTITCRASQDISNYLNWYQQKPGKAPKLLIY YTSKLHSGVPSRFSGSGSGTDYTLTISSLQPEDFATYYCQQGSALPWTF GQGTKVEIKRTVAAPSVFIFPPSDEQLKSGTASVVCLLNNFYPREAKVQ WKVDNALQSGNSQESVTEQDSKDSTYSLSSTLTLSKADYEKHKVYAC EVTHQGLSSPVTKSFNRGEC (SEQ ID NO: 32) |
| OX40SLR LCv kappa | DIQMTQSPSSLSASVGDRVTITCRASQDISNYLNWYQQKPGKAPKLLIY YTSKLHSGVPSRFSGSGSGTDYTLTISSLQPEDFATYYCQQGSALPWTF GQGTKVEIKRTVAAPSVFIFPPSDEQLKSGTASVVCLLNNFYPREAKVQ WKVDNALQSGNSQESVTEQDSKDSTYSLSSTLTLSKADYEKHKVYAC EVTHQGLSSPVTKSFNRGEC (SEQ ID NO: 93) |
| BiS2- PD-L1-OX40 HC- 4P | EIVLTQSPGTLSLSPGERATLSCRASQRVSSSYLAWYQQKPGQAPRLLI YDASSRATGIPDRFSGSGSGTDFTLTISRLEPEDFAVYYCQQYGSLPWT FGCGTKVEIKGGGGSGGGGSGGGGSGGGGSEVQLVESGGGLVQPGGS LRLSCAASGFTFSRYWMSWVRQAPGKCLEWVANIKQDGSEKYYVDS VKGRFTISRDNAKNSLYLQMNSLRAEDTAVYYCAREGGWFGELAFDY WGQGTLVTVSSGGGGSGGGGSQVQLQESGPGLVKPSQTLSLTCAVYG GSFSSGYWNWIRKHPGKGLEYIGYISYNGITYHNPSLKSRITINRDTSKN QYSLQLNSVTPEDTAVYYCARYKYDYDGGHAMDYWGQGTLVTVSSA STKGPSVFPLAPCSRSTSESTAALGCLVKDYFPEPVTVSWNSGALTSGV HTFPAVLQSSGLYSLSSVVTVPSSSLGTKTYTCNVDHKPSNTKVDKRV ESKYGPPCPPCPAPEFLGGPSVFLFPPKPKDTLMISRTPEVTCVVVDVSQ EDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQ VSLTCLVKGFYPSDIAVEWESNGQPENNYKTTPPVLDSDGSFFLYSRLT VDKSRWQEGNVFSCSVMHEALHNHYTQKSLSLSLGK (SEQ ID NO: 34) |
| BiS3- OX40 HC-4P-PD-L1 | QVQLQESGPGLVKPSQTLSLTCAVYGGSFSSGYWNWIRKHPGKGLEYI GYISYNGITYHNPSLKSRITINRDTSKNQYSLQLNSVTPEDTAVYYCAR YKYDYDGGHAMDYWGQGTLVTVSSASTKGPSVFPLAPCSRSTSESTA ALGCLVKDYFPEPVTVSWNSGALTSGVHTFPAVLQSSGLYSLSSVVTV PSSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNA KTKPREEQFNSTYRVVSVLTVLHQDWLNGKEYKCKVSNKGLPSSIEKT ISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLGKGGGGSGGGGSEIVLTQSPGTLSLSPGERATLSCR ASQRVSSSYLAWYQQKPGQAPRLLIYDASSRATGIPDRFSGSGSGTDFT LTISRLEPEDFAVYYCQQYGSLPWTFGCGTKVEIKGGGGSGGGGSGGG GSGGGGSEVQLVESGGGLVQPGGSLRLSCAASGFTFSRYWMSWVRQA PGKCLEWVANIKQDGSEKYYVDSVKGRFTISRDNAKNSLYLQMNSLR AEDTAVYYCAREGGWFGELAFDYWGQGTLVTVSS (SEQ ID NO: 35) |
| BiS5- OX40 HC-4P-PD-L1 | QVQLQESGPGLVKPSQTLSLTCAVYGGSFSSGYWNWIRKHPGKGLEYI GYISYNGITYHNPSLKSRITINRDTSKNQYSLQLNSVTPEDTAVYYCAR YKYDYDGGHAMDYWGQGTLVTVSSASTKGPSVFPLAPCSRSTSESTA ALGCLVKDYFPEPVTVSWNSGALTSGVHTFPAVLQSSGLYSLSSVVTV PSSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNA KTKPREEQFNSTYRVVSVLTVLHQDWLNGKEYKCKVSNKGLPSSIEKT ISKAKGQPREPQVYTLPPSQEEMTKNQVSLTCLVKGFYPSDIAVEWESN GGGGSGGGGSEIVLTQSPGTLSLSPGERATLSCRASQRVSSSYLAWYQ QKPGQAPRLLIYDASSRATGIPDRFSGSGSGTDFTLTISRLEPEDFAVYY CQQYGSLPWTFGCGTKVEIKGGGGSGGGGSGGGGSGGGGSEVQLVES |

TABLE 10-continued

BIS constructs for OX40/PD-L1

| Description | Sequence |
|---|---|
| | GGGLVQPGGSLRLSCAASGFTFSRYWMSWVRQAPGKCLEWVANIKQ<br>DGSEKYYVDSVKGRFTISRDNAKNSLYLQMNSLRAEDTAVYYCAREG<br>GWFGELAFDYWGQGTLVTVSSGGGGSGGGGSGQPENNYKTTPPVLDS<br>DGSFFLYSRLTVDKSRWQEGNVFSCSVMHEALHNHYTQKSLSLSLGK<br>(SEQ ID NO: 36) |
| BiS5-OX40SLR HC-<br>G1-N434A-PD-L1 | QVQLQESGPGLVKPSQTLSLTCAVYGGSFSSGYWNWIRKHPGKGLEYI<br>GYISYNAITYHNPSLKSRITINRDTSKNQYSLQLNSVTPEDTAVYYCAR<br>YKYDYEGGHAMDYWGQGTLVTVSSASTKGPSVFPLAPSSKSTSGGTA<br>ALGCLVKDYFPEPVTVSWNSGALTSGVHTFPAVLQSSGLYSLSSVVTV<br>PSSSLGTQTYICNVNHKPSNTKVDKRVEPKSCDKTHTCPPCPAPELLGG<br>PSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPI<br>EKTISKAKGQPREPQVYTLPPSREEMTKNQVSLTCLVKGFYPSDIAVEW<br>ESNGGGSGGGGSEVQLVESGGGLVQPGGSLRLSCAASGFTFSRYWM<br>SWVRQAPGKCLEWVANIKQDGSEKYYVDSVKGRFTISRDNAKNSLYL<br>QMNSLRAEDTAVYYCAREGGWFGELAFDYWGQGTLVTVSSGGGGSG<br>GGGSGGGGSGGGGSEIVLTQSPGTLSLSPGERATLSCRASQRVSSSYLA<br>WYQQKPGQAPRLLIYDASSRATGIPDRFSGSGSGTDFTLTISRLEPEDFA<br>VYYCQQYGSLPWTFGCGTKVEIKGGGGSGGGGSGQPENNYKTTPPVL<br>DSDGSFFLYSKLTVDKSRWQQGNVFSCSVMHEALHAHYTQKSLSLSP<br>GK (SEQ ID NO: 94) |

Octet Binding Assay

To evaluate binding of the bispecific binding molecules disclosed herein, an Octet QK equipped with Ni-NTA biosensor tips and 10× kinetics buffer were used (ForteBio, Menlo Park, Calif.). For this particular series of bispecific binding proteins, His-tagged PD-L1-Fc, his-tagged PD-1-Fc and hOX40-Fc (human recombinant proteins) were purchased from R&D Systems (Minneapolis, Minn.). All binding assays were performed at 25° C.

Figure 35:
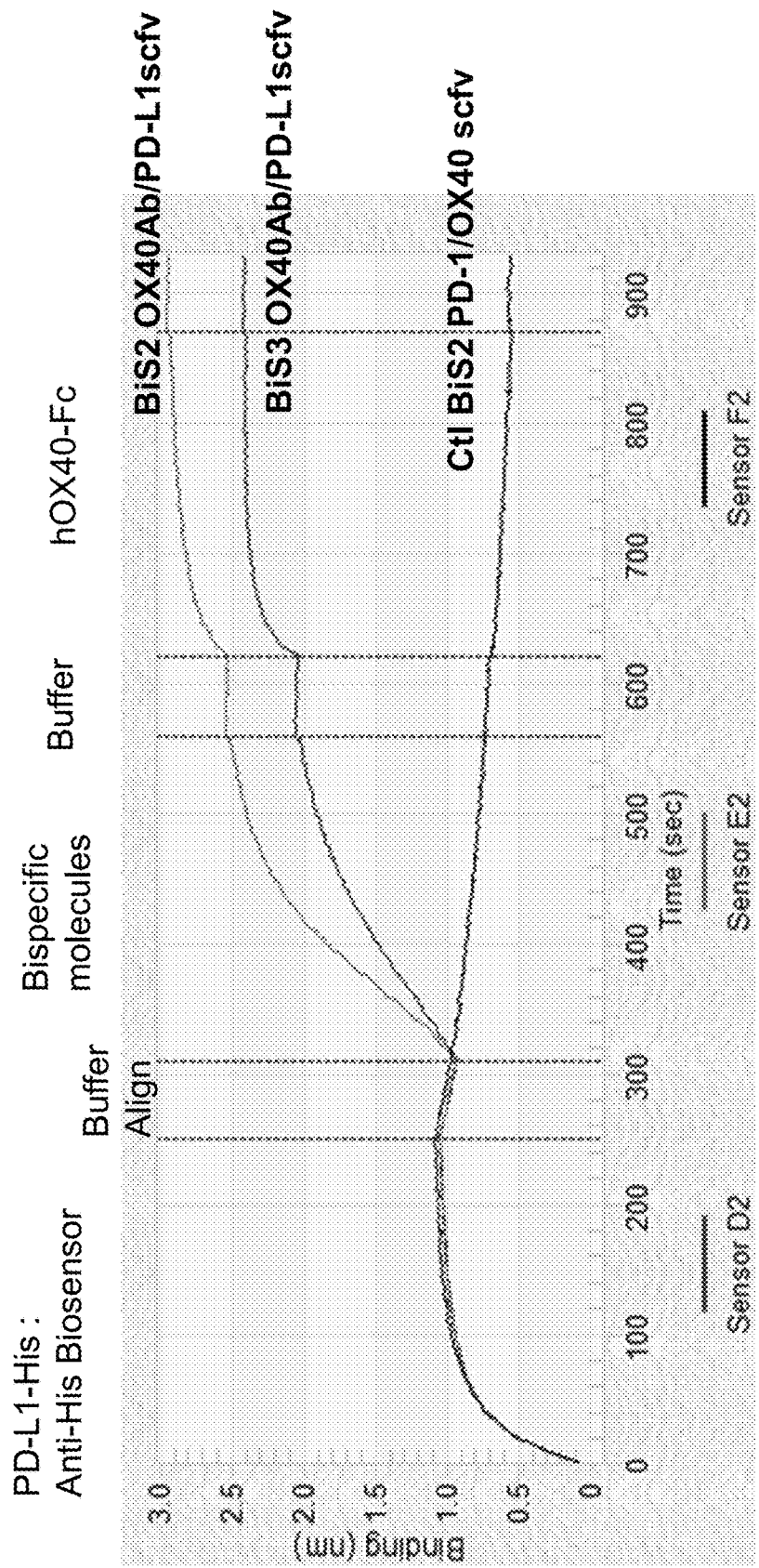
FIG. 35 shows the results of an octet assay using BiS2 and BiS3 OX40/PD-L1 bispecific molecules.

Sample plates were agitated at 1000 rpm prior to analysis. The Ni-NTA biosensor tips were pre-wetted for 5 min. in 1× kinetic buffer. The 1× kinetic buffer also served as the running buffer for baseline determination and as the dilution buffer for antigens and bispecific antibodies. Ni-NTA biosensor tips were dipped into 100 nM his-tagged PD-L1-Fc (see, (b), below) or his-tagged PD-1-Fc for antigen capture for about 1 min. The antigen-coated biosensor tips were each dipped into 10 μh/ml bispecific antibodies for ~5 minutes and then moved into a column of wells containing 100 nM hOX40-Fc antigen for 2 minutes. The binding results show that BiS2/BiS3 OX40Ab/PD-L1 molecules bind to both PD-L1-His and hOX40-Fc, and that BiS2 OX40Ab/PD-L1 binds with greater affinity than BiS3 OX40Ab/PD-L1. BiS2 PD-1/OX40 was used as a control (FIG. 35).

Staphylococcal Enterotoxin B (SEB) Assay

Figure 36A:
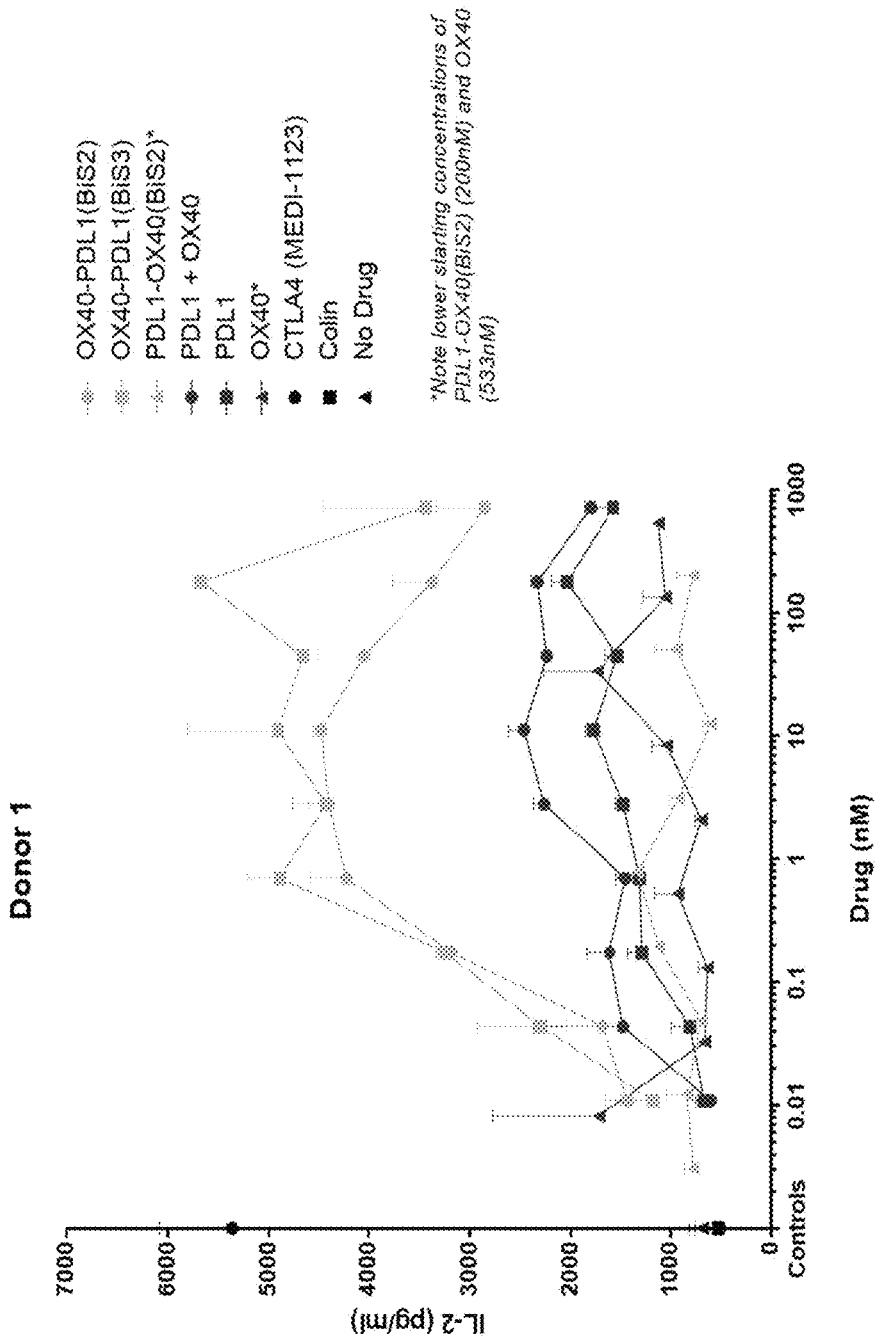
FIGS. 36A-B show the results of an SEB assay using BiS2 and BiS3 OX40/PD-L1 bispecific molecules.
Figure 36B:
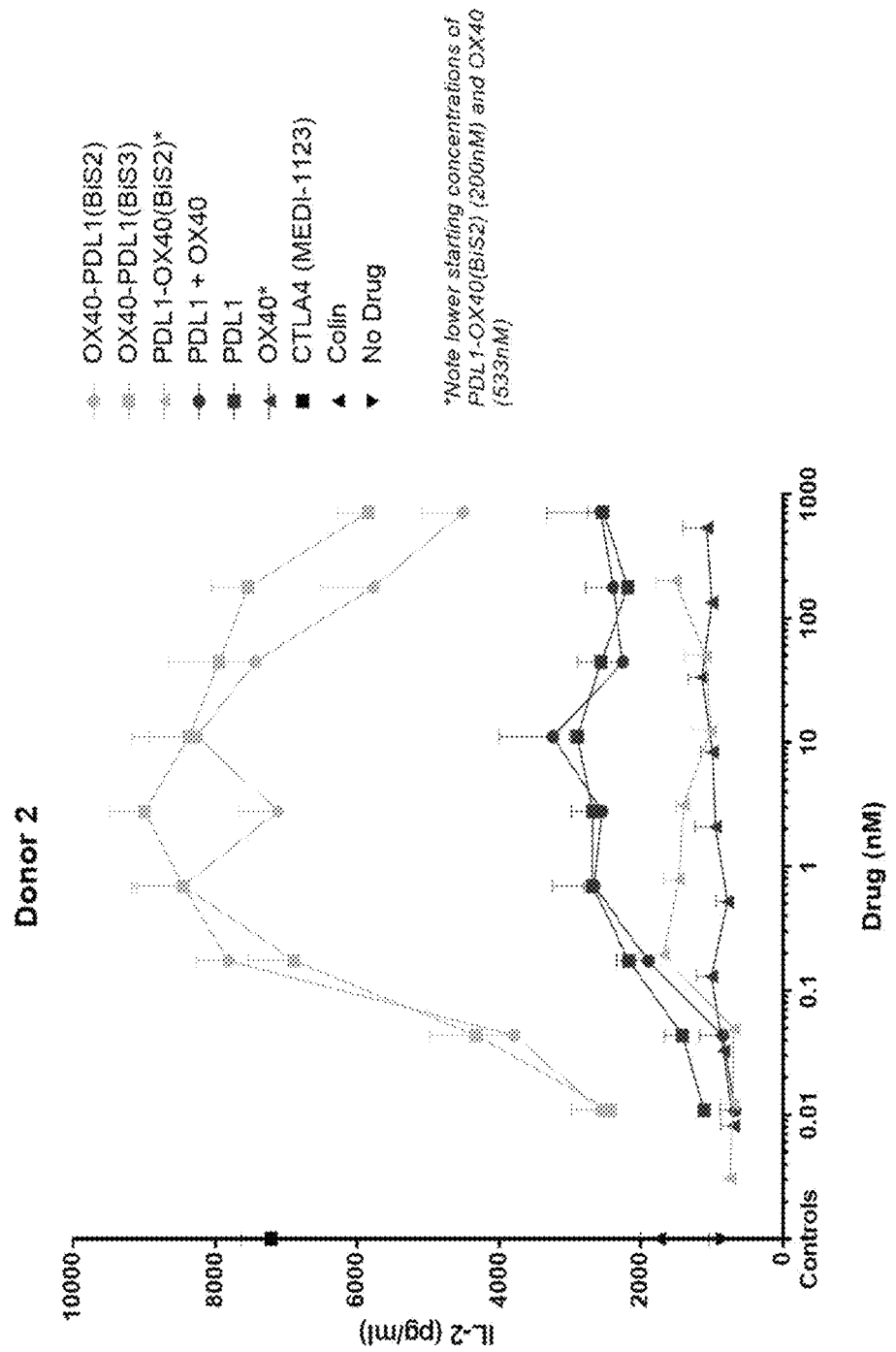

An SEB assay using the protocol described above showed that the OX40/PD-L1 bispecific molecule was active in both BiS2 and BiS3 formats (FIGS. 36A-B).

PD-L1 Reporter Assay

Materials:

Cell lines and culture conditions:

Human PD-1 Jurkat NFAT luciferase clone 2 reporter

PD-L1 expressing CHO scFv OKT3 (UBC) (All cells were maintained in RPMI 1640 media plus 10% FBS and 1× pen/strep antibiotics (RPMI complete media) at 37° C. in a humidified tissue culture incubator).

RPMI-1640, LifeTechnologies cat# A1049101

Heat inactivated newborn calf serum (FBS), LifeTechnologies cat#26010074

Complete RPMI medium: RPMI-1640 plus 10% FBS

100× Penicillin/Streptomycin, LifeTechnologies cat#15140-122

96 well TC treated flat bottom culture plates, Costar 3903, VWR cat#29444-010

SteadyGlo Luciferase Assay System, Promega, cat#E2510

Test Antibodies

EnVision Multilabel Plate Reader, Perkin Elmer

Methods:

For 2-cell bioactivity assay for neutralization of PD-L1 inhibition, PD-L1 expressing CHO scFv OKT3 cells were trypsinized, neutralized with warm RPMI complete media, and collected in a 50 mL conical tube. Cells were pelleted at 380 g for 5 min at RT, and then suspended in fresh RPMI complete media and counted on a Vi cell counter. PD-L1 expressing CHO scFv OKT3 cells were adjusted to 0.4e6/mL and 25 μL (10,000 cells) per well were plated as shown on the plate layout. Cells were allowed to adhere to plates for 3 hours. Thereafter, 50 μL of RPMI containing test reagents (2× final conc) were aliquoted onto the CHO cells and incubated for an additional 1 hour. This incubation gives the test reagent time to bind to PD-L1 on the surface of CHO cells. At 1 hour, PD-1 expressing Jurkat NFAT luciferase reporter cells were collected in a 50 mL conical tube, pelleted at 380 g for 5 min at RT, and re-suspended in fresh, warm RPMI complete media. Cells were adjusted to 1.2e6/mL and 25 μL (30,000) cells plated into wells with PD-L1 expressing CHO scFv OKT3 cells and test articles.

Cells and test reagent were further incubated for 18 hours for PD-1 Jurkat reporter cell activation. Thereafter, SteadyGlo luciferase reagent was prepared and 100 μL aliquoted to each well. Complete lysis was achieved by gentle shaking at RT (200 rpm orbital shaker) for 15 min. After lysis, luciferase activity was measured on an Envision Multilabel Plate Reader using the US96 luminescence protocol. Luciferase RLU was plotted versus log [test reagent] in Graphpad Prism software, and $EC_{50}$ values for PD-L1 antagonism determined using non-linear regression analysis, 4-parameter fit of sigmoidal dose-response curves.

Figure 37:
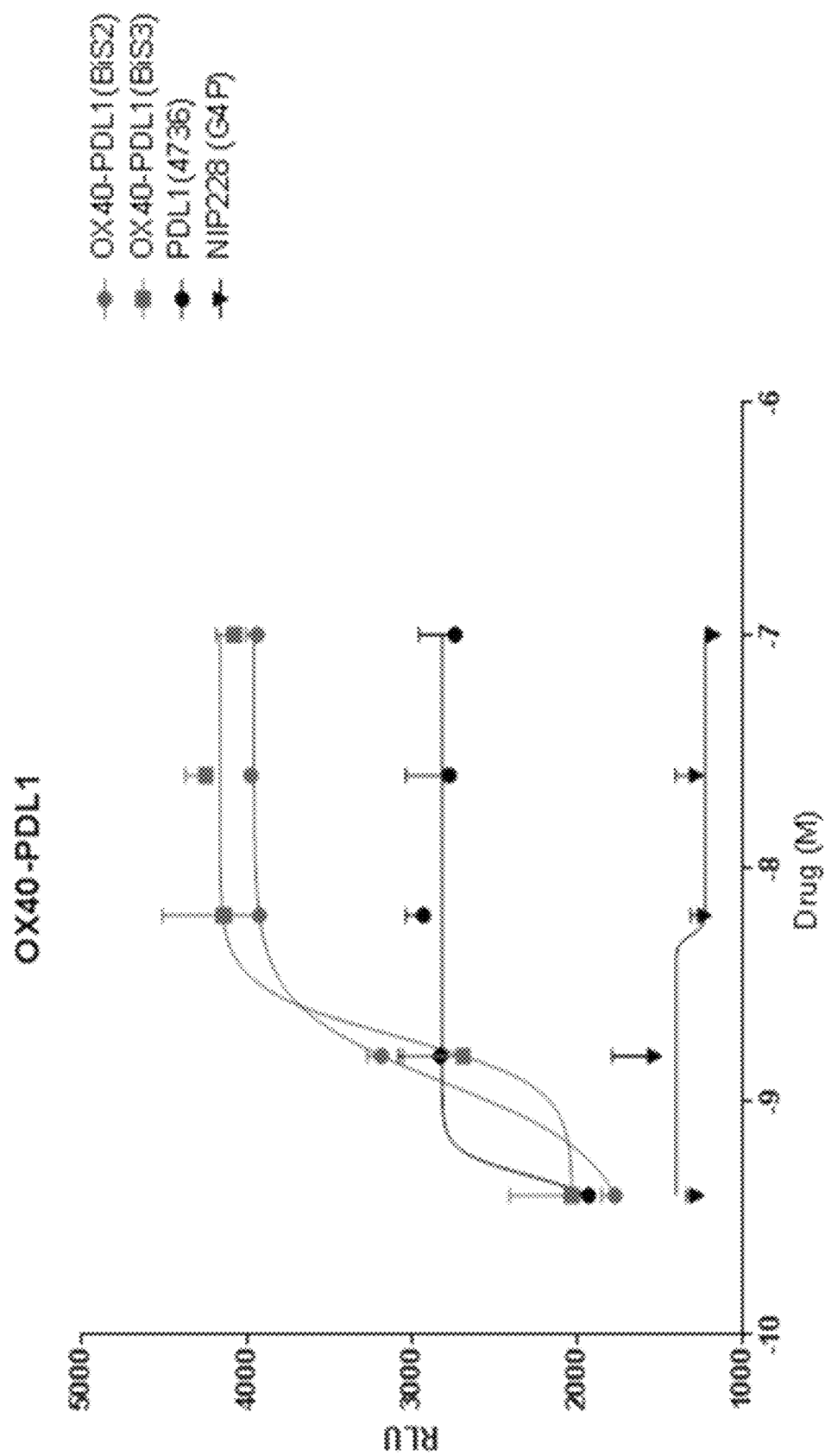
FIG. 37 shows the results of a PD-L1 reporter assay using BiS2 and BiS3 OX40/PD-L1 bispecific molecules.

Results:

OX40/PD-L1 BiS2/3 were tested against PD-L1/PD-1 parents and NIP228(G4P) controls using a five-point dose titration with a starting point of 100 nM (PD-L1). OX40-PD-L1 BisAbs were both shown to be active and have stronger agonism than PD-L1(4736) parent (FIG. 37) The BiS2 and BiS3 formats performed similarly.

CMV Ag Recall Assay

Figure 38:
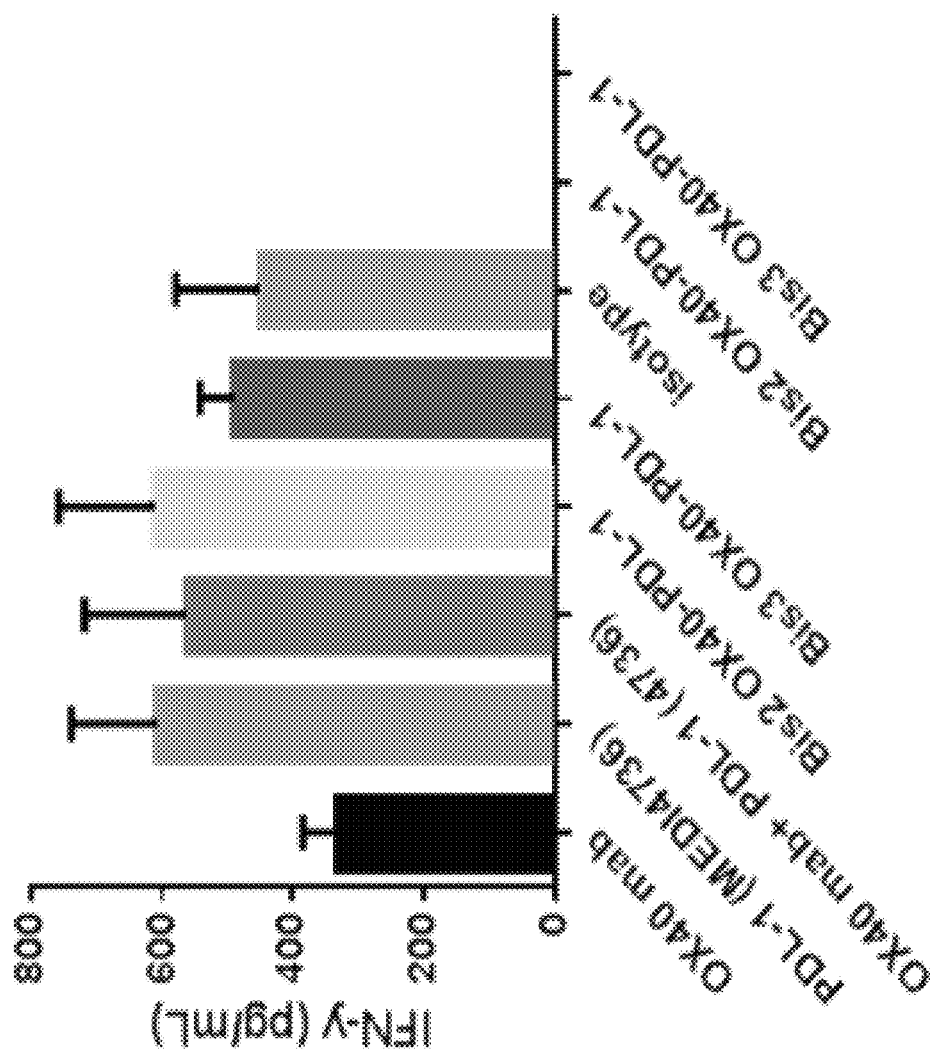
FIG. 38 shows the results of a CMV Ag recall assay using BiS2 and BiS3 OX40/PD-L1 bispecific molecules.

In the CMV Ag recall assay (using the protocol described above), the BiS2 and BiS3 molecules demonstrated equal activity relative to combination (FIG. 38).

All the binding and immune response assays discussed above provide illustrative data that the bispecific binding molecules disclosed herein exhibit specific binding for both target molecules—in some instances greater binding activity than the combination of individual monospecific parental binding molecules (antibodies), and can induce or enhance an immune response. Furthermore, the molecules are shown to have cell killing activity against a cancer cell line. As such, the data shows that these molecules and bispecific platform structure(s) represent excellent candidates for immuno-oncology therapeutics.

Octet Binding Assay (OX40(SLR)/PD-L1 BiS5)

Figure 39:
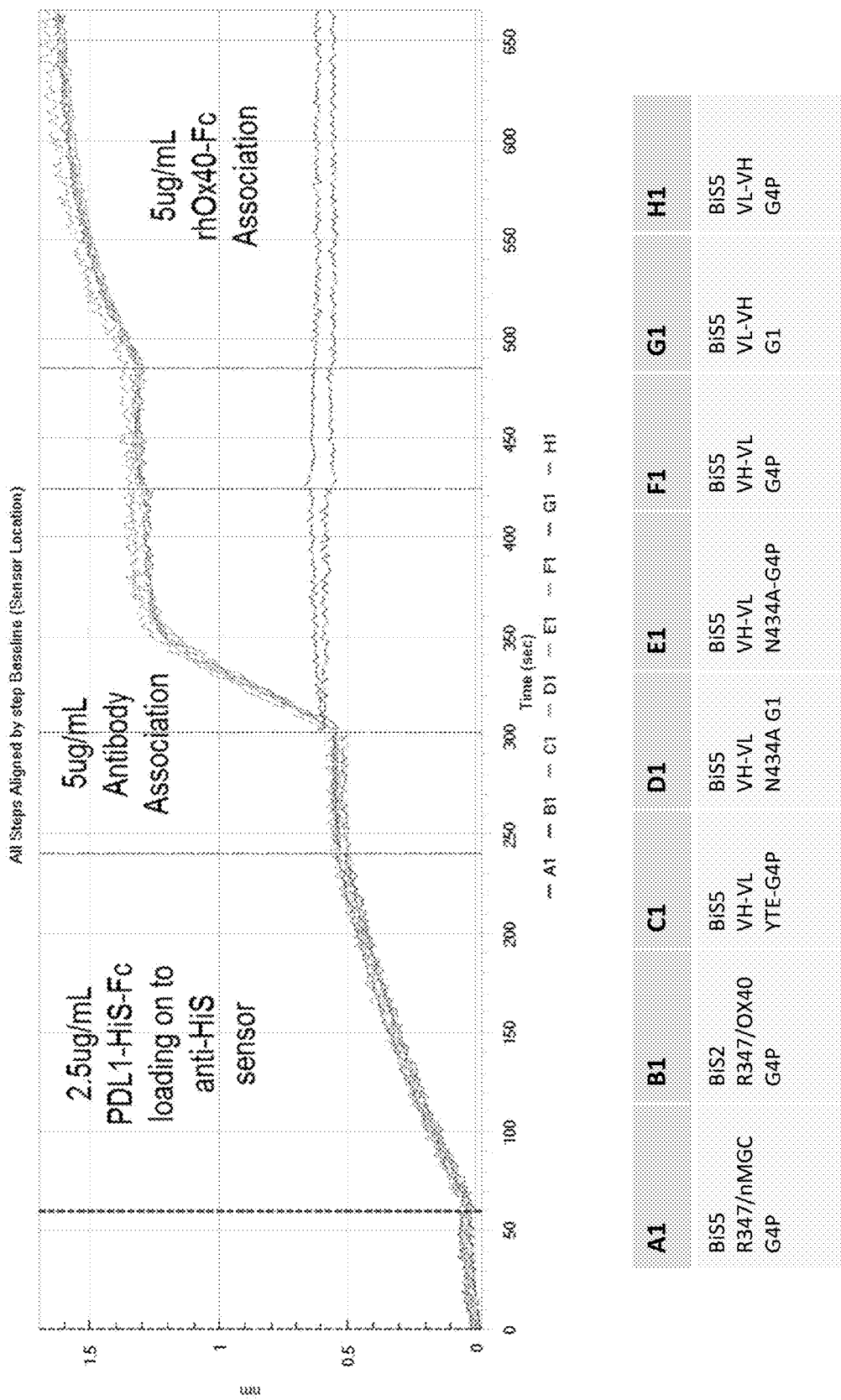
FIG. 39 shows the results of an octet binding assay which demonstrates the concurrent binding of the OX40(SLR)/PD-L1 BiS5 construct that targets PD-L1 and OX40.
Figure 40C:
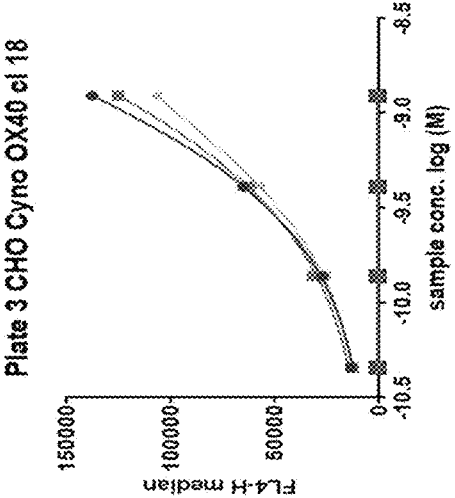
Figure 40B:
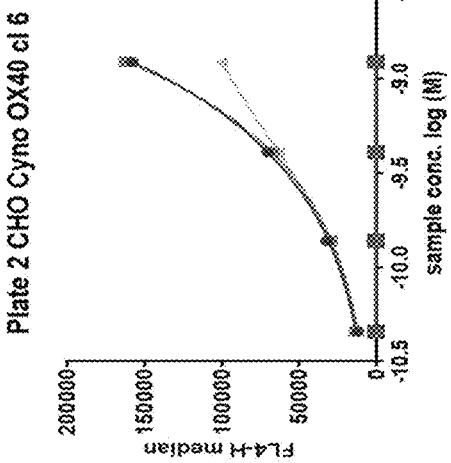
Figure 40A:
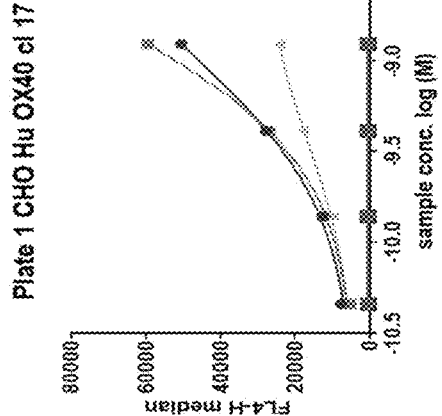

To evaluate binding of the bispecific binding molecules disclosed herein, an Octet QK equipped with Ni-NTA biosensor tips and 10× kinetics buffer were used (ForteBio, Menlo Park, Calif.). For this particular series of bispecific binding proteins, His-tagged PD-L1-Fc, his-tagged PD-1-Fc and hOX40-Fc (human recombinant proteins) were purchased from R&D Systems (Minneapolis, Minn.). All binding assays were performed at 25° C. The binding results show that BiS5 OX40Ab/PD-L1 molecules bind to both PD-L1-His and hOX40-Fc (FIG. 39).

PD-L1/OX40 BiS5 bound to CHO cells expressing CHO cells expressing human or cynomolgus OX40 and PD-L1/B7H1 (FIGS. 40A-F). Binding of PD-L1/OX40 BiS5 constructs was also measured by flow cytometry (HyperCyt) (FIG. 42). OX40 IgG4P and OX40/PD-L1 bispecifics bound to Jurkat OX40 reporter cells. PD-L1 IgG and OX40/PD-L1 bispecifics bound to NCI H358 and CHOK1 B7H1(PD-L1)/OKT3 cells. All IgG and bispecifics bound to HEK CD32a cells.

PD-L1 and OX40 Reporter Assay

Figure 42A:
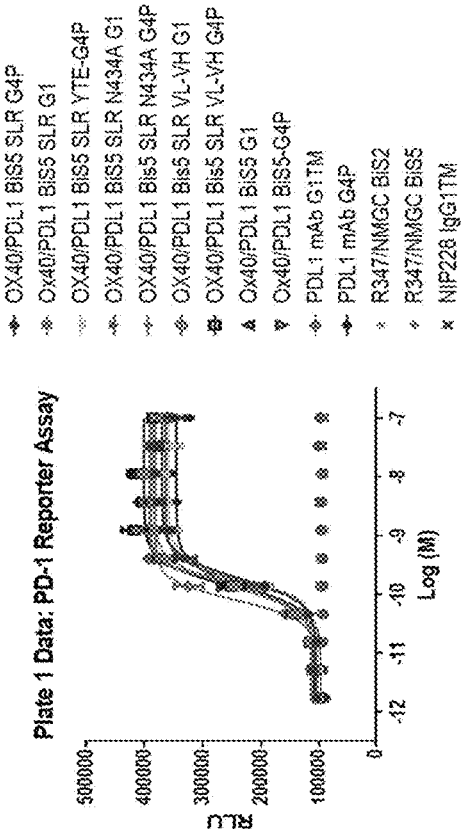
FIGS. 42A-B show the results of a PD-L1 reporter assay using OX40/PD-L1 bispecific molecules.
Figure 42B:
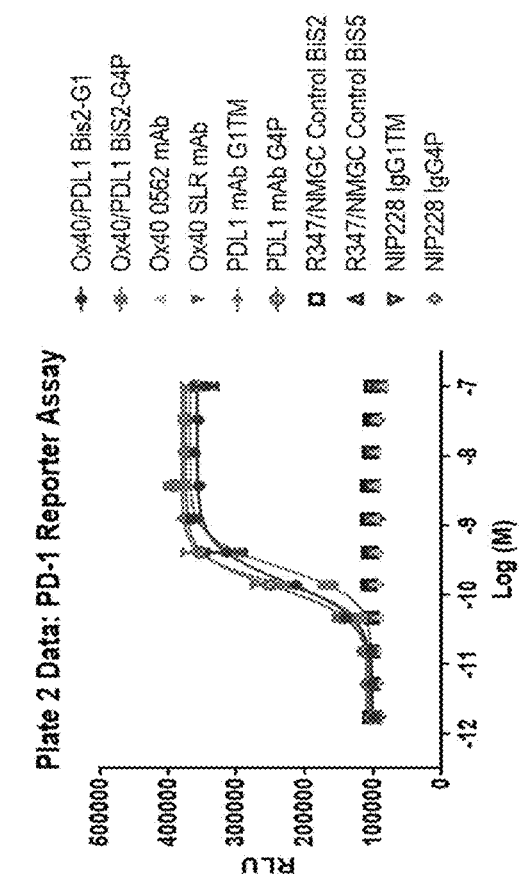
Figure 47:
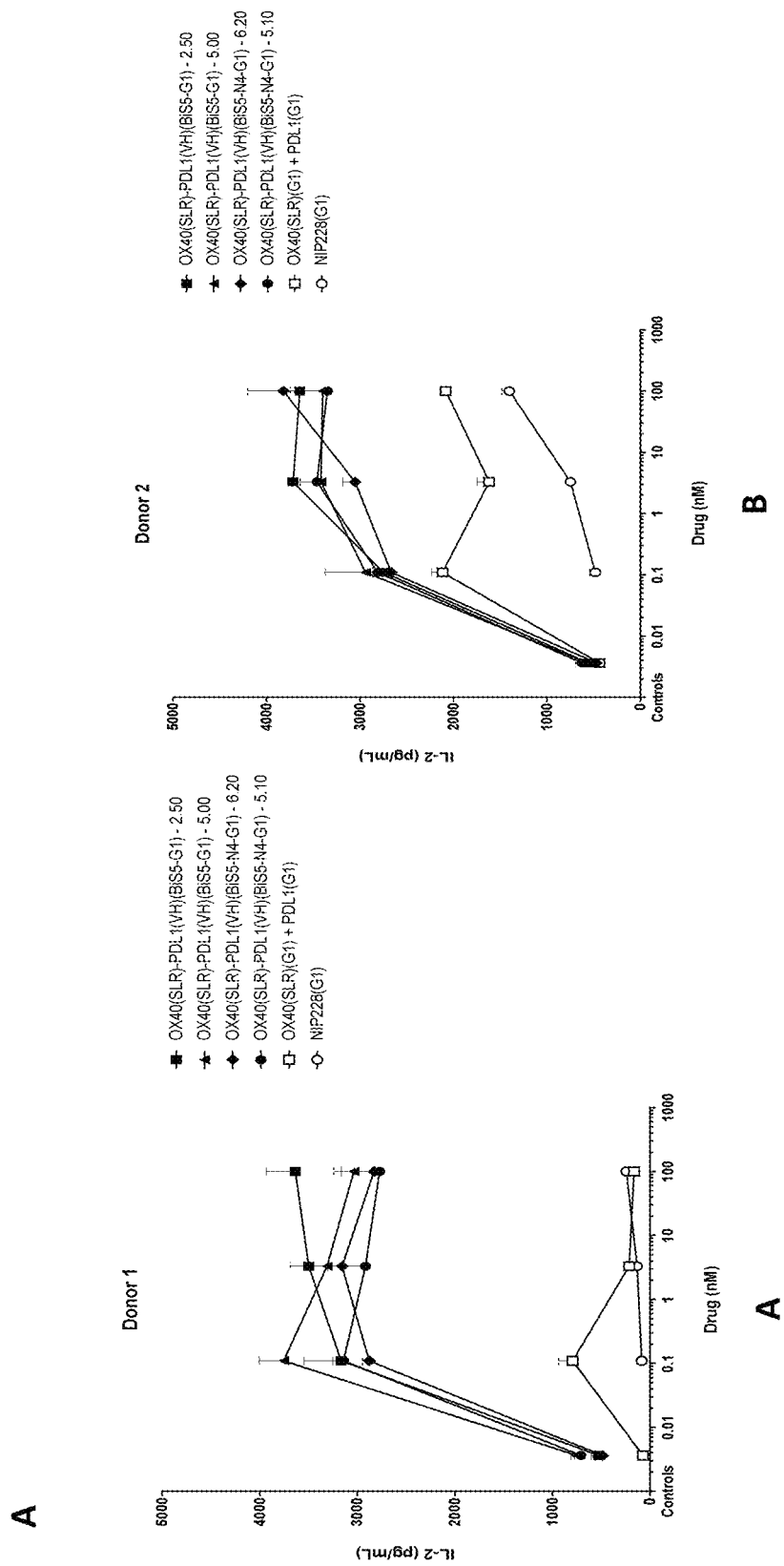
FIGS. 47A-D shows the results of an SEB assay using OX40/PD-L1 bispecific molecules.
Figure 47D:
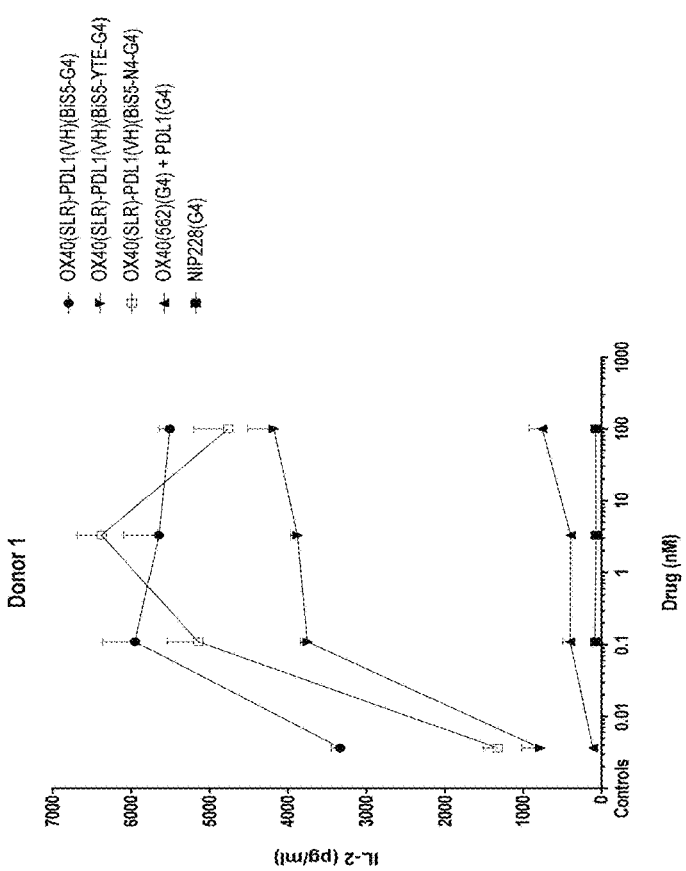
Figure 47C:
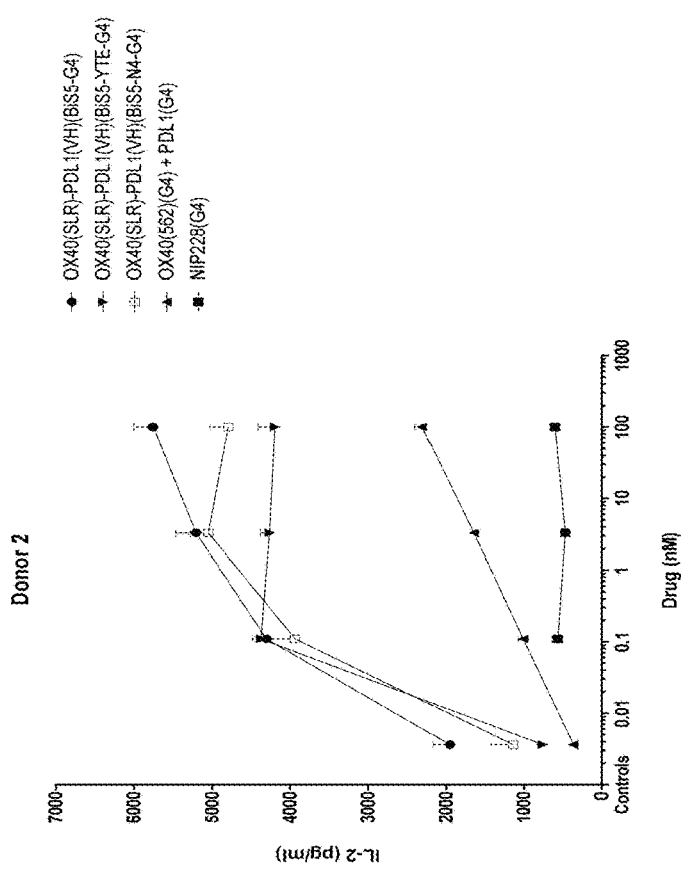

In the PD-L1 reporter assay (using the protocol described above), all PD-L1 scFv containing bispecifics and positive control IgGs displayed activity (FIGS. 42A-B). The single arm OX40 controls and isotype controls did not display any activity in this assay. The $EC_{50}$ values and hill slopes are consistent with values obtained in previous assays for the anti PD-L1 parental controls and the PD-L1 Bis2, Bis3 and Bis5 constructs.

In an OX40 reporter gene assay using HEK CD32a cells, the bispecific constructs had equal activity to each other, and Fc mediated agonism was observed (FIGS. 43A-B). OX40/PD-L1 Bis5 N434A IgG1 had equivalent $EC_{50}$ activity to OX40 IgG4P and MEDI0562 (OX40 IgG1).

In an OX40 reporter gene assay using CHOK1 PD-L1 over expressing cells, the OX40/PD-L1 bispecifics show equal agonism (FIGS. 44A-B). OX40/PD-L1 Bis5 N434A IgG1 had equivalent $EC_{50}$ activity to other Fc variants of the OX40/PD-L1 Bis5 bispecific Mab tested. No agonism with OX40 IgGs or PD-L1 IgGs was detected. Thus, PD-L1 mediated OX40 agonism was demonstrated.

PD-L1 mediated OX40 agonism with tumor cells using OX40/PD-L1 bispecific molecules was detected (FIGS. 45A-B). OX40/PD-L1 bispecific molecules showed equal agonism in this assay—bell shaped curves. No agonism with OX40 IgGs was observed, therefore demonstrating a benefit of using bispecifics over OX40 IgG plus PD-L1 IgG combination. No agonism was seen with NCI H358 PD-L1 KO cells (FIGS. 46A-D) showing that NCI H358 agonism seen with cells is PD-L1 specific.

Staphylococcal Enterotoxin B (SEB) Assay

In the SEB assay, OX40/PD-L1 bispecific molecules had greater activity than the combination of individual antibodies to OX40 and PD-L1 (FIGS. 47A-D). In particular, the G4P construct had greater activity than the G1 construct. Wild-type, a YTE containing variant, and the N434A variant had equivalent activity.

Treg Suppression Assay

Figure 49:
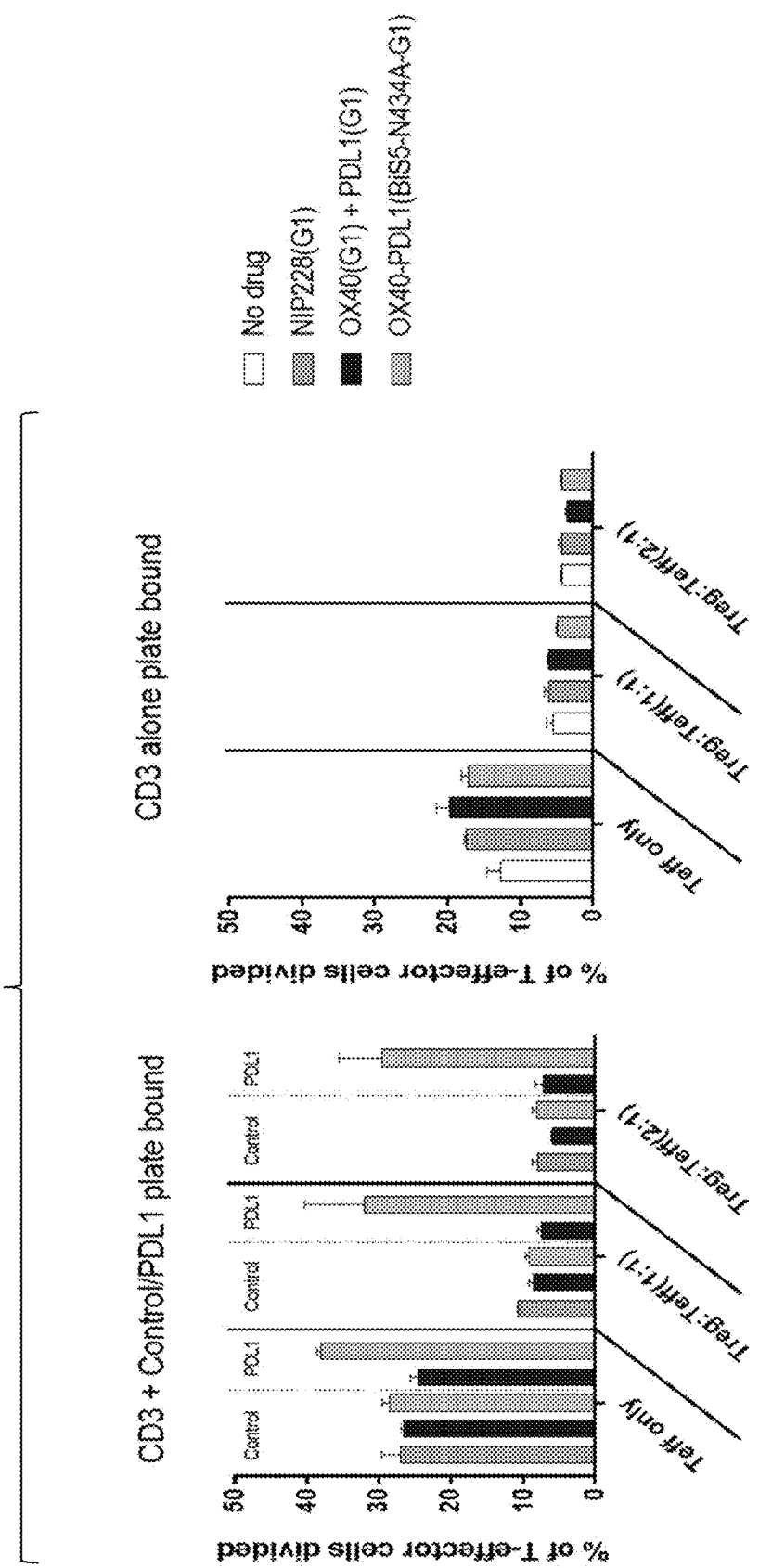
FIG. 49 depicts shows the results of the Treg suppression assay using the OX40/PD-L1 bispecific molecules.
Figure 50:
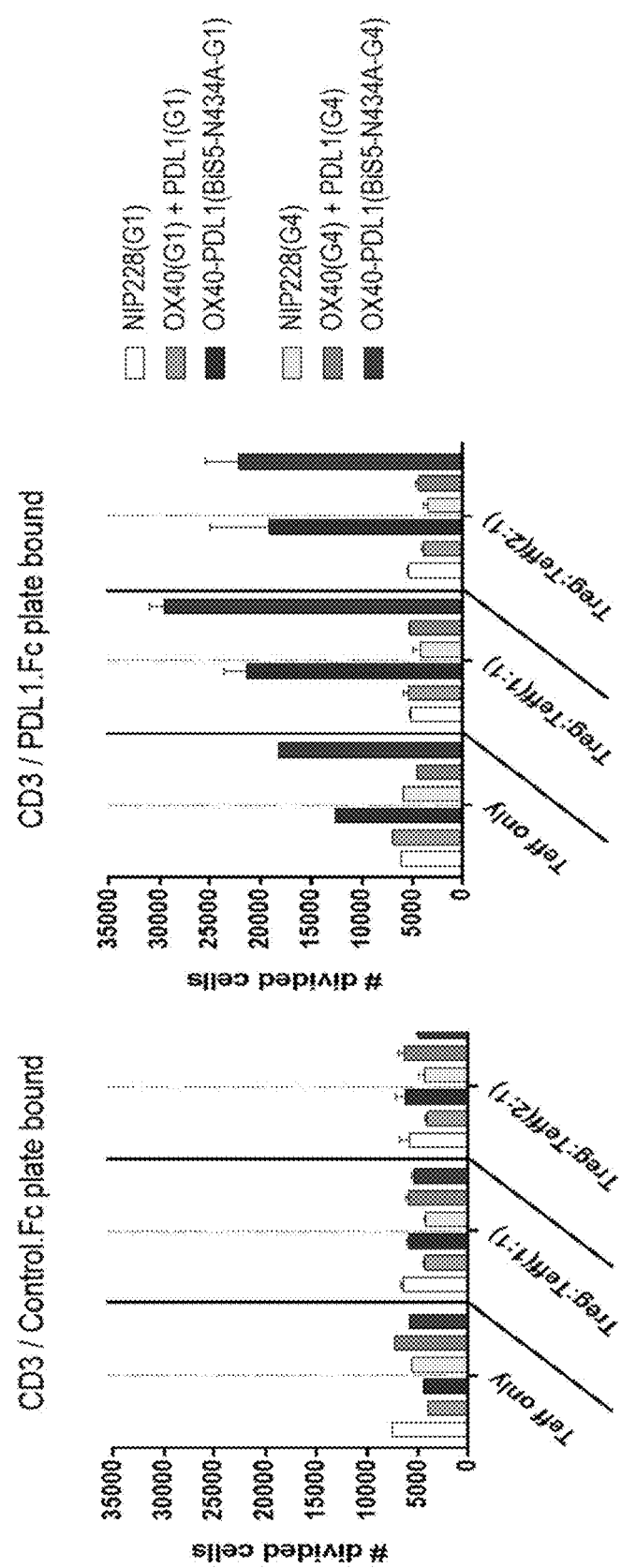
FIG. 50 depicts shows the results of the Treg suppression assay using the OX40/PD-L1 bispecific molecules.
Figure 52:
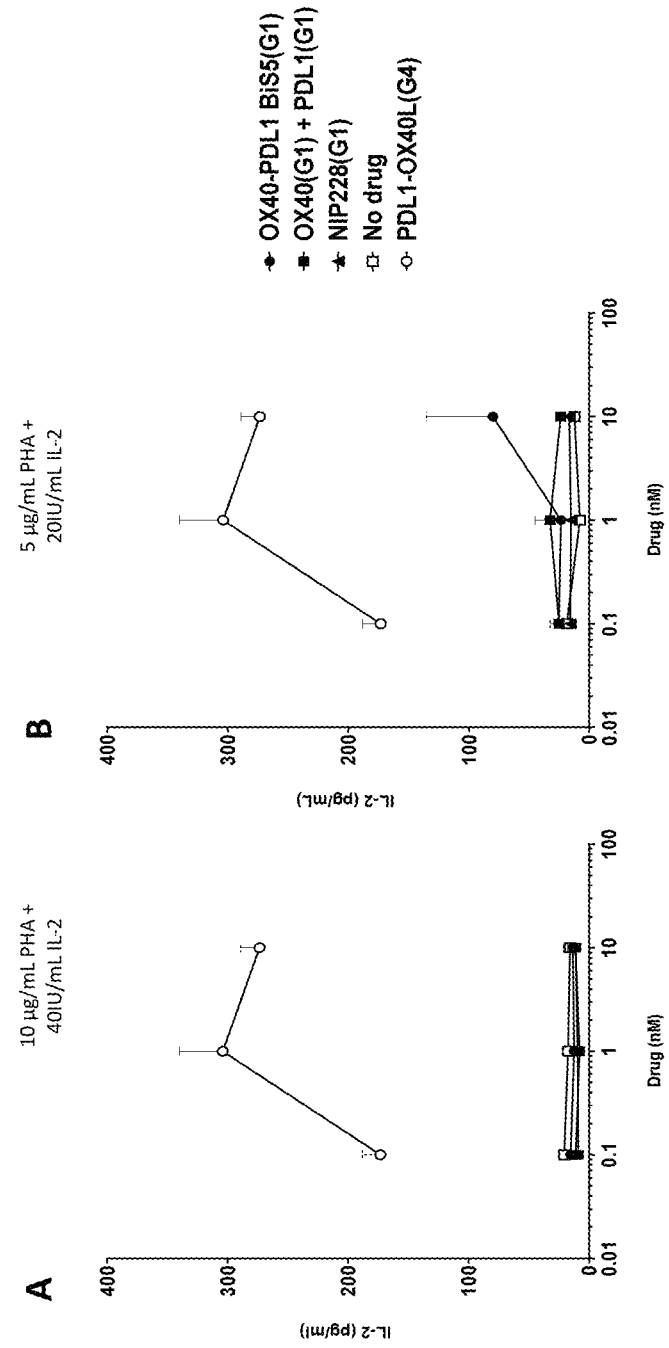
FIGS. 52A-E shows the results of the MLR assay using the OX40/PD-L1 bispecific molecules.
Figure 52:
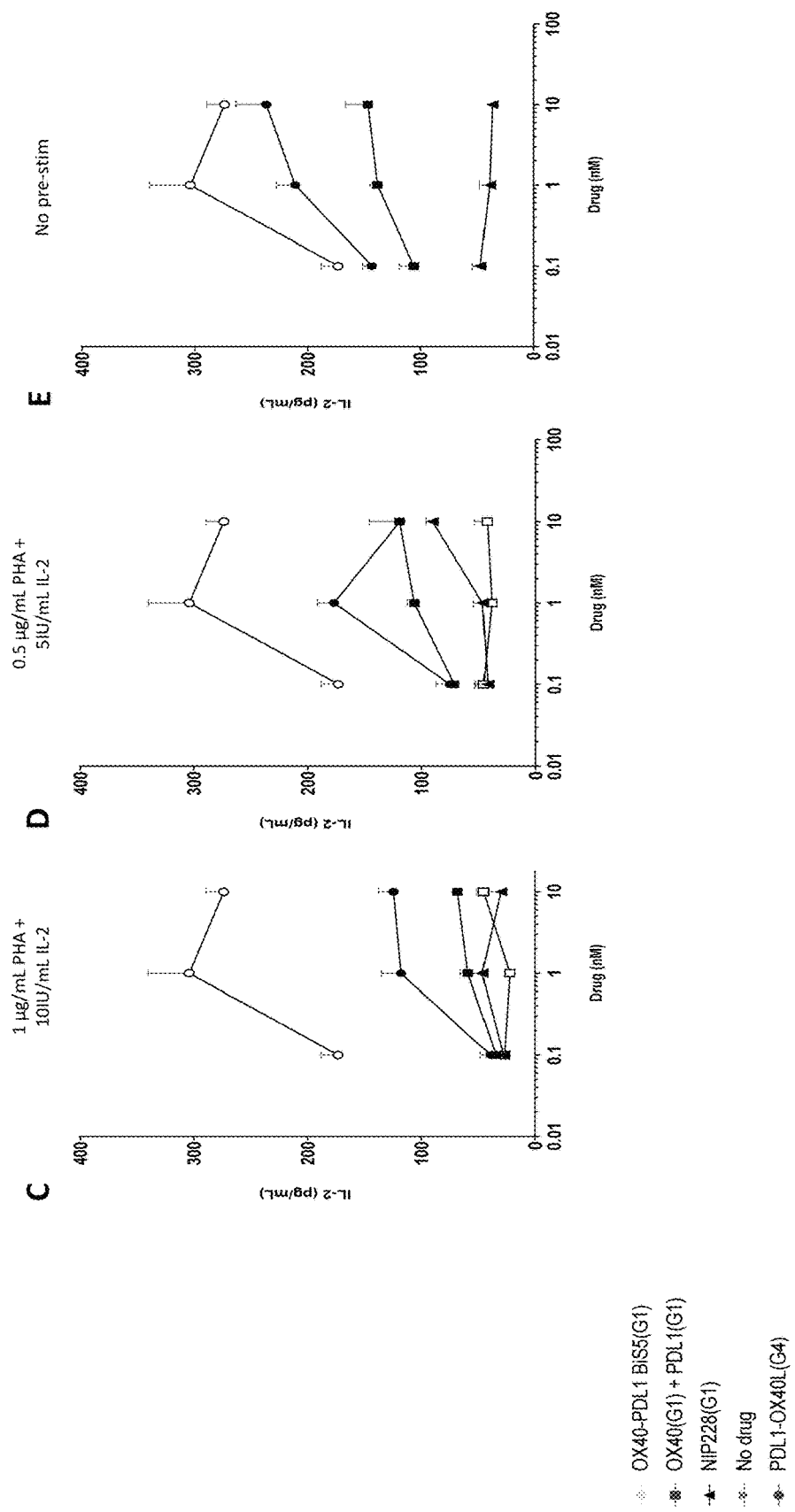

A Treg suppression assay was performed to test the OX40/PD-L1 bispecific molecules (FIGS. 4A-D). OX40/PD-L1 bispecific molecules were active on CD4+ $T_{eff}$ only in the presence of PD-L1 (FIGS. 49 and 50). Without being bound by theory, this indicated crosslinking of OX40 in trans. OX40/PD-L1 bispecific molecules suppressed $T_{reg}$ inhibitory effects, but only when crosslinked by binding to plate-immobilized PD-L1.

Mixed Leukocyte Reaction (MLR) Assay

A MLR assay was performed to test the OX40/PD-L1 bispecific molecules (FIGS. 51A-B). OX40/PD-L1 bispecific molecules had greater activity than the combination of individual antibodies to OX40 and PD-L1 (FIG. 52A-E).

Antibody-dependent Cell-mediated Cytotoxicity (ADCC) Assay

Figure 54:
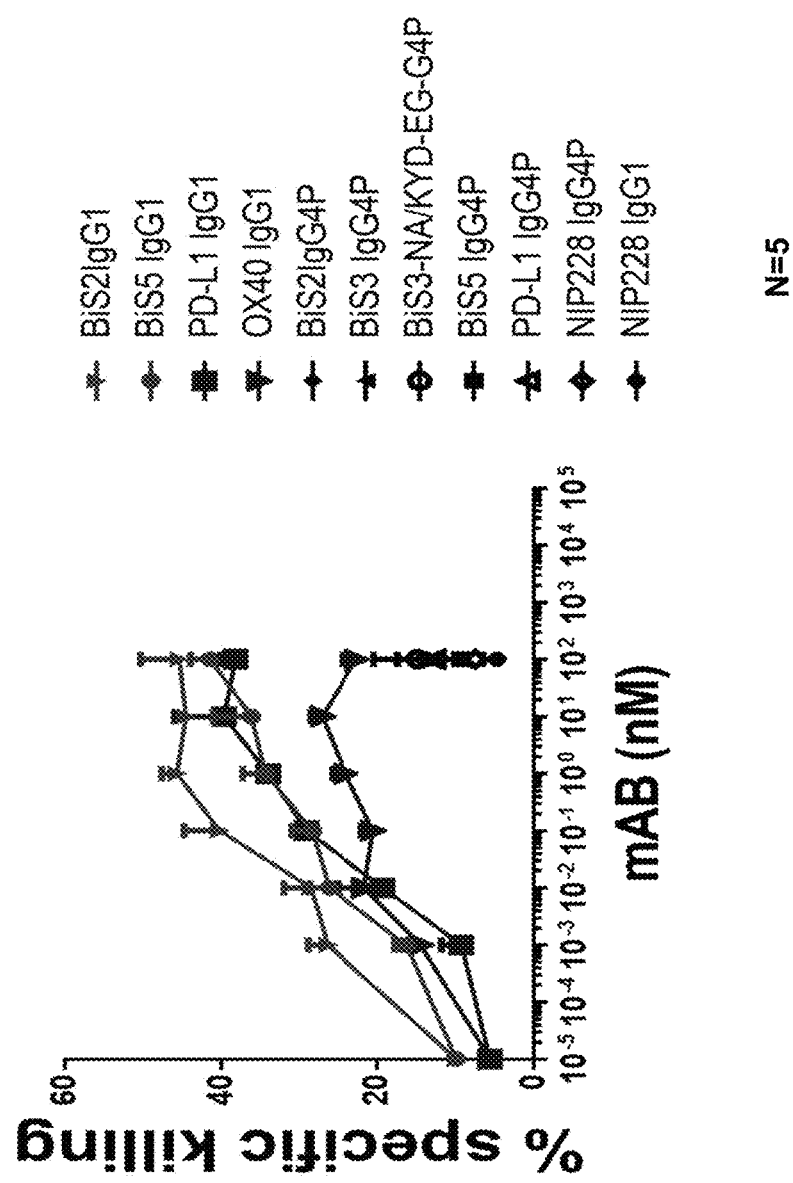
FIG. 54 shows that BiS2 and BiS5 OX40/PD-L1 bispecific molecules mediate antibody-dependent cell-mediated cytotoxicity (ADCC) of NK cells against PD-L1 and OX40 expressing CHO cells.

An ADCC assay was performed to test the OX40/PD-L1 bispecific molecules. ADCC assay using freshly isolated NK cells as effector cells and CHOK1 PD-L1 B7H1 and CHOK1 OX40 overexpressing cells, respectively, as target cells at an effector to target (E:T) ratio of 20:1. Target cell lysis was analyzed using release of Europium from labelled target cells after 5 hours. In the ADCC assay, OX40/PD-L1 BiS2 and BiS5 mediated ADCC against PD-L1 or OX40 expressing CHO cells (FIGS. 53A-B and 54).

Figure 55:
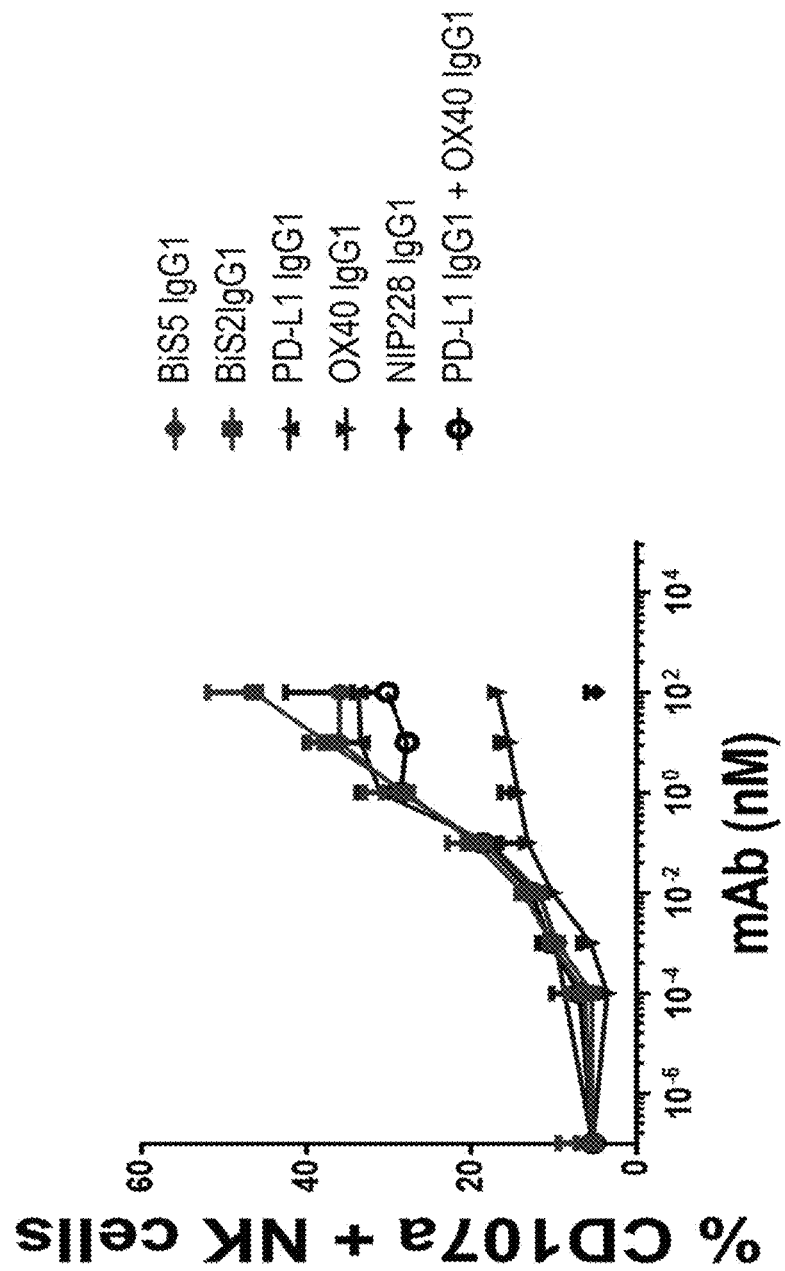
FIG. 55 shows that BiS2 and BiS5 OX40/PD-L1 bispecific molecules increased CD107a mobilization of NK cells against PD-L1 and OX40 expressing CHO cells in antibody-dependent cell-mediated cytotoxicity (ADCC).
Figure 56:
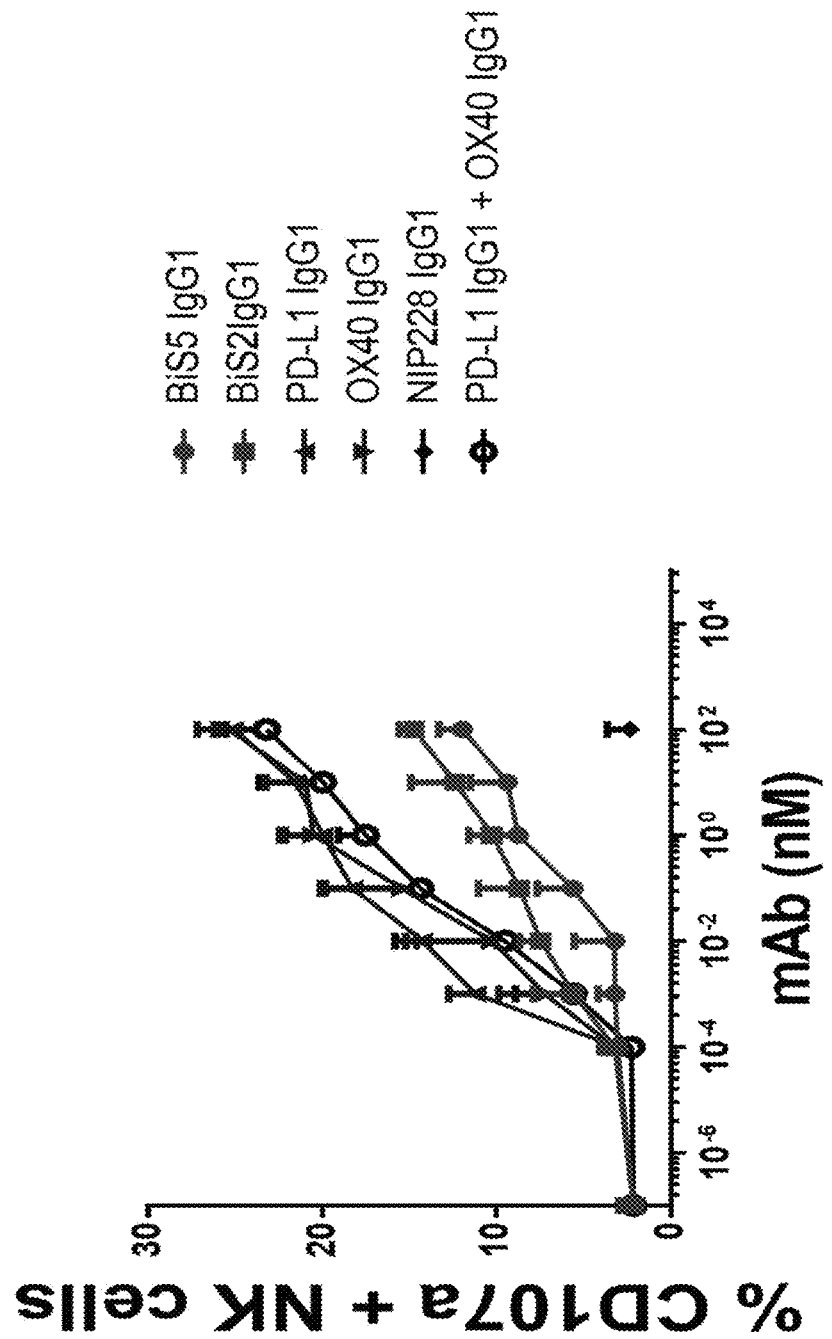
FIG. 56 shows that BiS2 and BiS5 OX40/PD-L1 bispecific molecules mediate antibody-dependent cell-mediated cytotoxicity (ADCC) of NK cells against activated allogeneic T cells.
Figure 57B:
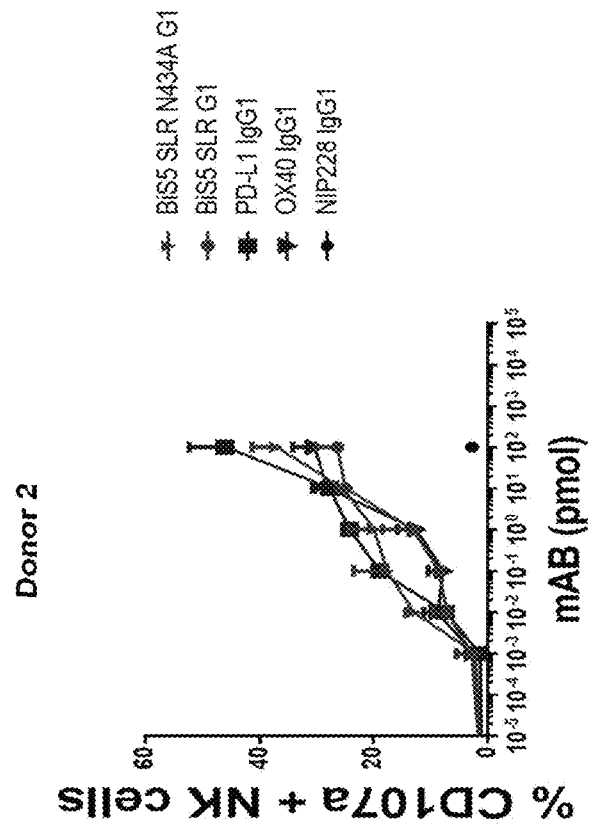
FIGS. 57A-B shows that BiS5 OX40/PD-L1 increased CD107a mobilization of NK cells from two different donors against activated allogeneic T cells in antibody-dependent cell-mediated cytotoxicity (ADCC).
Figure 57A:
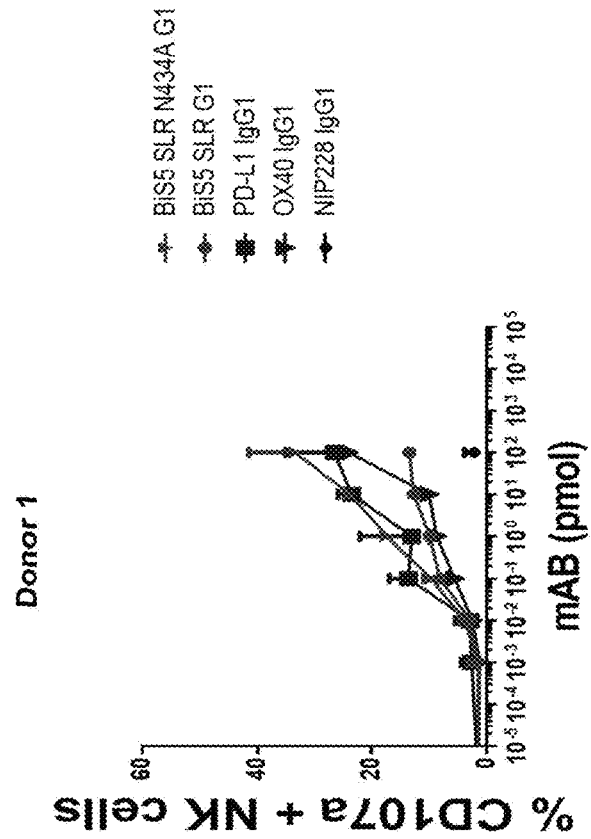

A CD107a mobilisation assay was performed using freshly isolated NK cells as effector cells and PD-L1 and OX40 overexpressing CHO K1 as target cells at a E:T ratio of 10:1. CD107a mobilisation to the cell surface of NK cells was analysed by flow cytometry after 4 hours. BiS2 and BiS5 OX40/PD-L1 bispecific molecules increased CD107a mobilization of NK cells against PD-L1 and OX40 expressing CHO cells in antibody-dependent cell-mediated cytotoxicity (ADCC) assays (FIG. 55). BiS2 and BiS5 OX40/PD-L1 bispecific molecules increased CD107a mobilization of NK cells against activated allogeneic T cells that have up-regulated OX40 and PD-L1 (FIG. 56). BiS5 OX40/PD-L1 increased CD107a mobilization of NK cells from two different donors against activated allogeneic T cells (FIGS. 57A-B).

Pharmacokinetic and Pharmacodynamic (PK/PD) Studies

Figure 58:
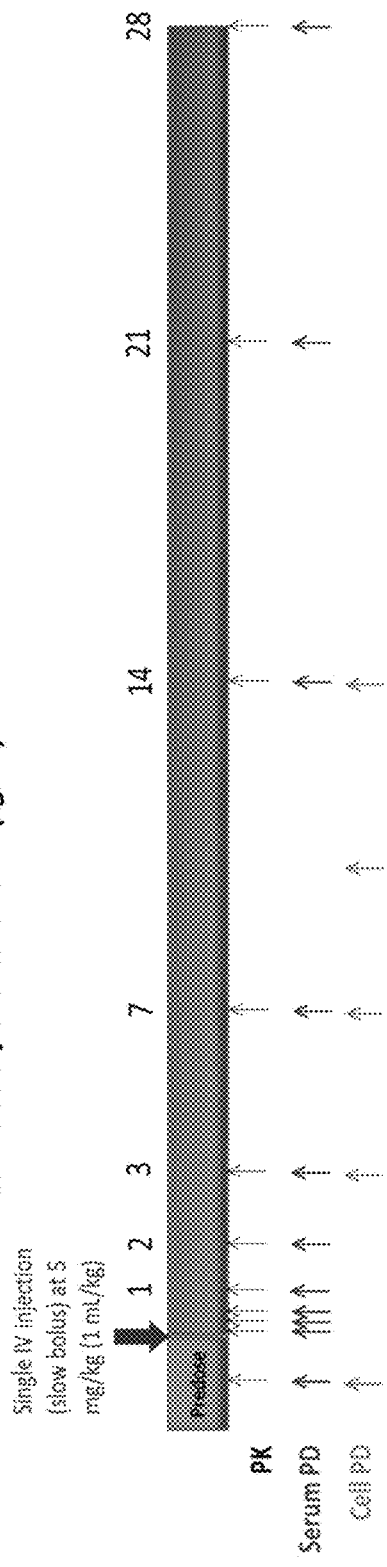
FIG. 58 shows a study design to compare PK/PD of OX40/PD-L1 bispecific molecules.
Figure 59:
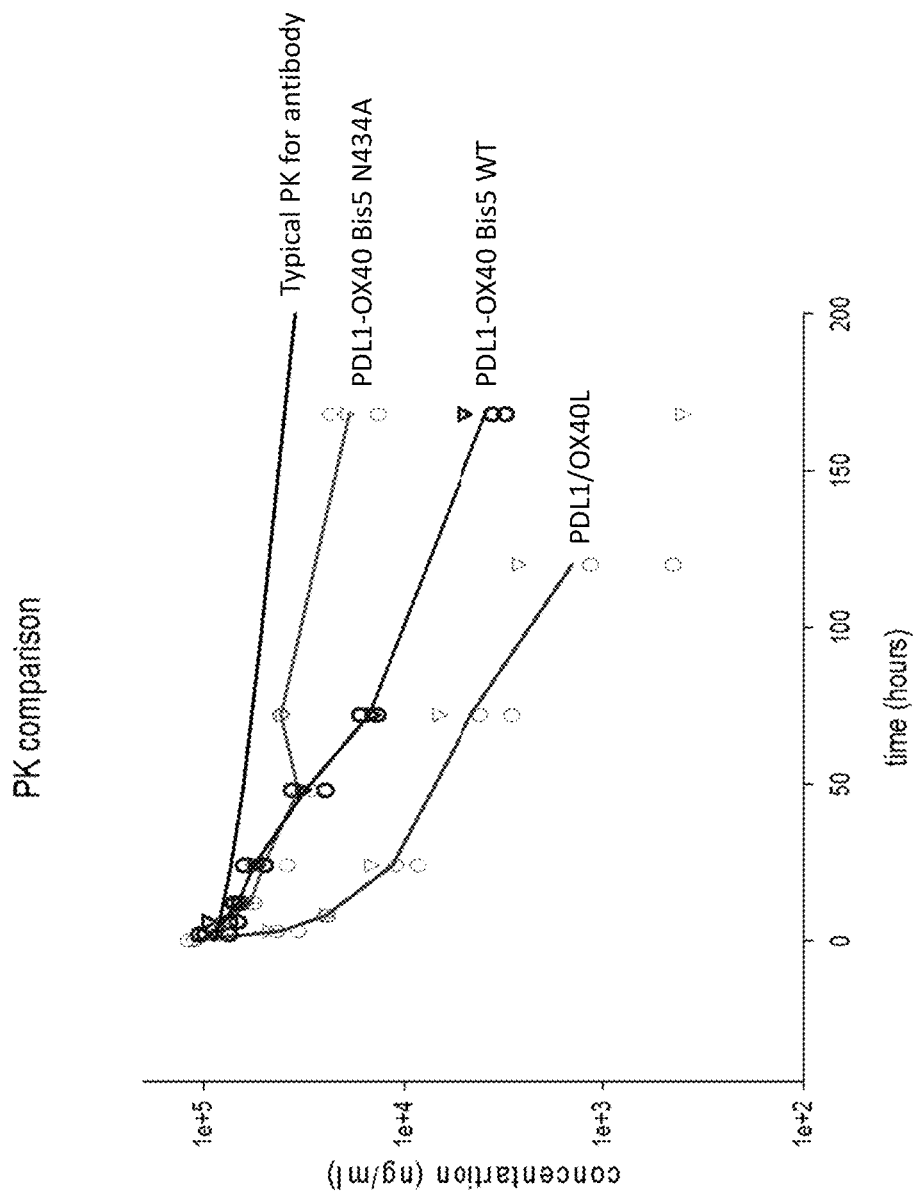
FIG. 59 shows a comparison of serum concentration time profiles for PD-L1/OX40 bispecific molecules in cynomolgus monkeys.

A study was designed to compare the PK/PD of OX40/PD-L1 bispecific molecules (FIG. 58). Serum concentration time profiles for PD-L1/OX40 bispecific molecules were compared in cynomolgus monkeys (FIG. 59 and Table 11). Mean T1/2 for the Bis5 OX40/PD-L1 IgG1 N434A molecule was greater than for the WT Bis5 molecule; clearance rate was less for the Bis5 OX40/PD-L1 IgG1 N434A molecule as compared to the WT Bis5 molecule. Both molecules similarly reduced soluble PD-L1 in the serum, and elicited a significant increase in the percentage of Ki67+ total memory CD4+ T cells, total memory CD8+ T cells and NK cells.

TABLE 11

| Test Article | Animal | AUClast (ng*h/mL) | AUCinf (ng*h/mL) | % AUCExtrap (%) | C0 (ng/mL) | Cmax (ng/mL) |
|---|---|---|---|---|---|---|
| BiS5-OX40/PD-L1-G1 N434A | 2028 | 5490000 | 6840000 | 19.8 | 82900 | 82300 |
| | 2033 | 6530000 | 10800000 | 39.7 | 77700 | 79100 |
| | 2059 | 6510000 | 9260000 | 29.7 | 94500 | 89800 |
| | Mean | 6180000 | 8980000 | 29.7 | 85000 | 83700 |
| | SD | 597000 | 2000000 | 9.91 | 8610 | 5520 |
| BiS5-OX40/PD-L1-G1 WT | 2032 | 4260000 | 4530000 | 6.08 | 104000 | 101000 |
| | 2047 | 3670000 | 3900000 | 5.84 | 131000 | 105000 |
| | 2056 | 4190000 | 4340000 | 3.45 | 74400 | 74400 |
| | Mean | 4040000 | 4260000 | 5.13 | 103000 | 93300 |
| | SD | 320000 | 324000 | 1.45 | 28200 | 16500 |

| Test Article | Animal | Tmax (h) | Cl (mL/min/kg) | Vss (L/kg) | T½ (h) | Rsq |
|---|---|---|---|---|---|---|
| BiS5-OX40/PD-L1-G1 N434A | 2028 | 2 | 0.0122 | 0.0773 | 70 | 0.836 |
| | 2033 | 6 | 0.0077 | 0.0842 | 128 | 0.873 |
| | 2059 | 2 | 0.00899 | 0.0746 | 97.1 | 0.933 |
| | Mean | 3.33 | 0.00963 | 0.0787 | 98.3 | 0.881 |
| | SD | 2.31 | 0.0023 | 0.00496 | 28.9 | 0.049 |
| BiS5-OX40/PD-L1-G1 WT | 2032 | 2 | 0.0184 | 0.0596 | 37.9 | 0.952 |
| | 2047 | 2 | 0.0214 | 0.0672 | 44.6 | 0.987 |
| | 2056 | 2 | 0.0192 | 0.0555 | 34 | 0.99 |
| | Mean | 2 | 0.0196 | 0.0608 | 38.9 | 0.976 |
| | SD | 0 | 0.00154 | 0.00593 | 5.35 | 0.0211 |

Figure 60:
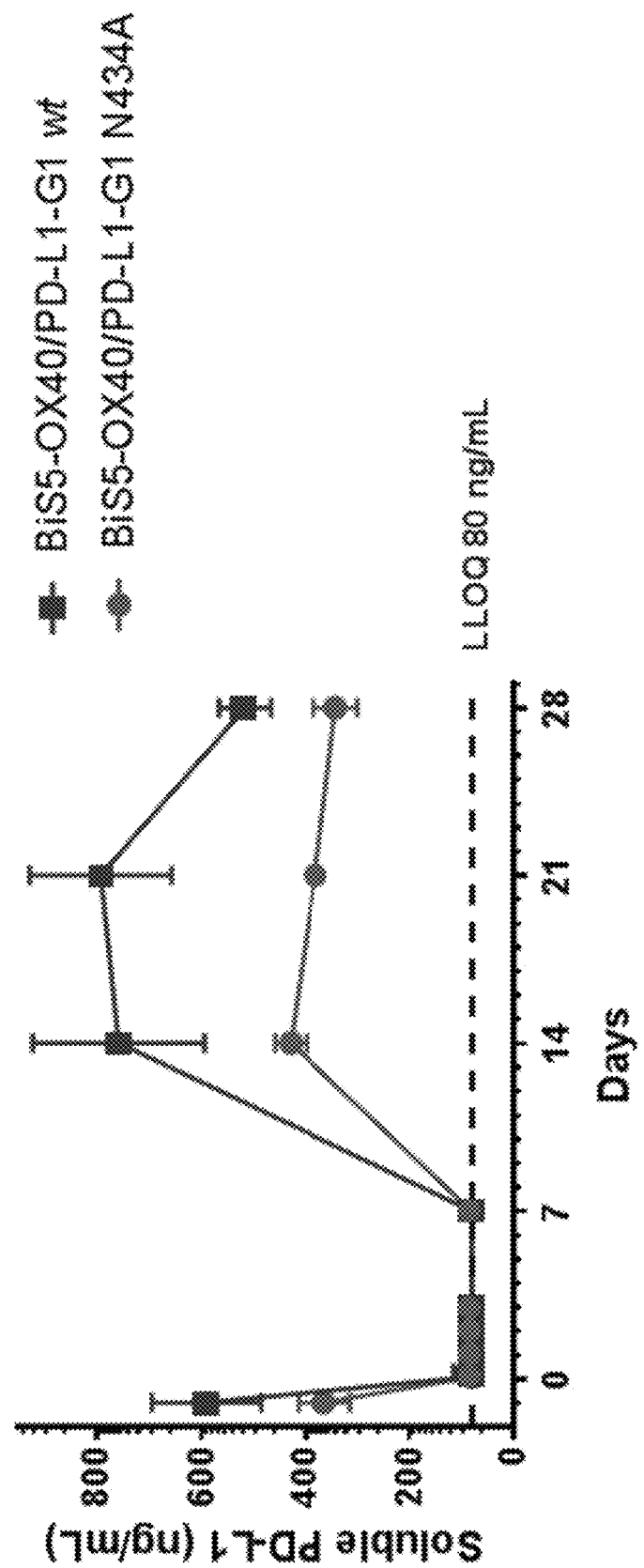
FIG. 60 shows depletion of soluble PD-L1 in serum by PD-L1/OX40 bispecific molecules.
Figure 61:
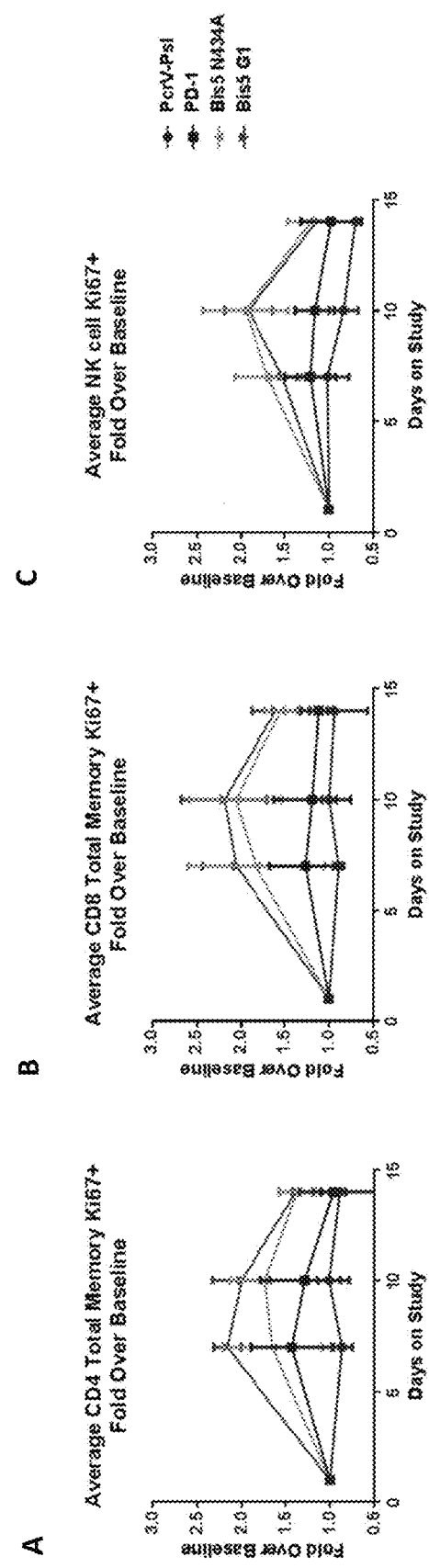
FIGS. 61A-F provides a summary of pharmacodynamic data for PD-L1/OX40 bispecific molecules. Baseline defined as mean of Day −5 and Day 0 pre-dose.
Figure 61E:
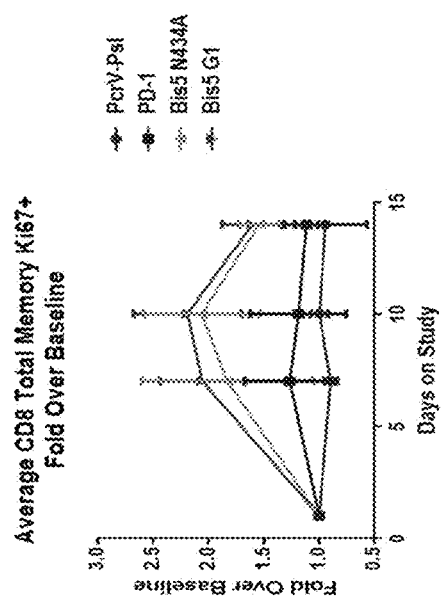
Figure 61D:
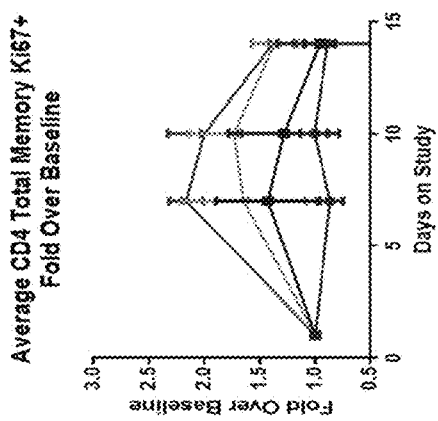
Figure 61F:
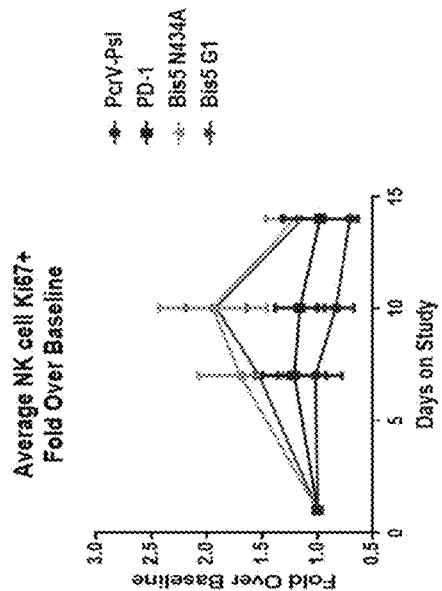

OX40/PD-L1 bispecific molecules reduced serum soluble PD-L1 concentrations below the assay LLOQ (FIG. 60). The N434A mutation improved pharmacokinetics of BiS5-OX40/PD-L1-G1. In particular, CL was reduced by approximately half; there was a corresponding 2-fold increase in T1/2 and AUCinf; and Cmax and Vss not impacted. This was consistent with previously reported effects of this mutation on the PK of monoclonal antibodies. Thus, progress was made towards mAb-like PK for BiS5-OX40/PD-L1-G1 IO BisAb. Serum concentrations of BiS5-OX40/PD-L1-G1 BiSAbs were below the limit of quantitation (BLOQ) at 2 weeks, and may have been related to ADA.

Substantial and statistically significant increases were seen in total memory CD4, total memory CD8, and NK cell proliferation (percentage of Ki67+ cells) comparing PD-L1 OX40 Bis5 groups to control (anti-PcrV-Psl control) Ab group (FIGS. 61A-F). A trend towards significant differences was seen between PD-1 LO115 and PD-L1 OX40 Bis5 groups in total memory CD4, total memory CD8, and NK cell proliferation (Ki67+). There were no statistically significant differences in proliferation between PD-L1 OX40 Bis5 N434A (half-life extended) version and the G1 version. PD-L1 OX40 Bis5 N434A and IgG1 versions are biologically active bispecific molecules.

Example 2(e). OX40/PD-1 Bispecific Binding Proteins

The following bispecific binding proteins that bind PD-1 and OX40 were created using the parental sequences identified above in Table 2. Proteins identified as Bis2 and Bis3 were generated with the sequences in Table 24 below and were assessed for concurrent antigen binding activity using the Octet binding assay as discussed below.

TABLE 24

| Description | Sequence |
|---|---|
| PD1 LCv kappa | QIVLTQSPATLSLSPGERATLSCSASSKHTNLYWSRHMYWYQQKPGQA PRLLIYLTSNRATGIPARFSGSGSGTDFTLTISSLEPEDFAVYYCQQWSS NPFTFGQGTKLEIKRTVAAPSVFIFPPSDEQLKSGTASVVCLLNNFYPRE AKVQWKVDNALQSGNSQESVTEQDSKDSTYSLSSTLTLSKADYEKHK VYACEVTHQGLSSPVTKSFNRGEC (SEQ ID NO: 97) |
| BiS2-PD-1-OX40 HC-4P | DIQMTQSPSSLSASVGDRVTITCRASQDISNYLNWYQQKPGKAPKLLIY YTSKLHSGVPSRFSGSGSGTDYTLTISSLQPEDFATYYCQQGSALPWTF GCGTKVEIKGGGGSGGGGSGGGGSGGGGSQVQLQESGPGLVKPSQTL SLTCAVYGGSFSSGYWNWIRKHPGKCLEYIGYISYNGITYHNPSLKSRI TINRDTSKNQYSLQLNSVTPEDTAVYYCARYKYDYDGGHAMDYWGQ GTLVTVSSGGGGSGGGGSEVQLVESGGGLVQPGGSLRLSCAASGFTFS DYGMHWVRQAPGKGLEWVAYISSGSYTIYSADSVKGRFTISRDNAKN SLYLQMNSLRAEDTAVYYCARRAPNSFYEYYFDYWGQGTTVTVSSAS TKGPSVFPLAPCSRSTSESTAALGCLVKDYFPEPVTVSWNSGALTSGVH TFPAVLQSSGLYSLSSVVTVPSSSLGTKTYTCNVDHKPSNTKVDKRVES KYGPPCPPCPAPEFLGGPSVFLFPPKPKDTLMISRTPEVTCVVVDVSQE DPEVQFNWYVDGVEVHNAKTKPREEQFNSTYRVVSVLTVLHQDWLN |

TABLE 24-continued

BIS constructs for OX40/PD-1

| Description | Sequence |
|---|---|
| | GKEYKCKVSNKGLPSSIEKTISKAKGQPREPQVYTLPPSQEEMTKNQVS<br>LTCLVKGFYPSDIAVEWESNGQPENNYKTTPPVLDSDGSFFLYSRLTVD<br>KSRWQEGNVFSCSVMHEALHNHYTQKSLSLSLGK (SEQ ID NO: 95) |
| BiS3-<br>OX40 HC-4P-PD-1 | EVQLVESGGGLVQPGGSLRLSCAASGFTFSDYGMHWVRQAPGKGLE<br>WVAYISSGSYTIYSADSVKGRFTISRDNAKNSLYLQMNSLRAEDTAVY<br>YCARRAPNSFYEYYFDYWGQGTTVTVSSASTKGPSVFPLAPCSRSTSES<br>TAALGCLVKDYFPEPVTVSWNSGALTSGVHTFPAVLQSSGLYSLSSVV<br>TVPSSSLGTKTYTCNVDHKPSNTKVDKRVESKYGPPCPPCPAPEFLGGP<br>SVFLFPPKPKDTLMISRTPEVTCVVVDVSQEDPEVQFNWYVDGVEVHN<br>AKTKPREEQFNSTYRVVSVLTVLHQDWLNGKEYKCKVSNKGLPSSIEK<br>TISKAKGQPREPQVYTLPPSQEEMTKNQVSLTCLVKGFYPSDIAVEWES<br>NGQPENNYKTTPPVLDSDGSFFLYSRLTVDKSRWQEGNVFSCSVMHE<br>ALHNHYTQKSLSLSLGKGGGGSGGGGSDIQMTQSPSSLSASVGDRVTI<br>TCRASQDISNYLNWYQQKPGKAPKLLIYYTSKLHSGVPSRFSGSGSGT<br>DYTLTISSLQPEDFATYYCQQGSALPWTFGCGTKVEIKGGGGSGGGGS<br>GGGGSGGGGSQVQLQESGPGLVKPSQTLSLTCAVYGGSFSSGYWNWI<br>RKHPGKCLEYIGYISYNGITYHNPSLKSRITINRDTSKNQYSLQLNSVTP<br>EDTAVYYCARYKYDYDGGHAMDYWGQGTLVTVSS (SEQ ID NO: 96) |

Figure 62:
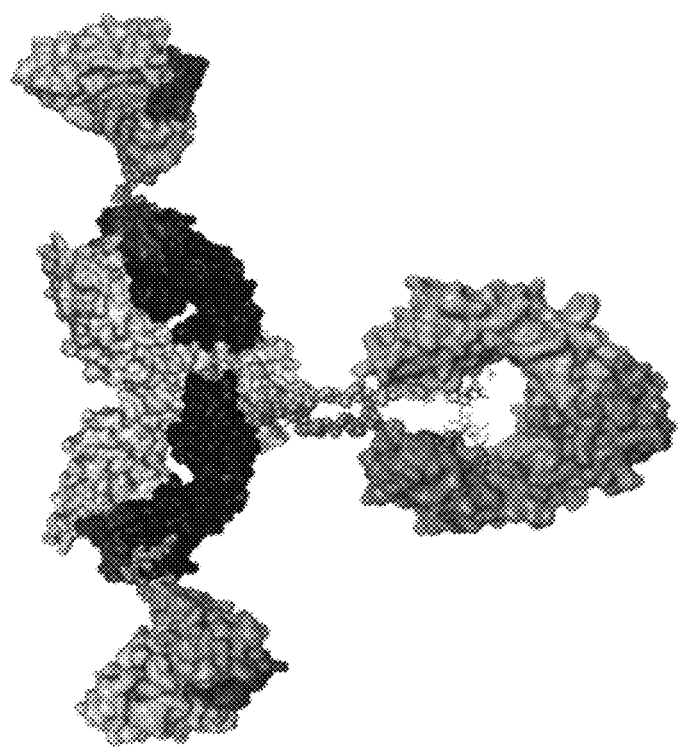
FIG. 62 depicts a schematic of a PD-1/OX40 BiS2 IgG4P monoclonal antibody (mAb).
Figure 63:
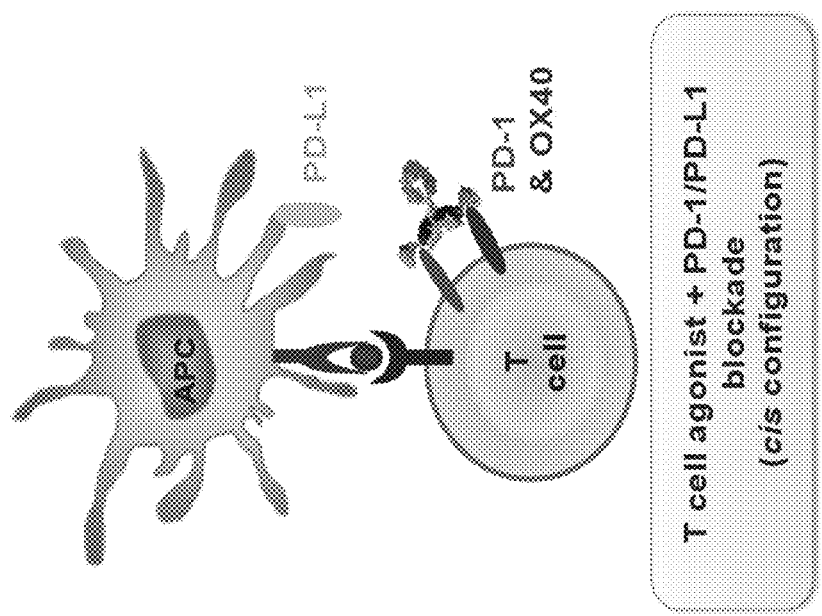
FIG. 63 depicts a potential mechanism of action of PD-1/OX40 BiS2 mAb.

PD-1/OX40 BiS2 monoclonal antibody (mAb) is a bispecific antibody (FIG. 62; PD-1 binding proteins depicted in gray and OX40 binding proteins depicted in light gray) engineered to bind concurrently to human and cynomolgus monkey PD-1 and human and cynomolgus monkey OX40. Without being bound by theory, a proposed mechanism of action suggests dual signaling effects on T cells after binding in cis to both OX40 and PD-1, agonism of the T cell co-stimulatory surface receptor OX40, and blockade of immunosuppressive PD-1 (FIG. 63).

Octet Binding Assay

Figure 64:
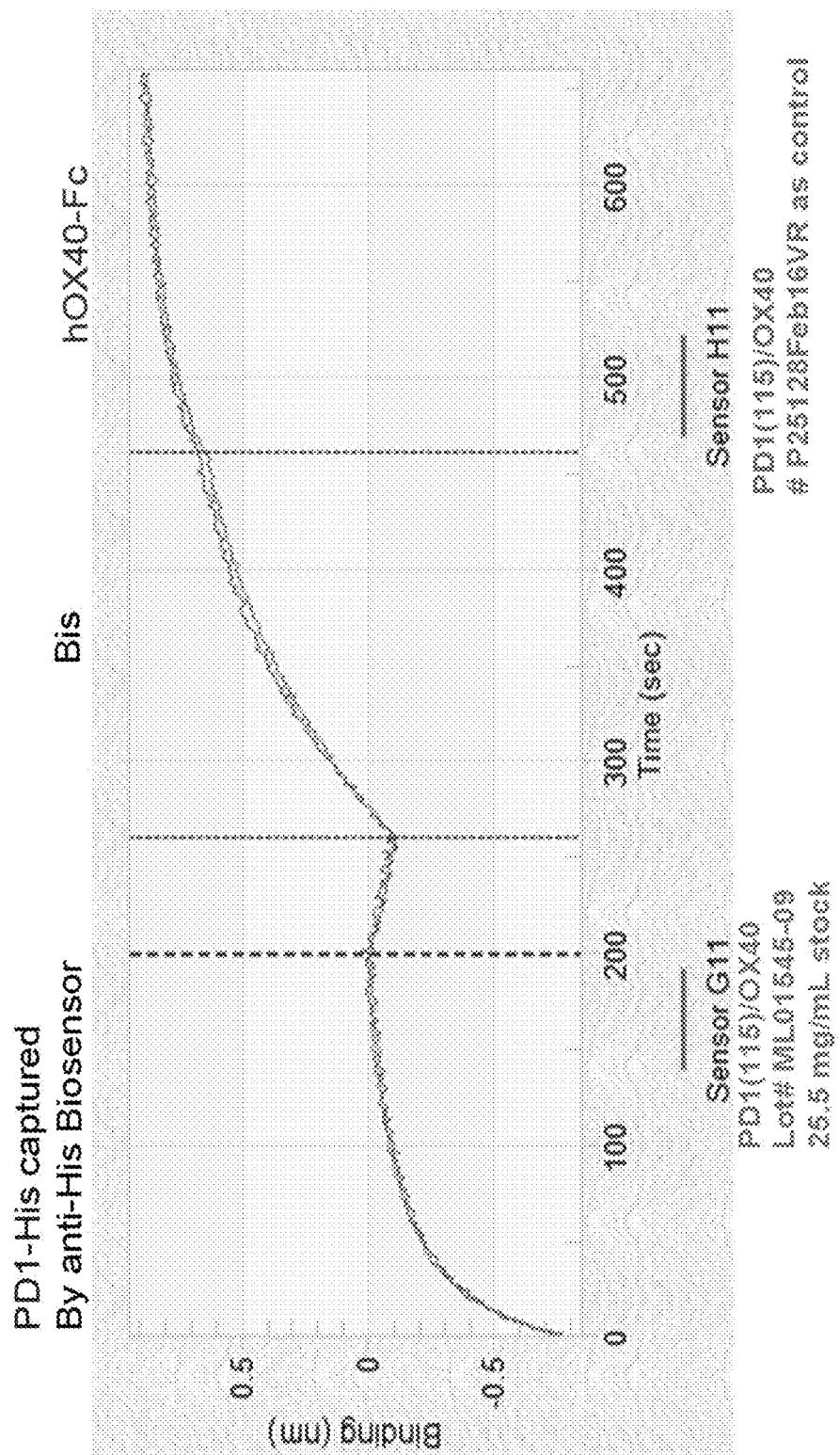
FIG. 64 depicts the concurrent binding activity for two different lots of the PD-1(LO115)/OX40 BiS2 mAb to PD1-His and human OX40-Fc.

Concurrent binding activity was shown for two different lots of the PD-1(LO115)/OX40 BiS2 mAb to PD1-His and human OX40-Fc (FIG. 64).

OX40 Reporter Assay

PD-1(LO115)/OX40 BiS2 mAb showed activity comparable to other OX40 agonists (FIGS. 65A-B). Proteins were stored at 4° C. and used immediately, freeze/thawed three times, stored at 4° C. for 7 days and stored at 40° C. for 7 days. Activity was reported as relative light units versus concentration of mAb. $EC_{50}$ was ~2 nM for PD1(LO115)/OX40 BiS2 mAb at 4° C. on day 0.

PD-1/PD-L1 Reporter Assay

Figures 66A, 66B:
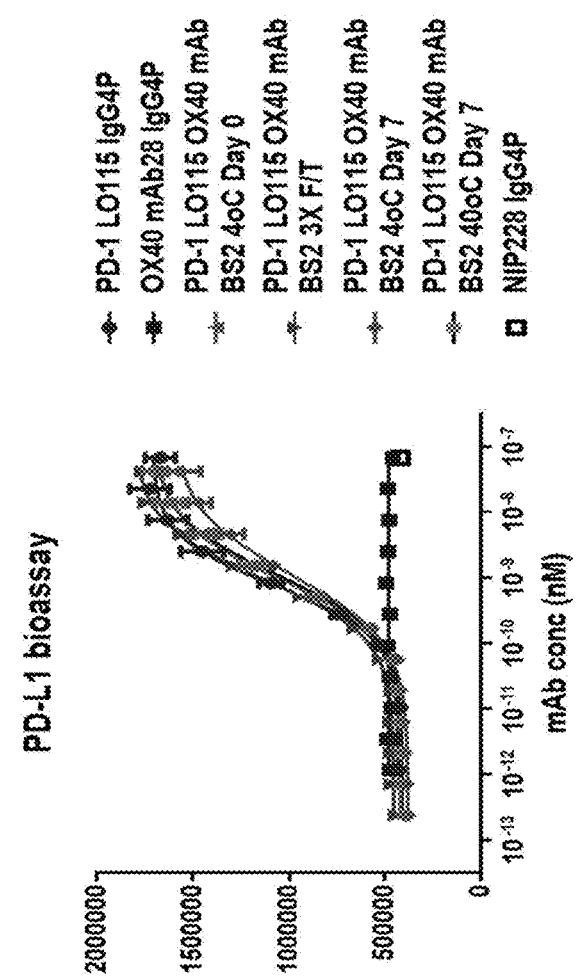
FIG. 66A depicts a schematic of a PD-1/PD-L1 reporter assay.
FIG. 66B shows results of the PD1/PD-L1 reporter assay using PD1 LO115 mAb, OX40 mAb, a control mAb and PD1(LO115)/OX40 BiS2 mAb.

PD-1(LO115)/OX40 BiS2 mAb showed activity comparable to other PD-1 agonists (FIGS. 66A-B). Proteins were stored at 4° C. and used immediately, freeze/thawed three times, stored at 4° C. for 7 days and stored at 40° C. for 7 days. Activity was reported as relative light units versus concentration of mAb. $EC_{50}$ was ~1 nM for PD1 (LO115)/OX40 BiS2 mAb at 4° C. on day 0. Two sets of primary human in vitro potency assays have been conducted; an antigen-recall T cell assay and a T cell co-stimulation using staphyloccal entertoxin B (SEB).

Staphylococcal Enterotoxin B (SEB) Assay

Figure 67:
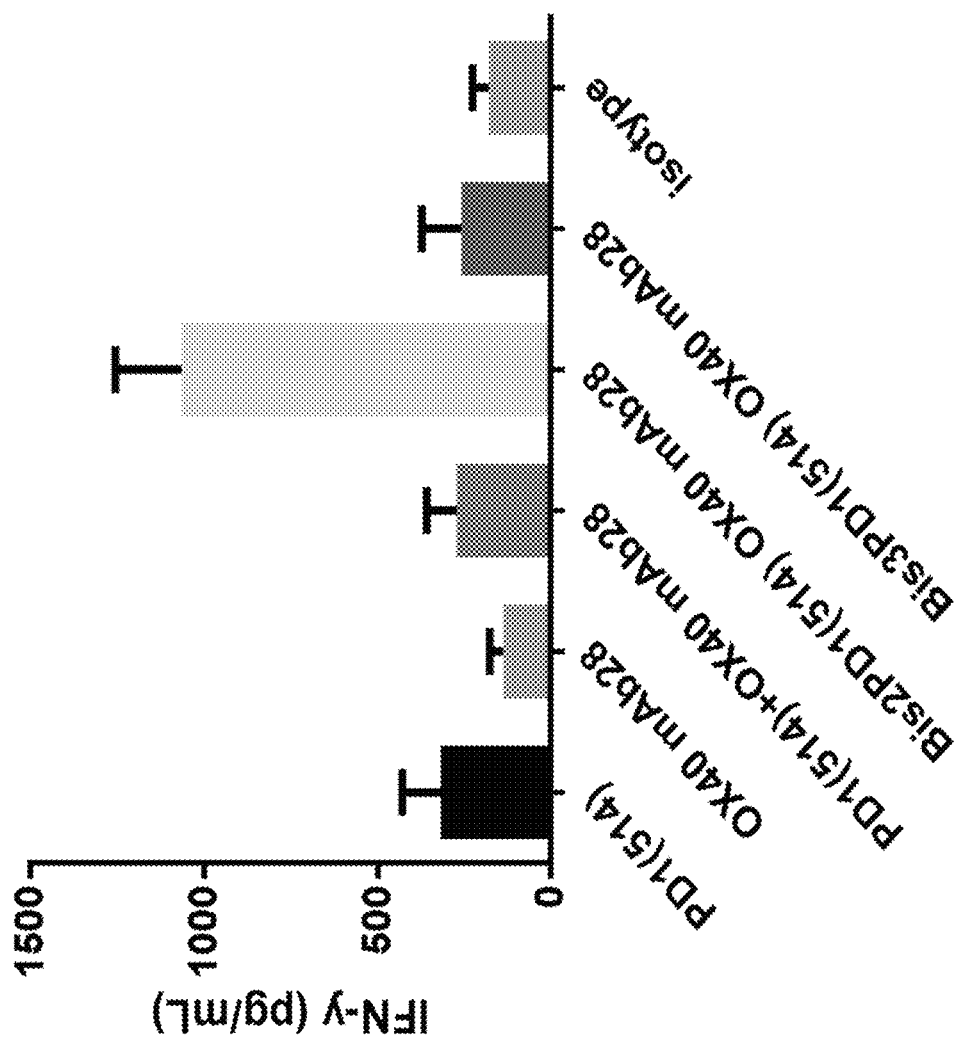
FIG. 67 shows the results of an SEB assay using the BiS2 variant of PD-1(LO115)/OX40 bispecific molecule and controls.

In the SEB assay, PD-1(LO115)/OX40 BiS2 mAb induced an increase in the levels of IL-2 detected in the supernatant of cells after 3 days in culture (FIG. 67). Thus, PD-1/OX40 BiS2 mAb can concurrently bind to its human target antigens and can co-stimulate T cells in vitro.

Figure 68:
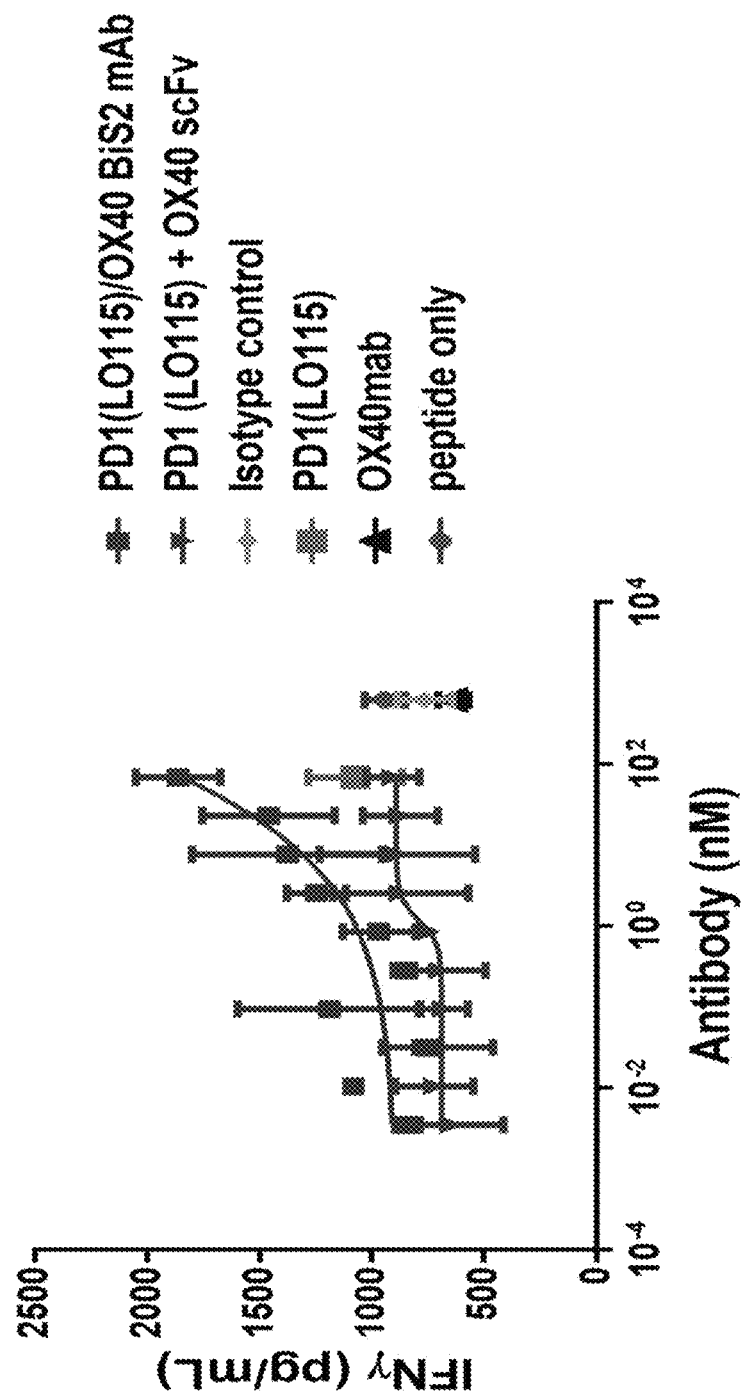
FIG. 68 shows the results of a CMV antigen recall assay using the BiS2 variant of PD-1(LO115)/OX40 bispecific molecule and controls.
Figure 69:
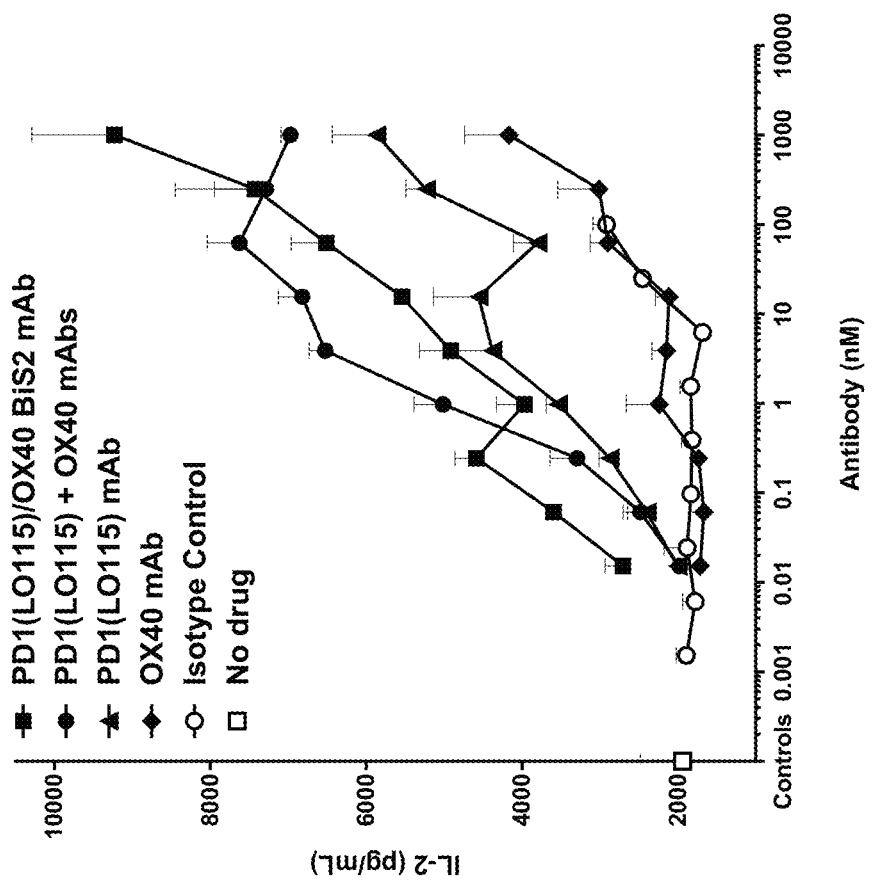
FIG. 69 shows the results of a CMV antigen recall assay using the BiS2 and BiS3 variants of PD-1(AMP514)/OX40 bispecific molecules and controls.

In the antigen-recall assay PD-1/OX40 BiS2 mAb drove an increase in the levels of interferon (IFN)-gamma as compared to the parent mAbs and the combination of the parent mAbs (FIGS. 68 and 69).

CMV Ag Recall Assay

Figure 70:
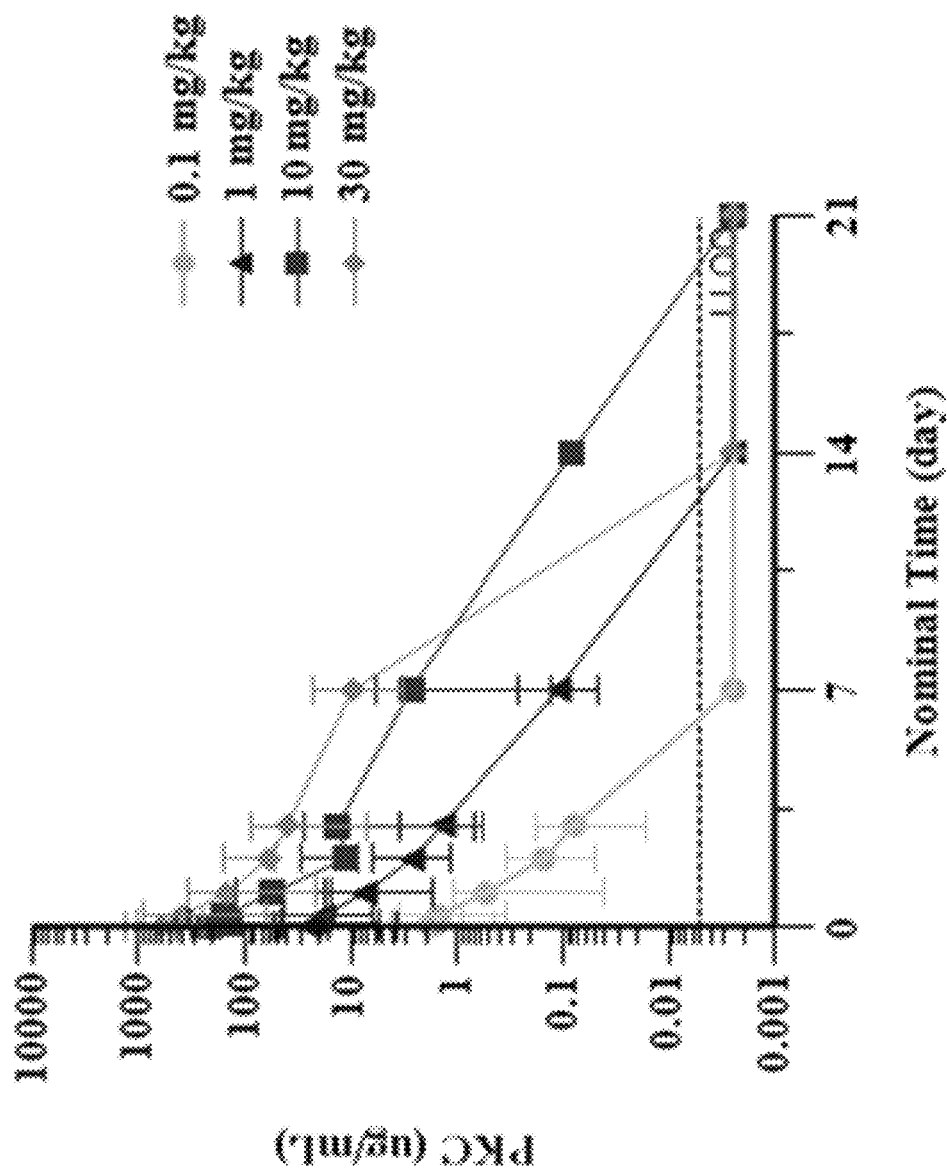
FIG. 70 shows Serum concentration-time profiles of PD1 (LO115)/OX40 BiS2 mAb after single IV dose in cynomolgus monkeys. Data represents the mean±standard deviation of 3 males/group. The LLOQ (5 ng/mL is shown by the dotted line. PKC=pharmacokinetic concentration; LLOQ=lower limit of quantitation.

Results of the CMV Ag recall assay (using the protocol described above), the BiS2 and BiS3 molecules did not demonstrate equal activity relative to combination (FIG. 70). The data show that PD-1/OX40 BiS2 IgG4P mAb is active in vitro and in vivo. PD-1/OX40 BiS3, which differs in structure from PD1/OX40 BiS2, was not detectably active. Thus, PD-1/OX40 BiS3 (not active) is different from BiS2 (active).

Pharmacokinetic and Pharmacodynamic (PK/PD) Studies

Cynomolgus monkey was considered to be a pharmacologically relevant nonclinical species to test the functional activity of PD-1/OX40 BiS2 mAb. The pharmacokinetics (PK) and pharmacodynamics (PD) of PD-1/OX40 BiS2 mAb were assessed in a non-GLP (Good Laboratory Practices) study in cynomolgus monkeys. PD-1(LO115)/OX40 BiS2 mAb PK and PD (percent Ki67 positive CD4+ and CD8+ total memory T cells) were evaluated in cynomolgus monkeys (n=3; males) following a single intravenous (IV) dose over the dose range of 0.1 mg/kg to 30 mg/kg. PBMC were collected pre-dose and on day 1, 8, 11 and 15 post-dose, cryopreserved and thawed before being analyzed by flow cytometry. In summary, PD1(LO115)/OX40 BiS2 mAb displayed approximately linear PK with a short half-life of 0.6-1.7 days (FIG. 70; Table 12).

TABLE 12

Mean pharmacokinetic parameters of PD1(LO115)/OX40 BiS2 mAb.

| Dose<br>(mg/kg) | $C_{max}$<br>(ug/mL) | $AUC_{last}$<br>(day*ug/mL) | $AUC_{INF}$<br>(day*ug/mL) | CL<br>(mL/day/kg) | $T_{1/2}$<br>(day) | Vss<br>(mL/kg) |
|---|---|---|---|---|---|---|
| 0.1 | 2.0 (0.5) | 1.6 (0.3) | 1.7 (0.3) | 60.2 (9.0) | 0.6 (0.1) | 47.4 (18.3) |
| 1 | 25.1 (3.1) | 24.8 (7.5) | 25.1 (7.3) | 41.8 (10.4) | 0.9 (0.3) | 43.2 (17.4) |

TABLE 12-continued

Mean pharmacokinetic parameters of PD1(LO115)/OX40 BiS2 mAb.

| Dose (mg/kg) | $C_{max}$ (ug/mL) | $AUC_{last}$ (day*ug/mL) | $AUC_{INF}$ (day*ug/mL) | CL (mL/day/kg) | $T_{1/2}$ (day) | Vss (mL/kg) |
|---|---|---|---|---|---|---|
| 10 | 211 (19) | 203 (9.2) | 207 (18.0) | 48.6 (4.2) | 1.7 (0.2) | 72.7 (8.8) |
| 30 | 607 (83) | 576 (49) | 577 (61) | 52.3 (5.5) | 1.5 (0.2) | 85.6 (4.3) |

Values are presented as Mean (Standard Deviation). $AUC_{last}$ = area under the concentration time curve up to the last measurable concentration; $AUC_{INF}$ = area under the concentration time curve up to infinite time; $C_{max}$ = maximum observed concentration; CL: systemic clearance; $T_{1/2}$ = half-life; Vss: terminal phase volume of distribution; $V_{ss}$: Steady-state volume of distribution.

Figure 71:
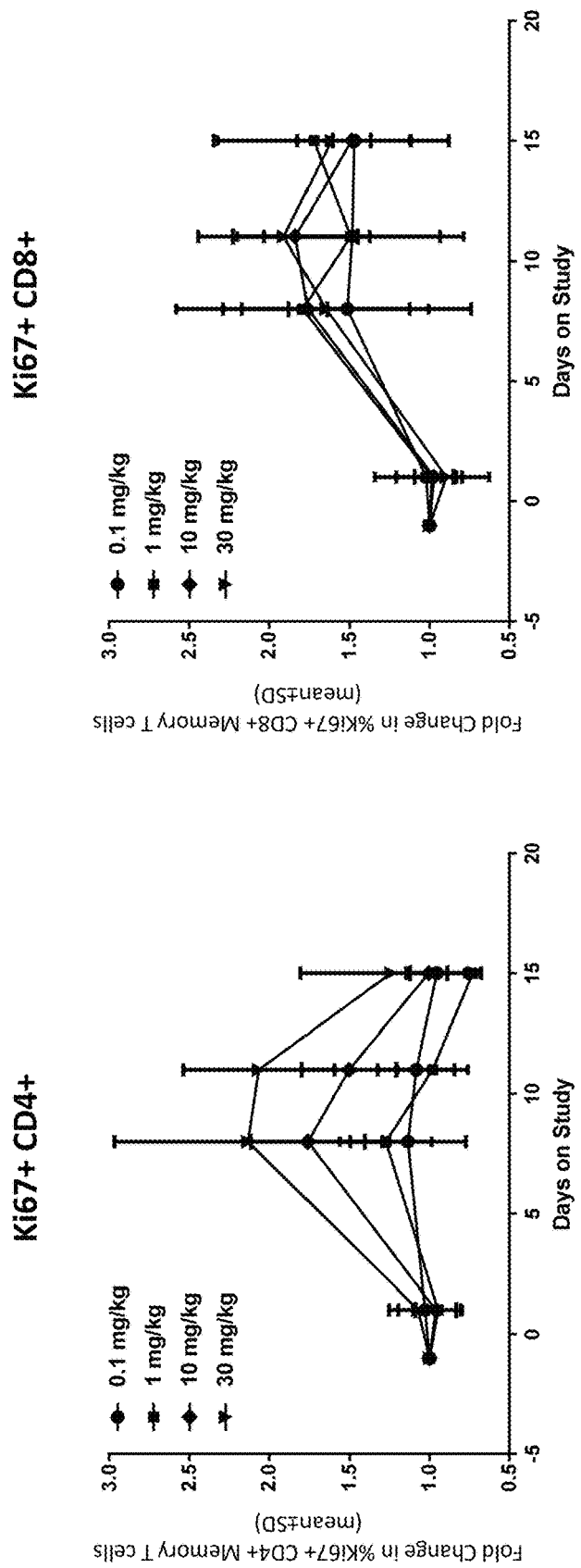
FIG. 71 shows percent Ki67 positive CD4+ and CD8+ memory T cells after single IV administration of PD-1 (LO115)/OX40 BiS2 mAb in cynomolgus monkeys. Data represent the mean±standard deviation of 3 males/group. Left panel A represents CD4+ memory T cells and right panel shows CD8+ memory T cells. IV=intravenous.
Figure 72:
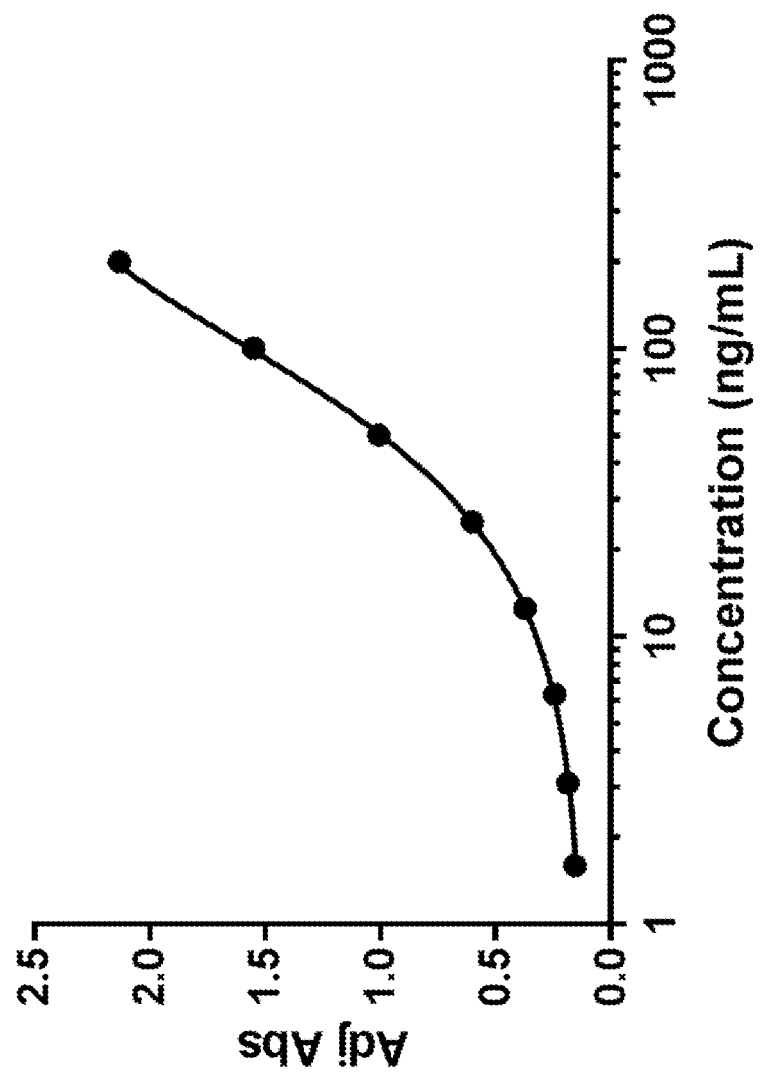
FIG. 72 shows a representative standard curve for quantitation of PD-1/OX40 in cynomolgus monkey serum.

Mean peak concentrations ($C_{max}$) increased approximately dose proportionately from 2.0 µg/mL at 0.1 mg/kg to 607 µg/mL at 30 mg/kg. AUC∞ increased approximately dose-proportionally from 1.7 µg·day/mL at 0.1 mg/kg to 577 µg·day/mL at 30 mg/kg. Mean serum clearance ranged from 41.8 mL/day/kg to 60.2 mL/day/kg. The steady-state volume of distribution ranged from 43.2 mL/kg to 85.6 mL/kg. PD results (FIG. 71) showed a dose-dependent increase in CD4+ total memory T cell proliferation (Ki67) and an increase in CD8+ total memory T cell proliferation (Ki67). A representative standard curve for quantitation of PD-1/OX40 in cynomolgus monkey serum is shown (FIG. 72).

Example 3. Physical and Chemical Stability of BiSAb Constructs

A series of experiments were performed in order to evaluate and assess the physical and chemical stability of the BiSAb constructs as described herein, relative to other bispecific binding protein structural strategies and platforms. In particular, the series of stability studies discussed below identified and analyzed the effect of various pH ranges on stability of the BiSAbs (e.g., hydrolysis, fragmentation, aggregation, thermal stability). As the data show, for the different illustrative embodiments of the various BiSAb formats, the BiSAb disclosed herein (identified as "BiS5" in the studies below, and in D/H format as shown in Table 13) demonstrated unexpected and surprising physical and chemical stability relative to all the other BiSAb structural motifs.

TABLE 13

BiS5 Stability study constructs

| Construct | Sequence |
|---|---|
| D<br>IgG: LC10<br>scFv: 2F4<br>SN-(scFv)-G<br>Amino acid | EVQLVESGGGLVQPGGSLRLSCAASGFTFSSHDMHWVRQATGKGLE<br>WVSGIGTAGDTYYPDSVKGRFTISRENAKNSLYLQMNSLRAGDTAVY<br>YCARDRYSPTGHYYGMDVWGQGTTVTVSSASTKGPSVFPLAPSSKST<br>SGGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPAP<br>ELLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFYPS<br>DIAVEWESN*GGGGSGGGGS*EIVMTQSPATLSVSPGERATLSCRASQSV<br>SSYLGWYQQKPGQAPRLLIYGASTRATGIPARFSGSGSGTEFTLTISSLQ<br>SEDFAVYYCQQYQNWPLLTFGCGTKLEIK*GGGGSGGGGSGGGGSGGG<br>GS*EVQLLESGGGLVQPGGSLRLSCAASGFTFSPYMMQWVRQAPGKCL<br>EWVSSIWPSGGKTYYADSVKGRFTISRDNSKNTLYLQMNSLRAEDTA<br>VYYCARVRRGGATDYWGQGTLVTVSS*GGGGSGGGGS*GQPENNYKTT<br>PPVLDSDGSFFLYSKLTVDKSRWQQGNVFSCSVMHEALHNHYTQKSL<br>SLSPGK (SEQ ID NO: 37) |

V regions are underlined, linkers are in italics. Sequence is as follows: LC10VH, CH1, hinge, CH2, CH3 (N-term), L1-2F4VL-linker-2F4VH-L2, CH3 (C-term)

| H<br>IgG: 2F4<br>scFv: LC10<br>SN-(scFv)-G<br>Amino acid | EVQLLESGGGLVQPGGSLRLSCAASGFTFSPYMMQWVRQAPGKGLE<br>WVSSIWPSGGKTYYADSVKGRFTISRDNSKNTLYLQMNSLRAEDTAV<br>YYCARVRRGGATDYWGQGTLVTVSSASTKGPSVFPLAPSSKSTSGGT<br>AALGCLVKDYFPEPVTVSWNSGALTSGVHTFPAVLQSSGLYSLSSVVT<br>VPSSSLGTQTYICNVNHKPSNTKVDKRVEPKSCDKTHTCPPCPAPELLG<br>GPSVFLFPPKPKDTLMISRTPEVTCVVVDVSHEDPEVKFNWYVDGVEV<br>HNAKTKPREEQYNSTYRVVSVLTVLHQDWLNGKEYKCKVSNKALPA<br>PIEKTISKAKGQPREPQVYTLPPSREEMTKNQVSLTCLVKGFYPSDIAV<br>EWESN*GGGGSGGGGS*DIQMTQSPSTLSASVGDRVTITCRASQSISSWLA<br>WYQQKPGKAPKLLIYKASSLESGVPSRFSGSGSGTEFTLTISSLQPDDF<br>ATYYCKQYADYWTFGCGTKVEIK*GGGGSGGGGSGGGGSGGGGS*EVQ<br>LVESGGGLVQPGGSLRLSCAASGFTFSSHDMHWVRQATGKCLEWVS<br>GIGTAGDTYYPDSVKGRFTISRENAKNSLYLQMNSLRAGDTAVYYCA<br>RDRYSPTGHYYGMDVWGQGTTVTVSS*GGGGSGGGGS*GQPENNYKTT<br>PPVLDSDGSFFLYSKLTVDKSRWQQGNVFSCSVMHEALHNHYTQKSL<br>SLSPGK (SEQ ID NO: 38) |

TABLE 13-continued

BiS5 Stability study constructs

Construct    Sequence

V regions are underlined, linkers are in italics. Sequence is as follows:
2F4VH, CH1, hinge, CH2, CH3 (N-term), L1-LC10VL-linker-
LC10VH-L2, CH3 (C-term)

Example 3.1

Further comparison was performed between the BiS format disclosed herein ("BiS5") and another BiS format that includes two binding domains (scFv domains) linked at the hinge region (i.e., between the Fc and Fab regions), identified as "BiS4". The BiS4 and BiS5 proteins were expressed in Chinese hamster ovary (CHO), and purified by routine chromatographic methods. As noted above, these two formats have similar Fab and scFv sequences, with the primary difference between them being the location of the scFv domain (for BiS4, the scFv is located in the hinge region; for this particular BiS5, a scFv is located in the SNG loop in the $C_H3$ domain, as discussed herein). The purified BiS molecules were supplied in PBS buffer and protein concentration was determined using NanoDrop ND-1000 (Thermo Scientific, Wilmington, Del.) using an extinction coefficient of 1.54 $M^{-1}$ $cm^{-1}$.

pH Screen and Short-term Stability Study

For pH screen studies, BiS4 and BiS5 antibodies were concentrated to ~12 mg/mL and dialyzed against 6 different pH conditions, 20 mM sodium succinate (pH 5.0), histidine/histidine HCl (pH 5.5, 6.0, and 6.5), and sodium phosphate (pH 7.0 and 7.5), all containing 240 mM sucrose. Dialysis was performed by using Slide-A-Lyzer dialysis cassettes (10 kDa molecular weight cutoff (MWCO), Thermo-Fisher, Rockford, Ill.). After completion of the dialysis, 0.02% polysorbate 80 was spiked and the final concentration of the protein was adjusted ~10 mg/mL. The BiS4 and BiS5 formulations were sterilized using a 0.22 μm filter (Millipore, Billerica, Mass.) in a pre-sanitized laminar flow hood. One milliliter aliquots were dispensed into 3 mL borosilicate glass type I vials (West Pharmaceutical Services, Exton, Pa.). Samples were stored at 40° C. and analyzed by SEC at time zero and after storage for 1, 2, 3, and 4 weeks.

Differential Scanning Calorimetry (DSC)

Differential scanning calorimetry thermograms for time zero samples were obtained using a VP-Capillary DSC connected to a temperature regulated auto-sampler (Malvern Instruments Ltd., Westborough, Mass.). To acquire the thermograms protein concentration of 1 mg/mL was used along with a scan rate of 90° C./h over the temperature range 20° C.-100° C. The thermograms of BiS4 and BiS5 in different pH conditions ranging from 5.0 to 7.5 were buffer subtracted and baseline corrected. Data analysis was performed using the DSC plug-in for the Origin 7 SR4 software package. The experimental results were fit to a multistate model with three transitions to calculate the melting temperature ($T_m$) values. The point where the heat capacity ($C_p$) value for the first thermal transition reached 500 cal $mol^{-1}$° $C.^{-1}$ was considered as onset temperature ($T_{onset}$).

High-Performance Size-Exclusion Chromatography (HP-SEC)

To separate aggregate and fragment species from monomer based on size, stability samples were analyzed using an Agilent high-performance liquid chromatography system with a photodiode array detector capable of recording 200-400 nm UV absorbance spectra with a 7.8×30 $cm^2$, 5 μm, 250A, Tosho TSKgel G3000SWxl (TOSOH Biosciences, King of Prussia, Pa.) and a corresponding guard column. To separate the species a mobile phase containing 0.1M sodium phosphate dibasic anhydrous, 0.1M sodium sulfate, 0.01% sodium azide, pH 6.8, and a flow rate of 1 mL $min^{-1}$ were used. The amount of protein injected was about 250 μg. The separation of BiS4 and BiS5 was monitored using the absorbance spectrum of 280 nm. The peak areas for soluble aggregates (multimer and dimer), monomer, and fragments were quantified. Then, the percentage of each of the species was calculated and plotted against incubation time to develop kinetic plots. pH profile curves for the rate of monomer loss, fragmentation and aggregation per month were developed by calculating the slop of each kinetic plot.

Thermal Stability of BiS4 and BiS5

Figures 73A, 73B, 73C, 73D:
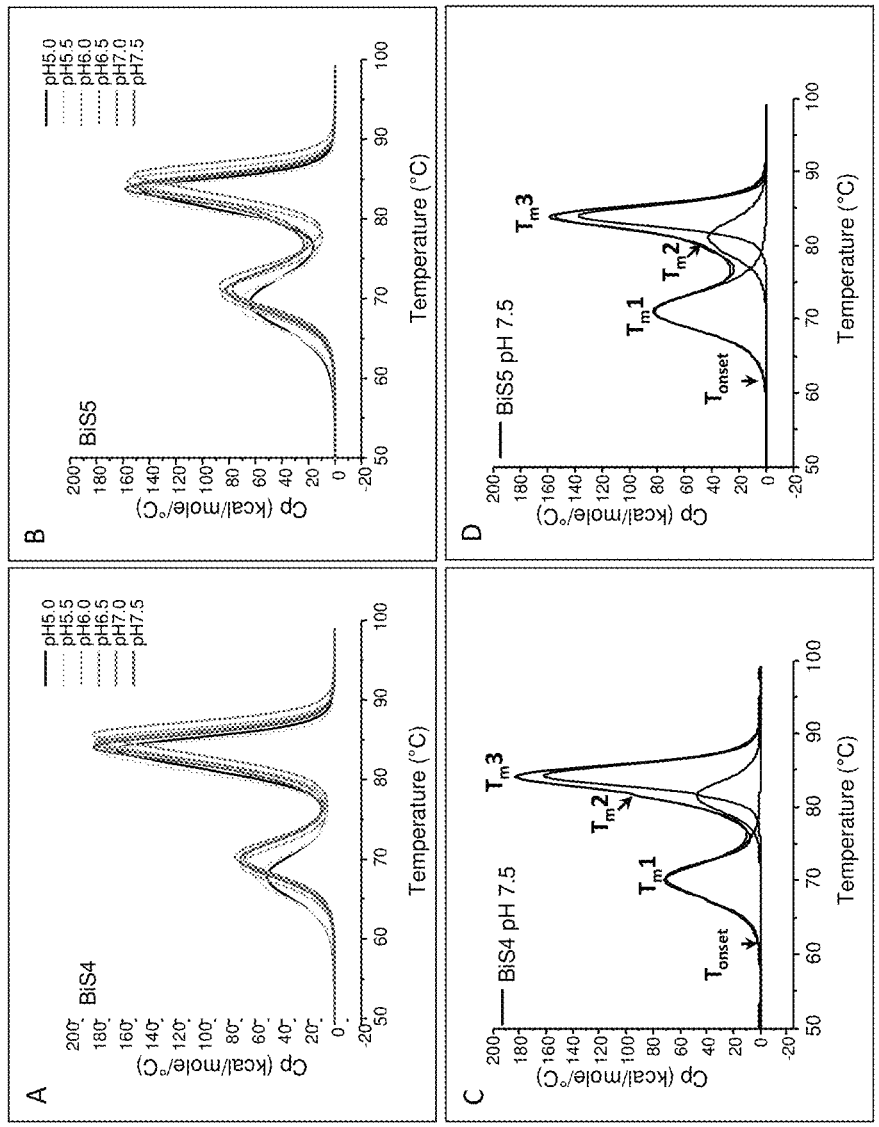
FIGS. 73A-73E provide illustrative DSC thermograms of the bispecific binding protein disclosed herein ("BiS5") relative to a different BiS format ("BiS4") at different pH values.
Figure 73E:
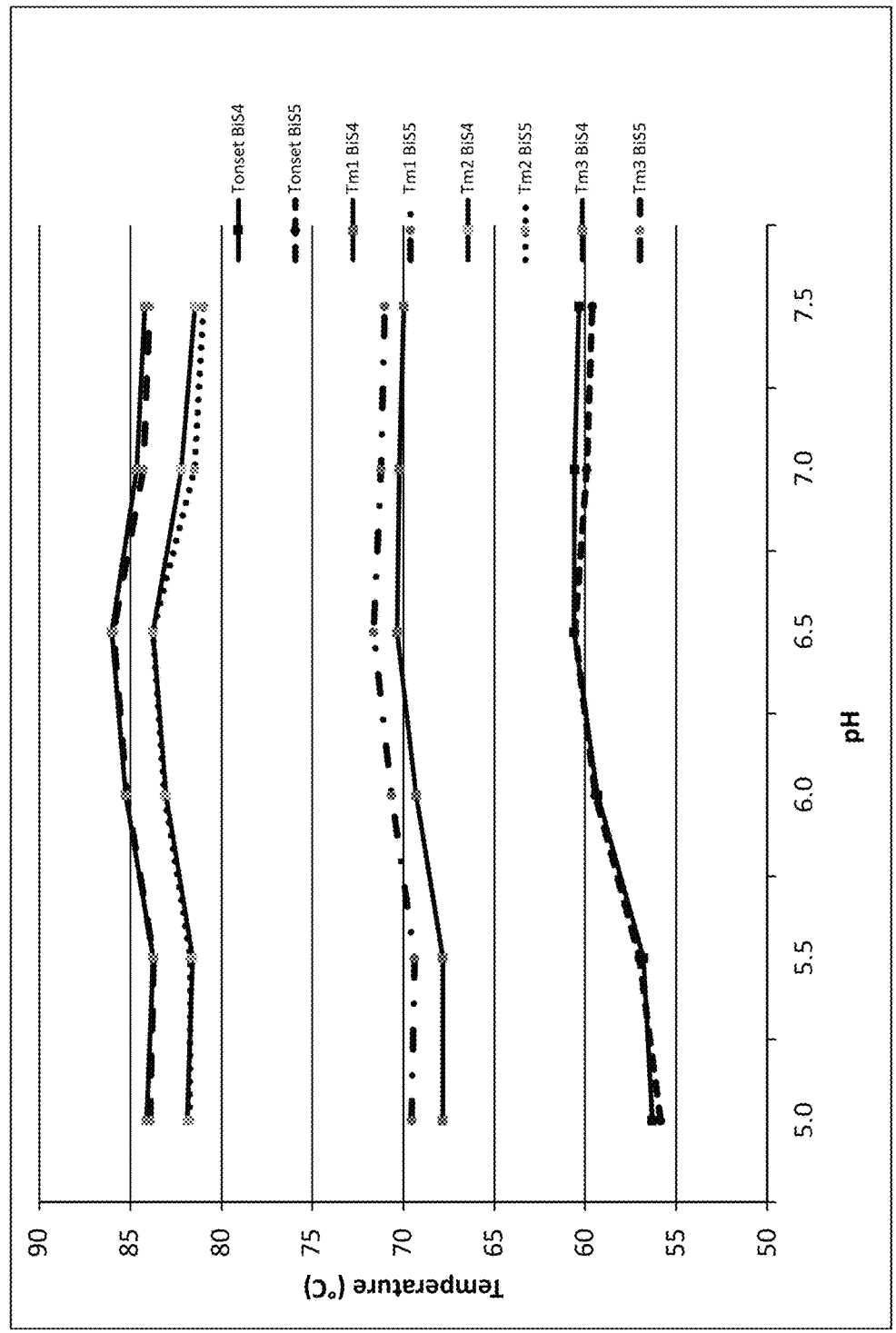
Figure 74A:
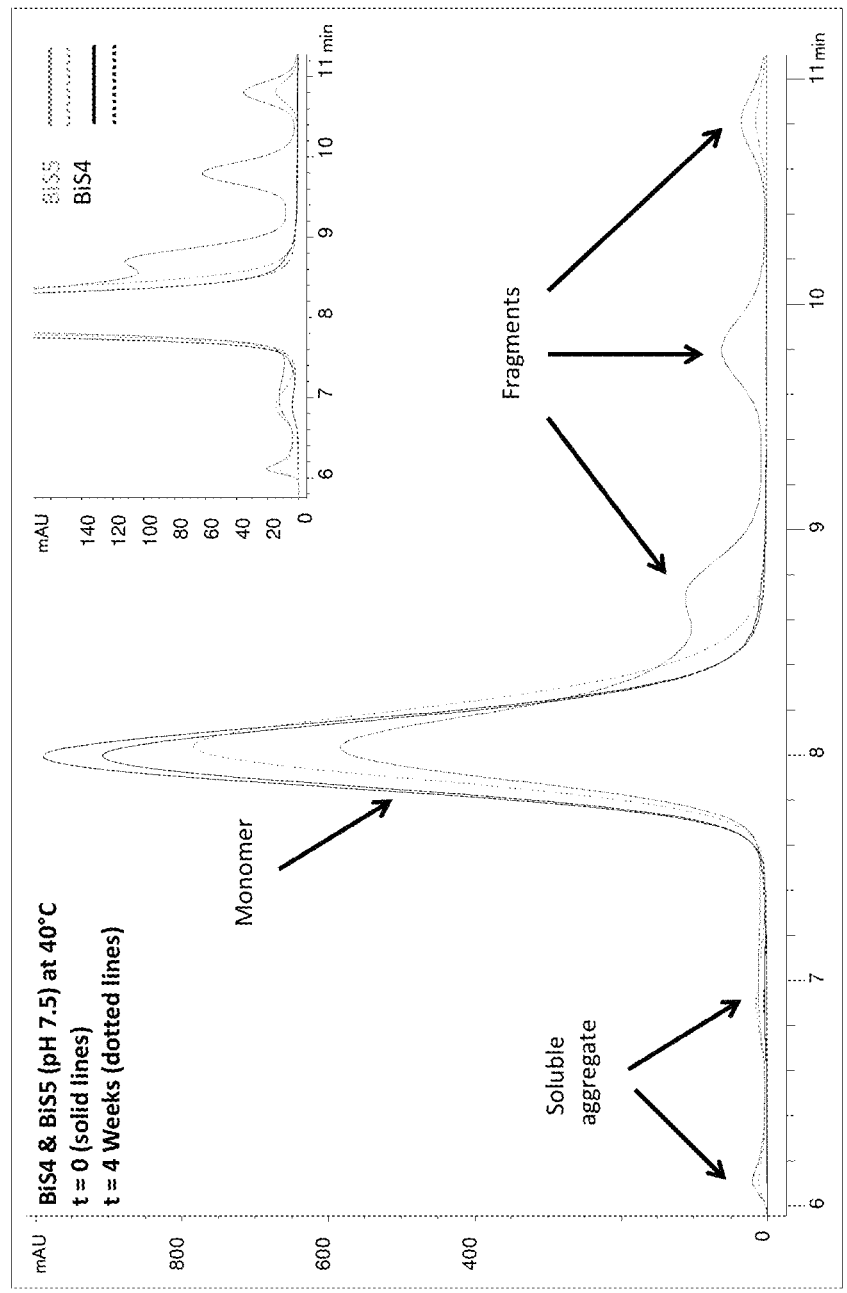
FIGS. 74A and 74B depict HP-SEC analysis of samples at pH 7.5 before and after storage at 40° C. for 4 weeks.
Figure 74B:
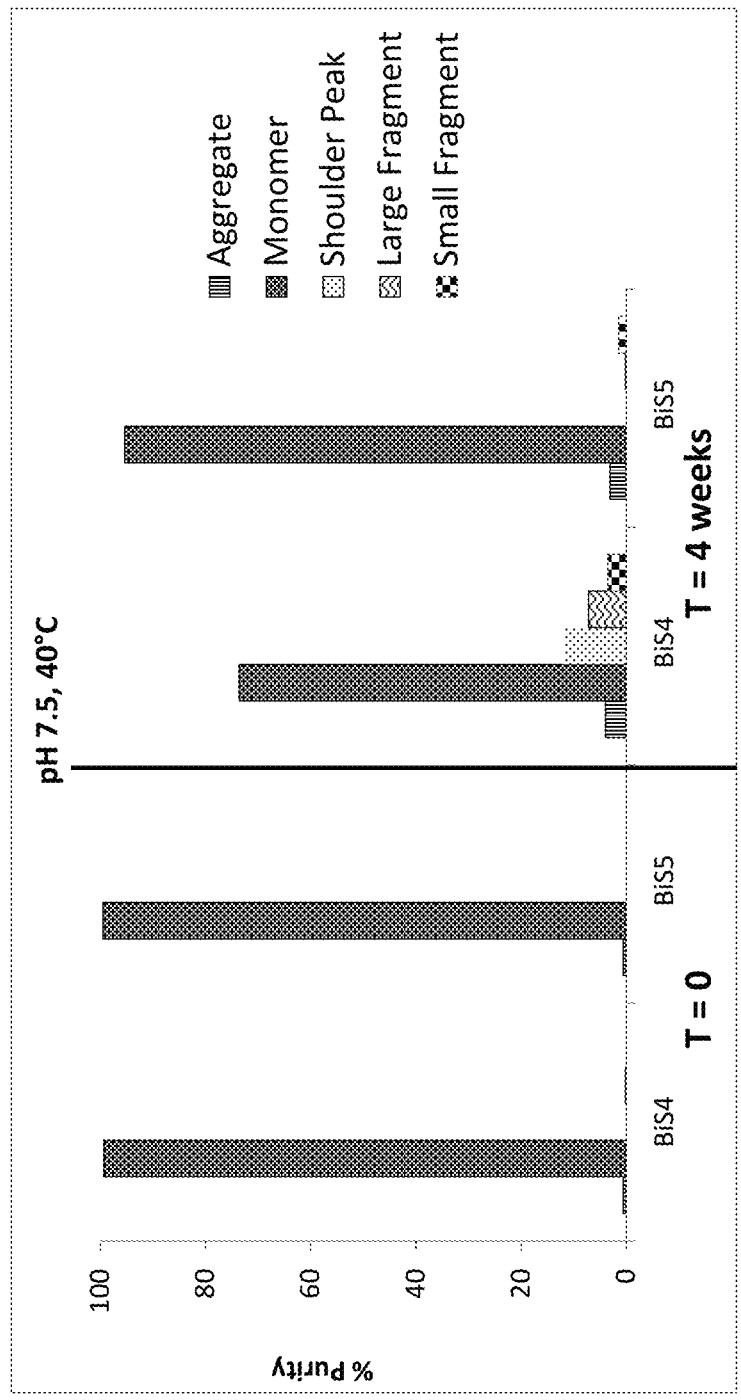

The effect of pH on thermal stability of BiS4 and BiS5 was evaluated through analysis of the thermograms obtained by using capillary DSC, and generated at six different pH conditions. FIGS. 74A and 74B shows overlays of DSC thermograms of BiS4 and BiS5, respectively, from pH 5.0 to 7.5. As shown in FIG. 73, each thermogram shows three thermal unfolding events with transition temperatures $T_m1$, $T_m2$, and $T_m3$. The first transition ($T_m1$) likely to be associated with the simultaneous unfolding of the $C_H2$ and scFv domains whereas the second ($T_m2$) and third ($T_m3$) transitions are associated with the unfolding of the $C_H3$ and Fab domains. For both the formats, an increase in $T_{onset}$, $T_m1$, $T_m2$ and $T_m3$ were observed with increase in pH up to 6.5 (FIGS. 73A, 73B, 73E and Table 14, below). For BiS4 and BiS5, no differences were observed in $T_{onset}$, $T_m2$, and $T_m3$ at all pH conditions (FIG. 73E and Table 15) indicating that the presence of scFv either in the hinge region or $C_H3$ domain does not impact thermal stability of $C_H3$ and $F_{ab}$. Interestingly, a slight increase in $T_m1$ was observed for BiS5 at all pH conditions indicating an increase in thermal stability of either scFv, $C_H2$, or both when scFv is located in the $C_H3$ domain.

TABLE 14

Effect of pH on thermal onset temperature ($T_{onset}$) and thermal melting temperatures ($T_m1$, $T_m2$, and $T_m3$) for BiS4 and BiS5 as measured by capillary DSC.

| | BiS4 | | | | BiS5 | | | |
|---|---|---|---|---|---|---|---|---|
| pH | $T_{onset}$ | $T_m1$ | $T_m2$ | $T_m3$ | $T_{onset}$ | $T_m1$ | $T_m2$ | $T_m3$ |
| 5.0 | 56.3 | 67.8 | 81.9 | 84.1 | 55.9 | 69.5 | 81.8 | 83.9 |
| 5.5 | 56.8 | 67.8 | 81.6 | 83.8 | 57.0 | 69.4 | 81.7 | 83.7 |
| 6.0 | 59.3 | 69.3 | 83.1 | 85.3 | 59.4 | 70.7 | 83.1 | 85.2 |
| 6.5 | 60.6 | 70.3 | 83.8 | 86.0 | 60.6 | 71.6 | 83.8 | 85.9 |
| 7.0 | 60.6 | 70.2 | 82.2 | 84.7 | 59.9 | 71.2 | 81.5 | 84.3 |
| 7.5 | 60.3 | 70.0 | 81.5 | 84.2 | 59.6 | 71.0 | 81.0 | 83.9 |

Physical and Chemical Stability of BiS4 and BiS5

The physical and chemical stability of the BiS4 and BiS5 formats at different pH values (ranging from 5.0 to 7.5) was evaluated at 40° C. for up 4 weeks. HP-SEC chromatograms at "time zero" were used to compare the total area, monomer, aggregate, and fragment content of HP-SEC chromatograms for other time points. Representative chromatograms of BiS4 and BiS5 at pH 7.5 time zero compared to 4 weeks are shown in FIG. 74A. All the samples contain primarily monomer with low levels of soluble aggregates and with or without fragments. At time zero (solid lines), majority of the sample is monomer, with no other notable differences except a small difference in the peak height between the two samples likely due to a slight difference in the concentration (FIG. 74A). Dotted lines show an overlay of HP-SEC chromatograms of both the formats in the same pH conditions after storage for 4 weeks at 40° C. Under accelerated temperature stress condition both the formats show an additional peak, early-eluting peak (multimeric species), a decrease in the monomer, and elevated levels of fragments (FIG. 74A). The loss of monomer due to fragmentation was more prominent in BiS4 compared to BiS5 indicating that the BiS5 is more chemically stable. Based on their structure, possible fragmentation sites, and retention time, we speculate that the small fragment peak (RT ~10.8 min) is a Fab, and large fragment peak (RT ~9.8 min) and the shoulder peak (RT ~8.7 min) is a Fab with scFv and its corresponding higher molecular weight fragment (HMWF) with Fab, scFv, and Fc, respectively.

Figure 89:
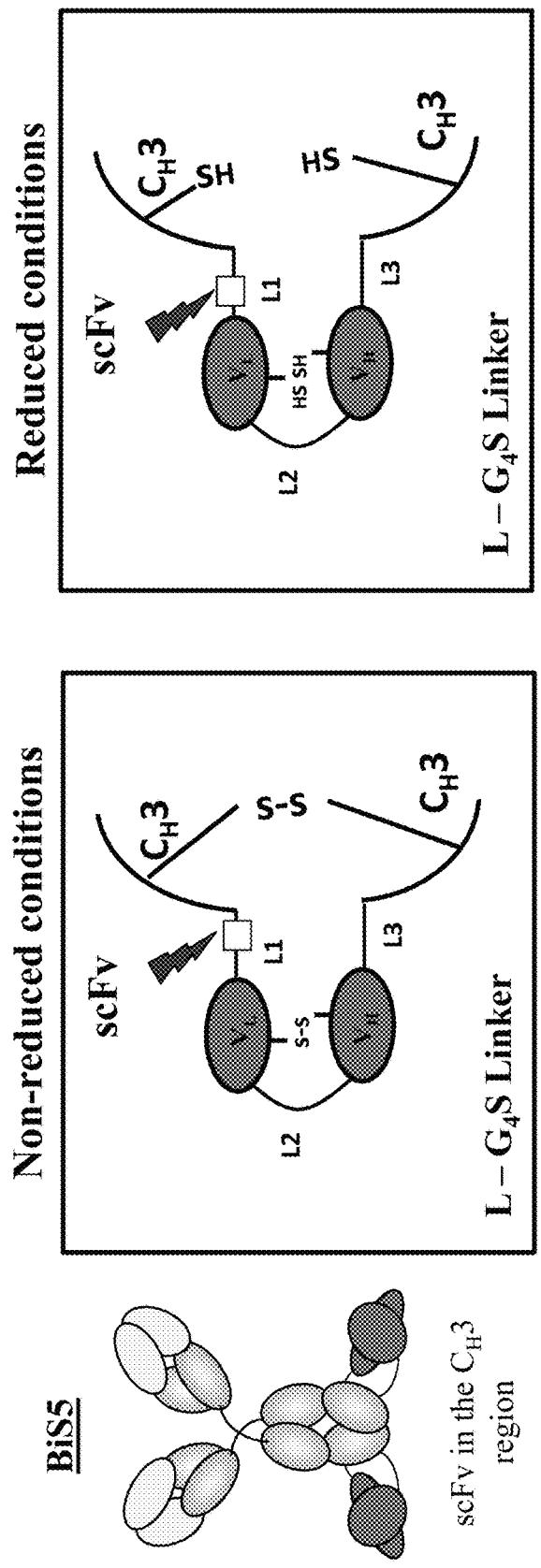
FIG. 89 depicts the structural arrangement of BiS5 under reducing and non-reducing conditions.

To better evaluate the effect of the location of scFv on the physical and chemical stability of BiS4 and BiS5, percent total area for each species were plotted in a bar chart for time zero and 4 weeks at 40° C. for pH 7.5 (FIG. 74B). As shown in FIG. 74B, at time zero, the monomer purity for BiS4 and BiS5 are similar. Samples incubated at 40° C. for up to 4 weeks showed significant differences in the type and extent of fragments formed. For BiS4 samples, 11.8%, 7.2%, and 3.5% of shoulder peak (RT ~8.7 min), large fragment (RT ~9.8 min) and small fragment (RT ~10.8 min) were formed, respectively (FIG. 74B). Surprisingly, BiS5 sample showed only 1.4% of small fragment (RT ~10.8 min) likely due to tethering of scFv from both the sides of the domain to Fc (FIG. 89).

Figure 75A:
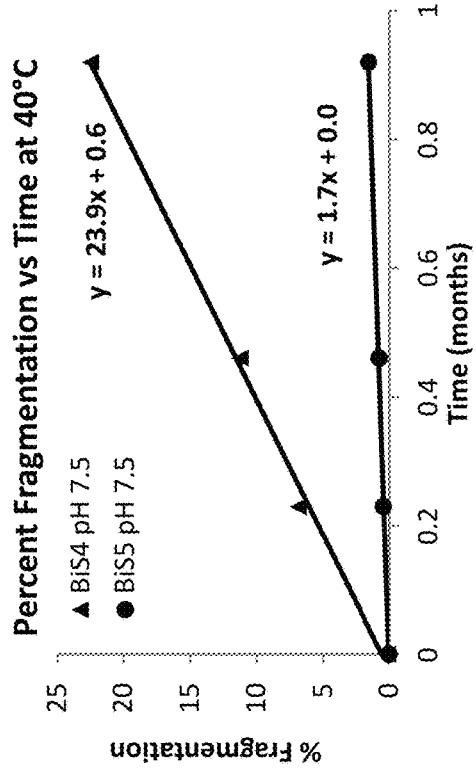
FIGS. 75A-75C provide kinetics plots showing the effect of pH 7.5 on accelerated and short-term storage stability at 40° C. for BiS4 (triangle trace) and BiS5 (circle trace).
Figure 75B:
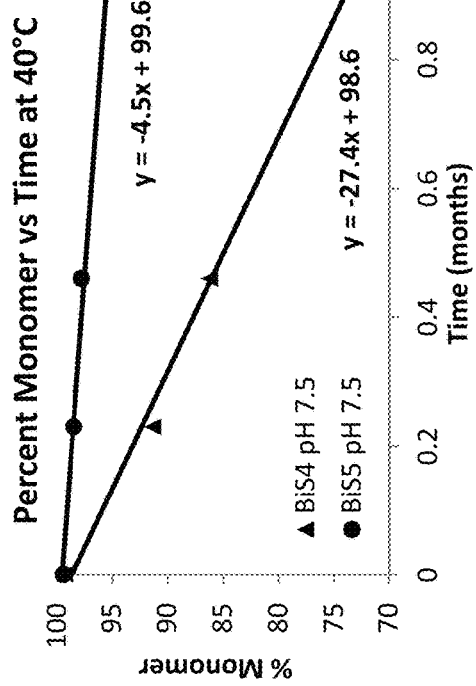
Figure 75C:
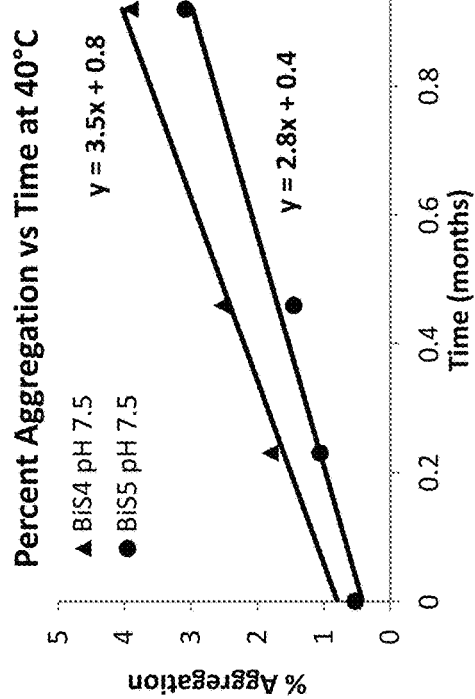

FIGS. 75A-75C show the kinetics of aggregation, fragmentation and monomer loss for BiS4 and BiS5 at incubated at 40° C. for pH 7.5 samples. BiS4 samples showed more rapid rate of loss of monomer compared to BiS5 (FIG. 75A). The rate of monomer loss for BiS4 and BiS5 at pH 7.5 was 27.4%/month and 4.5%/month, respectively (FIG. 75A). For BiS4, majority of monomer loss is due to fragmentation which was 23.9%/month and to a lesser extent due to aggregation which was 3.5%/month (FIGS. 75B and 75C). Interestingly, for BiS5, aggregation seemed to be at slightly higher rate (2.8%/month) compared to fragmentation rate (1.7%/month) (FIGS. 75B-75C).

Figure 76A:
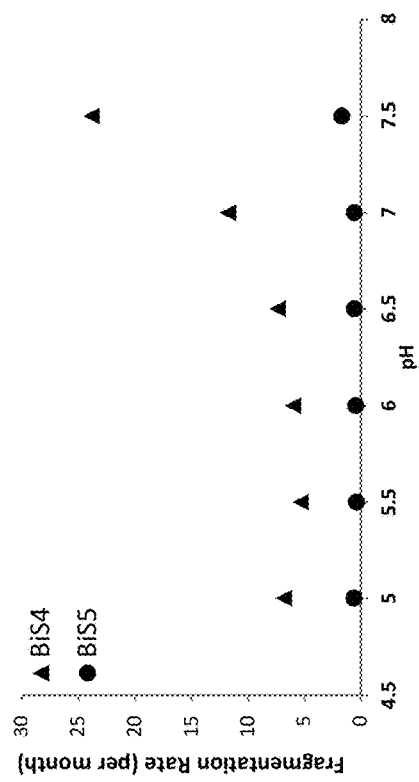
FIGS. 76A-76C depict pH rate profile plots for BiS4 (triangles) and BiS5 (circles).
Figure 76B:
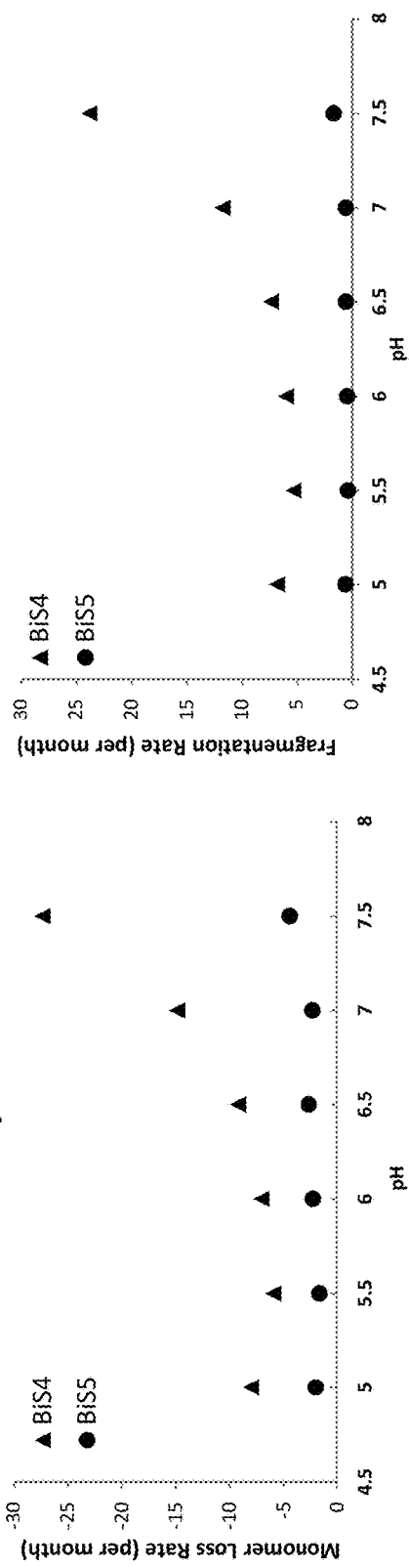
Figure 76C:
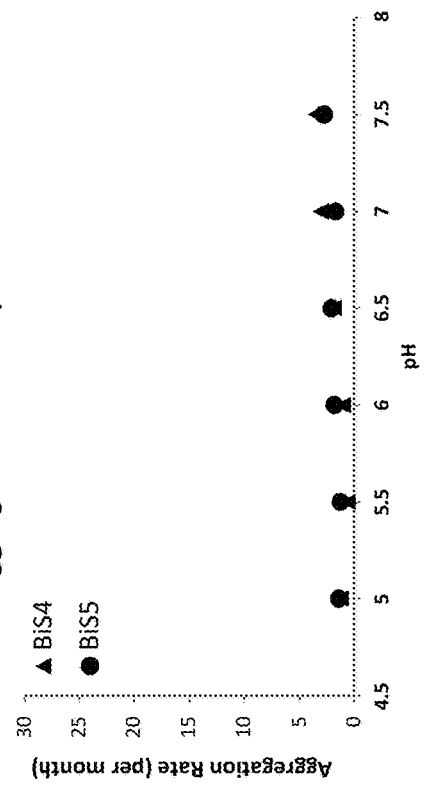
Figure 77A:
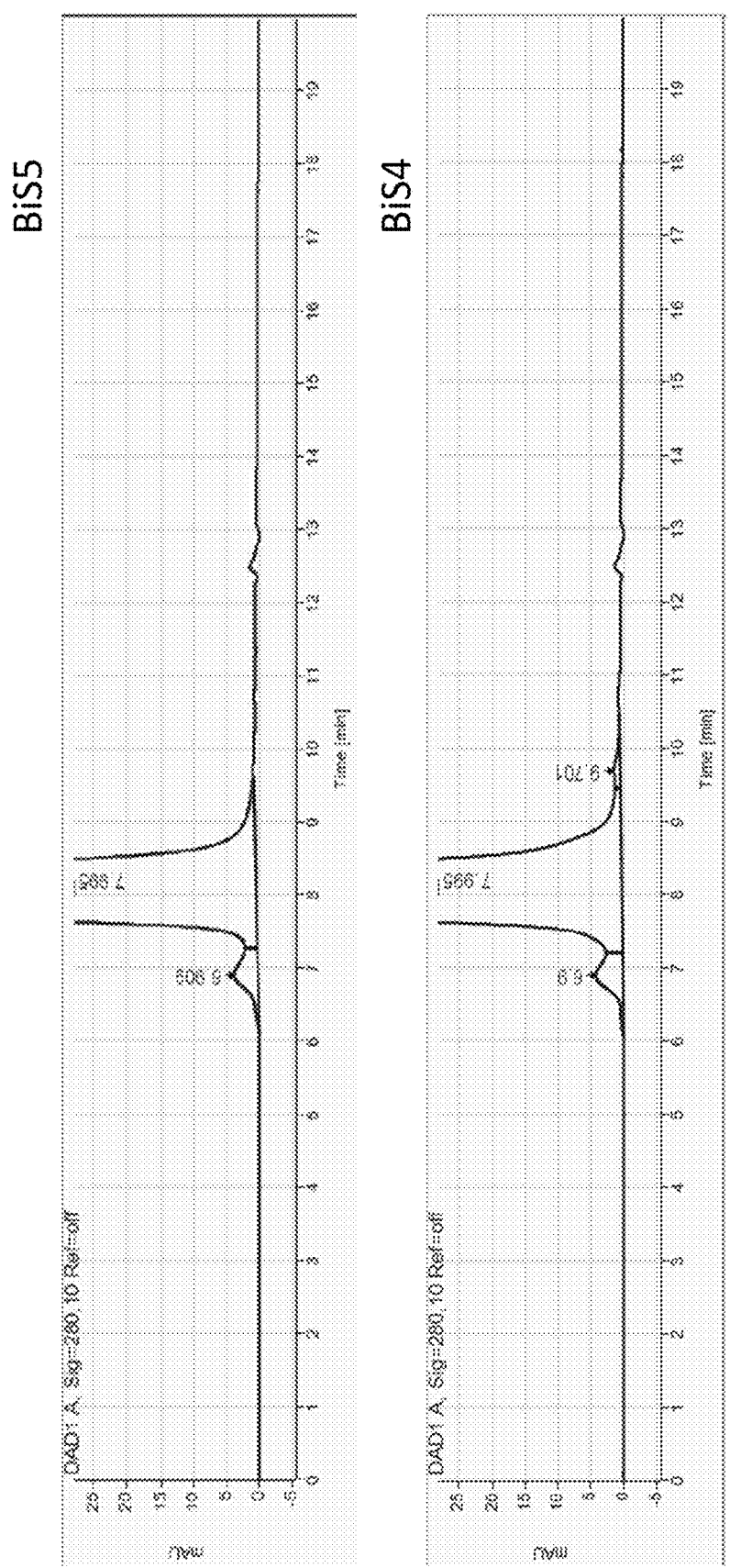
FIGS. 77A and 77B depict additional analysis of BiS4 and BiS5 fragmentation.
Figure 77B:
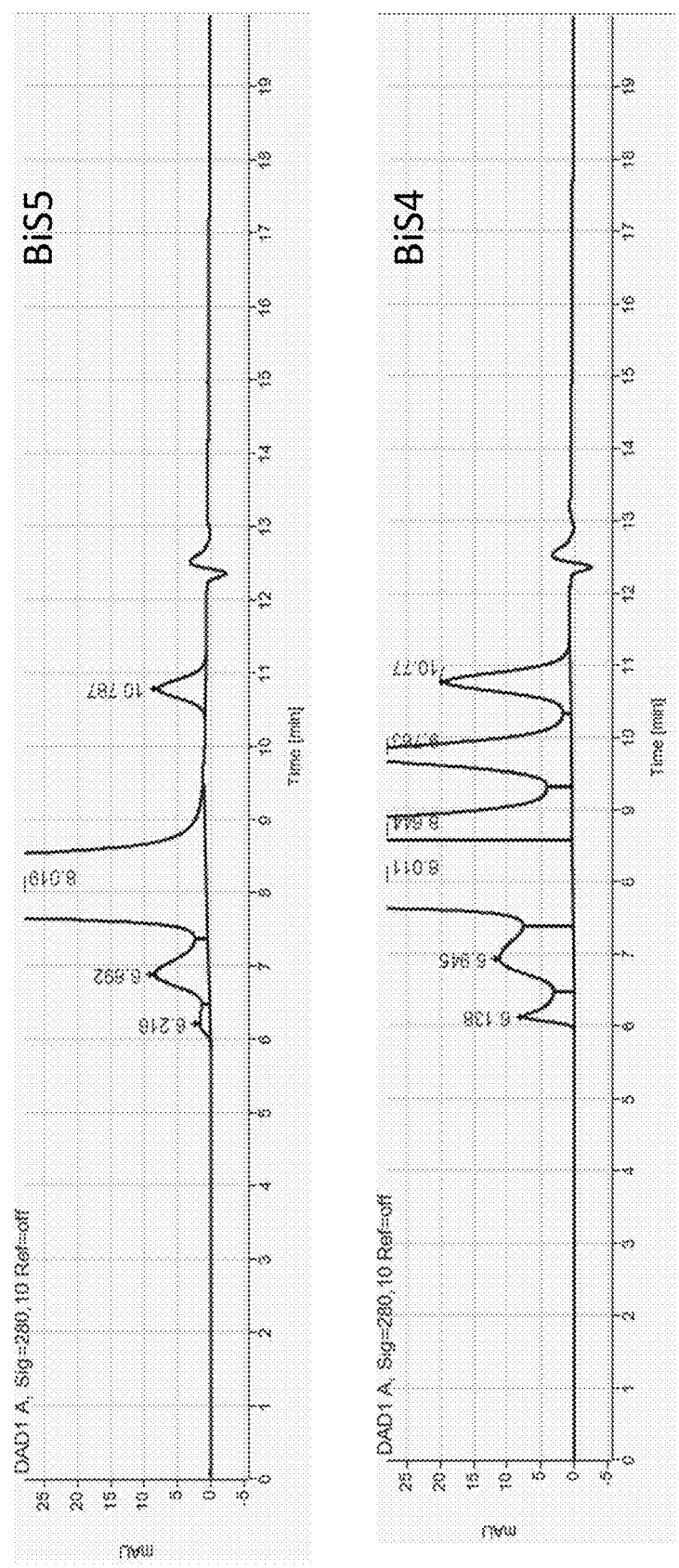
Figure 78:
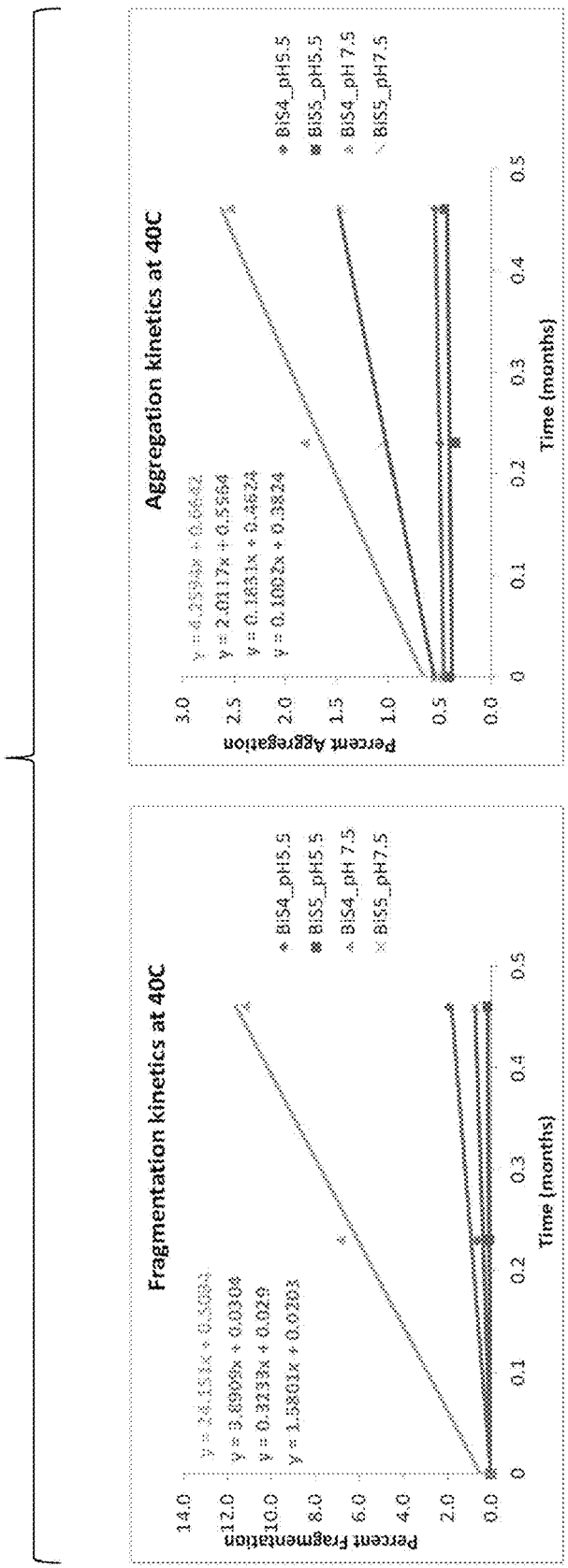
FIG. 78 depicts analysis of BiS4 and BiS5 fragmentation (left panel) and aggregation (right panel) as a function of pH. Both formats have reduced fragmentation and aggregation at lower (5.5) pH, while BiS5 has superior performance at both pH values for both fragmentation and aggregation.

Further analysis of the effect of pH on physical and chemical stability of BiS4 and BiS5 formats, the rate of monomer loss, fragmentation and aggregation per month was performed by plotting those values against the 6 pH conditions (FIGS. 76A-76C). Throughout all six pH conditions ranging from pH 5.0-7.5, the rate of monomer loss was lower for the BiS5 format compared to BiS4 (FIG. 76A), which suggests that the BiS5 format disclosed herein possesses unexpectedly superior physical and chemical stability to other bispecific protein formats. For BiS4, the majority of monomer degradation was due to fragmentation even at lower pH conditions (FIG. 76B). BiS5 showed lower fragmentation rates compared to BiS4 in all the pH conditions tested. Surprisingly, the fragmentation rates in BiS5 seemed to be flat and lower across wider pH range compared to BiS4. Without being bound by any particular theory, it may be that the lower fragmentation rates observed in BiS5 may arise from the G45 linkers on either end of the scFv connecting it to the Fc. Fragmentation on one of the G45 linkers connecting to Fc, may not release the scFv, as it may be still connected to the Fc via the other G45 linker. In BiS4 and BiS5, aggregation rates seemed to be similar throughout all the pH conditions tested (FIG. 76C), suggesting that the location of scFv has minimal effect on aggregation kinetics, which is also supported by the observed no change in the $T_{onset}$ between the two formats at all pH conditions as measured using capillary DSC (FIG. 73E and Table 14, discussed above). At pH 7.5 and 40° C. (at time=0), neither molecule exhibited appreciable fragmentation (FIG. 77A), but under the same conditions after 2 weeks storage at 40° C., appreciable fragmentation is observed for BiS4 and minimal fragmentation for BiS5 (FIG. 77B). Both BiS4 and BiS5 have reduced fragmentation and aggregation at lower (5.5) pH, while BiS5 has superior performance at both pH values for both fragmentation and aggregation (FIG. 78). This series of experiments demonstrate that the BiS5, disclosed herein, possesses superior chemical stability and similar physical stability to that of BiS4.

Example 3.2

Additional studies were performed in order to evaluate the physical and chemical stability of different embodiments of the bispecific binding proteins that are disclosed herein and identified as Constructs A-H (see, e.g., Table 13 and related Examples, above). These constructs were analyzed using DSC, accelerated storage stability, and FcRn and FcgR binding assays, as follows below.

Differential Scanning Calorimetry Analysis

The DSC experiments for this data set were performed using a Microcal VP-DSC scanning microcalorimeter (Microcal). All solutions and samples used for DSC were filtered using a 0.22 μm filter and degassed prior to loading into the calorimeter. Antibodies used for the DSC studies were >98% monomeric as determined by analytical SEC. Prior to DSC analysis all samples were exhaustively dialyzed (at least 3 buffer exchanges) in 25 mM histidine-HCl (pH 6.0). Buffer from this dialysis was used as reference buffer for subsequent DSC experiments. Prior to sample measurement, baseline measurements (buffer versus buffer) were subtracted from the sample measurement. Dialyzed samples (at a concentration of 1 mg/ml) were added to the sample well and DSC measurements were performed at a 1° C./min scan rate. Data analysis and deconvolution were carried out using the Origin™ DSC software provided by Microcal. Deconvolution analysis was performed using a non-2-state model and best fits were obtained using 100 iteration cycles. The $T_{onset}$ is defined as the qualitative temperature at which the thermogram appears to have a nonzero slope, The $T_m$ is defined as the temperature at which half of the molecules in a set are unfolded, and is calculated as the temperature value corresponding to each peak maximum on the thermogram.

Figure 79:
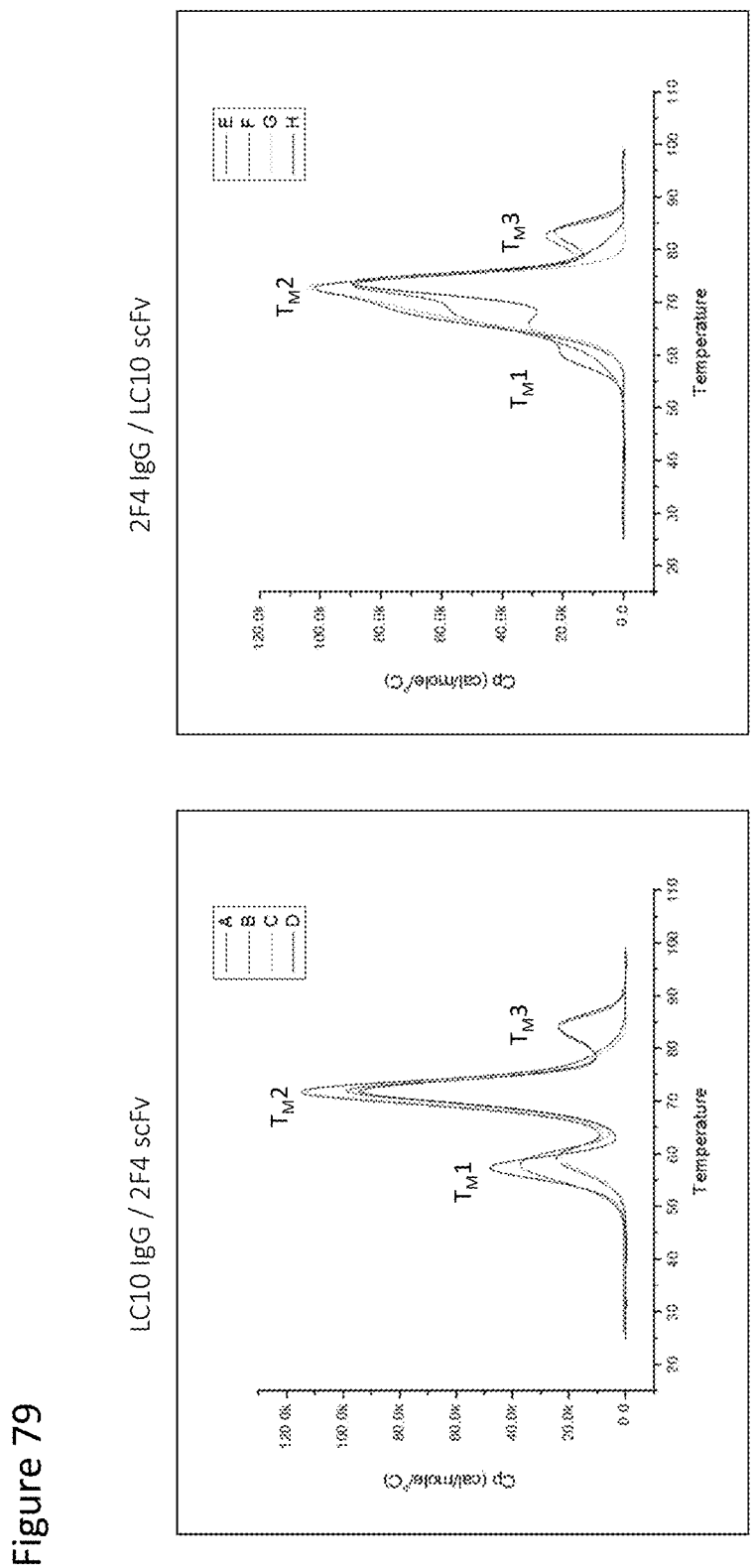
FIG. 79 depicts DSC thermograms of several of the BiS5 bispecific binding protein disclosed herein for constructs (left panel) A, B, C, and D, as well as (right panel) E, F, G, and H. Constructs A and E include the scFv at IS-RTP; B and F include the scFv at AK-GQP; C and G include the scFv at S-NG; and D and H include the scFv at SN-G. The scFv for constructs A, B, C, and D is 2F4 (IgG is LC10), while the scFv for E, F, G, and H is LC10 (IgG is 2F4). The various $T_M$ values are associated with the following domains, $T_M1$=CH2/scFv; $T_M2$=Fab; $T_M3$=CH3.

The results for the different constructs are presented in FIG. 79. Generally, constructs A, C, D that include 2F4 as scFv have lower $T_M1$ when compared to constructs E, G, H that include LC10 as scFv. Without being bound by theory, the difference in the TM1 value may be due to an inherently better thermal stability of the LC10 scFv domain relative to the 2F4 variable domain. The data suggest that constructs A-D, having 2F4 as scFv, would be less thermally stable than constructs E-H with LC10 as scFv.

Accelerated Storage Stability Analysis

The concentrations of the constructs were normalized to 1 mg/mL. 1 mL of each bispecific construct or IgG control was aliquoted into 1.5 ml Eppendorf tubes. Samples were incubated in a static incubator for 2 weeks at 45° C. Samples were analyzed at 3, 7, and 14 days and assessed for stability. At each time point, a visual inspection was performed to record any increased turbidity or precipitation. The samples were filtered using a 0.2 um spin column and 120 ul of sample was aliquoted into a HPLC vial, making sure there is no air bubble left at the bottom of the vial. Samples were then tested on an Agilent 1100 series HPLC-SEC to check for aggregation and degradation using a TSK-GEL G3000SW$_{XL}$ (300×7.8 mm) Tosoh Bioscience column with 0.1M sodium phosphate, 0.1M sodium sulphate, pH6.8 as the running buffer. 60 μL of sample was injected and run at a flow rate of 1 mL/min. The monomer retention time (mins), Total peak area, % monomer, % aggregate, % fragment, % monomer loss were captured and used for analytical SEC analysis. The results are summarized in Table 15.

TABLE 15

Accelerated stability studies.

| Construct | $T_M1$ (° C.) | Monomer % Day 0 | Monomer % Day 0 | Aggreg % Day 0 | Aggreg % Day 7 | Degrad % Day 0 | Degrad % Day 7 |
|---|---|---|---|---|---|---|---|
| A | 57.11 | 97.1 | 68.4 | 2.2 | 30.0 | .64 | 1.7 |
| C | 59.01 | 80.4 | 79.7 | 9.7 | 20.4 | 0.0 | 0.0 |
| D | 58.82 | 92.2 | 90.8 | 7.2 | 8.6 | 0.5 | 0.6 |
| E | 65.83 | 91.3 | 91.2 | 1.7 | 0.0 | 7.0 | 8.2 |
| G | 68.7 | 99.3 | 99.1 | 0.0 | 0.0 | 0.7 | 0.9 |
| H | 67.5 | 99.4 | 99.2 | 0.0 | 0.0 | 0.6 | 0.8 |

As described herein, the location of the scFv domain in the above constructs is as follows (where the "-" indicates the scFv): A and E are at IS-RTP; B and F are at AK-GQP; C and G are at S-NG; and D and H are at SN-G. The various $T_M$ values are associated with the following domains, $T_M1$=CH2/scFv; $T_M2$=Fab; $T_M3$=CH3. The data tend to show that constructs A and C with 2F4 scFv inserted into ISRTP (A) and SNG (C) loops are more prone to aggregation than are constructs E and G that have the LC10 scfv inserted at the same locations. This observation suggests that the sequence identity and behavior of the scFv domain can have an effect on the stability of the bispecific binding protein constructs. Further, from the above, it could be predicted that construct D, which contains the 2F4 scFv, would have lower stability similar to A and C; however it seems that inserting the 2F4 scFv into the SNG loop stabilizes the molecule and reduces tendency to form aggregates. Taken together this accelerated stability study indicates that scFv sequence and location within the Fc region can play a measurable role in the stability of the BiSAb construct.

FcRn and FcγR Binding Analysis

Binding experiments were carried out using a BIAcore 3000 instrument (BIAcore). To capture the antibody, 1000 RU IsdH (Fab) antigen was immobilized on a CM5 chip. 100 nM of the BiSAb construct or mAb controls were flowed at 20 μL/min for 5 min to capture antibody. 5 uM huFcRn or FcγR I, IIa, IIb, IIIa-158V or IIIA158F were flowed at 5 μL/min for 20 min. FcRn binding was performed in PBS+5 uM EDTA at pH 6.0 while FcRn binding was performed in PBS+5 uM EDTA at pH 7.4.

Figure 80:
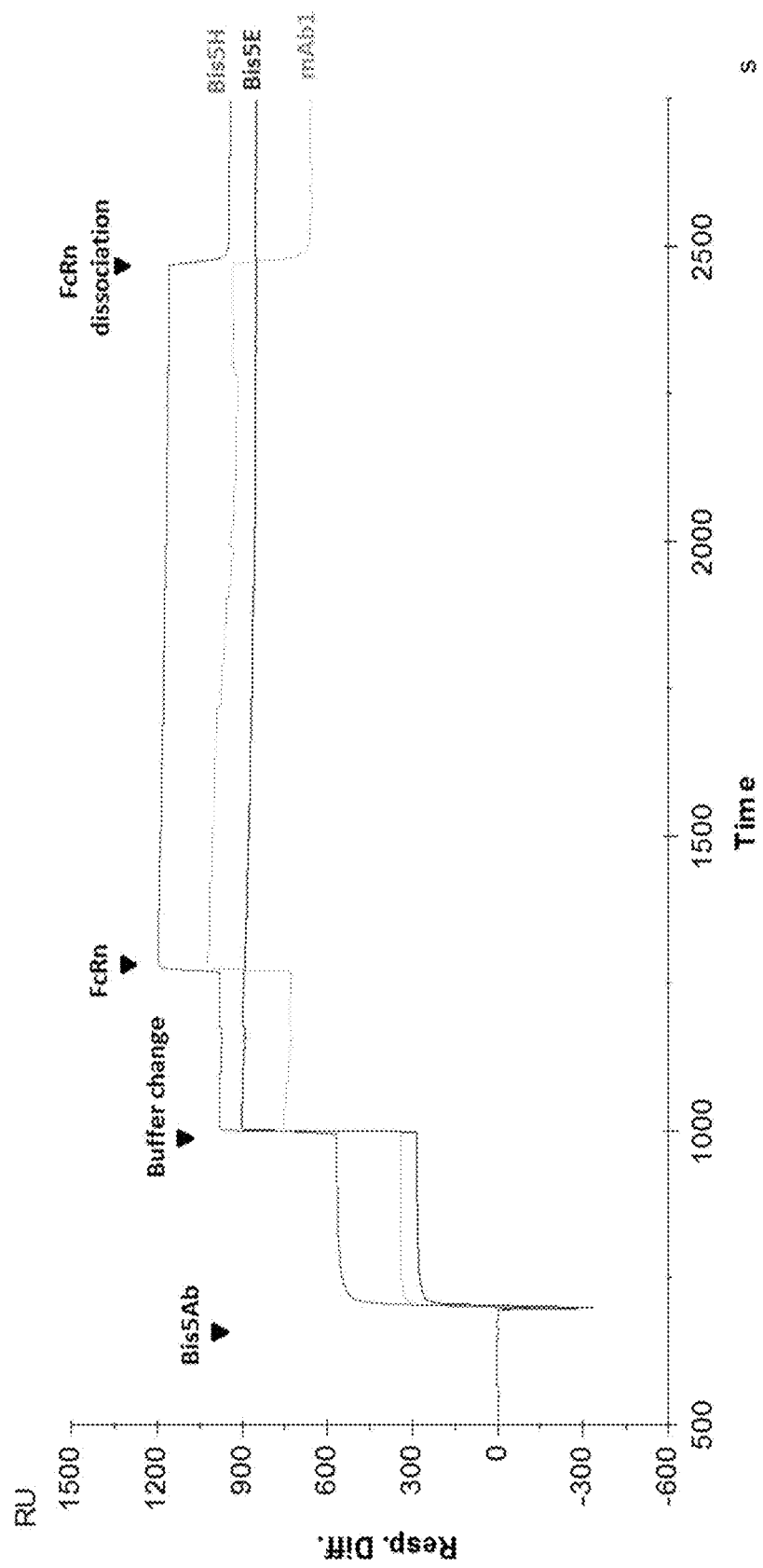
FIG. 80 depicts a representative data set for FcRn binding with the bispecific binding protein disclosed herein (constructs D and H). The location of the scFv in the CH2-CH3 domain (i.e., within the ISTRP loop) can have an effect on FcRn binding activity.

Constructs A, C, D, E, G and H were evaluated for FcRn binding. Representative data are shown in FIG. 80 for each of the bispecific constructs E and H, and for 2F4 IgG binding to FcRn. The constructs having scFv downstream of the CH2-CH3 interface appear to retain FcRn binding (e.g., D & H constructs). Constructs having scFv located within the ISRTP loop upstream of the CH2-CH3 interface appear to remove detectable FcRn binding (e.g., A & E constructs). The ISRTP loop is within the region of known half-life extending YTE mutations in the Fc (M252Y/S254T/T256E) that are known to be important for FcRn binding.

Figure 81:
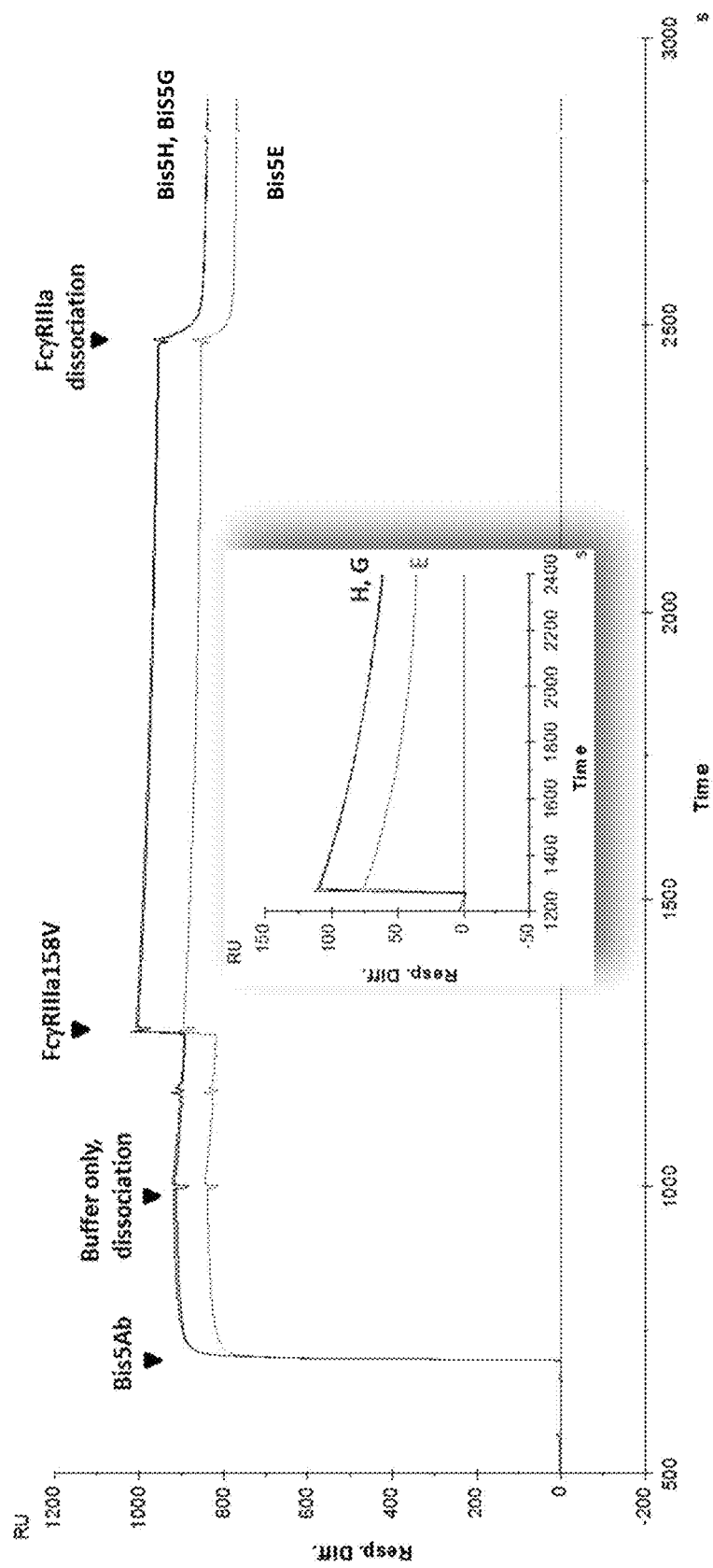
FIG. 81 depicts a representative data set for FcγR binding with the bispecific binding protein disclosed herein (constructs E, G, and H with FcγRIIIa-158V). The inset reflects the same data as the main figure, renormalized at the FcγRIIIa-158V injection. All constructs were able to bind FcγRs with an observable difference in affinities based on location of the scFv domains.

Constructs A, C, D, E, G, and H were tested for binding to FcγRI, FcγRIIa, FcγRIIb, FcγRIIIa-158F, and FcγRIIIa-158V. Representative data are shown in FIG. 81 for constructs E, G, and H binding to FcγRIIIa-158V. All constructs tested retained binding to FcγRs, though with different affinities (FIG. 81, inset). Table 16 shows the observed binding trends of the various constructs to FcγRs.

TABLE 16

| FcγR binding trends. | | | | |
|---|---|---|---|---|
| FcγRI | FcγRIIa | FcγRIIb | FcγRIIIa158F | FcγRIIIa158V |
| D > C > A | D > C > A | D > C > A | D > C > A | D > C > A |
| H > G > E | H > G > E | H > G > E | H > G > E | H > G > E |

The differences observed in FcγR binding with constructs having scFv inserted in the ISRTP loop upstream of CH2-CH3 interface (A and E) show consistently reduced FcγR binding when compared to the other constructs having the scFv inserted into the SNG loop downstream of the CH2-CH3 interface (C, D, G, and H).

Figure 82:
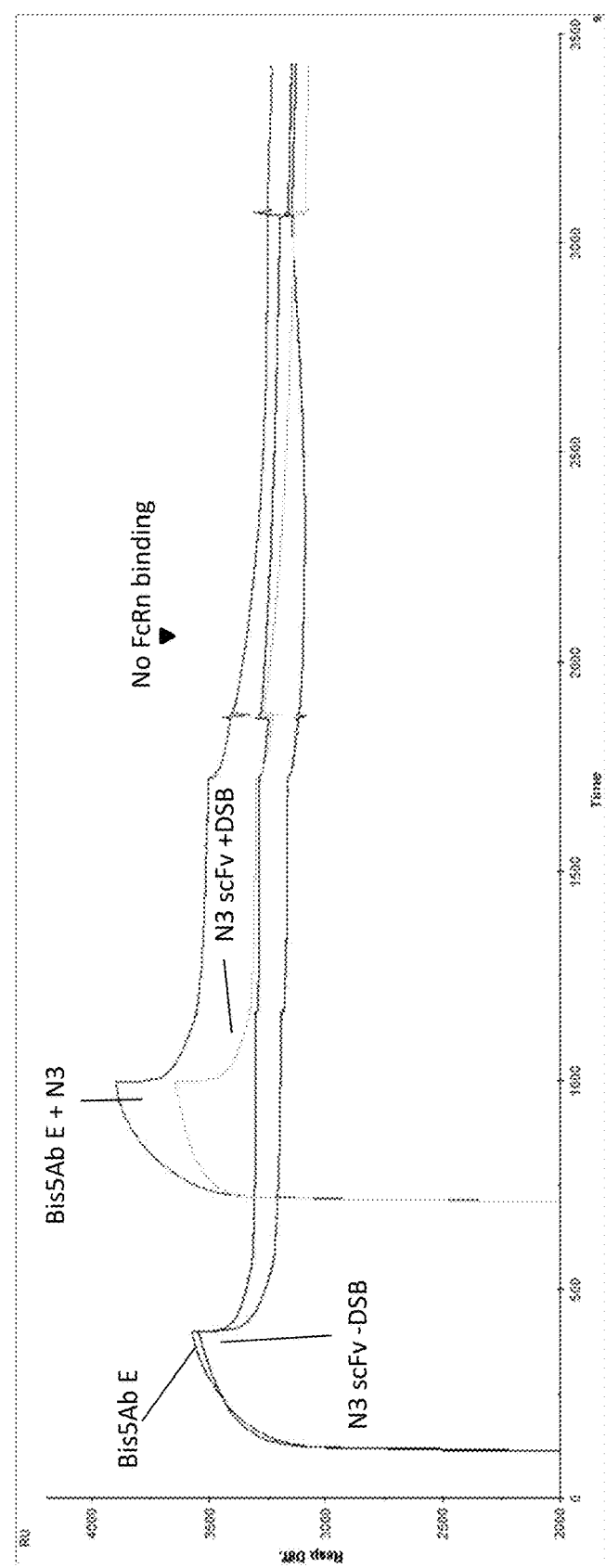
FIG. 82 shows that an intact ISRTP loop is important for FcRn binding of the illustrative bispecific binding constructs (e.g., A and E). Introduction of the N3 loop does not compensate for interruption of the ISRTP loop (BiS5E+N3). An scFv introduced into an N3 loop inserted into an IgG1 Fc renders the IgG unable to bind FcRn. Time in the x-axis is measured in seconds.

Attempts to evaluate whether FcRn binding in the constructs A and E could be improved or restored were made by introducing a half-life extending loop (N3) to the Fc region. FIG. 82 is representative of the data and shows that for the E constructs, neither BiS5Ab E nor construct E with the N3 loop introduced (BiS5Ab E+N3) were able to bind FcRn. Furthermore, inserting the LC10 scFv into the N3 loop (N3 scFv) and keeping the ISRTP loop intact also diminished FcRn binding below detectable levels. These data indicate that at least for the E construct, if not for each construct disclosed herein, both the ISRTP loop and N3 loop, if present, need to be intact and unmodified in order to retain FcRn binding.

Example 3.3

Figure 83:
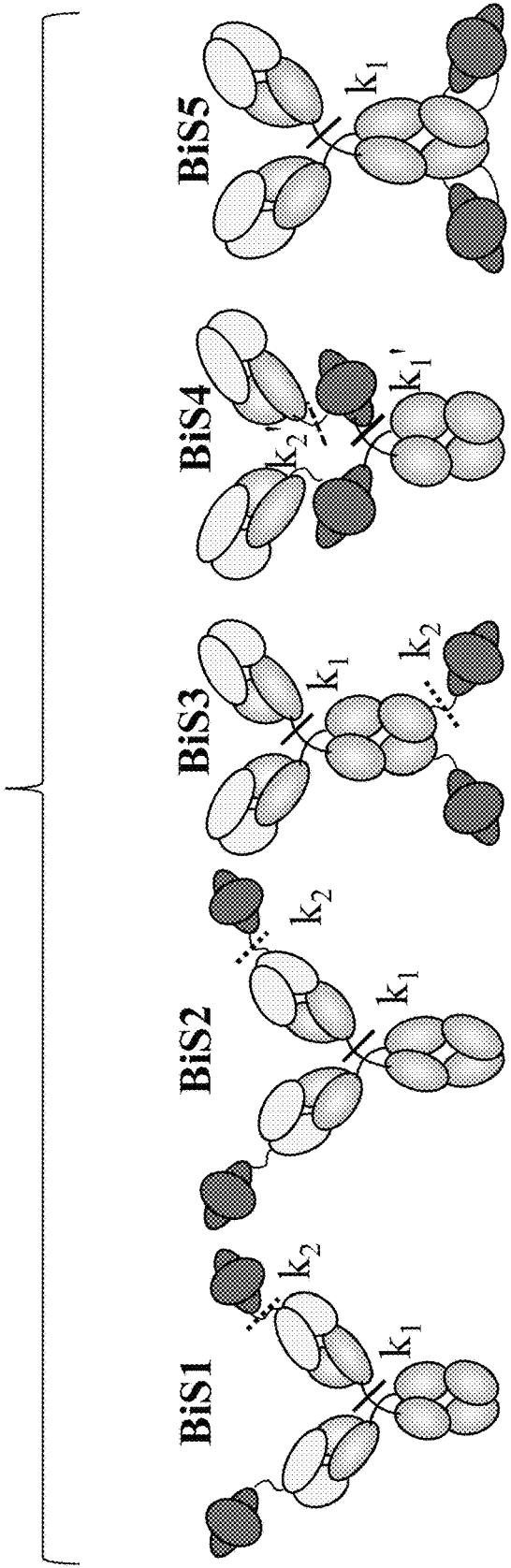
FIG. 83 depicts the general schematic structural format of each BiS1, BiS2, BiS3, BiS4, and BiS5 constructs. The denotations of "k1" and "k2" indicate the fragmentation patterns as used in the kinetic analysis discussed in Example 3.

In addition to the comparison between BiS4 and the bispecific binding constructs disclosed herein (BiS5), a study was performed in order to evaluate three other BiS structural motif platforms, identified as BiS1, BiS2 and BiS3 (see, FIG. 83). As will be appreciated by reference to FIG. 83, these platforms vary in terms of the location of one of the binding domains (illustrated as an scFv domain). Of the five motifs, only BiS4 and BiS5 include two linker moieties as points of attachment to the larger protein, the others (BiS1, BiS2, and BiS3) are attached by a single linker.

Figure 84:
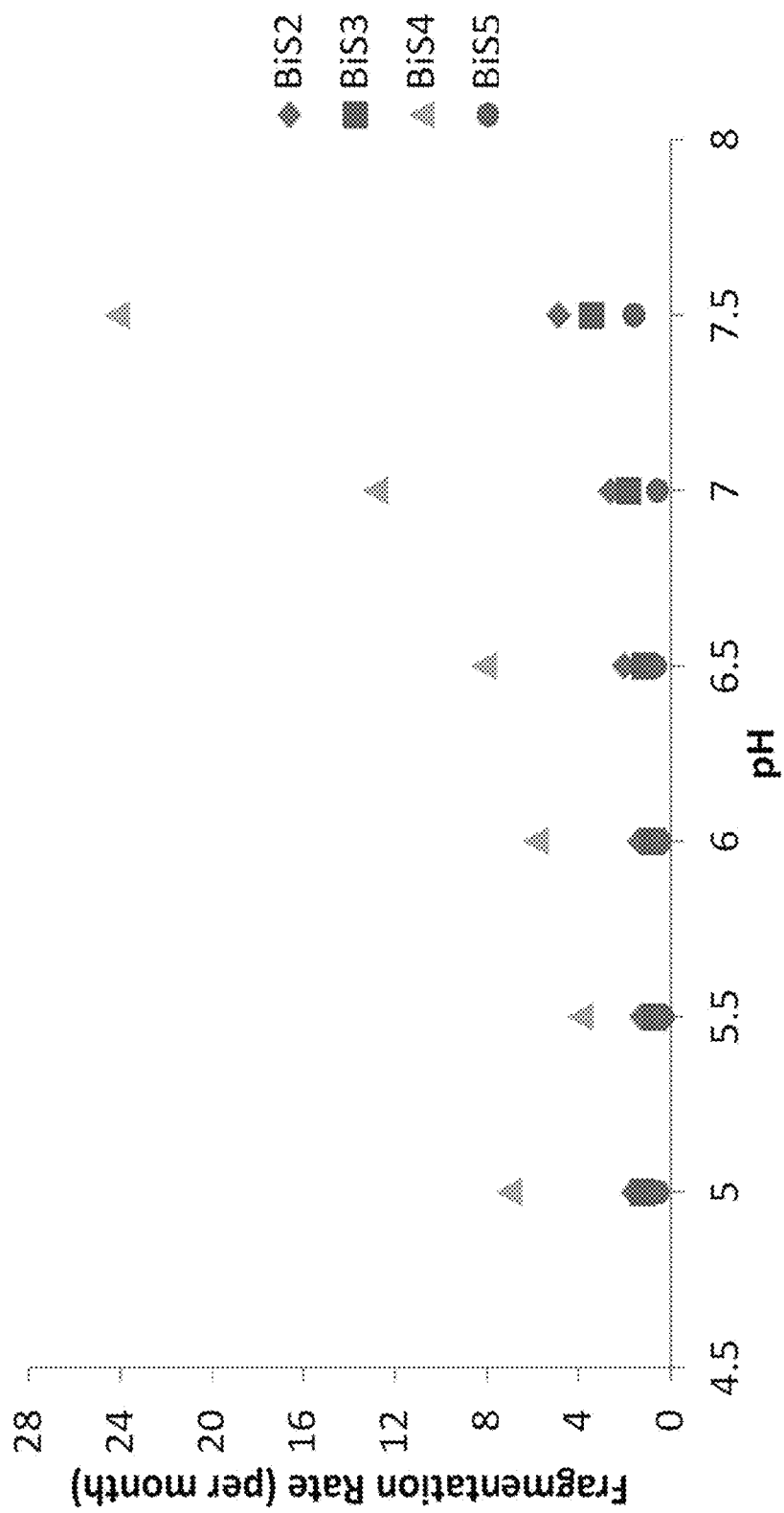
FIG. 84 depicts the fragmentation rate of each BiS1, BiS2, BiS3, BiS4, and BiS5 as a function of pH.
Figure 85:
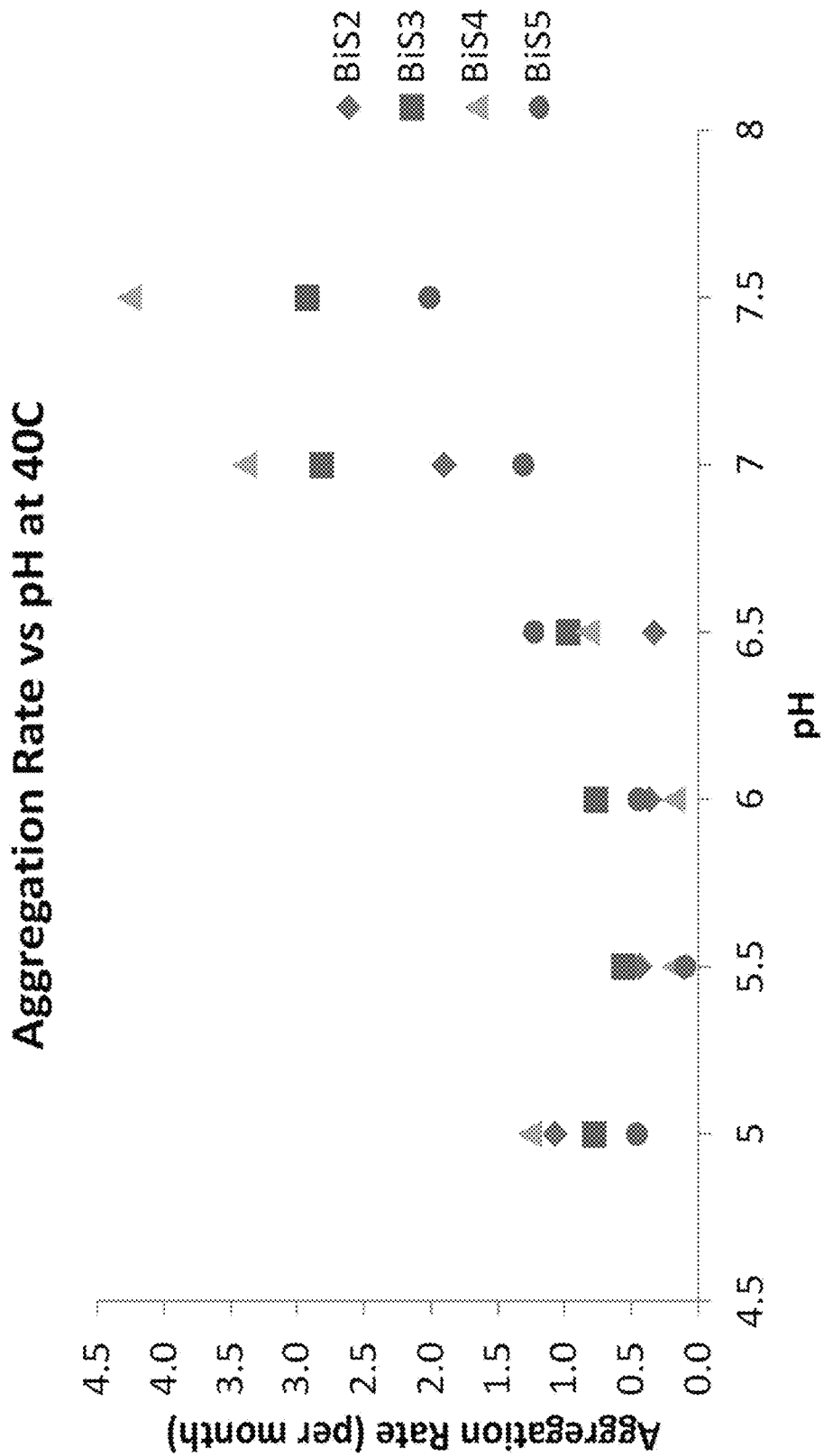
FIG. 85 depicts the aggregation rate of each BiS1, BiS2, BiS3, BiS4, and BiS5 as a function of pH.

Briefly, representative molecules of each construct were analyzed for stability using the techniques discussed above in Examples 3.1 and 3.2. Samples of each construct were added to buffers of pH 5.0, 5.5, 6.0, 6.5, 7.0, and 7.5 and were stored at 40° C. over a period of two months. The samples were then analyzed for fragmentation rate (FIG. 84), aggregation rate (FIG. 85), and monomer loss rate (FIG. 86) using HP-SEC. Under these conditions, the analysis indicated that the bispecific binding protein format disclosed herein ("BiS5"; and in D/H format as denoted above in Table 13) had superior physical and chemical stability relative to all the other formats at all pH conditions.

Figure 87:
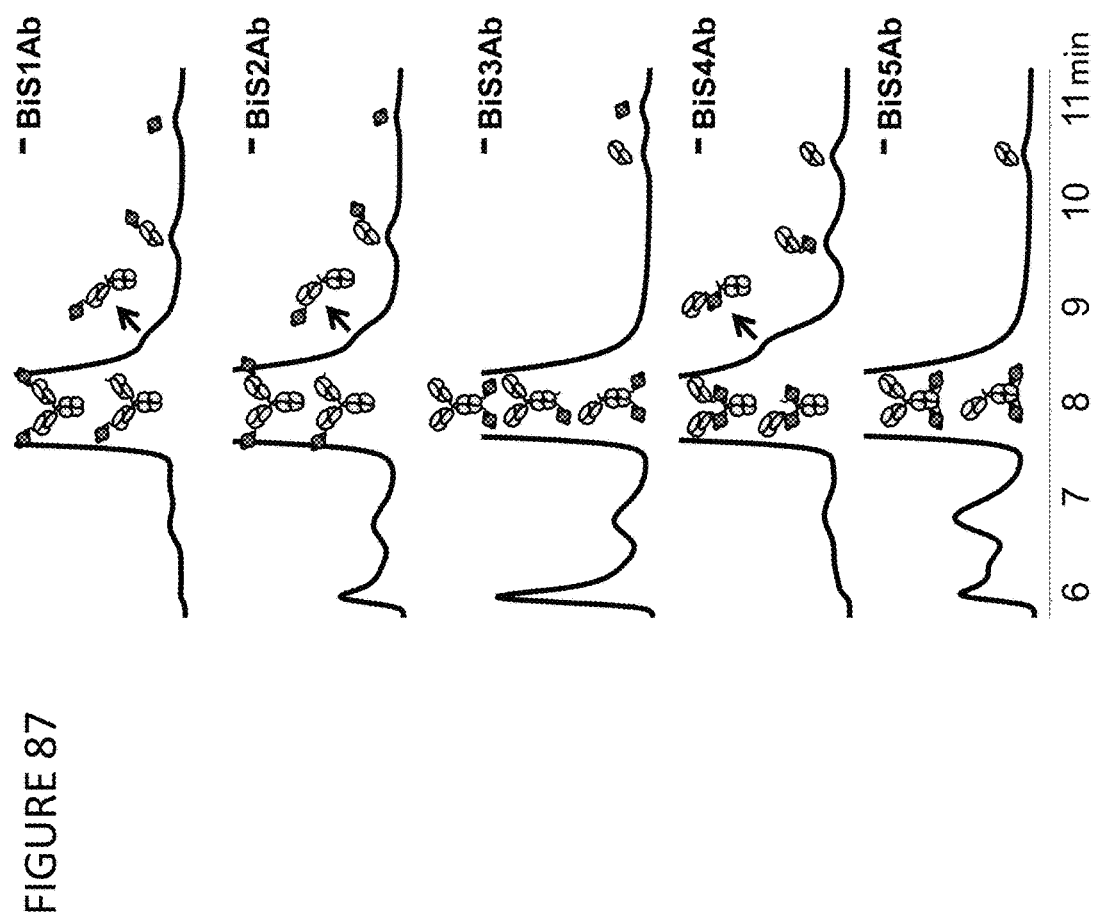
FIG. 87 depicts a representation of the fragmentation pattern and the correspondence to the peaks on HPSEC chromatograms for of each BiS1, BiS2, BiS3, BiS4, and BiS5.
Figure 88:
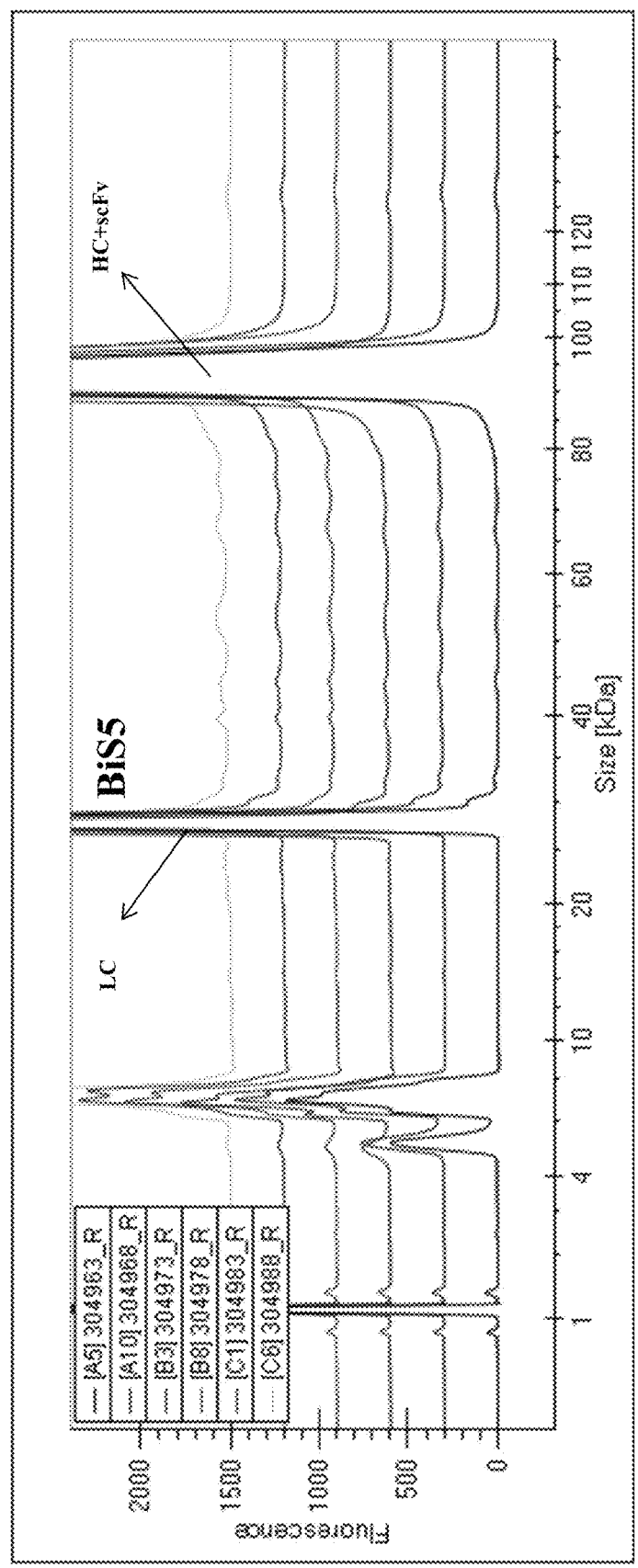
FIG. 88 depicts representative analysis of the fragmentation pattern under reducing conditions.

The SEC data were also used to map the various peaks to the corresponding fragments of the BiS molecules (FIG. 87). The mapping was based on assumptions that include that fragmentation occurs in the hinge and linker region of the molecules, the size of the fragment, the theoretical fragmentation, and how the expected fragment species align with respect to the fragment species observed in other formats. While there is good resolution between lower molecular weight fragments (LMWF) in each format, there is also poor or no resolution between monomer and higher molecular weight fragments (HMWF) in all formats. Based on the information in Table 17, it was concluded that the HP-SEC technique underestimates the fragmentation in BiS formats to a greater extent than for monoclonal antibodies. An alternate analysis was developed as discussed below.

TABLE 17

Fragmentation analysis - SEC underestimates fragmentation rates of BiS formats.

| Species | Mol. Wt. (kDa) | RT* (min) | % frag. per month at 40° C. (2 months) | | | | |
|---|---|---|---|---|---|---|---|
| | | | BiS1 | BiS2 | BiS3 | BiS4 | BiS5 |
| BiSAb monomer[1] | 200 | 7.9 | 3.4 | 3.4 | 0.8 | 6.2 | 0.5 |
| 2Fab + 1scFv + Fc[2] | 175 | 7.9 | x ($k_2$) | x ($k_2$) | x ($k_2$) | | |
| 1Fab + 2scFv + Fc[2] | 150 | 7.9 | | | x ($k_1$) | x ($k_2'$) | x ($k_1$) |
| 1Fab + 1scFv + Fc[3] | 125 | 8.7 | 1.7 ($k_1$) | 0.8 ($k_1$) | — | 3.4 ($k_1'$) | — |
| 1Fab + 1scFv | 75 | 9.7 | 0.9 ($k_1$) | 1.0 ($k_1$) | — | 1.5 ($k_1'$) | — |
| 1Fab | 50 | 10.6 | — | — | 0.4 ($k_1$) | 1.2 ($k_2'$) | 0.5 ($k_1$) |
| 1scFv | 25 | 11.0 | 0.8 ($k_2$) | 0.6 ($k_2$) | 0.4 ($k_2$) | — | — |

*Retention Time
[1]Monomer loss includes loss due to fragmentation only and does not include aggregation.
[2]Rates may be underestimated due to co-elution of HMWF with monomer.
[3]Rates for the shoulder peak may vary because of drop down integration.

An alternative analysis was developed in order to calculate fragmentation rates of HMWF using a molar extinction coefficient based on the assumptions that (i) during degradation, if a small fragment is detected then there should also be a corresponding large fragment present; (ii) secondary fragmentation (fragments of fragments) does not significantly occur during the duration of the stability study; and (iii) fragmentation occurs in the linker region and/or the hinge region. Fragmentation rates were determined based on the following relationships:

$$\text{Monomer} = \frac{k_t}{mEC_m} \quad \frac{LMWF}{k_{LMWF}} + \frac{HMWF}{k_{HMWF}}$$
$$\phantom{\text{Monomer} = \frac{k_t}{mEC_m}} \quad mEC_{LMWF} \quad mEC_{HMWF}$$

$$k_{HMWF} = \frac{k_{LMWF}}{mEC_{LMWF}} \times mEC_{HMWF}$$

Table 18: Inferred fragmentation analysis.

| Species | Mol. Wt. (kDa) | RT (min) | % frag. per month at 40° C. (2 months) | | | | |
|---|---|---|---|---|---|---|---|
| | | | BiS1 | BiS2 | BiS3 | BiS4 | BiS5 |
| BiSAb monomer[1] | 200 | 7.9 | 3.4 | 3.4 | 0.8 | 6.2 | 0.5 |
| 2Fab + 1scFv + Fc[2] | 175 | 7.9 | 3.6 ($k_2$) | 2.7 ($k_2$) | 1.9 ($k_2$) | | |
| 1Fab + 2scFv + Fc[2] | 150 | 7.9 | | | 1.6 ($k_1$) | 4.7 ($k_2'$) | 1.8 ($k_1$) |

-continued

| Species | Mol. Wt. (kDa) | RT (min) | % frag. per month at 40° C. (2 months) | | | | |
|---|---|---|---|---|---|---|---|
| | | | BiS1 | BiS2 | BiS3 | BiS4 | BiS5 |
| 1Fab + 1scFv + Fc[3] | 125 | 8.7 | 1.4 ($k_1$) | 1.6 ($k_1$) | — | 2.5 ($k_1'$) | — |
| 1Fab + 1scFv | 75 | 9.7 | 0.9 ($k_1$) | 1.0 ($k_1$) | — | 1.5 ($k_1'$) | — |
| 1Fab | 50 | 10.6 | — | — | 0.4 ($k_1$) | 1.2 ($k_2'$) | 0.5 ($k_1$) |
| 1scFv | 25 | 11.0 | 0.8 ($k_2$) | 0.6 ($k_2$) | 0.4 ($k_2$) | — | — |
| Total $k_1$ (hinge) | | | 2.3 | 2.6 | 2.0 | 4.0 | 2.3 |
| Total $k_2$ ($G_4S$ linker) | | | 4.4 | 3.3 | 2.3 | 5.9 | — |
| Total ($k = k_1 + k_2$) | | | 6.7 | 5.9 | 4.3 | 9.9 | 2.3 |

[1]Monomer loss includes loss due to fragmentation only and does not include aggregation.
[2]Rates may be underestimated due to co-elution of HMWF with monomer.
[3]Rates for the shoulder peak may vary because of integration of incompletely resolved peaks.

Figure 86:
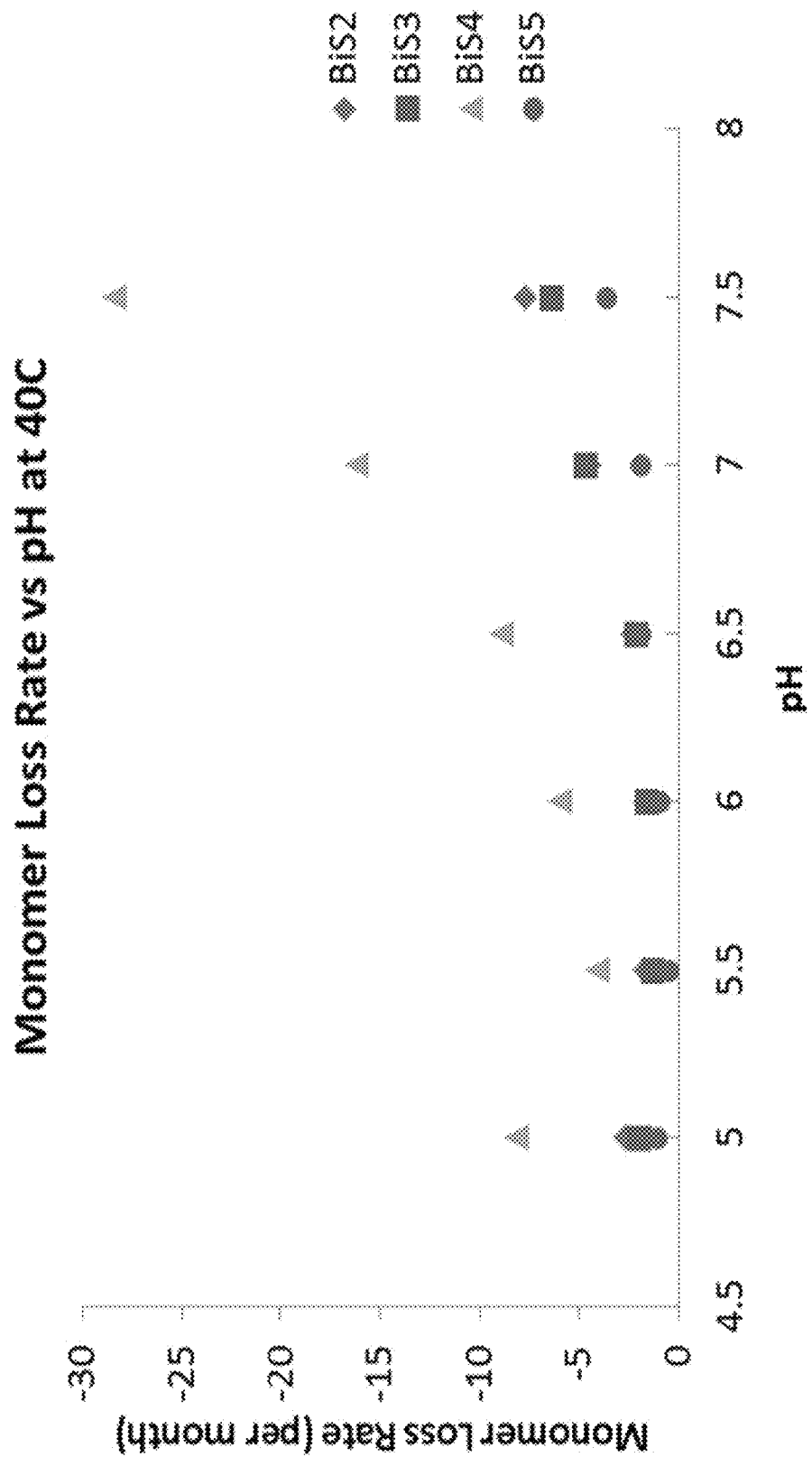
FIG. 86 depicts the monomer loss rate of each BiS1, BiS2, BiS3, BiS4, and BiS5 as a function of pH.

Further an analysis of fragmentation rates was conducted with the constructs under reducing conditions, in order to identify whether formation of disulfide bonds had an effect on fragmentation and stability. Representative data of this assay are presented in (FIG. 86). Under reducing conditions, higher fragmentation rates were observable for all BiS formats, except for BiS1 (Table 19). It was concluded that the higher fragmentation rates under reducing conditions confirms that the scFv moiety in the BiS5 construct is tethered to the CH3 region (FIG. 89).

TABLE 19

Fragmentation analysis - reducing conditions.

| Species | Mol. Wt. (kDa) | RT (min) | % frag. per month at 40° C. (2 months) (SEC/Red-GXII) | | | | |
|---|---|---|---|---|---|---|---|
| | | | BiS1 | BiS2 | BiS3 | BiS4 | BiS5 |
| BiSAb monomer[1] | 200 | 7.9 | 3.4/2.3 | 3.4/3.9 | 0.8/3.3 | 6.2/8.8 | 0.5/6.1 |
| 2Fab + 1scFv + Fc[2] | 175 | 7.9 | x ($k_2$) | x ($k_2$) | x ($k_2$) | | |
| 1Fab + 2scFv + Fc[2] | 150 | 7.9 | | | x ($k_1$) | x ($k_2'$) | x ($k_1$) |
| 1Fab + 1scFv + Fc[3] | 125 | 8.7 | 1.7 ($k_1$) | 0.8 ($k_1$) | — | 3.4 ($k_1'$) | — |
| 1Fab + 1scFv | 75 | 9.7 | 0.9 ($k_1$) | 1.0 ($k_1$) | — | 1.5 ($k_1'$) | — |
| 1Fab | 50 | 10.6 | — | — | 0.4 ($k_1$) | 1.2 ($k_2'$) | 0.5 ($k_1$) |
| 1scFv | 25 | 11.0 | 0.8 ($k_2$) | 0.6 ($k_2$) | 0.4 ($k_2$) | — | — |

TABLE 20

Overview of fragmentation analyses.

| Analytical Method | % frag. per month at 40° C. (2 months) | | | | |
|---|---|---|---|---|---|
| | BiS1 | BiS2 | BiS3 | BiS4 | BiS5 |
| Std. HPSEC | 3.4 | 3.4 | 0.8 | 6.4 | 0.5 |
| Alt. analysis of std. HPSEC | 6.7 | 5.9 | 4.3 | 9.9 | 2.3 |
| Non-red. GXII | 3.0 | 2.7 | 2.0 | 6.4 | 1.2 |
| Red. GXII | 2.3 | 3.9 | 3.3 | 8.8 | 6.1 |
| Total no. of $G_4S$ linker/molecule | 4 | 4 | 4 | 6 | 6 |

The characteristics of the stabilizing disulfide bonds disclosed above were further investigated. Results are shown in Tables 23 and 24 below. Bispecific antibodies corresponding to two different specificities were generated in BiS4 and BiS5 (scFv inserted in SN-G loop) formats with and without the stabilizing disulfide bond in the scFv. Accelerated stability study indicated that BiS4 constructs without a stabilizing disulfide bond had substantial monomer loss due to degradation which was prevented by introducing the stabilizing VL-VH disulfide bond. These results indicate that removal of stabilizing disulfide bond in the scFv in the BiS5 construct did not have a significant effect on its stability.

TABLE 21

| Anti-EGFR IgG/ anti-Her2 scFv | $T_M1$ (° C.) | Monomer % Day 0 | Monomer % Day 14 | Aggregation % Day 0 | Aggregation % Day 14 | Degradation % Day 0 | Degradation % Day 14 |
|---|---|---|---|---|---|---|---|
| BiS5 with DSB | 71.17 | 100 | 100 | 0.0 | 0.0 | 0.0 | 0.0 |
| BiS5 without DSB | 69.83 | 95.1 | 97.0 | 4.9 | 3.0 | 0.0 | 0.0 |
| BiS4 with DSB | 72.28 | 100 | 98.4 | 0.0 | 0.0 | 0.0 | 1.6 |
| BiS4 without DSB | 69.34 | 95.7 | 86.7 | 4.3 | 2.3 | 0.0 | 11.1 |

TABLE 22

| D-LC10 IgG/ 2F4 scFv | $T_M1$ (° C.) | Monomer % Day 0 | Monomer % Day 14 | Aggregation % Day 0 | Aggregation % Day 14 | Degradation % Day 0 | Degradation % Day 14 |
| --- | --- | --- | --- | --- | --- | --- | --- |
| BIS5 with DSB | 58.82 | 92.2 | 89.6 | 7.2 | 9.7 | 0.5 | 0.7 |
| BIS5 without DSB | 54.22 | 92.4 | 86.1 | 4.4 | 10.1 | 3.0 | 3.9 |
| BIS4 with DSB | 66.74 | 99.0 | 98.2 | 1.0 | 0.0 | 0.0 | 1.9 |
| BIS4 without DSB | 56.10 | 97.7 | 83.9 | 2.0 | 7.7 | 0.3 | 8.5 |

Based on all the above data it seems that the bispecific binding protein format disclosed herein is the most stable of all the formats tested. Furthermore, the BiSAb5 appears to be most stable at the lower pH values tested (e.g., 5.0, 5.5, and 6.0) in terms of minimizing both fragmentation and aggregation. As such the unexpected and surprising stability characteristics of the BisAbs disclosed herein provide a further advantage relative to other structural platforms and formats that are used in engineering bispecific binding molecules.

INCORPORATION BY REFERENCE

All publications and patents mentioned herein are hereby incorporated by reference in their entirety as if each individual publication or patent was specifically and individually indicated to be incorporated by reference.

While specific aspects of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

What is claimed is:

1. A bispecific binding protein that binds to PD-1 and CTLA-4 comprising a first heavy chain comprising the amino acid sequence of SEQ ID NO: 9, a first light chain comprising the amino acid sequence of SEQ ID NO: 7, a second heavy chain comprising the amino acid sequence of SEQ ID NO: 12, and a second light chain comprising the amino acid sequence of SEQ ID NO: 4.

2. The protein of claim 1 comprising an Fc region, wherein the Fc region is aglycosylated.

3. The protein of claim 1 comprising an Fc region, wherein the Fc region is deglycosylated.

4. The protein of claim 1 comprising an Fc region, wherein the Fc region has reduced fucosylation or is afucosylated.

5. A composition comprising the protein of claim 1 and a pharmaceutically acceptable carrier.

6. A nucleic acid molecule comprising a nucleotide sequence encoding a protein of claim 1.

7. A vector comprising the nucleic acid molecule of claim 6.

8. An isolated host cell comprising the vector of claim 7.

9. A method of treating or preventing cancer in a subject, the method comprising administering the protein of claim 1 to the subject.

10. The method of claim 9, wherein the cancer is one or more of ovarian cancer, breast cancer, colorectal cancer, prostate cancer, cervical cancer, uterine cancer, testicular cancer, bladder cancer, head and neck cancer, melanoma, pancreatic cancer, renal cell carcinoma, and lung cancer.

11. A method of enhancing an immune response in a subject, the method comprising administering the protein of claim 1 to the subject.

12. The nucleic acid molecule of claim 6, wherein the nucleotide encoding the protein of claim 1 comprises a nucleotide sequence encoding a first heavy chain, comprising the nucleotide sequence of SEQ ID NO: 10; a nucleotide sequence encoding a first light chain, comprising the nucleotide sequence of SEQ ID NO: 8; a nucleotide sequence encoding a second heavy chain, comprising the nucleotide sequence of SEQ ID NO: 13; and a nucleotide sequence encoding a second light chain, comprising the nucleotide sequence of SEQ ID NO: 11.

* * * * *